(12) United States Patent
Davidson et al.

(10) Patent No.: US 10,577,358 B2
(45) Date of Patent: Mar. 3, 2020

(54) STRIGOLACTONE FORMULATIONS AND USES THEREOF

(71) Applicant: SOUND AGRICULTURE COMPANY, San Francisco, CA (US)

(72) Inventors: Eric A. Davidson, San Francisco, CA (US); Travis S. Bayer, San Francisco, CA (US); Oliver Windram, London (GB); Yonek Hleba, London (GB)

(73) Assignee: SOUND AGRICULTURE COMPANY, Emeryville, CA (US)

( * ) Notice: Subject to any disclaimer, the term of this patent is extended or adjusted under 35 U.S.C. 154(b) by 0 days.

(21) Appl. No.: 15/947,508

(22) Filed: Apr. 6, 2018

(65) Prior Publication Data

US 2019/0084970 A1  Mar. 21, 2019

Related U.S. Application Data

(63) Continuation of application No. 14/856,908, filed on Sep. 17, 2015, now Pat. No. 9,994,557, which is a continuation of application No. PCT/US2014/062297, filed on Oct. 24, 2014.

(60) Provisional application No. 61/918,552, filed on Dec. 19, 2013, provisional application No. 61/895,893, filed on Oct. 25, 2013.

(51) Int. Cl.

| | | |
|---|---|---|
| *C07D 407/12* | (2006.01) | |
| *C07D 307/93* | (2006.01) | |
| *C07D 307/92* | (2006.01) | |
| *A01N 43/08* | (2006.01) | |
| *A01N 43/90* | (2006.01) | |
| *A01N 43/12* | (2006.01) | |
| *C07K 14/47* | (2006.01) | |
| *C12N 9/02* | (2006.01) | |
| *C12N 9/10* | (2006.01) | |
| *C12N 9/90* | (2006.01) | |

(52) U.S. Cl.
CPC .......... *C07D 407/12* (2013.01); *A01N 43/08* (2013.01); *A01N 43/12* (2013.01); *A01N 43/90* (2013.01); *C07D 307/92* (2013.01); *C07D 307/93* (2013.01); *C07K 14/47* (2013.01); *C12N 9/001* (2013.01); *C12N 9/0069* (2013.01); *C12N 9/1085* (2013.01); *C12N 9/90* (2013.01); *C12Y 103/99031* (2013.01); *C12Y 113/1107* (2015.07); *C12Y 113/11068* (2015.07); *C12Y 205/01029* (2013.01); *C12Y 205/01099* (2015.07); *C12Y 502/01014* (2015.07)

(58) Field of Classification Search
USPC ...................................................... 435/252
See application file for complete search history.

(56) References Cited

U.S. PATENT DOCUMENTS

| | | |
|---|---|---|
| 7,038,064 B2 | 5/2006 | Ishii et al. |
| 7,825,268 B2 | 11/2010 | Stumpe et al. |
| 8,101,171 B2 | 1/2012 | Becard et al. |
| 8,946,280 B2 | 2/2015 | Lachia et al. |
| 9,131,685 B2 | 9/2015 | Dahman et al. |
| 9,994,557 B2 | 6/2018 | Davidson et al. |
| 2008/0318773 A1 | 12/2008 | Becard et al. |
| 2011/0207608 A1 | 8/2011 | Zhu et al. |
| 2011/0230352 A1 | 9/2011 | Rameau et al. |
| 2012/0046169 A1 | 2/2012 | Dahman et al. |
| 2015/0274690 A1 | 10/2015 | Davidson et al. |

FOREIGN PATENT DOCUMENTS

| | | |
|---|---|---|
| CN | 1141952 A | 2/1997 |
| CN | 103068241 A | 4/2013 |
| CN | 103396390 A | 11/2013 |
| WO | WO-9831837 A1 | 7/1998 |
| WO | WO-2010125065 A2 | 11/2010 |
| WO | WO-2012057404 A1 | 5/2012 |
| WO | WO-2013092430 A1 | 6/2013 |
| WO | WO-2015061764 A1 | 4/2015 |
| WO | WO-2016172655 A1 | 10/2016 |

OTHER PUBLICATIONS

Heetika Malik et al., Aromatic A-ring analogues of orobanchol, new germination stimulants for seeds of parasitic weeds, Org. Biomol. Chem, Sep. 2011, 2286-2293.*
CAS Registry No. 1401956-60-2, STN Entry Date Oct. 24, 2012.
Co-pending U.S. Appl. No. 15/568,716, filed Oct. 23, 2017.
International Search Report and Written Opinion dated Sep. 14, 2016 for International Application No. PCT/US2016/029080.
Mwakaboko, et al. Single step synthesis of strigolactone analogues from cyclic keto enols, germination stimulants for seeds of parasitic weeds. Bioorg Med Chem. Aug. 15, 2011;19(16):5006-11.
Pubchem, Substance Record for SID 54096325 Create Date: Oct. 8, 2008. [retrieved on Aug. 16, 2016]. Retrieved from the Internet: https://pubchem.ncbi.nlm.nih.gov/substance/54096325.
Pubchem, Substance Record for SID 55052802 Create Date: Oct. 8, 2008. [retrieved on Jun. 1, 2016]. Retrieved from the Internet: https://pubchem.ncbi.nlm.nih.gov/substance/55052802.

(Continued)

*Primary Examiner* — Johann R Richter
*Assistant Examiner* — Courtney A Brown
(74) *Attorney, Agent, or Firm* — Wilson Sonsini Goodrich & Rosati

(57) ABSTRACT

Disclosed herein are plant propagation materials, methods of manufacturing, formulations and uses thereof. The plant propagation materials disclosed herein may comprise a strigolactone obtained by a biosynthetic process. The plant propagation material may comprise a chemical mimic of a strigolactone. The strigolactone may be 5-deoxystrigol. Methods of manufacturing the plant propagation materials may comprise a chemical process. Alternatively, methods of manufacturing the plant propagation material may comprise a biosynthetic process. The methods may comprise use of one or more polynucleotides. The polynucleotides may encode a metabolite. The polynucleotides may comprise one or more genes encoding one or more components of a strigolactone pathway.

14 Claims, 23 Drawing Sheets

(56) References Cited

OTHER PUBLICATIONS

CAS Registry No. 920959-02-0, STN Entry Date Feb. 14, 2007.
Toh, et al. Thermoinhibition uncovers a role for strigolactones in *Arabidopsis* seed germination. Plant Cell Physiol. Jan. 2012;53(1):107-17.
Akiyama, et al. Strigolactones: chemical signals for fungal symbionts and parasitic weeds in plant roots. Ann Bot. Jun. 2006;97(6):925-31. Epub Mar. 30, 2006.
Alder, et al. The path from β-carotene to carlactone, a strigolactone-like plant hormone. Science. Mar. 16, 2012;335(6074):1348-51. doi: 10.1126/science.1218094.
Besserer, et al. GR24, a synthetic analog of strigolactones, stimulates the mitosis and growth of the arbuscular mycorrhizal fungus *Gigaspora rosea* by boosting its energy metabolism. Plant Physiol. Sep. 2008;148(1):402-13. doi: 10.1104/pp.108.121400. Epub Jul. 9, 2008.
Bouwmeester, et al. Secondary metabolite signalling in host-parasitic plant interactions. Curr Opin Plant Biol. Aug. 2003;6(4):358-64.
Boyer, et al. Grain yields with limited water. J Exp Bot. Nov. 2004;55(407):2385-94. Epub Jul. 30, 2004.
Boyer, et al. New Strigolactone Analogs as Plant Hormones with Low Activities in the Rhizosphere. Molecular Plant Advance Access, published Dec. 26, 2013.
Boyer, et al. Structure-activity relationship studies of strigolactone-related molecules for branching inhibition in garden pea: molecule design for shoot branching. Plant Physiol. Aug. 2012;159(4):1524-44. doi: 10.1104/pp.112.195826. Epub Jun. 21, 2012.
Bruce, et al. Molecular and physiological approaches to maize improvement for drought tolerance. J Exp Bot. Jan. 2002;53(366):13-25.
Chadwick, et al. Sesquiterpenoids lactones: benefits to plants and people. Int J Mol Sci. Jun. 19, 2013;14(6):12780-805. doi: 10.3390/ijms140612780.
Chugh, et al. Differential antioxidative response of tolerant and sensitive maize (*Zea mays* L.) genotypes to drought stress at reproductive stage. Indian J Biochem Biophys. Apr. 2013;50(2):150-8.
Clark, et al. Agronomic, economic, and environmental comparison of pest management in conventional and alternative tomato and corn systems in northern California. Agriculture, Ecosystems & Environment. vol. 68, Issues 1-2, Mar. 1998, pp. 51-71.
Climate Stabilization Targets: Emissions, Concentrations, and Impacts over Decades to Millenina. 2011: The National Academies Press.
Cohen, et al. Structure-function relations of strigolactone analogs: activity as plant hormones and plant interactions. Mol Plant. Jan. 2013;6(1):141-52. doi: 10.1093/mp/sss134. Epub Dec. 8, 2012.
Eddy, et al. Optimizing Greenhouse Corn Prduction: Summary. Purdue Methods for Corn Growth, 2012.
Eddy, et al. Optimizing Greenhouse Corn Production: Materials and Methods. Purdue Methods for Corn Growth, 2010.
Eddy, et al. Optimizing Greenhouse corn Production: What is the Best Lighting and Plant Density? Purdue Methods for Corn Growth, 2010.
European search report and search opinion dated Jun. 8, 2017 for EP Application No. 14855263.1.
Gambrel, et al. Optimizing Greenhouse Corn Production: What Is the Best Pot Size? Purdue Methods for Corn Growth, 2010.
Gambrel, et al. Optimizing Greenhouse Corn Production: What Is the Best Root Medium? Purdue Methods for Corn Growth, 2010.
Goulet, et al. Climbing the branches of the strigolactones pathway one discovery at a time. Plant Physiol. Oct. 2010;154(2):493-6. doi: 10.1104/pp.110.161026.
Harrigan, et al. The forage and grain of MON 87460, a drought-tolerant corn hybrid, are compositionally equivalent to that of conventional corn. J Agric Food Chem. Oct. 28, 2009;57(20):9754-63. doi: 10.1021/jf9021515.

Harris, et al. Water-stress-induced changes in the abscisic acid content of guard cells and other cells of *Vicia faba* L. leaves as determined by enzyme-amplified immunoassay. Proc Natl Acad Sci USA. Apr. 1988;85(8):2584-8.
International search report and written opinion dated Jan. 16, 2015 for PCT Application No. US2014/062297.
Kim, et al. Guard cell signal transduction network: advances in understanding abscisic acid, CO2, and Ca2+ signaling. Annu Rev Plant Biol. 2010;61:561-91. doi: 10.1146/annurev-arplant-042809-112226.
Lake, et al. Regulation of Biochemical Plant Growth Regulators at the U.S. Environmental Protection Agency. HortTechnology Jan.-Mar. 2002, vol. 12, No. 1, pp. 55-58.
Lawrence, B. Production of clary sage oil and sclareol in North America. In Proceedings of the 4th international symposium on medicinal and aromatic plants. 1994.
Leonberger, et al. Optimizing Greenhouse Corn Production: What Is the Best Open Pollination Method? Purdue Methods for Corn Growth, 2010.
Lopez-Raez, et al. Does abscisic acid affect strigolactone biosynthesis? New Phytol. Jul. 2010;187(2):343-54. doi: 10.1111/j.1469-8137.2010.03291.x. Epub May 10, 2010.
Lopez-Raez, et al. Strigolactones: ecological significance and use as a target for parasitic plant control. Pest Manag Sci. May 2009;65(5):471-7. doi: 10.1002/ps.1692.
Macias, et al. New Chemical Clues for Broomrape-Sunflower Host—Parasite Interactions: Synthesis of Guaianestrigolactones. Journal of agricultural and food chemistry 57.13 (2009): 5853-5864.
Magnus, et al. Tentative Molecular Mechanism for Germination Stimulation of Striga and Orobanche Seeds by Strigol and Its Synthetic Analogues. J. Agric. Food. Chem. 1992, 40 1066-1070.
Malik, et al. Aromatic A-ring analogues of orbanchol, new germination stimulants for seeds of parasitic weeds. Organic & Biomolecular Chemistry. Apr. 7, 2011. 9(7), pp. 2286-2293.
"Mwakaboko, A. S. Synthesis and Biological Evaluation of new Strigolactone Analogues as Germination Stimulants for the Seeds of the Parasitic Weeds Striga and *Orobanche* spp. Thesis. Catholic University Nijmegen, Netherlands. Mar. 25, 2003.".
Mwakaboko, et al. Strigolactone analogs derived from ketones using a working model for germination stimulants as a blueprint. Plant Cell Physiol. Apr. 2011;52(4):699-715. doi: 10.1093/pcp/pcr031. Epub Mar. 18, 2011.
Nielsen, R. Corn growth and development, what goes on from planting to harvest? Extension University, 1997.
O'Connor, C. Soil Matters: How the Federal Crop Insurance Program should be reformed to encourage low-risk farming methods with high-reward environmental outcomes. 2013.
Okamoto, et al. Activation of dimeric ABA receptors elicits guard cell closure, ABA-regulated gene expression, and drought tolerance. Proc Natl Acad Sci U S A. Jul. 16, 2013;110(29):12132-7. doi: 10.1073/pnas.1305919110. Epub Jul. 1, 2013.
Peleg, et al. Hormone balance and abiotic stress tolerance in crop plants. Curr Opin Plant Biol. Jun. 2011;14(3):290-5. doi: 10.1016/j.pbi.2011.02.001. Epub Mar. 4, 2011.
Peppi, et al. Abscisic Acid Application Timing and Concentration Affect Firmness, Pigmentation, and Color of 'Flame Seedless' Grapes. HortScience Oct. 2006, vol. 41, No. 6, 1440-1445.
Pimentel, et al. Environmental and Economic Costs of Pesticide Use. BioScience, vol. 42, No. 10, 1992.
Prasch, et al. Simultaneous application of heat, drought, and virus to *Arabidopsis* plants reveals significant shifts in signaling networks. Plant Physiol. Aug. 2013;162(4):1849-66. doi: 10.1104/pp.113.221044. Epub Jun. 10, 2013.
Qin, et al. Sesquiterpene lactones from Inula hupehensis inhibit nitric oxide production in RAW264.7 macrophages. Planta Med. Jun. 2012;78(10):1002-9. doi: 10.1055/s-0031-1298621. Epub May 30, 2012.
Raupp, et al. New sesquiterpene lactones from sunflower root exudate as germination stimulants for Orobanche cumana. J Agric Food Chem. Nov. 6, 2013;61(44):10481-7. doi: 10.1021/jf402392e. Epub Oct. 24, 2013.

(56) References Cited

OTHER PUBLICATIONS

Ren, et al. Cytotoxic and NF-κB inhibitory sesquiterpene lactones from Piptocoma rufescens. Tetrahedron. Mar. 25, 2012;68(12):2671-2678. Epub Jan. 26, 2012.
Rink, et al. Optimizing Greenouse Corn Production: What is the Best Irrigation Strategy? Purdue Methods for Corn Growth, 2010.
Rivero, et al. Enhanced cytokinin synthesis in tobacco plants expressing PSARK::IPT prevents the degradation of photosynthetic protein complexes during drought. Plant Cell Physiol. Nov. 2010;51(11):1929-41. doi: 10.1093/pcp/pcq143. Epub Sep. 24, 2010.
Rungeler, et al. Germacranolides from Mikania guaco. Phytochemistry. Mar. 2001;56(5):475-89.
Ruyter-Spira, et al. Physiological effects of the synthetic strigolactone analog GR24 on root system architecture in *Arabidopsis*: another belowground role for strigolactones? Plant Physiol. Feb. 2011;155(2):721-34. doi: 10.1104/pp.110.166645. Epub Nov. 30, 2010.
Schoper, et al. Plant factors controlling seed set in maize : the influence of silk, pollen, and ear-leaf water status and tassel heat treatment at pollination. Plant Physiol. Jan. 1987;83(1):121-5.
Shin, et al. Sesquiterpenes and other constituents from *Dendranthema zawadskii* var. *latilobum*. Chem Pharm Bull (Tokyo). 2012;60(3):306-14.
Stephanopoulous, G. Synthetic biology and metabolic engineering. ACS Synth Biol. Nov. 16, 2012;1(11):514-25. doi: 10.1021/sb300094q.
Tanaka, et al. Synthesis of 7-oxo-5-deoxystrigol, a 7-oxygenated strigolactone analog. Biosci Biotechnol Biochem. 2013;77(4):832-5. Epub Apr. 7, 2013.
Tarklason, et al. Effect of Nitrogen Application Timing on Corn Production Using Subsurface Drip Irrigation. Soil Science, Mar. 2009, vol. 174, Issue 3, pp. 174-179.
Tollefson, J. Drought-tolerant maize gets US debut. Nature. Jan. 13, 2011;469(7329):144. doi: 10.1038/469144a.
Tsuchiya, et al. Strigolactones: a new hormone with a past. Curr Opin Plant Biol. Oct. 2009;12(5):556-61. doi: 10.1016/j.pbi.2009.07.018. Epub Aug. 31, 2009.

United States Department of Agriculture, National Agricultural Statistics Service Crop production report released Sep. 2013.
United States Department of Agriculture, Risk Management Agency RMA Indemnities (AS of Jul. 8, 2013). Accessed Sep. 26, 2013 from: http://www.rma.usda.gov/data/indemnity/2013/070813table.pdf.
Upar, et al. Efficient enantioselective synthesis of (+)-sclareolide and (+)-tetrahydroactinidiolide: chiral LBA-induced biomimetic cyclization. Tetrahedron: Asymmetry vol. 20, Issue 14, Jul. 29, 2009, pp. 1637-1640.
Wigchert, et al. Dose-response of seeds of the parasitic weeds *Striga* and *Orobanche* toward the synthetic germination stimulants GR 24 and Nijmegen 1. J Agric Food Chem. Apr. 1999;47(4):1705-10.
Witt, et al. Metabolic and phenotypic responses of greenhouse-grown maize hybrids to experimentally controlled drought stress. Mol Plant. Mar. 2012;5(2):401-17. doi: 10.1093/mp/ssr102. Epub Dec. 15, 2011.
Xie, et al. Fabacyl acetate, a germination stimulant for root parasitic plants from Pisum sativum. Phytochemistry 70.2 (2009): 211-215.
Yoneyama, et al. Characterization of strigolactones exuded by Asteraceae plants. Plant growth regulation 65.3 (2011): 495-504.
Yoneyma, et al. Strigolactones as a new plant growth regulator. Presentation at the MARCO Symposium 2009, Tsukuba, Japan, on Oct. 6, 2009.
Yoshida, et al. Plants that attack plants: molecular elucidation of plant parasitism. Curr Opin Plant Biol. Dec. 2012;15(6):708-13. doi: 10.1016/j.pbi.2012.07.004. Epub Aug. 13, 2012.
Zwanenburg, et al. Structure and Activity of Strigolactones: New Plant Hormones with a Rich Future. Mol. Plant, vol. 6, Issue 1, pp. 38-62.
Zwanenburg, et al. Structure and function of natural and synthetic signalling molecules in parasitic weed germination. Pest Manag Sci 2009; 65: 478-491.
Office action dated Apr. 17, 2017 for U.S. Appl. No. 14/856,908.
Office action dated Oct. 21, 2016 for U.S. Appl. No. 14/856,908.
Office action dated Dec. 14, 2017 for U.S. Appl. No. 14/856,908.
U.S. Appl. No. 14/856,908 Notice of Allowance dated Mar. 29, 2018.

\* cited by examiner

AB01 treatment enables salinity tolerance in tomato

Control    + AB01

Reduction of *Striga* parasite in field trials

STRIGOLACTONE FORMULATIONS AND USES THEREOF

CROSS-REFERENCE

This application is a continuation of U.S. patent application Ser. No. 14/856,908, filed on Sep. 17, 2015, which is a continuation of PCT/US2014/062297, filed Oct. 24, 2014, which claims priority to U.S. Provisional Patent Application 61/895,893, filed Oct. 25, 2013, and U.S. Provisional Patent Application 61/918,552, filed Dec. 19, 2013, which are entirely incorporated herein by reference.

BACKGROUND OF THE INVENTION

Drought is a major constraint on crop productivity and a significant risk for farmers. The challenges associated with drought are likely to increase due to climate change, which will increase temperatures and alter precipitation patterns. Adapting the nation's agricultural system to water-limited conditions is a major priority to ensure food security and sustainable farm economics. Current drought management strategies are limited to soil management practices and crop variety choice. A crop protection product that could be sprayed on or applied to drought-affected fields at the onset of drought to protect or enhance yields would be a valuable tool for growers to adapt to drought and climate change in real time.

Strigolactones are a recently discovered class of hormones known to regulate development and stress response. Strigolactone has not been evaluated as a product due to its high cost of production. We have developed novel and economical routes to produce plant propagation materials. The plant propagation materials may comprise strigolactone. Alternatively, or additionally, the plant propagation materials comprise chemical mimics of strigolactone. The plant propagation materials may be administered to plants, such as maize. Plants treated with strigolactones may show a significant resistance to the adverse effects of water-limited conditions. In addition, plants treated with strigolactones may show increased plant yield. Further disclosed herein are uses of plant propagation materials.

SUMMARY OF THE INVENTION

Disclosed herein is a compound of Formula (I), a salt, solvate, polymorph, stereoisomer, or isomer thereof:

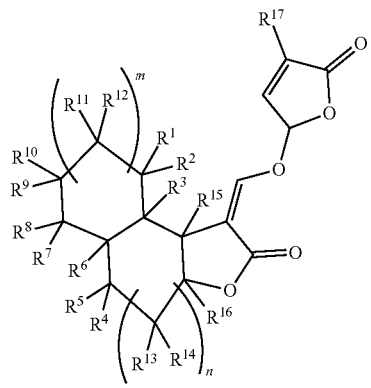

Formula (I)

wherein:
$R^1$, $R^2$, $R^4$, $R^5$, $R^7$, $R^8$, $R^9$, $R^{10}$, $R^{11}$, $R^{12}$, $R^{13}$, $R^{14}$, $R^{15}$, $R^{16}$, and $R^{17}$ are each independently H, alkyl, haloalkyl, amino, halo, or —$OR^{18}$;
$R^3$ and $R^6$ are each independently H, alkyl, haloalkyl, amino, halo, or —$OR^{18}$; or $R^3$ and $R^6$ together form a direct bond to provide a double bond;
each $R^{18}$ is independently H, alkyl, haloalkyl, aryl, heteroaryl, or —$C(O)R^{19}$;
each $R^{19}$ is independently alkyl, haloalkyl, aryl, or heteroaryl;
m is 0, 1, or 2; and
n is 1 or 2.

In some instances, m is 0 and n is 1. In some instances, m is 0 and n is 2. In some instances, m is 1 and n is 2. In some instances, m is 2 and n is 1. In some instances, m is 2 and n is 2. In some instances, m is 1 and n is 1.

Further disclosed herein is a compound having the structure of Formula (II):

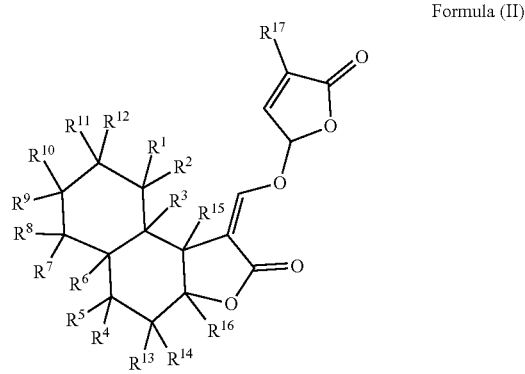

Formula (II)

or a salt, solvate, polymorph, stereoisomer, or isomer thereof, wherein:
$R^1$, $R^2$, $R^4$, $R^5$, $R^7$, $R^8$, $R^9$, $R^{10}$, $R^{11}$, $R^{12}$, $R^{13}$, $R^{14}$, $R^{15}$, $R^{16}$, and $R^{17}$ are each independently H, alkyl, haloalkyl, amino, halo, or —$OR^{18}$;
$R^3$ and $R^6$ are each independently H, alkyl, haloalkyl, amino, halo, or —$OR^{18}$; or $R^3$ and $R^6$ together form a direct bond to provide a double bond;
each $R^{18}$ is independently H, alkyl, haloalkyl, aryl, heteroaryl, or —$C(O)R^{19}$; and
each $R^{19}$ is independently alkyl, haloalkyl, aryl, or heteroaryl Further disclosed herein is a compound having a structure of Formula (III)

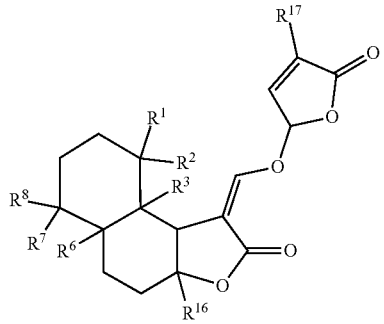

Formula (III)

or a salt, solvate, polymorph, stereoisomer, or isomer thereof, wherein:

$R^1$, $R^2$, $R^7$, $R^8$, $R^9$, $R^{16}$, and $R^{17}$ are each independently H, alkyl, haloalkyl, amino, halo, or —$OR^{18}$; $R^3$ and $R^6$ are each independently H, alkyl, haloalkyl, amino, halo, or —$OR^{18}$; or $R^3$ and $R^6$ together form a direct bond to provide a double bond;

each $R^{18}$ is independently H, alkyl, haloalkyl, aryl, heteroaryl, or —$C(O)R^{19}$; and each $R^{19}$ is independently alkyl, haloalkyl, aryl, or heteroaryl.

In some instances, $R^1$, $R^2$, $R^4$, $R^5$, $R^7$, $R^8$, $R^9$, $R^{10}$, $R^{11}$, $R^{12}$, $R^{13}$, $R^{14}$, $R^{15}$, $R^{16}$, and $R^{17}$ are each independently H, alkyl, or —$OR^{18}$. In some instances, $R^3$ and $R^6$ together form a direct bond to provide a double bond. In some instances, $R^3$ and $R^6$ are each independently H, alkyl, haloalkyl, amino, halo, or —$OR^{18}$. In some instances, $R^3$ and $R^6$ are each independently H, alkyl, or —$OR^{18}$. In some instances, $R^{17}$ is alkyl.

Further disclosed herein are compounds having the structure of Formula IV:

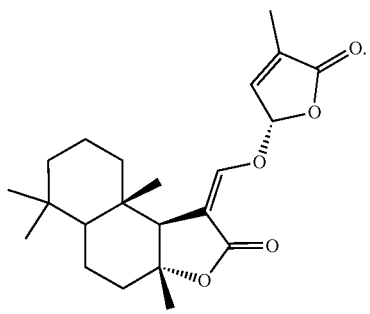

and Formula V:

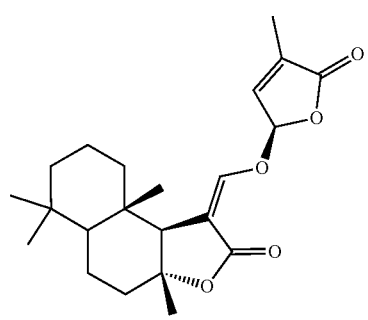 [SMILES: CC1=C[C@H](O/C=C2\C(=O)O[C@]3(C)CCC4C(C)(C)CCC[C@]4(C)[C@@H]23)OC1=O]

Further disclosed herein are compounds having the structure of Formula (VI)

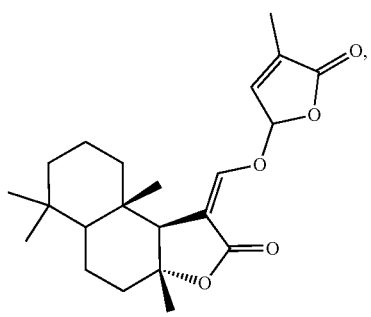 [SMILES: CC1=CC(O/C=C2\C(=O)O[C@]3(C)CCC4C(C)(C)CCC[C@]4(C)[C@@H]23)OC1=O]

or a salt, solvate, polymorph, stereoisomer, or isomer thereof.

Disclosed herein is another chemical mimic of Strigolactone. The chemical mimic of Strigolactone can be compound of Formula (VII), a salt, solvate, polymorph, diastereoisomer, stereoisomer, or isomer thereof:

Formula (VII)

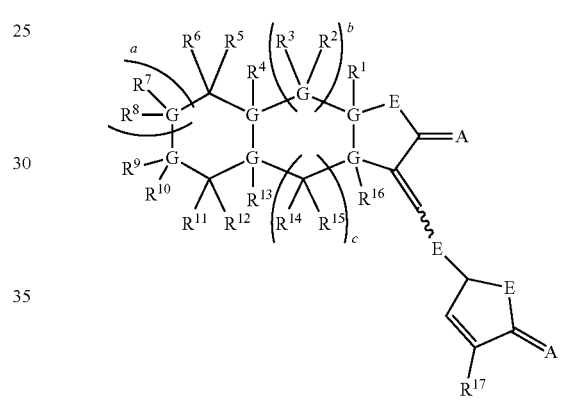

wherein:

a, b, c are each independently 0, 1, or 2;

each A is independently O, or S;

each E is independently O, S, or —$NR^{18}$;

each G is independently C or N;

$R^5$, $R^6$, $R^{11}$, $R^{12}$, $R^{14}$, $R^{15}$ and $R^{17}$ are each independently H, alkyl, haloalkyl, amino, halo, or —$OR^{18}$;

$R^2$, $R^3$, $R^7$, $R^8$, $R^9$, and $R^{10}$ are each independently H, alkyl, haloalkyl, amino, halo, —$OR^{18}$ or a lone electron pair;

$R^1$ and $R^{16}$ are each independently H, alkyl, haloalkyl, amino, halo, lone electron pair, or —$OR^{18}$; or $R^1$ and $R^{16}$ together form a direct bond to provide a double bond;

$R^4$ and $R^{13}$ are each independently H, alkyl, haloalkyl, amino, halo, lone electron pair, or —$OR^{18}$; or $R^1$ and $R^{16}$ together form a direct bond to provide a double bond;

each $R^{18}$ is independently H, alkyl, haloalkyl, aryl, heteroaryl, —$C(O)R^{19}$ or

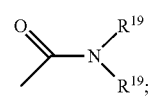

and each $R^{19}$ is independently H, alkyl, haloalkyl, aryl, or heteroaryl.

Another chemical mimic of Strigolactone can be compound of Formula (VIII), a salt, solvate, polymorph, diastereoisomer, stereoisomer, or isomer thereof:

Formula (VIII)

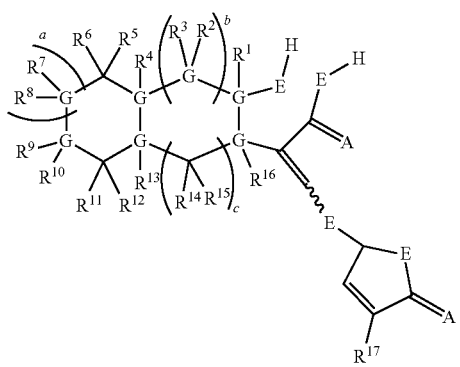

wherein:
a, b, c are each independently 0, 1, or 2;
each A is independently O, or S;
each E is independently O, S, or —NR$^{18}$;
each G is independently C or N;
R$^5$, R$^6$, R$^{11}$, R$^{12}$, R$^{14}$, R$^{15}$ and R$^{17}$ are each independently H, alkyl, haloalkyl, amino, halo, or —OR$^{18}$;
R$^2$, R$^3$, R$^7$, R$^8$, R$^9$, and R$^{10}$ are each independently H, alkyl, haloalkyl, amino, halo, —OR$^{18}$ or a lone electron pair;
R$^1$ and R$^{16}$ are each independently H, alkyl, haloalkyl, amino, halo, lone electron pair, or —OR$^{18}$; or R$^1$ and R$^{16}$ together form a direct bond to provide a double bond;
R$^4$ and R$^{13}$ are each independently H, alkyl, haloalkyl, amino, halo, lone electron pair, or —OR$^{18}$; or R$^1$ and R$^{16}$ together form a direct bond to provide a double bond;
each R$^{18}$ is independently H, alkyl, haloalkyl, aryl, heteroaryl, —C(O)R$^{19}$ or

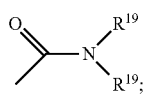

and
each R$^{19}$ is independently H, alkyl, haloalkyl, aryl, or heteroaryl.

In an embodiment, each A in the compound, salt, solvate, polymorph, diastereoisomer, stereoisomer, or isomer of the chemical mimic of strigolactone is independently O. In another embodiment, each E in the compound, salt, solvate, polymorph, diastereoisomer, stereoisomer, or isomer of the chemical mimic of strigolactone is independently O. In another embodiment, each G in the compound, salt, solvate, polymorph, diastereoisomer, stereoisomer, or isomer of the chemical mimic of strigolactone is independently C. In another embodiment, the compound, salt, solvate, polymorph, diastereoisomer, stereoisomer, or isomer of the chemical mimic of strigolactone, wherein R$^2$, R$^3$, R$^4$, R$^7$, R$^8$, R$^9$, R$^{10}$, R$^{11}$, R$^{12}$, and R$^{16}$ are each independently H. In another embodiment, the compound, salt, solvate, polymorph, diastereoisomer, stereoisomer, or isomer of the chemical mimic of strigolactone, wherein R$^1$, R$^5$, R$^6$, R$^{13}$, and R$^{17}$ are each independently alkyl. In another embodiment, the compound, salt, solvate, polymorph, diastereoisomer, stereoisomer, or isomer of the chemical mimic of strigolactone, wherein R$^1$, R$^5$, R$^6$, R$^{13}$, and R$^{17}$ are each independently methyl.

In one embodiment, the compound, salt, solvate, polymorph, diastereoisomer, stereoisomer, or isomer disclosed herein is not (+)-Strigol

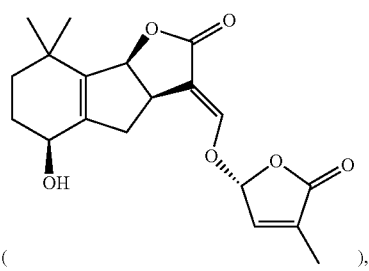 [SMILES: CC1=C[C@H](O/C=C2/C(=O)O[C@@H]3C4=C(C[C@H]23)[C@@H](O)CCC4(C)C)OC1=O]

(+)-Strigyl acetate

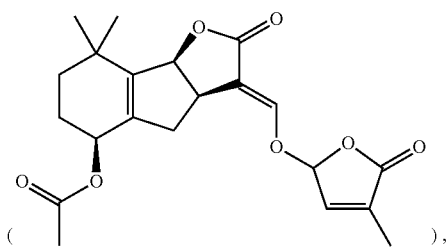 [SMILES: CC(=O)O[C@H]1CCC(C)(C)C2=C1C[C@@H]1/C(=C\OC3C=C(C)C(=O)O3)C(=O)O[C@H]21]

(+)-Orobanchol

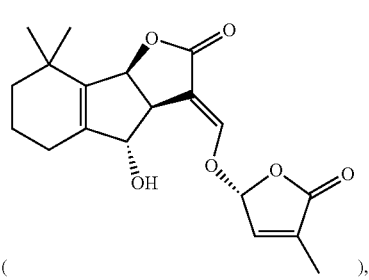 [SMILES: CC1=C[C@H](O/C=C2/C(=O)O[C@@H]3C4=C(CCCC4(C)C)[C@@H](O)[C@H]23)OC1=O]

(+)-Orobanchyl acetate

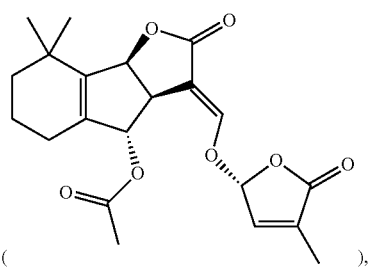 [SMILES: CC(=O)O[C@@H]1C2=C([C@H]3OC(=O)/C(=C/O[C@H]4C=C(C)C(=O)O4)[C@@H]13)C(C)(C)CCC2]

(+)-5-Deoxystrigol

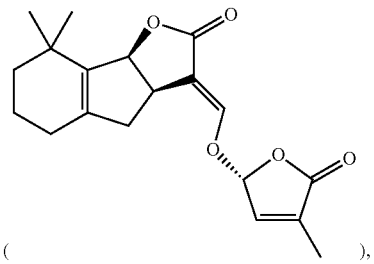 [SMILES: CC1=C[C@H](O/C=C2/C(=O)O[C@@H]3C4=C(CCCC4(C)C)C[C@H]23)OC1=O]

( ),

Sorgolactone

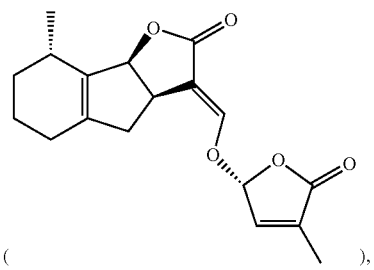 [SMILES: CC1=C[C@H](O/C=C2/C(=O)O[C@@H]3C4=C(CCC[C@@H]4C)C[C@H]23)OC1=O]

( ), or any combination thereof.

The compound, salt, solvate, polymorph, diastereoisomer, stereoisomer, or isomer can be isolated and purified. In one embodiment, $R^4$ and $R^{13}$ together do not form a direct bond to provide a double bond. In another embodiment, $R^4$ and $R^{13}$ together forms a direct bond to provide a double bond. In another embodiment, b+c equals at least 2. In another embodiment, b is 1 or 2.

The compound, salt, solvate, polymorph, diastereoisomer, stereoisomer, or isomer may be one of the following:

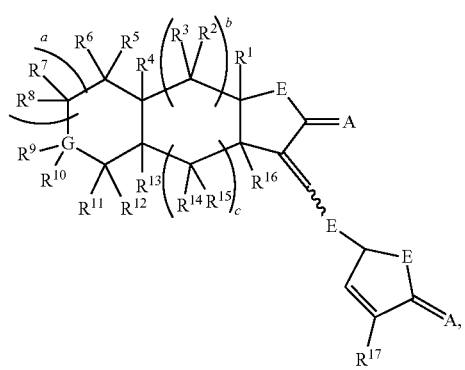

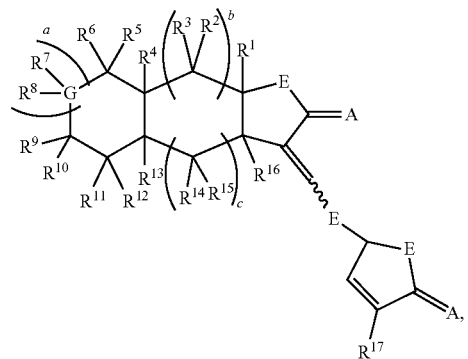

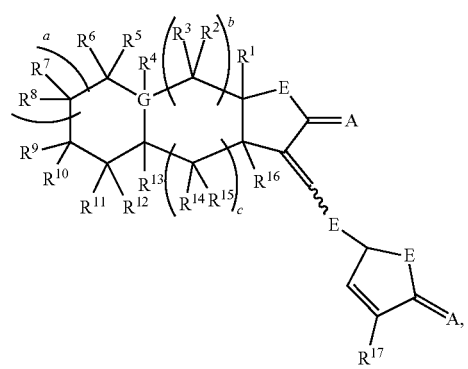

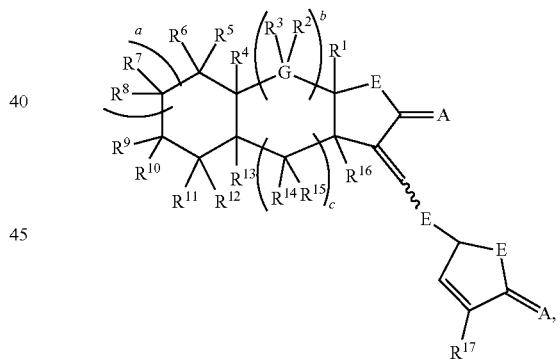

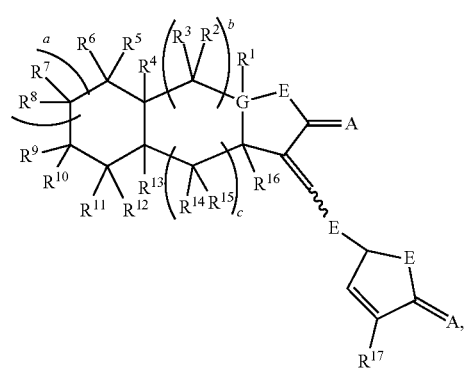

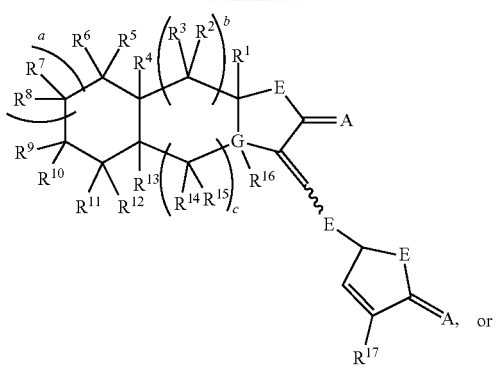

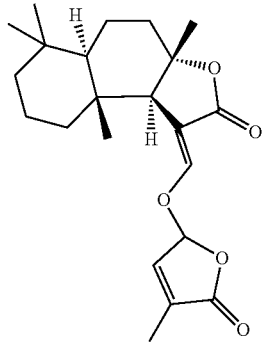

Formula (X)

The chemical mimic of strigolactone may be a compound, salt, solvate, polymorph, diastereoisomer, stereoisomer, or isomer, having the structure of Formula (IX):

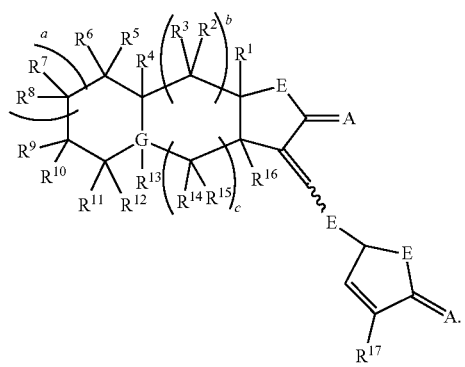

Formula (IX)

The chemical mimic of strigolactone may be a compound, salt, solvate, polymorph, diastereoisomer, stereoisomer, or isomer, having the structure of Formula (X):

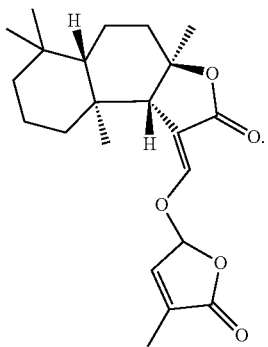

The compound, salt, solvate, polymorph, diastereoisomer, stereoisomer, or isomer disclosed herein, may have a diastereomeric excess of at least about 15%, 20%, 30%, 40%, 50%, 60%, 70%, 80%, 85%, 90%, 95%, or 99%. The compound, salt, solvate, polymorph, diastereoisomer, stereoisomer, or isomer disclosed herein, may have a diastereomeric excess of about 15%-99%, 20%-99%, 30%-99%, 40-99%, 50-99%, 60-99%, 70-99%, 80-99%, 90-99%, 15%-90%, 20%-90%, 30%-90%, 40-90%, 50-90%, 60-90%, 70-90%, 80-90%, 15%-80%, 20%-80%, 30%-80%, 40-80%, 50-80%, 60-80%, 70-80%, 15%-70%, 20%-70%, 30%-70%, 40-70%, 50-70%, 60-70%, 15%-60%, 20%-60%, 30%-60%, 40-60%, 50-60%, 15%-50%, 20%-50%, 30%-50%, 40-50%, 15%-40%, 20%-40%, 30%-40%, 15%-30%, 20%-30%, or 15-20%. In one embodiment, the compound, salt, solvate, polymorph, diastereoisomer, stereoisomer, or isomer disclosed herein, may have a diastereomeric excess of from at least about 50% to 100%.

The compound, salt, solvate, polymorph, diastereoisomer, stereoisomer, isomer or formulation disclosed herein may comprise about: 2, 3, 4, 5, 6, 7, 8, 9, or 10 individual diastereoisomer of Formula I, II, III, IV, V, VI, VII, VIII, IX, or X.

Disclosed herein are formulations comprising the compound, salt, solvate, polymorph, diastereoisomer, stereoisomer, or isomer disclosed herein. The formulation may further comprise an excipient. In one embodiment, the excipient comprises water, a surfactant, an alcohol, or any combination thereof. In another embodiment, the formulation comprises the surfactant, wherein the surfactant comprises sulfosuccinate, naphthalene sulfonate, sulfated ester, phosphate ester, sulfated alcohol, alkyl benzene sulfonate, polycarboxylate, naphthalene sulfonate condensate, phenol sulfonic acid condensate, lignosulfonate, methyl oleyl taurate, polyvinyl alcohol, or any combination thereof.

The formulation may further comprise a fertilizer. In one embodiment, the fertilizer comprises nitrogen fertilizer, phosphate fertilizer, potassium fertilizer, calcium fertilizer, magnesium fertilizer, sulfur fertilizer, compound fertilizer, organic fertilizer, or any combination thereof.

The formulation may further comprise an insecticide, a fungicide, a herbicide, or any combination thereof. In one embodiment, the herbicide comprises a glyphosate. In another embodiment, the glyphosate comprises N-(phosphonomethyl)glycine.

Disclosed herein can be a method comprising contacting a plant with the compound, salt, solvate, polymorph, diastereoisomer, stereoisomer, isomer, or formulation disclosed herein. In one embodiment, the contacting the plant comprises administering the compound, salt, solvate, polymorph, stereoisomer, isomer or formulation as a spray. In another embodiment, the contacting the plant further comprises adding the compound, salt, solvate, polymorph, stereoisomer, isomer or formulation to irrigation water of the plant.

The plant disclosed herein can be cereals, such as millet, barley, maize, oats, triticale, rye, buckwheat, fonio, quinoa, sorghum, corn, wheat, and rice. The plant can be staple crops such as potato, cassava, and legumes. The plant can be vegetables, spices, fruits, nuts, herbs, and edible flowers. The plant can be sugar cane and sugar beet. The plant can be maize, soybean, rapeseed, safflower, sunflower, and olive. In one embodiment, the plant is soybean, tomato, soybean, corn, rice, tomato, alfalfa, wheat, green algae or any combination thereof.

In one embodiment of the method, a yield of the contacted plant is increased as compared to an uncontacted plant, a life of the contacted plant is extended as compared to an uncontacted plant, a wilting of the contacted plant is reduced or delayed as compared to an uncontacted plant, a turgidity of the contacted plant is prolonged or maintained as compared to an uncontacted plant, a loss of one or more petals of the contacted plant is reduced or delayed as compared to an uncontacted plant, a chlorophyll content of the contacted plant is maintained as compared to an uncontacted plant, a loss of the chlorophyll content of the contacted plant is reduced or delayed as compared to an uncontacted plant, a chlorophyll content of the contacted plant is increased as compared to an uncontacted plant, a salinity tolerance of the contacted plant is increased as compared to an uncontacted plant, a water consumption of the contacted plant is reduced as compared to an uncontacted plant, a drought tolerance of the contacted plant is increased as compared to an uncontacted plant, a pest resistance of the contacted plant is increased as compared to an uncontacted plant, a pesticides consumption of the contacted plant is reduced as compared to an uncontacted plant, or any combination thereof.

In one embodiment of the method, a yield of the contacted plant is increased as compared to an uncontacted plant. In another embodiment of the method, a life of the contacted plant is extended as compared to an uncontacted plant. In another embodiment of the method, a wilting of the contacted plant is reduced or delayed as compared to an uncontacted plant. In another embodiment of the method, a turgidity of the contacted plant is prolonged or maintained as compared to an uncontacted plant. In another embodiment of the method, a loss of one or more petals of the contacted plant is reduced or delayed as compared to an uncontacted plant. In another embodiment of the method, a chlorophyll content of the contacted plant is maintained as compared to an uncontacted plant. In another embodiment of the method, a loss of the chlorophyll content of the contacted plant is reduced or delayed as compared to an uncontacted plant. In another embodiment of the method, a chlorophyll content of the contacted plant is increased as compared to an uncontacted plant. In another embodiment of the method, a salinity tolerance of the contacted plant is increased as compared to an uncontacted plant. In another embodiment of the method, a water consumption of the contacted plant is reduced as compared to an uncontacted plant. In another embodiment of the method, a drought tolerance of the contacted plant is increased as compared to an uncontacted plant. In another embodiment of the method, a pest resistance of the contacted plant is increased as compared to an uncontacted plant. In another embodiment of the method, a pesticides consumption of the contacted plant is reduced as compared to an uncontacted plant.

In another embodiment, the method comprises contacting a plant with the compound, salt, solvate, polymorph, diastereoisomer, stereoisomer, isomer or formulation disclosed herein, in an amount effective to increase a yield of the contacted plant as compared to an uncontacted plant, extend a life of the contacted plant as compared to an uncontacted plant, reduce or delay a wilting of the contacted plant as compared to an uncontacted plant, prolong or maintain a turgidity of the contacted plant as compared to an uncontacted plant, reduce or delay a loss of one or more petals of the contacted plant as compared to an uncontacted plant, maintain a chlorophyll content of the contacted plant as compared to an uncontacted plant, reduce or delay a loss of the chlorophyll content of the contacted plant as compared to an uncontacted plant, increase a chlorophyll content of the contacted plant as compared to an uncontacted plant, increase a salinity tolerance of the contacted plant as compared to an uncontacted plant, reduce a water consumption of the contacted plant as compared to an uncontacted plant, increase a drought tolerance of the contacted plant as compared to an uncontacted plant, increase a pest resistance of the contacted plant as compared to an uncontacted plant, reduce a pesticides consumption of the contacted plant as compared to an uncontacted plant, or any combination thereof.

The method may comprise contacting a plant with the compound, salt, solvate, polymorph, diastereoisomer, stereoisomer, isomer or formulation disclosed herein. In one embodiment, the method contacts the plant in an amount effective to increase a yield of the contacted plant as compared to an uncontacted plant. In another embodiment, the method contacts the plant in an amount effective to extend a life of the contacted plant as compared to an uncontacted plant. In another embodiment, the method contacts the plant in an amount effective to reduce or delay a wilting of the contacted plant as compared to an uncontacted plant. In another embodiment, the method contacts the plant in an amount effective to prolong or maintain a turgidity of the contacted plant as compared to an uncontacted plant. In another embodiment, the method contacts the plant in an amount effective to reduce or delay a loss of one or more petals of the contacted plant as compared to an uncontacted plant. In another embodiment, the method contacts the plant in an amount effective to maintain a chlorophyll content of the contacted plant as compared to an uncontacted plant. In another embodiment, the method contacts the plant in an amount effective to reduce or delay a loss of the chlorophyll content of the contacted plant as compared to an uncontacted plant. In another embodiment, the method contacts the plant in an amount effective to increase a chlorophyll content of the contacted plant as compared to an uncontacted plant. In another embodiment, the method contacts the plant in an amount effective to increase a salinity tolerance of the contacted plant as compared to an uncontacted plant. In another embodiment, the method contacts the plant in an amount effective to reduce a water consumption of the contacted plant as compared to an uncontacted plant. In another embodiment, the method contacts the plant in an amount effective to increase a drought tolerance of the contacted plant as compared to an uncontacted plant. In another embodiment, the method contacts the plant in an amount effective to increase a pest resistance of the contacted plant as compared to an uncontacted plant. In another embodiment, the method contacts the plant in an amount effective to reduce a pesticides consumption of the contacted plant as compared to an uncontacted plant.

The method may comprise increasing the yield of the contacted plant, wherein the yield of the contacted plant is increased by at least about 5%, 10%, 15%, 20%, 25%, 30%, 35%, 40%, 45%, 50%, 55%, 60%, 65%, 70%, 75%, 80%, 85%, or 90% as compared to an uncontacted plant. The yield of the contacted plant may be increased from about 5% to 90%, for example, 5%-25%, 10%-30%, 20%-40%, 30%-50%, 40%-50%, 50%-60%, 60%-70%, or 70%-90% as compared to an uncontacted plant. In one example, the yield of the contacted plant is increased from about 5% to 50% as compared to an uncontacted plant. The yield of the contacted plant may be increased under adequately irrigated condition. The yield of the contacted plant may be increased under drought condition.

The method may comprise extending the life of the contacted plant, wherein the life of the contacted plant is extended by at least about 5%, 10%, 15%, 20%, 25%, 30%, 35%, 40%, 45%, 50%, 55%, 60%, 65%, 70%, 75%, 80%, 85%, or 90% as compared to an uncontacted plant. The life of the contacted plant may be extended from about 5% to 90%, for example, 5%-25%, 10%-30%, 20%-40%, 30%-50%, 40%-50%, 50%-60%, 60%-70%, or 70%-90% as compared to an uncontacted plant. In one example, the life of the contacted plant is extended from about 5% to 50% as compared to an uncontacted plant.

In some embodiments, a plant is determined to be dead if the metabolic activity of the plant has ceased. In some embodiments, a plant is determined to be dead if the vegetative growth of the plant has ceased.

The method may comprise extending the life of the contacted plant, wherein the life of the contacted plant is extended by at least about 6 hours, 12 hours, 24 hours, 36 hours, or 48 hours as compared to an uncontacted plant. The life of the contacted plant may be extended by at least about 1 day, 2 days, 3 days, 4 days, 5 days, 6 days, 7 days, 8 days, 9 days, or 10 days as compared to an uncontacted plant. The life of the contacted plant may be extended by at least about 1 week, 2 weeks, 3 weeks, 4 weeks, 5 weeks, or 6 weeks as compared to an uncontacted plant. The life of the contacted plant may be extended by at least about 1 month, 2 months, 3 months, 4 months, 5 months, or 6 months as compared to an uncontacted plant. The life of the contacted plant may be extended from 6 hours to 48 hours as compared to an uncontacted plant. The life of the contacted plant may be extended from 1 day to 10 days as compared to an uncontacted plant. The life of the contacted plant may be extended from 1 week to 6 weeks as compared to an uncontacted plant. The life of the contacted plant may be extended from 1 month to 6 months as compared to an uncontacted plant. In one example, the life of the contacted plant is extended from at least about 6 hours to 1 month as compared to an uncontacted plant.

The method may comprise reducing the wilting of the contacted plant, wherein the wilting of the contacted plant is reduced by at least about 5%, 10%, 15%, 20%, 25%, 30%, 35%, 40%, 45%, 50%, 55%, 60%, 65%, 70%, 75%, 80%, 85%, or 90% as compared to an uncontacted plant. The wilting of the contacted plant may be reduced from about 5% to 90%, for example, 5%-25%, 10%-30%, 20%-40%, 30%-50%, 40%-50%, 50%-60%, 60%-70%, or 70%-90% as compared to an uncontacted plant. In one example, the wilting of the contacted plant is reduced from about 5% to 50% as compared to an uncontacted plant.

In some embodiments, the wilting can be determined by visual inspection. In some embodiments, the wilting can be determined by the change in leaf angle. The angle between the stem and leaf can change drastically during wilting. For example, it is determined to be wilting when the angle between the stem and leaf changes 10°, 20°, 30°, 40°, 50°, 60°, 70°, 80°, 90°, 100°, 110°, 120°, 130°, 140°, 150°, 160°, 170°, or 180°. In some embodiments, the wilting can be determined by the total leaf volume.

The method may comprise delaying the wilting of the contacted plant, wherein the wilting of the contacted plant is delayed by at least about 6 hours, 12 hours, 24 hours, 36 hours, or 48 hours as compared to an uncontacted plant. The wilting of the contacted plant may be delayed by at least about 1 day, 2 days, 3 days, 4 days, 5 days, 6 days, 7 days, 8 days, 9 days, or 10 days as compared to an uncontacted plant. The wilting of the contacted plant may be delayed by at least about 1 week, 2 weeks, 3 weeks, 4 weeks, 5 weeks, or 6 weeks as compared to an uncontacted plant. The wilting of the contacted plant may be delayed by at least about 1 month, 2 months, 3 months, 4 months, 5 months, or 6 months as compared to an uncontacted plant. The wilting of the contacted plant may be delayed from 6 hours to 48 hours as compared to an uncontacted plant. The wilting of the contacted plant may be delayed from 1 day to 10 days as compared to an uncontacted plant. The wilting of the contacted plant may be delayed from 1 week to 6 weeks as compared to an uncontacted plant. The wilting of the contacted plant may be delayed from 1 month to 6 months as compared to an uncontacted plant. In one example, the wilting of the contacted plant is delayed from at least about 6 hours to 1 month as compared to an uncontacted plant.

The method may comprise prolonging or maintaining the turgidity of the contacted plant, wherein the turgidity of the contacted plant is prolonged or maintained by at least about 6 hours, 12 hours, 24 hours, 36 hours, or 48 hours as compared to an uncontacted plant. The turgidity of the contacted plant may be prolonged or maintained by at least about 1 day, 2 days, 3 days, 4 days, 5 days, 6 days, 7 days, 8 days, 9 days, or 10 days as compared to an uncontacted plant. The turgidity of the contacted plant may be prolonged or maintained by at least about 1 week, 2 weeks, 3 weeks, 4 weeks, 5 weeks, or 6 weeks as compared to an uncontacted plant. The turgidity of the contacted plant may be prolonged or maintained by at least about 1 month, 2 months, 3 months, 4 months, 5 months, or 6 months as compared to an uncontacted plant. The turgidity of the contacted plant may be prolonged or maintained from 6 hours to 48 hours as compared to an uncontacted plant. The turgidity of the contacted plant may be prolonged or maintained from 1 day to 10 days as compared to an uncontacted plant. The turgidity of the contacted plant may be prolonged or maintained from 1 week to 6 weeks as compared to an uncontacted plant. The turgidity of the contacted plant may be prolonged or maintained from 1 month to 6 months as compared to an uncontacted plant. In one example, the turgidity of the contacted plant is prolonged or maintained from at least about 6 hours to 1 month as compared to an uncontacted plant.

The method may comprise reducing the loss of one or more petals of the contacted plant, wherein the loss of one or more petals of the contacted plant is reduced by at least about 5%, 10%, 15%, 20%, 25%, 30%, 35%, 40%, 45%, 50%, 55%, 60%, 65%, 70%, 75%, 80%, 85%, or 90% as compared to an uncontacted plant. The loss of one or more petals of the contacted plant may be reduced from about 5% to 90%, for example, 5%-25%, 10%-30%, 20%-40%, 30%-50%, 40%-50%, 50%-60%, 60%-70%, or 70%-90% as compared to an uncontacted plant. In one example, the loss of one or more petals of the contacted plant is reduced from about 5% to 50% as compared to an uncontacted plant.

The method may comprise delaying the loss of one or more petals of the contacted plant, wherein the loss of one or more petals of the contacted plant is delayed by at least about 6 hours, 12 hours, 24 hours, 36 hours, or 48 hours as compared to an uncontacted plant. The loss of one or more petals of the contacted plant may be delayed by at least about 1 day, 2 days, 3 days, 4 days, 5 days, 6 days, 7 days, 8 days, 9 days, or 10 days as compared to an uncontacted plant. The loss of one or more petals of the contacted plant may be delayed by at least about 1 week, 2 weeks, 3 weeks, 4 weeks, 5 weeks, or 6 weeks as compared to an uncontacted plant. The loss of one or more petals of the contacted plant may be delayed by at least about 1 month, 2 months, 3 months, 4 months, 5 months, or 6 months as compared to an uncontacted plant. The loss of one or more petals of the contacted plant may be delayed from 6 hours to 48 hours as compared to an uncontacted plant. The loss of one or more petals of the contacted plant may be delayed from 1 day to 10 days as compared to an uncontacted plant. The loss of one or more petals of the contacted plant may be delayed from 1 week to 6 weeks as compared to an uncontacted plant. The loss of one or more petals of the contacted plant may be delayed from 1 month to 6 months as compared to an uncontacted plant. In one example, the loss of one or more petals of the contacted plant is delayed from at least about 6 hours to 1 month as compared to an uncontacted plant.

The method may comprise delaying the chlorophyll content of the contacted plant, wherein the chlorophyll content of the contacted plant is maintained for at least about 6 hours, 12 hours, 24 hours, 36 hours, or 48 hours as compared to an uncontacted plant. The chlorophyll content of the contacted plant may be maintained for at least about 1 day, 2 days, 3 days, 4 days, 5 days, 6 days, 7 days, 8 days, 9 days, or 10 days as compared to an uncontacted plant. The chlorophyll content of the contacted plant may be maintained for at least about 1 week, 2 weeks, 3 weeks, 4 weeks, 5 weeks, or 6 weeks as compared to an uncontacted plant. The chlorophyll content of the contacted plant may be maintained for at least about 1 month, 2 months, 3 months, 4 months, 5 months, or 6 months as compared to an uncontacted plant. The chlorophyll content of the contacted plant may be maintained from 6 hours to 48 hours as compared to an uncontacted plant. The chlorophyll content of the contacted plant may be maintained from 1 day to 10 days as compared to an uncontacted plant. The chlorophyll content of the contacted plant may be maintained from 1 week to 6 weeks as compared to an uncontacted plant. The chlorophyll content of the contacted plant may be maintained from 1 month to 6 months as compared to an uncontacted plant. In one example, the chlorophyll content of the contacted plant is maintained from at least about 6 hours to 1 month as compared to an uncontacted plant.

The method may comprise delaying the loss of the chlorophyll content of the contacted plant, wherein the loss of the chlorophyll content of the contacted plant is delayed by at least about 6 hours, 12 hours, 24 hours, 36 hours, or 48 hours as compared to an uncontacted plant. The loss of the chlorophyll content of the contacted plant may be delayed by at least about 1 day, 2 days, 3 days, 4 days, 5 days, 6 days, 7 days, 8 days, 9 days, or 10 days as compared to an uncontacted plant. The loss of the chlorophyll content of the contacted plant may be delayed by at least about 1 week, 2 weeks, 3 weeks, 4 weeks, 5 weeks, or 6 weeks as compared to an uncontacted plant. The loss of the chlorophyll content of the contacted plant may be delayed by at least about 1 month, 2 months, 3 months, 4 months, 5 months, or 6 months as compared to an uncontacted plant. The loss of the chlorophyll content of the contacted plant may be delayed from 6 hours to 48 hours as compared to an uncontacted plant. The loss of the chlorophyll content of the contacted plant may be delayed from 1 day to 10 days as compared to an uncontacted plant. The loss of the chlorophyll content of the contacted plant may be delayed from 1 week to 6 weeks as compared to an uncontacted plant. The loss of the chlorophyll content of the contacted plant may be delayed from 1 month to 6 months as compared to an uncontacted plant. In one example, the loss of the chlorophyll content of the contacted plant is delayed from at least about 6 hours to 1 month as compared to an uncontacted plant.

In some embodiments, the chlorophyll can be measured by using a chlorophyll meter, such as a SPAD 502 PLUS meter. In some embodiments, the chlorophyll meter measures absorbance at 502 nm through the leaf.

The method may comprise increasing the chlorophyll content of the contacted plant, wherein the chlorophyll content of the contacted plant is increased by at least about 5%, 10%, 15%, 20%, 25%, 30%, 35%, 40%, 45%, 50%, 55%, 60%, 65%, 70%, 75%, 80%, 85%, or 90% as compared to an uncontacted plant. The chlorophyll content of the contacted plant may be increased from about 5% to 90%, for example, 5%-25%, 10%-30%, 20%-40%, 30%-50%, 40%-50%, 50%-60%, 60%-70%, or 70%-90% as compared to an uncontacted plant. In one example, the chlorophyll content of the contacted plant is increased from about 5% to 50% as compared to an uncontacted plant.

The method may comprise increasing the salinity tolerance of the contacted plant, wherein the yield of the contacted plant under salinity condition is increased by at least about 5%, 10%, 15%, 20%, 25%, 30%, 35%, 40%, 45%, 50%, 55%, 60%, 65%, 70%, 75%, 80%, 85%, or 90% as compared to an uncontacted plant. The yield of the contacted plant under salinity condition may be increased from about 5% to 90%, for example, 5%-25%, 10%-30%, 20%-40%, 30%-50%, 40%-50%, 50%-60%, 60%-70%, or 70%-90% as compared to an uncontacted plant. In one example, the yield of the contacted plant under salinity condition is increased from about 5% to 50% as compared to an uncontacted plant. In some embodiments, the yield of the contacted plant is measured by weight.

The method may comprise increasing the salinity tolerance of the contacted plant, wherein a water consumption per weight unit of the contacted plant produced is reduced by at least about 5%, 10%, 15%, 20%, 25%, 30%, 35%, 40%, 45%, 50%, 55%, 60%, 65%, 70%, 75%, 80%, 85%, or 90% as compared to an uncontacted plant. The water consumption per weight unit of the contacted plant produced is reduced from about 5% to 90%, for example, 5%-25%, 10%-30%, 20%-40%, 30%-50%, 40%-50%, 50%-60%, 60%-70%, or 70%-90% as compared to an uncontacted plant. In one example, the water consumption per weight unit of the contacted plant produced is reduced from about 5% to 50% as compared to an uncontacted plant. In some embodiments, the water consumption is measured by weight.

The method may comprise increasing the drought tolerance of the contacted plant, wherein the yield of the contacted plant under drought condition is increased by at least about 5%, 10%, 15%, 20%, 25%, 30%, 35%, 40%, 45%, 50%, 55%, 60%, 65%, 70%, 75%, 80%, 85%, or 90% as compared to an uncontacted plant. The yield of the contacted plant under drought condition may be increased from about 5% to 90%, for example, 5%-25%, 10%-30%, 20%-40%, 30%-50%, 40%-50%, 50%-60%, 60%-70%, or 70%-90% as compared to an uncontacted plant. In one example, the yield of the contacted plant under drought condition is increased from about 5% to 50% as compared to an uncontacted plant. In some embodiments, the yield of the contacted plant is measured by weight.

The method may comprise increasing the pest resistance of the contacted plant, wherein the yield of the contacted plant without using any pesticides is increased by at least about 5%, 10%, 15%, 20%, 25%, 30%, 35%, 40%, 45%, 50%, 55%, 60%, 65%, 70%, 75%, 80%, 85%, or 90% as compared to an uncontacted plant. The yield of the contacted plant without using any pesticides may be increased from about 5% to 90%, for example, 5%-25%, 10%-30%, 20%-40%, 30%-50%, 40%-50%, 50%-60%, 60%-70%, or 70%-90% as compared to an uncontacted plant. In one example, the yield of the contacted plant without using any pesticides is increased from about 5% to 50% as compared to an uncontacted plant. In some embodiments, the yield of the contacted plant is measured by weight.

The method may comprise reducing the pesticides consumption of the contacted plant, wherein a pesticides consumption per weight unit of the contacted plant produced is reduced by at least about 5%, 10%, 15%, 20%, 25%, 30%, 35%, 40%, 45%, 50%, 55%, 60%, 65%, 70%, 75%, 80%, 85%, or 90% as compared to an uncontacted plant. The pesticides consumption per weight unit of the contacted plant produced is reduced from about 5% to 90%, for example, 5%-25%, 10%-30%, 20%-40%, 30%-50%, 40%-50%, 50%-60%, 60%-70%, or 70%-90% as compared to an uncontacted plant. In one example, the pesticides consumption per weight unit of the contacted plant produced is reduced from about 5% to 50% as compared to an uncontacted plant. In some embodiments, the pesticides consumption is measured by weight.

In one embodiment, the contacted plant comprises a corn. A production of the corn may be increased as compared to an uncontacted plant. The method may comprise increasing the production of the corn, wherein an average kernel mass of the corn is increased by at least about 5%, 10%, 15%, 20%, 25%, 30%, 35%, 40%, 45%, 50%, 55%, 60%, 65%, 70%, 75%, 80%, 85%, or 90% as compared to an uncontacted corn. The average kernel mass of the corn may be increased from about 5% to 90%, for example, 5%-25%, 10%-30%, 20%-40%, 30%-50%, 40%-50%, 50%-60%, 60%-70%, or 70%-90% as compared to an uncontacted corn. In one example, the average kernel mass of the corn is increased from about 5% to 50% as compared to an uncontacted corn.

In another embodiment, the method may comprise increasing the production of the corn, wherein an average ear volume of the corn is increased by at least about 5%, 10%, 15%, 20%, 25%, 30%, 35%, 40%, 45%, 50%, 55%, 60%, 65%, 70%, 75%, 80%, 85%, or 90% as compared to an uncontacted corn. The average ear volume of the corn may be increased from about 5% to 90%, for example, 5%-25%, 10%-30%, 20%-40%, 30%-50%, 40%-50%, 50%-60%, 60%-70%, or 70%-90% as compared to an uncontacted corn. In one example, the average ear volume of the corn is increased from about 5% to 50% as compared to an uncontacted corn.

The method may inhibit the growth of a weed. In one embodiment, the weed comprises a parasitic weed. In another embodiment, the parasitic weed comprises a weed from the genus of Striga. The Striga genus may comprise species such as Striga asiatica, S. gesnerioides, and S. hermonthica. In some embodiments, the growth of the weed is measured in biomass (grams) over time.

Further disclosed is a method of making a formulation comprising forming the formulation with the compound, salt, solvate, polymorph, diastereoisomer, stereoisomer, or isomer disclosed herein. In one embodiment, the formulation further comprises an excipient. In another embodiment, the excipient comprises water, a surfactant, an alcohol, or any combination thereof.

The amount of the compound, salt, solvate, polymorph, diastereoisomer, stereoisomer, isomer, or formulation disclosed herein may comprise from at least about 1 mg to 1000 kg. The amount of the compound, salt, solvate, polymorph, diastereoisomer, stereoisomer, isomer, or formulation disclosed herein may comprise at least about 1 mg, 5 mg, 10 mg, 20 mg, 30 mg, 40 mg, 50 mg, 100 mg, 200 mg, 300 mg, 400 mg, 500 mg, 1 g, 5 g, 10 g, 50 g, 100 g, 500 g, 1 kg, 5 kg, 10 kg, 50 kg, 100 kg, or 1000 kg. The amount of the compound, salt, solvate, polymorph, diastereoisomer, stereoisomer, isomer, or formulation disclosed herein may comprise from at least about 1% to 99% of the total weight. The amount of the compound, salt, solvate, polymorph, diastereoisomer, stereoisomer, isomer, or formulation disclosed herein may comprise comprises about 1%, 5%, 10%, 20%, 30%, 40%, 50%, 60%, 70%, 80%, 90%, 95%, or 99% of the total weight.

In one embodiment, disclosed herein is a soil comprising the compound, salt, solvate, polymorph, diastereoisomer, stereoisomer, isomer, or formulation disclosed herein. In another embodiment, disclosed herein is a plant grown using the method disclosed herein, or an edible portion thereof. In another embodiment, disclosed herein is a food comprising an ingredient from the plant disclosed herein, or an edible portion thereof. In another embodiment, disclosed herein is a food comprising the compound, salt, solvate, polymorph, diastereoisomer, stereoisomer, isomer, or formulation disclosed herein. In another embodiment, disclosed herein is a seed comprising the compound, salt, solvate, polymorph, diastereoisomer, stereoisomer, isomer, or formulation disclosed herein.

Disclosed herein may be an engineered cell comprising a plurality of polynucleotides, wherein (i) the plurality of polynucleotides encode one or more metabolites; and/or (ii) the plurality of polynucleotides comprise one or more genes selected from a group comprising crtE, crtB, crtI, D27, CCD7, CCD8, and MAX1.

Disclosed herein is a method of producing the compound, salt, solvate, polymorph, diastereoisomer, stereoisomer, isomer, or formulation comprising alkylating

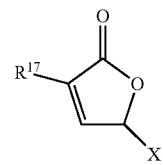

or a salt thereof, wherein $R^{17}$ is H, alkyl, halo, or haloalkyl and X is Cl, Br, or I. In one embodiment, the method comprises: i) hydroxymethylation of an optionally substituted decahydronaphtho[2,1-b]furan-2(3aH)-one; and ii) subsequent alkylation of

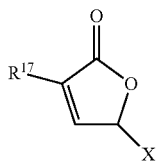

or a salt thereof, wherein $R^{17}$ is H, alkyl, halo, or haloalkyl and X is Cl, Br, or I. In another embodiment, the hydroxymethylation comprises a reaction between sclareolide and methyl formate in the presence of potassium tert-butoxide and the alkylation comprises a reaction between the hydroxymethylation product and 5-bromo-3-methylfuran-2 (5H)-one. In another embodiment, the optionally substituted decahydronaphtho[2,1-b]furan-2(3aH)-one comprises sclareolide. In another embodiment, the $R^{17}$ is alkyl. In another embodiment, the $R^{17}$ is methyl. In another embodiment, the X is Cl. In another embodiment, the hydroxymethylation and alkylation are a one pot procedure.

Further disclosed herein are methods of preparing the compounds disclosed herein. The method may comprise (i) hydroxymethylation of an optionally substituted decahydronaphtho[2,1-b]furan-2(3aH)-one; and (ii) subsequent alkylation with

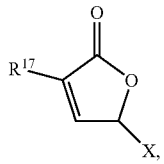

wherein $R^{17}$ is H, alkyl, halo, or haloalkyl and X is Cl, Br, or I.

In some instances, hydroxymethylation and alkylation is a one pot procedure. In some instances, the optionally substituted decahydronaphtho[2,1-b]furan-2(3aH)-one is sclareolide.

In some instances, $R^{17}$ is alkyl. In some instances, X is Br.

In some instances, the hydroxymethylation is a reaction between sclareolide and methyl formate in the presence of potassium tert-butoxide and the alkylation is a reaction between the hydroxymethylation product and 5-bromo-3-methylfuran-2(5H)-one.

Further disclosed herein are plant propagation materials comprising chemical mimics of strigolactone. Examples of strigolactone include, but are not limited to strigol, strigyl acetate, orobanchol, orobanchyl acetate, 7-orobanchyl acetate, 7-hydroxy-orobanchyl acetate, sorgomol, fabacyl acetate, 5-deoxystrigol, and sorgolactone. Examples of orobanchol include, but are not limited to, 7-oxo-orobanchol, 2'epi-orobanchol, ent-2'-epi-orobanchol and ent-orobanchol. Examples of 5-deoxystrigol include, but are not limited to, 2'-epi-5-deoxystrigol, ent-2'-epi-5-deoxystrigol, and ent-5-deoxystrigol.

The chemical mimics of strigolactone may be based on or derived from a plant. The plant may be rice. The plant may be tobacco.

Further disclosed herein are plant propagation materials comprising chemical mimics of strigolactone analogues. Examples of strigolactone analogs include, but are not limited to, 3'-methyl-GR24, thia-3'-methyl-debranone-like molecule, AR36, and CISA-1 (Boyer F D, *Mol Plant*, 2013 November). Additional examples of strigolactone analogs have been disclosed in Cohen (2013, *Mol Plant*, 2013, (6):1:141-52), Ruyter-Spira (2011, *Plant Physiol*, 155(2): 721-34), Tanaka M (2013, *Biosci Biotechnol Biochem*, 77(4):832-5), Mwakaboko (2011, *Plant Cell Physiol*, 52(4): 699-715), and Besserer (2008, *Plant Physiol*, 148(1); 402-13).

Further disclosed herein are plant propagation materials comprising the compounds disclosed herein. The plant propagation material may comprise a compound having of Formula I, or a salt, solvate, polymorph, stereoisomer, or isomer thereof. The plant propagation material may comprise a compound of Formula II, or a salt, solvate, polymorph, stereoisomer, or isomer thereof. The plant propagation material may comprise a compound of Formula III, or a salt, solvate, polymorph, stereoisomer, or isomer thereof. The plant propagation material may comprise a compound having a structure of Formula (VI)

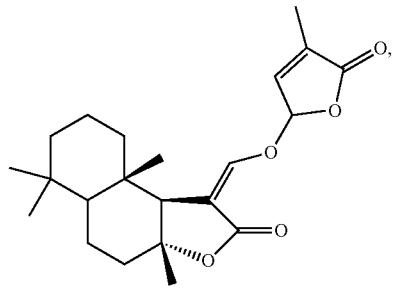 [SMILES: CC1=CC(O/C=C2\C(=O)O[C@]3(C)CCC4C(C)(C)CCC[C@]4(C)[C@@H]23)OC1=O]

or a salt, solvate, polymorph, stereoisomer, or isomer thereof.

Further disclosed herein are plant propagation materials comprising one or more compounds having the structure of Formula IV, Formula V, or a salt, solvate, polymorph, stereoisomer, or isomer thereof. Further disclosed herein are plant propagation materials comprising two or more compounds having the structure of Formula IV and Formula V.

Further disclosed herein are plant propagation materials comprising mixtures of strigolactones, or salts, solvates, polymorphs, stereoisomers, or isomers thereof. The mixture of strigolactones may comprise two or more of strigol, strigyl acetate, orobanchol, orobanchyl acetate, 7-orobanchyl acetate, 7-hydroxy-orobanchyl acetate, sorgomol, fabacyl acetate, 5-deoxystrigol, sorgolactone, 7-oxo-orobanchol, 2'epi-orobanchol, ent-2'-epi-orobanchol, ent-orobanchol, 2'-epi-5-deoxystrigol, ent-2'-epi-5-deoxystrigol, and ent-5-deoxystrigol. The mixture of strigolactones may comprise three or more of strigol, strigyl acetate, orobanchol, orobanchyl acetate, 7-orobanchyl acetate, 7-hydroxy-orobanchyl acetate, sorgomol, fabacyl acetate, 5-deoxystrigol, sorgolactone, 7-oxo-orobanchol, 2'epi-orobanchol, ent-2'-epi-orobanchol, ent-orobanchol, 2'-epi-5-deoxystrigol, ent-2'-epi-5-deoxystrigol, and ent-5-deoxystrigol. The mixture of strigolactones may comprise four or more of strigol, strigyl acetate, orobanchol, orobanchyl acetate, 7-orobanchyl acetate, 7-hydroxy-orobanchyl acetate, sorgomol, fabacyl acetate, 5-deoxystrigol, sorgolactone, 7-oxo-orobanchol, 2'epi-orobanchol, ent-2'-epi-orobanchol, ent-orobanchol, 2'-epi-5-deoxystrigol, ent-2'-epi-5-deoxystrigol, and ent-5-deoxystrigol. The mixture of strigolactones may comprise five or more of strigol, strigyl acetate, orobanchol, orobanchyl acetate, 7-orobanchyl acetate, 7-hydroxy-orobanchyl acetate, sorgomol, fabacyl acetate, 5-deoxystrigol, sorgolactone, 7-oxo-orobanchol, 2'epi-orobanchol, ent-2'-epi-orobanchol, ent-orobanchol, 2'-epi-5-deoxystrigol, ent-2'-epi-5-deoxystrigol, and ent-5-deoxystrigol.

The mixture of strigolactones may comprise two or more of strigol, strigyl acetate, orobanchol, orobanchyl acetate, 7-orobanchyl acetate, 7-hydroxy-orobanchyl acetate, sorgomol, fabacyl acetate, 5-deoxystrigol, and sorgolactone. The mixture of strigolactones may comprise three or more of strigol, strigyl acetate, orobanchol, orobanchyl acetate, 7-orobanchyl acetate, 7-hydroxy-orobanchyl acetate, sorgomol, fabacyl acetate, 5-deoxystrigol, and sorgolactone. The mixture of strigolactones may comprise four or more of strigol, strigyl acetate, orobanchol, orobanchyl acetate, 7-orobanchyl acetate, 7-hydroxy-orobanchyl acetate, sorgomol, fabacyl acetate, 5-deoxystrigol, and sorgolactone. The mixture of strigolactones may comprise five or more of strigol, strigyl acetate, orobanchol, orobanchyl acetate, 7-orobanchyl acetate, 7-hydroxy-orobanchyl acetate, sorgomol, fabacyl acetate, 5-deoxystrigol, and sorgolactone.

Disclosed herein are methods of producing a plant propagation material. The method may comprise chemical synthesis of the plant propapagation material. The plant propagation material may be a chemical mimic of strigolactone, or a salt, solvate, polymorph, stereoisomer, or isomer thereof. The plant propagation material may be a chemical mimic of 5-deoxystrigol, or a salt, solvate, polymorph, stereoisomer, or isomer thereof. The plant propagation material may be a chemical mimic of strigol, or a salt, solvate, polymorph, stereoisomer, or isomer thereof. The plant propagation material may be a chemical mimic of orobanchol, or a salt, solvate, polymorph, stereoisomer, or isomer thereof. The plant propagation material may be a chemical mimic of orobanchol acetate, or a salt, solvate, polymorph, stereoisomer, or isomer thereof. The plant propagation material may be a chemical mimic of strigyl acetate, or a salt, solvate, polymorph, stereoisomer, or isomer thereof. The plant propagation material may be a chemical mimic of sorgolactone, or a salt, solvate, polymorph, stereoisomer, or isomer thereof.

Further disclosed herein are methods of producing a plant propagation comprising conducting a condensation reaction on a sesquiterpene lactone, salt, solvate, polymorph, stereoisomer, isomer or derivative thereof, thereby producing a plant propagation material. In some instances, the plant propagation material is a compound having the structure of Formula I or a salt, solvate, polymorph, stereoisomer, or isomer thereof. In some instances, the plant propagation material is a compound having the structure of Formula II or a salt, solvate, polymorph, stereoisomer, or isomer thereof. In some instances, the plant propagation material is a compound having the structure of Formula III or a salt, solvate, polymorph, stereoisomer, or isomer thereof. In some instances, the plant propagation material is a compound having the structure of Formula IV or a salt, solvate, polymorph, stereoisomer, or isomer thereof. In some instances, the plant propagation material is a compound having the structure of Formula V or a salt, solvate, polymorph, stereoisomer, or isomer thereof. In some instances, the plant propagation material is a compound having the structure of Formula VI or a salt, solvate, polymorph, stereoisomer, or isomer thereof.

Alternatively, or additionally, the method of producing a plant propagation material may comprise conducting a hydroxymethylation and/or alkylation reaction on a sesquiterpene lactone, salt, solvate, polymorph, stereoisomer, isomer or derivative thereof, thereby producing a plant propagation material.

The sesquiterpene lactone for use in the methods disclosed herein may be sclareolide. The sesquiterpene lactone may be extracted from a sage plant. The sage plant may be a clary sage plant.

The condensation reaction may comprise condensing the sesquiterpene lactone, salt, solvate, polymorph, stereoisomer, isomer or derivative thereof, with methyl formate to produce a hydroxymethylene lactone. The condensation reaction may further comprise potassium tert-butoxide.

The method may comprise condensing the sesquiterpene lactone, salt, solvate, polymorph, stereoisomer, isomer or derivative thereof with an excess of methyl formate. The method may comprise condensing the sesquiterpene lactone, salt, solvate, polymorph, stereoisomer, isomer or derivative thereof with two-fold excess of methyl formate. The method may comprise condensing the sesquiterpene lactone, salt, solvate, polymorph, stereoisomer, isomer or derivative thereof with three-fold excess of methyl formate. The method may comprise condensing the sesquiterpene lactone, salt, solvate, polymorph, stereoisomer, isomer or derivative thereof with four-fold excess of methyl formate. The method may comprise condensing the sesquiterpene lactone, salt, solvate, polymorph, stereoisomer, isomer or derivative thereof with five-fold excess of methyl formate.

The method may further comprises conducting an alkylation reaction. The alkylation reaction may comprise alkylating the condensation reaction product with a bromobutenolide. The alkylation reaction may comprise alkylating the hydroxymethylene lactone with a bromobutenolide.

The alkylation reaction may produce a mixture of two diastereomers. In some instances, the two diasteromers are

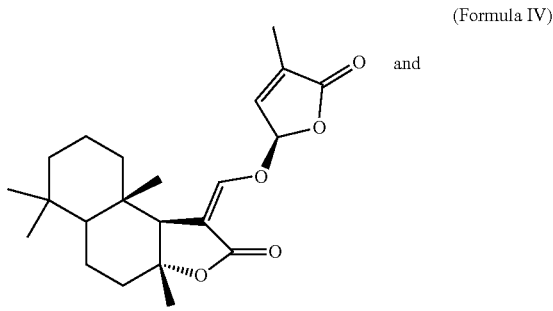

(Formula IV)

and

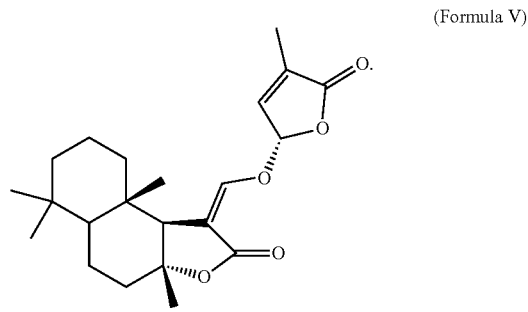

(Formula V)

In some instances, the method of producing the plant propagation material does not require a catalyst. In some instances, the method of producing the plant propagation material does not require two or more reaction volumes. In some instances, the method of producing the plant propagation material not require a chromatographic purification.

In some instances, the efficiency of producing the plant propagation material is at least about 50%. The efficiency of producing the plant propagation material may be at least about 60%. The efficiency of producing the plant propagation material may be at least about 70%. The efficiency of producing the plant propagation material may be at least about 75%. The efficiency of producing the plant propagation material may be at least about 80%. The efficiency of producing the plant propagation material may be at least about 85%. The efficiency of producing the plant propagation material may be at least about 90%.

The plant propagation material may be used to inhibit one or more weeds. The one or more weeds may be a parasitic weed. The parasitic weed may be *Striga*. The parasitic weed may be Orobanche.

Further disclosed herein are methods of producing a plant propagation material via a biosynthetic process. The biosynthetic process may comprise introducing one or more genes into a cell. The biosynthetic process may comprise transfecting one or more genes into a cell. The biosynthetic process may comprise transforming one or more cells with one or more genes. The one or more genes may encode a component of a strigolactone pathway. The one or more genes may encode a metabolite. In some instances, the one or more genes are not natural to the cell.

Further disclosed herein is a method of producing a plant propagation material, the method comprising expressing a plurality of polynucleotides in a cell to produce a plant propagation material, wherein (i) the plurality of polynucleotides encode one or more metabolites; and/or (ii) the plurality of polynucleotides may comprise one or more genes selected from a group comprising crtE, crtB, crtI, D27, CCD7, CCD8, and MAX1.

Further disclosed herein are polynucleotides encoding the one or more genes for use in the production of a plant propagation material. Further disclosed herein are vectors comprising the one or more polynucleotides encoding the one or more genes for use in the production of a plant propagation material. Further disclosed herein are cells for use in producing the plant propagation material disclosed herein. The cell may be an engineered cell. The engineered cell may comprise a plurality of polynucleotides, wherein (i) the plurality of polynucleotides encode one or more metabolites; and/or (ii) the plurality of polynucleotides comprise one or more genes selected from a group comprising crtE, crtB, crtI, D27, CCD7, CCD8, and MAX1. The plurality of polynucleotides may encode one or more metabolites and comprise one or more genes selected from a group comprising crtE, crtB, crtI, D27, CCD7, CCD8, and MAX1.

The plurality of polynucleotides may encode one or more metabolites. The one or more metabolites may comprise lycopene. In some instances, the one or more metabolites are not natural to the cell.

The plurality of polynucleotides may comprise one or more genes selected from a group comprising crtE, crtB, crtI, D27, CCD7, CCD8, and MAX1. The plurality of polynucleotides may comprise two or more genes selected from a group comprising crtE, crtB, crtI, D27, CCD7, CCD8, and MAX1. The plurality of polynucleotides may comprise three or more genes selected from a group comprising crtE, crtB, crtI, D27, CCD7, CCD8, and MAX1. The plurality of polynucleotides may comprise four or more genes selected from a group comprising crtE, crtB, crtI, D27, CCD7, CCD8, and MAX1. The plurality of polynucleotides may comprise five or more genes selected from a group comprising crtE, crtB, crtI, D27, CCD7, CCD8, and MAX1. The plurality of polynucleotides may comprise six or more genes selected from a group comprising crtE, crtB, crtI, D27, CCD7, CCD8, and MAX1. The plurality of polynucleotides mah comprise seven or more genes selected from a group comprising crtE, crtB, crtI, D27, CCD7, CCD8, and MAX1. The plurality of polynucleotides may comprise a crtE gene. The plurality of polynucleotides may comprise a crtB gene. The plurality of polynucleotides may comprise a crtI gene. The plurality of polynucleotides may comprise a D27 gene. The plurality of polynucleotides may comprise a CCD7 gene. The plurality of polynucleotides may comprise a CCD8 gene. The plurality of polynucleotides may comprise a MAX1 gene.

The one or more genes may be based on or derived from a plant. The plant may be a tobacco plant. The plant may be a rice plant. The one or more genes may be based on or derived from a fungi. The one or more genes may be based on or derived from yeast. The yeast may be a *Pantoea*. The yeast may be *P. ananatis*.

The cell may be a prokaryotic cell. The cell may be a eukaryotic cell. The eukaryotic cell may be a yeast cell. The yeast cell may be a *Pichia* cell. The *Pichia* cell may be a *Pichia pastoris* cell. The *Pichia* cell may be a *Pichia anantais* cell. The yeast cell may be a *Saccharomyces* cell. The *Saccharomyces* cell may be a *Saccharaomyces cerevesiae*.

The one or more cells may be cultured. The cells may be cultured under conditions to express the one or more genes that were introduced into the cell. The cells may be cultured to express the plurality of polynucleotides.

Further disclosed herein are methods of purifying the plant propagation material from the cell. Purifying the plant propagation material may comprise extracting the plant propagation material from the cell. Purifying the plant propagation material may comprise an ethyl acetate purification.

Further disclosed herein are formulations comprising the compounds disclosed herein. Further disclosed herein are formulations comprising the plant propagation materials disclosed herein. The formulation may be formulated as a powder, seed coating, or granule. The powder may be a wettable powder. The formulation may be formulated as a spray. The formulation may be formulated as an irrigation supplement. The formulation may be formulated as a seed coating.

Further disclosed herein are methods of improving agriculture. The method may comprise administering a formulation comprising a plant propagation material disclosed herein to a plant, thereby improving agriculture. The plant propagation material may comprise strigolactone, wherein the strigolactone is obtained by a biosynthetic process. The plant propagation material may comprise a chemical mimic of strigolactone, wherein the chemical mimic of strigolactone is obtained by a chemical process. The plant propagation material may comprise a compound having the structure of Formula I or a salt, solvate, polymorph, stereoisomer, or isomer thereof. The plant propagation material may comprise a compound having the structure of Formula II or a salt, solvate, polymorph, stereoisomer, or isomer thereof. The plant propagation material may comprise a compound having the structure of Formula III or a salt, solvate, polymorph, stereoisomer, or isomer thereof. The plant propagation material may comprise a compound having the structure of Formula IV or a salt, solvate, polymorph, stereoisomer, or isomer thereof. The plant propagation material may comprise a compound having the structure of Formula V or a salt, solvate, polymorph, stereoisomer, or isomer thereof. The plant propagation material may comprise a compound having the structure of Formula VI or a salt, solvate, polymorph, stereoisomer, or isomer thereof.

The plant propagation material may be applied directly to the plant. The plant propagation may be applied indirectly to the plant. The plant propagation material may be applied to the plant's habitat. The plant propagation material may be applied to the soil.

Further disclosed herein are methods for controlling phytopathogenic fungi. The method may comprise causing a formulation comprising a plant propagation material disclosed herein to act on the phytopathogenic fungi. The plant propagation material may comprise strigolactone, wherein the strigolactone is obtained by a biosynthetic process. The plant propagation material may comprise a chemical mimic of strigolactone, wherein the chemical mimic of strigolactone is obtained by a chemical process. The plant propagation material may comprise a compound having the structure of Formula I or a salt, solvate, polymorph, stereoisomer, or isomer thereof. The plant propagation material may comprise a compound having the structure of Formula II or a salt, solvate, polymorph, stereoisomer, or isomer thereof. The plant propagation material may comprise a compound having the structure of Formula III or a salt, solvate, polymorph, stereoisomer, or isomer thereof. The plant propagation material may comprise a compound having the structure of Formula IV or a salt, solvate, polymorph, stereoisomer, or isomer thereof. The plant propagation material may comprise a compound having the structure of Formula V or a salt, solvate, polymorph, stereoisomer, or isomer thereof. The plant propagation material may comprise a compound having the structure of Formula VI or a salt, solvate, polymorph, stereoisomer, or isomer thereof. The plant propagation material may be applied directly to the phytopathogenic fungi. The plant propagation may be applied indirectly to the phytopathogenic fungi. The plant propagation material may be applied to the phytopathogenic fungi's habitat. The plant propagation material may be applied to the soil. The plant propagation material may be applied to a plant within the vicinity of the phytopathogenic fungi. The plant within the vicinity of the phytopathogenic fungi may be a plant targeted by the phytopathogenic fungi. The plant propagation material may be applied directly to the plant. The plant propagation may be applied indirectly to the plant. The plant propagation material may be applied to the plant's habitat.

Further disclosed herein are methods for controlling unwanted plant growth. The method may comprise causing a formulation comprising a plant propagation material disclosed herein to act on the unwanted plant. The unwanted plant may be a *Striga* plant or Orobanche plant. The plant propagation material may comprise strigolactone, wherein the strigolactone is obtained by a biosynthetic process. The plant propagation material may comprise a chemical mimic of strigolacatone, wherein the chemical mimic of strigolactone is obtained by a chemical process. The plant propagation material may comprise a compound having the structure of Formula I or a salt, solvate, polymorph, stereoisomer, or isomer thereof. The plant propagation material may comprise a compound having the structure of Formula II or a salt, solvate, polymorph, stereoisomer, or isomer thereof. The plant propagation material may comprise a compound having the structure of Formula III or a salt, solvate, polymorph, stereoisomer, or isomer thereof. The plant propagation material may comprise a compound having the structure of Formula IV or a salt, solvate, polymorph, stereoisomer, or isomer thereof. The plant propagation material may comprise a compound having the structure of Formula V or a salt, solvate, polymorph, stereoisomer, or isomer thereof. The plant propagation material may comprise a compound having the structure of Formula VI or a salt, solvate, polymorph, stereoisomer, or isomer thereof. The plant propagation material may be applied directly to the unwanted plant. The plant propagation may be applied indirectly to the unwanted plant. The plant propagation material may be applied to the unwanted plant's habitat. The plant propagation may be applied to the soil. The plant propagation material may be applied to another plant within the vicinity of the unwanted plant. The plant within the vicinity of the unwanted plant may be a desirable plant. The plant propagation material may be applied directly to the desirable plant. The plant propagation may be applied indirectly to the desirable plant. The plant propagation material may be applied to the desirable plant's habitat.

Further disclosed herein are methods for controlling unwanted insect or mite infestation. The method may comprise causing a formulation comprising a plant propagation material disclosed herein to act on the unwanted insect or mite. The plant propagation material may comprise strigolactone, wherein the strigolactone is obtained by a biosynthetic process. The plant propagation material may comprise a chemical mimic of strigolacatone, wherein the chemical mimic of strigolactone is obtained by a chemical process. The plant propagation material may comprise a compound having the structure of Formula I or a salt, solvate, polymorph, stereoisomer, or isomer thereof. The plant propagation material may comprise a compound having the structure of Formula II or a salt, solvate, polymorph, stereoisomer, or isomer thereof. The plant propagation material may comprise a compound having the structure of Formula III or a salt, solvate, polymorph, stereoisomer, or isomer thereof. The plant propagation material may comprise a compound having the structure of Formula IV or a salt, solvate, polymorph, stereoisomer, or isomer thereof. The plant propagation material may comprise a compound having the structure of Formula V or a salt, solvate, polymorph, stereoisomer, or isomer thereof. The plant propagation material may comprise a compound having the structure of Formula VI or a salt, solvate, polymorph, stereoisomer, or isomer thereof. The plant propagation material may be applied to directly to the mite or insect. The plant propagation material may be applied indirectly to the mite or insect. The plant propagation material may be ingested by the mite or insect. The plant propagation material may be applied to a plant targeted by the mite or insect. The plant propagation material may be applied directly to the plant. The plant propagation may be applied indirectly to the plant. The plant propagation material may be applied to the plant's habitat. The plant propagation material may be applied to the soil.

Further disclosed herein are methods for regulating the growth of plants. The method may comprise causing a formulation comprising a plant propagation material disclosed herein to act on the plant or its habitat. The plant propagation material may comprise strigolactone, wherein the strigolactone is obtained by a biosynthetic process. The plant propagation material may comprise a chemical mimic of strigolactone, wherein the chemical mimic of strigolactone is obtained by a chemical process. The plant propagation material may comprise a compound having the structure of Formula I or a salt, solvate, polymorph, stereoisomer, or isomer thereof. The plant propagation material may comprise a compound having the structure of Formula II or a salt, solvate, polymorph, stereoisomer, or isomer thereof. The plant propagation material may comprise a compound having the structure of Formula III or a salt, solvate, polymorph, stereoisomer, or isomer thereof. The plant propagation material may comprise a compound having the structure of Formula IV or a salt, solvate, polymorph, stereoisomer, or isomer thereof. The plant propagation material may comprise a compound having the structure of Formula V or a salt, solvate, polymorph, stereoisomer, or isomer thereof. The plant propagation material may comprise a compound having the structure of Formula VI or a salt, solvate, polymorph, stereoisomer, or isomer thereof. The plant propagation material may be applied directly to the plant. The plant propagation may be applied indirectly to the plant. The plant propagation material may be applied to the plant's habitat. The plant propagation material may be applied to the soil.

The plant, desirable plant or plant targeted by the phytopathogenic fungi or mite/insect may be a crop plant. Crop plants include, but are not limited to, corn, rice, sorghum, millets, and sugar cane. The plant, desirable plant or plant targeted by the phytopathogenic fungi or mite/insect may be tobacco.

Further disclosed herein are methods of preserving or extending the life of a plant. Generally, the method may comprise contacting the plant with a plant propagation material disclosed herein. The plant propagation material may comprise a compound of Formula (I) or a salt, solvate, polymorph, stereoisomer, or isomer thereof. The plant propagation material may comprise a compound of Formula (II) or a salt, solvate, polymorph, stereoisomer, or isomer thereof. The plant propagation material may comprise a compound of Formula (III) or a salt, solvate, polymorph, stereoisomer, or isomer thereof. The plant propagation material may comprise a strigolactone or a salt, solvate, polymorph, stereoisomer, or isomer thereof. The plant propagation material may comprise a strigolactone mimic or a salt, solvate, polymorph, stereoisomer, or isomer thereof.

The plant propagation material for use in preserving or extending the life of a plant may be produced by any of the methods disclosed herein. For example, the plant propagation material is produced by conducting a condensation reaction on a sesquiterpene lactone, salt, solvate, polymorph, stereoisomer, isomer or derivative thereof. The plant propagation material may be produced by conducting a hydroxymethylation on a sesquiterpene lactone, salt, solvate, polymorph, stereoisomer, isomer or derivative thereof. The plant propagation material may be produced by (a) conducting a hydroxymethylation on a sesquiterpene lactone, salt, solvate, polymorph, stereoisomer, isomer or derivative thereof to produce a first product; and (b) conducting an alkylation reaction on the first product.

The plant may be a cut plant. The plant may be an uncut plant. The plant may be a potted plant. The plant may be a flower. The plant may be a bush or shrub. The plant may be a tree.

Preserving or extending the life of a plant may comprise contacting the plant with a plant propagation material disclosed herein. Contacting the plant with the plant propagation material may comprise administering the plant propagation material as a spray. Contacting the plant with the plant propagation material may comprise adding the plant growth material to the irrigation water of the plant. Contacting the plant with the plant propagation material may comprise applying the plant propagation material to the habitat of the plant. Contacting the plant with the plant propagation material may comprise adding the plant propagation material to a plant container (e.g., vase) and placing the plant in the plant container. Contacting the plant with the plant propagation material may comprise adding the plant propagation material to soil.

The life of the plant may be extended by at least about 20% as compared to an untreated plant. The life of the plant may be extended by at least about 30% as compared to an untreated plant. The life of the plant may be extended by at least about 40% as compared to an untreated plant. The life of the plant may be extended by at least about 50% as compared to an untreated plant. The life of the plant may be extended by at least about 55% as compared to an untreated plant. The life of the plant may be extended by at least about 60% as compared to an untreated plant. The life of the plant may be extended by at least about 65% as compared to an untreated plant. The life of the plant may be extended by at least about 70% as compared to an untreated plant.

The life of the plant may be extended by at least about 6, 12, 24, 30, 36, 42, 48, 54, 60, 66, or 72 hours as compared to an untreated plant. The life of the plant may be extended by at least about 24 hours as compared to an untreated plant. The life of the plant may be extended by at least about 36 hours as compared to an untreated plant. The life of the plant may be extended by at least about 48 hours as compared to an untreated plant. The life of the plant may be extended by at least about 72 hours as compared to an untreated plant.

The life of the plant may be extended by at least about 1, 1.5, 2, 2.5, 3, 3.5, 4, 4.5, 5, 5.5, 6, 6.5, or 7 days as compared to an untreated plant. The life of the plant may be extended by at least about 8, 9, 10, 11, 12, 13, 14, 15, 16, 17, 18, 19, or 20 days as compared to an untreated plant. The life of the plant may be extended by at least about 1 day as compared to an untreated plant. The life of the plant may be extended by at least about 2 days as compared to an untreated plant. The life of the plant may be extended by at least about 2.5 days as compared to an untreated plant. The life of the plant may be extended by at least about 3 days as compared to an untreated plant.

The life of the plant may be extended by at least about 1, 1.5, 2, 2.5, 3, 3.5, 4, 4.5, 5, 5.5, 6, 6.5, or 7 weeks as compared to an untreated plant. The life of the plant may be extended by at least about 8, 9, 10, 11, 12, 13, 14, 15, 16, 17, 18, 19, or 20 weeks as compared to an untreated plant. The life of the plant may be extended by at least about 1, 1.5, 2, 2.5, 3, 3.5, 4, 4.5, 5, 5.5, 6, 6.5, or 7 months as compared to an untreated plant. The life of the plant may be extended by at least about 8, 9, 10, 11, 12, 13, 14, 15, 16, 17, 18, 19, or 20 months as compared to an untreated plant.

Preserving or extending the life of the plant may comprise reducing wilting of the plant. Reducing wilting of the plant may comprise reducing flower or leaf rolling of the plant. The wilting of the plant may be reduced by at least about 20% as compared to an untreated plant. The wilting of the plant may be reduced by at least about 40% as compared to an untreated plant. The wilting of the plant may be reduced by at least about 60% as compared to an untreated plant.

Reducing the wilting of the plant may comprise delaying the wilting of the plant as compared to an untreated plant. The wilting of the plant may be delayed by at least about 2, 3, 4, 5, 6, 7, 8, 9, 10, 11, 12, 13, 14, 15, 16, 17, 18, 19, 20, 21, 22, 23, or 24 hours as compared to an untreated plant. The wilting of the plant may be delayed by at least about 12 hours as compared to an untreated plant. The wilting of the plant may be delayed by at least about 24 hours as compared to an untreated plant. The wilting of the plant may be delayed by at least about 36 hours as compared to an untreated plant. The wilting of the plant may be delayed by at least about 48 hours as compared to an untreated plant.

Preserving or extending the life of the plant may comprise prolonging or maintaining turgidity of the plant. The turgidity of the plant may be greater than the turgidity of an untreated plant. The turgidity of the plant may be at least about 20% greater than the turgidity of an untreated plant. The turgidity of the plant may be at least about 30% greater than the turgidity of an untreated plant. The turgidity of the plant may be at least about 40% greater than the turgidity of an untreated plant. The turgidity of the plant may be at least about 50% greater than the turgidity of an untreated plant.

Preserving or extending the life of the plant may comprise prolonging the turgid state of the plant. The turgid state of the plant may be increased by at least about 20% as compared to an untreated plant. The turgid state of the plant may be increased by at least about 30% as compared to an untreated plant. The turgid state of the plant may be increased by at least about 40% as compared to an untreated plant. The turgid state of the plant may be increased by at least about 50% as compared to an untreated plant.

The turgid state of the plant may be increased by at least about 2, 3, 4, 5, 6, 7, 8, 9, 10, 11, 12, 13, 14, 15, 16, 17, 18, 19, 20, 21, 22, 23, or 24 hours as compared to an untreated plant. The turgid state of the plant may be increased by at least about 6 hours as compared to an untreated plant. The turgid state of the plant may be increased by at least about 12 hours as compared to an untreated plant. The turgid state of the plant may be increased by at least about 24 hours as compared to an untreated plant.

Preserving or extending the life of the plant may comprise reducing or delaying the loss of one or more petals of the plant. The loss of the one or more petals of the plant may be reduced by least about 20% as compared to the loss of the one or more petals of an untreated plant. The loss of the one or more petals of the plant may be reduced by least about 30% as compared to the loss of the one or more petals of an untreated plant. The loss of the one or more petals of the plant may be reduced by least about 40% as compared to the loss of the one or more petals of an untreated plant.

The loss of the one or more petals of the plant may be delayed by at least about 2, 3, 4, 5, 6, 7, 8, 9, 10, 11, 12, 13, 14, 15, 16, 17, 18, 19, 20, 21, 22, 23, or 24 hours as compared to the loss of one or more petals of an untreated plant. The loss of the one or more petals of the plant may be delayed by at least about 6 hours as compared to the loss of one or more petals of an untreated plant. The loss of the one or more petals of the plant may be delayed by at least about 12 hours as compared to the loss of one or more petals of an untreated plant. The loss of the one or more petals of the plant may be delayed by at least about 18 hours as compared to the loss of one or more petals of an untreated plant.

Preserving or extending the life of the plant may comprise maintaining the chlorophyll content of the plant. The chlorophyll content of the plant may be maintained for at least about 2, 3, 4, 5, 6, 7, 8, 9, 10, 11, 12, 13, 14, 15, 16, 17, 18, 19, 20, 21, 22, 23, or 24 hours. The chlorophyll content of the plant may be maintained for at least about 6 hours. The chlorophyll content of the plant may be maintained for at least about 12 hours. The chlorophyll content of the plant may be maintained for at least about 24 hours.

Preserving or extending the life of the plant may comprise reducing or delaying the loss of the chlorophyll content of the plant. The chlorophyll content of the plant may be greater than the chlorophyll content of an untreated plant. The chlorophyll content of the plant may be at least about 1%, 5%, 10%, 15%, 20%, 25%, 30%, 35%, 40%, 45%, or 50% greater than the content of an untreated plant. The chlorophyll content of the plant may be at least about 20% greater than the content of an untreated plant. The chlorophyll content of the plant may be at least about 1.5, 2, 2.5, 3, 3.5, 4, 4.5, 5, 5.5, 6, 6.5, 7, 8, 9, or 10-fold greater than the content of an untreated plant. The chlorophyll content of the plant may be at least about 2-fold greater than the content of an untreated plant.

The loss of the chlorophyll content of the plant may be delayed by at least about 2, 3, 4, 5, 6, 7, 8, 9, 10, 11, 12, 13, 14, 15, 16, 17, 18, 19, 20, 21, 22, 23, or 24 hours as compared to the loss of the chlorophyll content of an untreated plant. The loss of the chlorophyll content of the plant may be delayed by at least about 6 hours as compared to the loss of the chlorophyll content of an untreated plant. The loss of the chlorophyll content of the plant may be delayed by at least about 12 hours as compared to the loss of the chlorophyll content of an untreated plant.

The loss of the chlorophyll content of the plant may be less than the loss of the chlorophyll content of an untreated plant. The loss of the chlorophyll content of the plant may be at least about 1%, 5%, 10%, 15%, 20%, 25%, 30%, 35%, 40%, 45%, 50%, 55%, or 60% less than the loss of the chlorophyll content of an untreated plant. The loss of the chlorophyll content of the plant may be at least about 10% less than the loss of the chlorophyll content of an untreated plant. The loss of the chlorophyll content of the plant may be at least about 20% less than the loss of the chlorophyll content of an untreated plant.

In one embodiment, the compound, salt, solvate, polymorph, diastereoisomer, stereoisomer, or isomer, wherein in the moiety:

the stereocenter * is selected from the group consisting of: (S), (R), racemic, and a non-racemic mixture of (R) and (S). In another embodiment, the compound, salt, solvate, polymorph, diastereoisomer, stereoisomer, or isomer, wherein in the moiety:

the stereocenter * is selected from the group consisting of: (S), (R), racemic, and a non-racemic mixture of (R) and (S). In another embodiment, in the compound, salt, solvate, polymorph, diastereoisomer, stereoisomer, or isomer disclosed herein, any stereocenter can be selected from the group consisting of: (S), (R), racemic, and a non-racemic mixture of (R) and (S).

Figure 2:
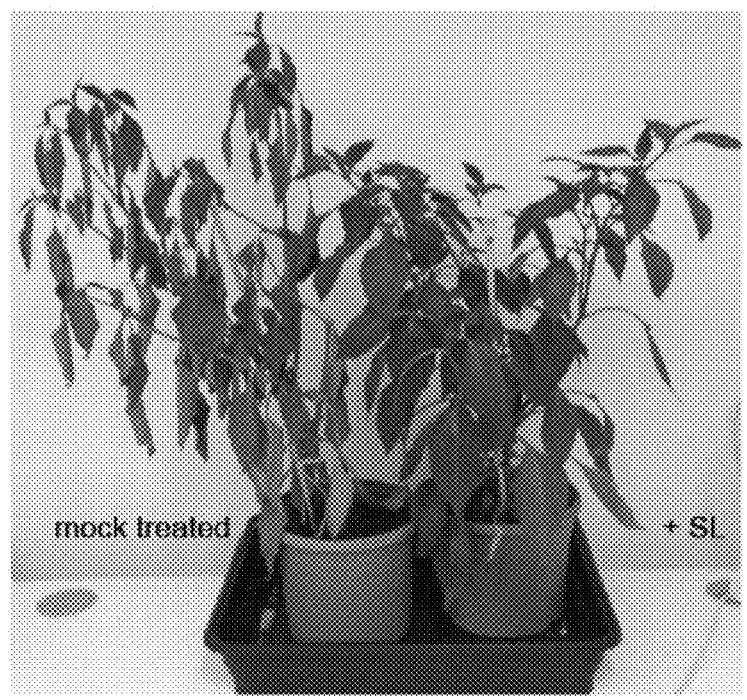

FIG. 2 Effect of SL on tolerance to water stress in *Capsicum annum*. Plants were either treated with SL or mock treated. Irrigation was stopped for 4 weeks. Untreated plant displayed symptoms of severe water stress and chlorosis, while the SL-treated plant appeared healthy and unstressed.

Figure 3:
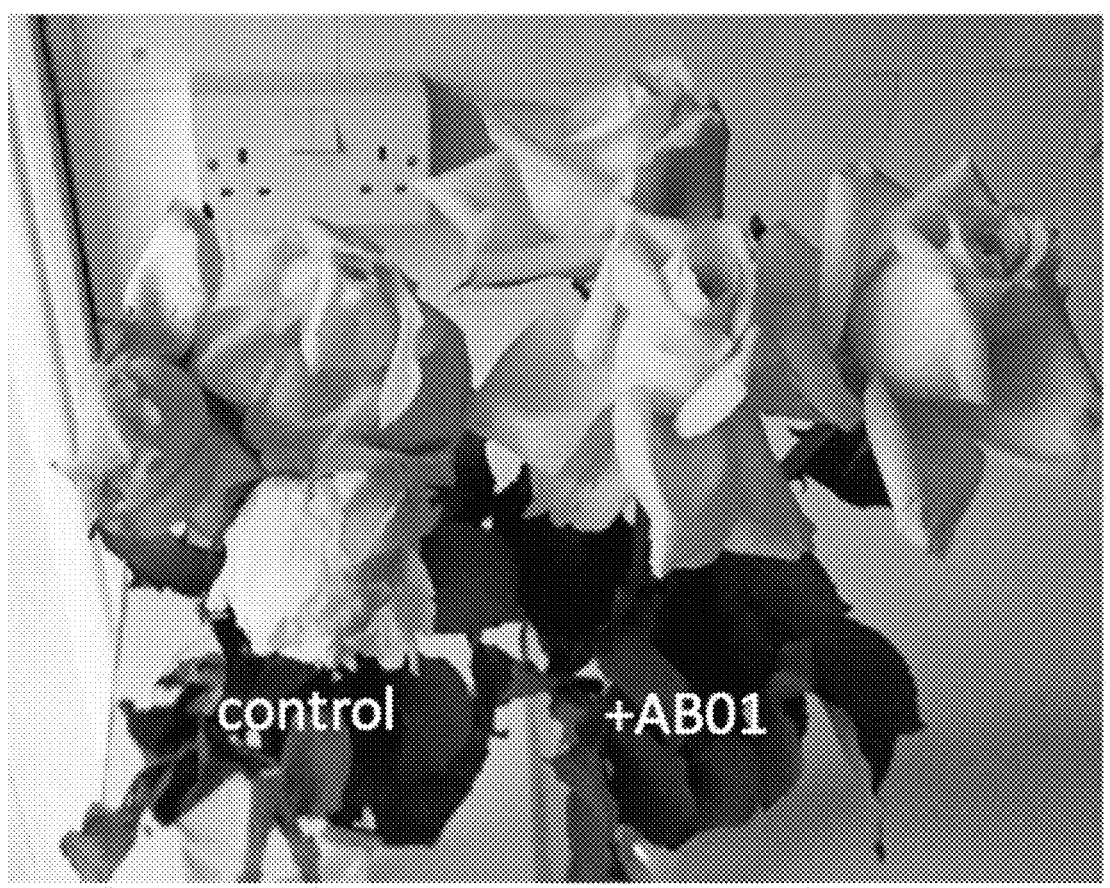

FIG. 3 shows the effect of a plant propagation material on vase life extension of cut flowers.

Figure 4:
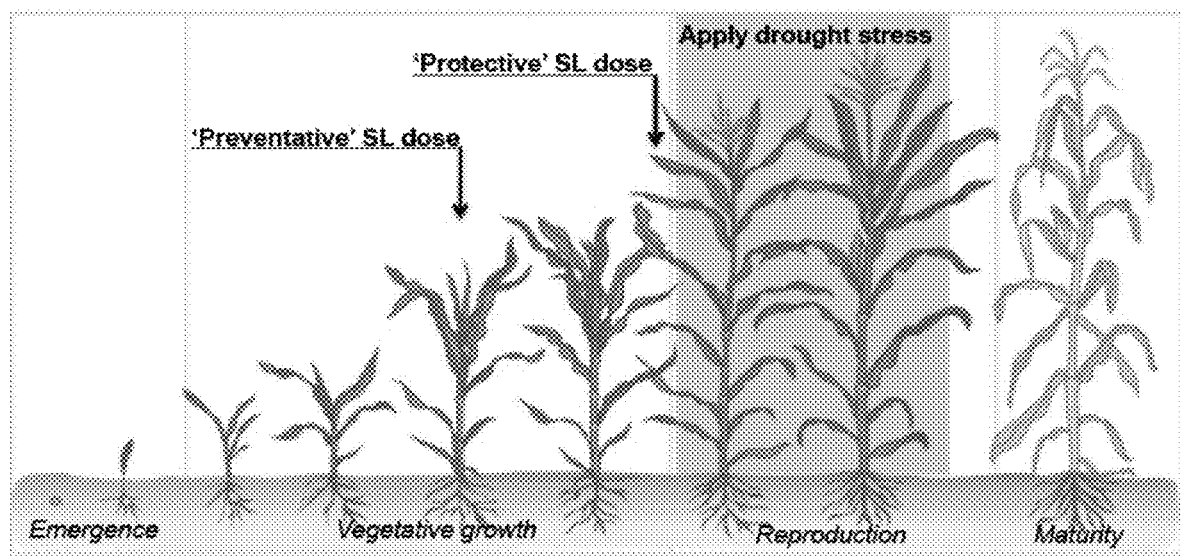

FIG. 4 Timeline of experiments to determine effect of SL application on yield. Plants are water-stressed starting in the early reproductive stage, prior to tasseling. SL is applied as either a 'preventative' dose during vegetative growth or as a 'protective' dose at the onset of water stress. Irrigation resumes during grain fill and grain yield is determined at maturity.

Figure 5:
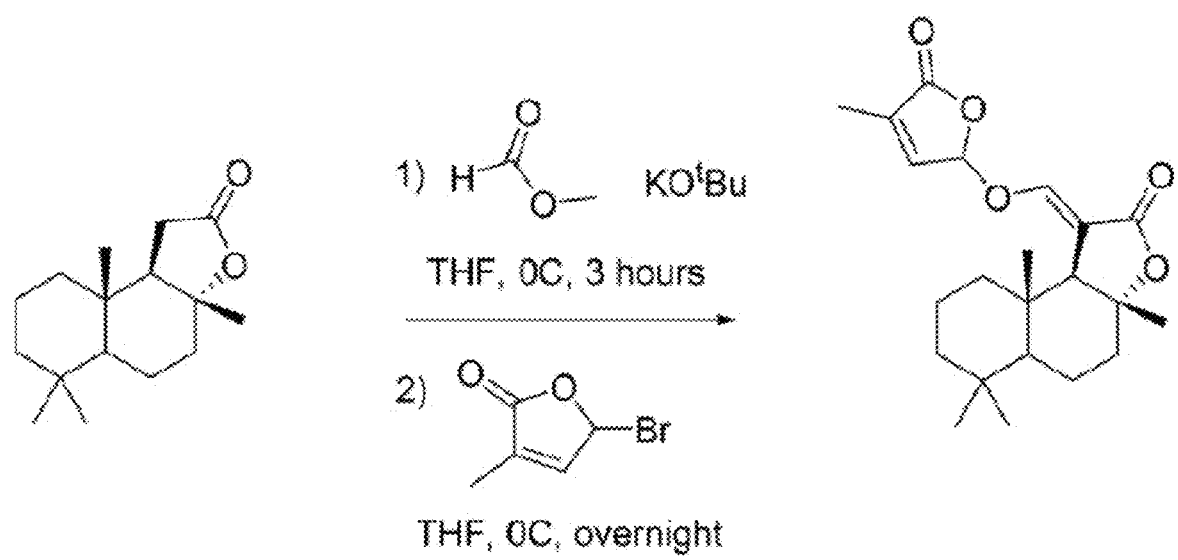

FIG. 5 shows a schematic for the synthesis of AB01.

Figure 6:
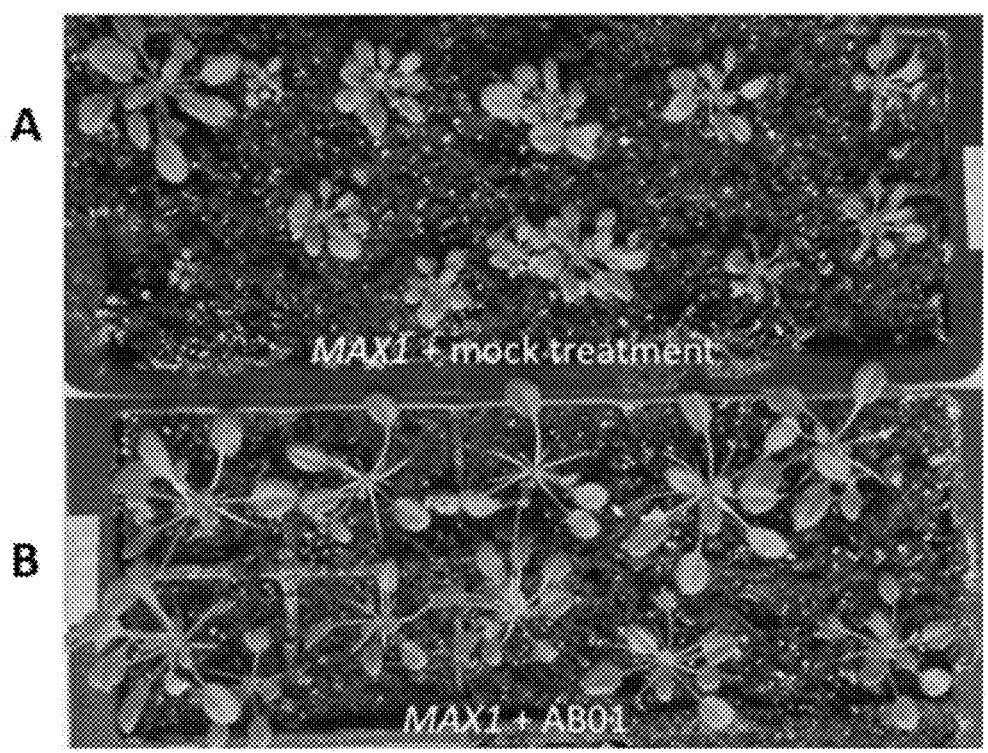

FIG. 6 shows bioactivity of AB01 in *Arabidopsis*. (A) Max1+mock treated; (B) Max1+AB01.

Figure 7:
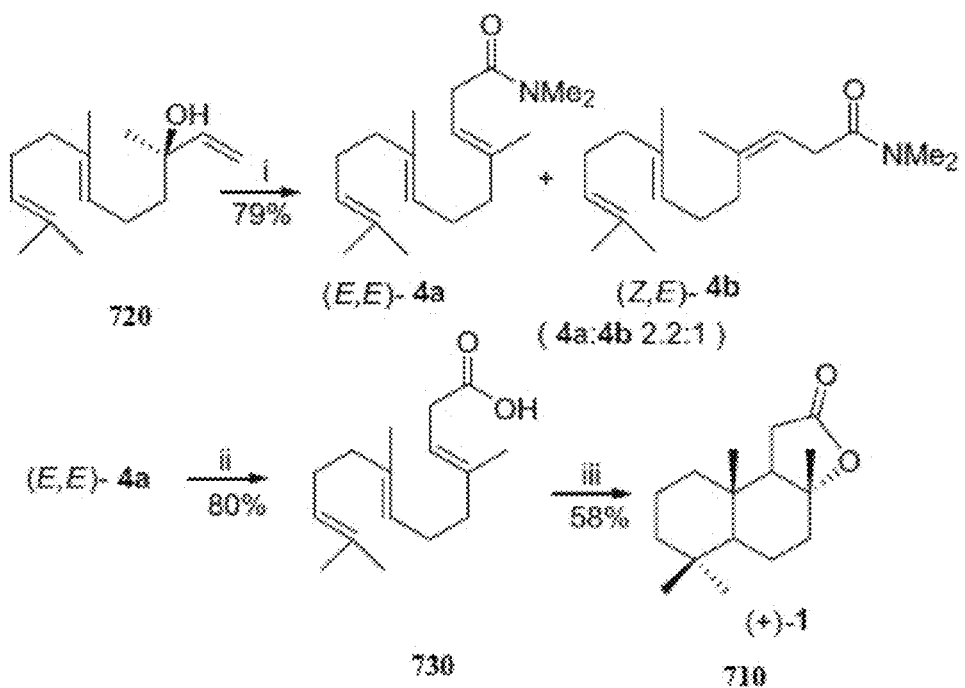

FIG. 7 shows an exemplary synthetic approach for (+)-sclareolide.

Figure 8:
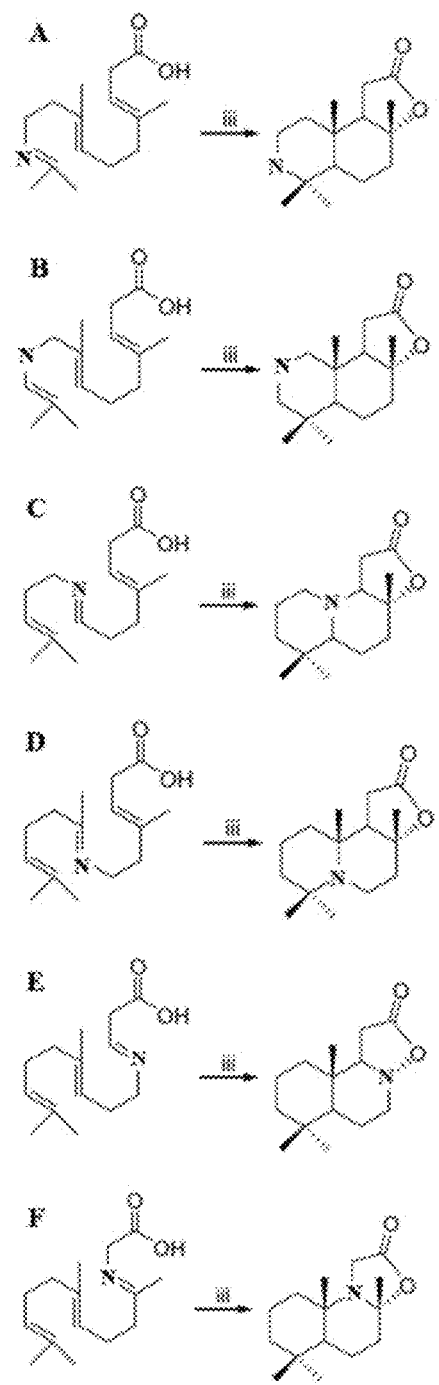

FIG. 8 shows exemplary synthetic approaches for nitrogen-containing compounds.

Figure 9:
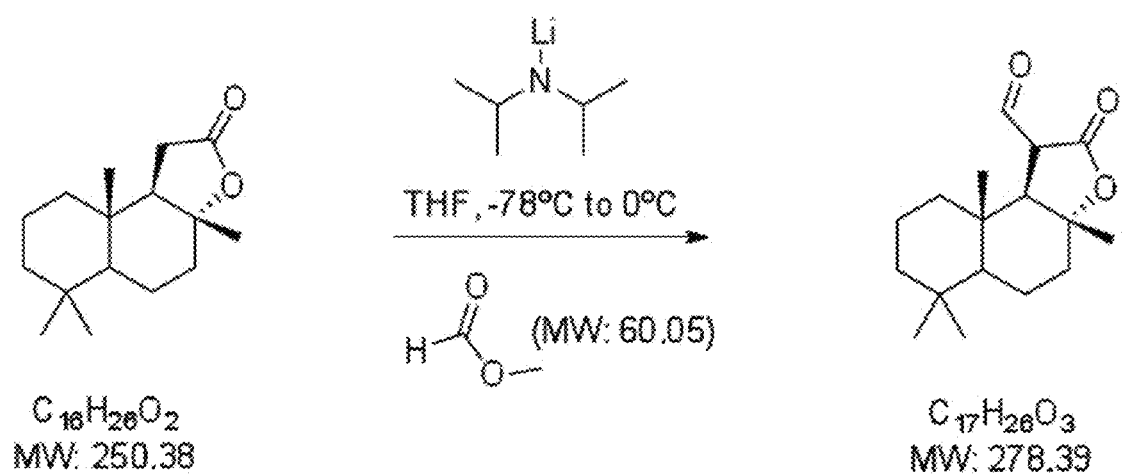

FIG. 9 shows the synthesis of formyl sclareolide.

Figure 10:
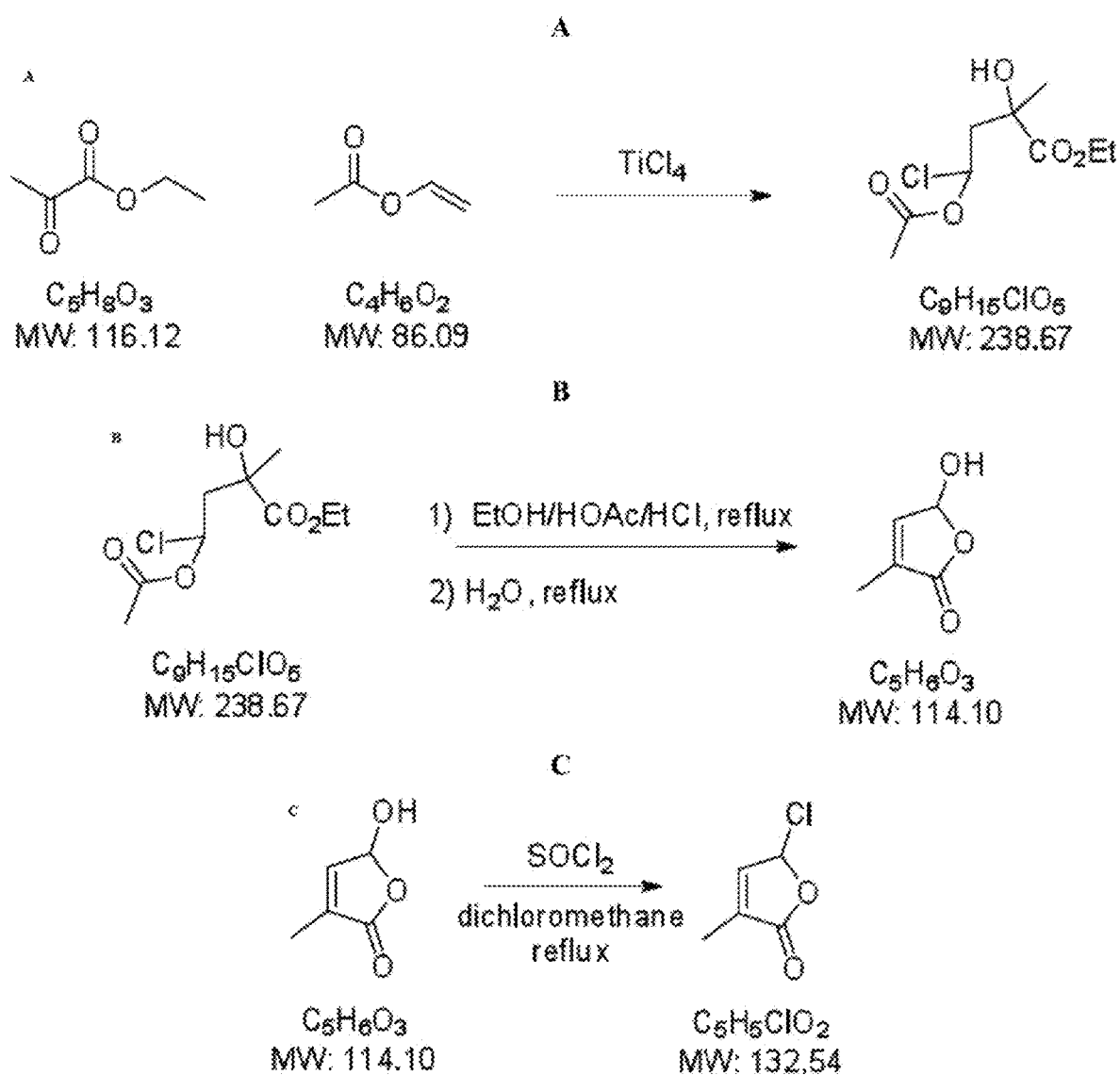

FIG. 10 shows the synthesis of chlorobutenolide. A) Step 1: TiCl4 aldol; B) Step 2: Hydrolysis and cyclization; C) Step 3: Chlorination.

Figure 11:
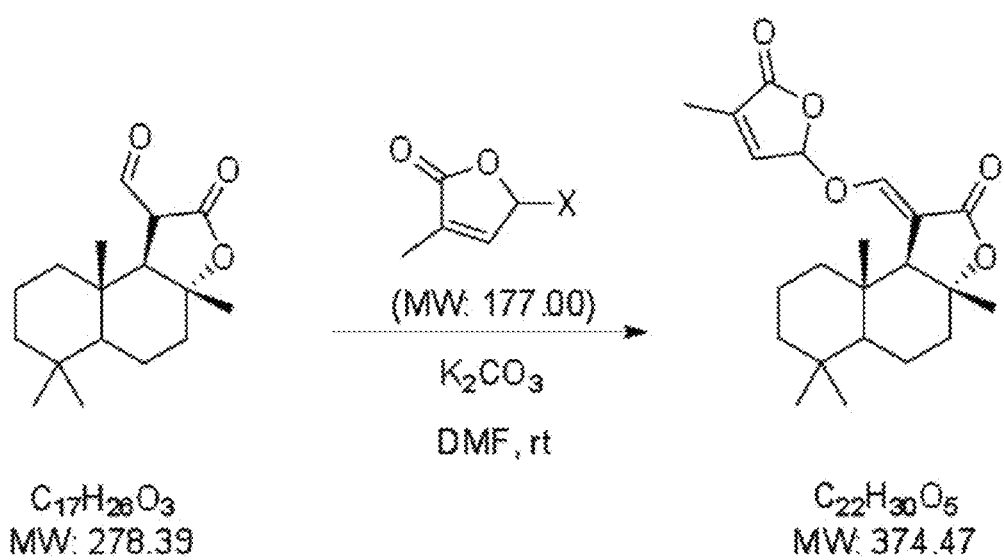

FIG. 11 shows the Synthesis of AB01.

Figure 12:
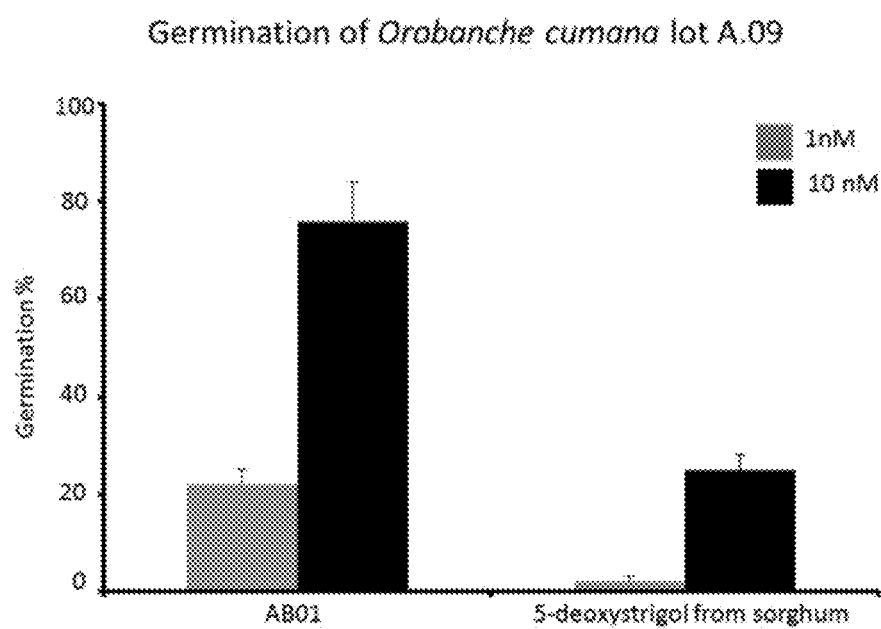

FIG. 12 shows improved germination triggering of parasitic weeds.

Figure 13:
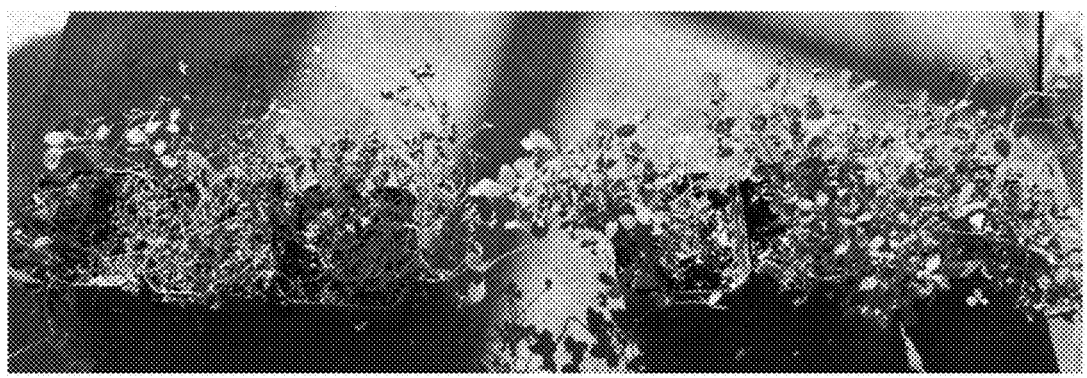

FIG. 13 shows drought tolerance in alfalfa enabled by AB01 treatment.

Figure 14:
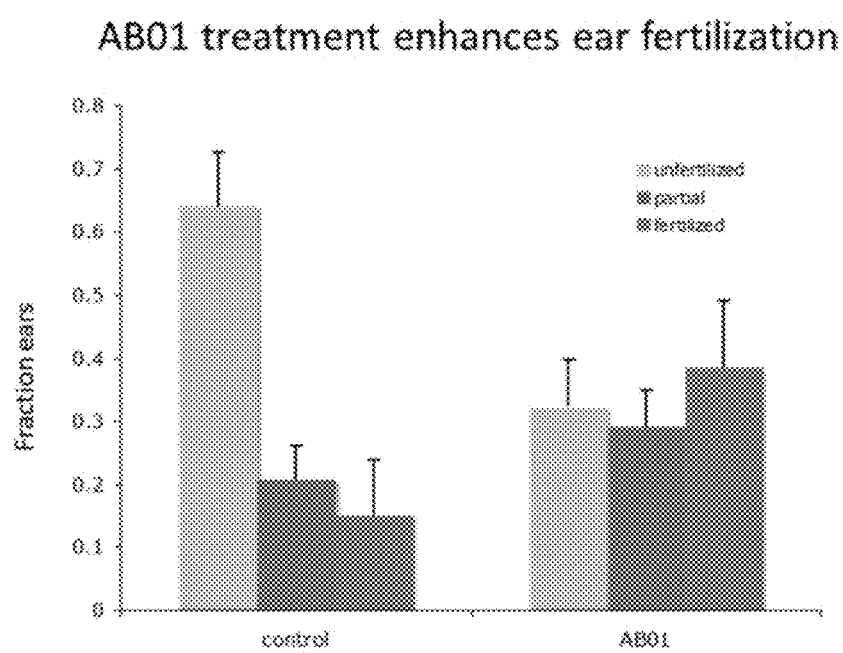

FIG. 14 shows AB01 enhances ear fertilization in corn field trial.

Figure 15:
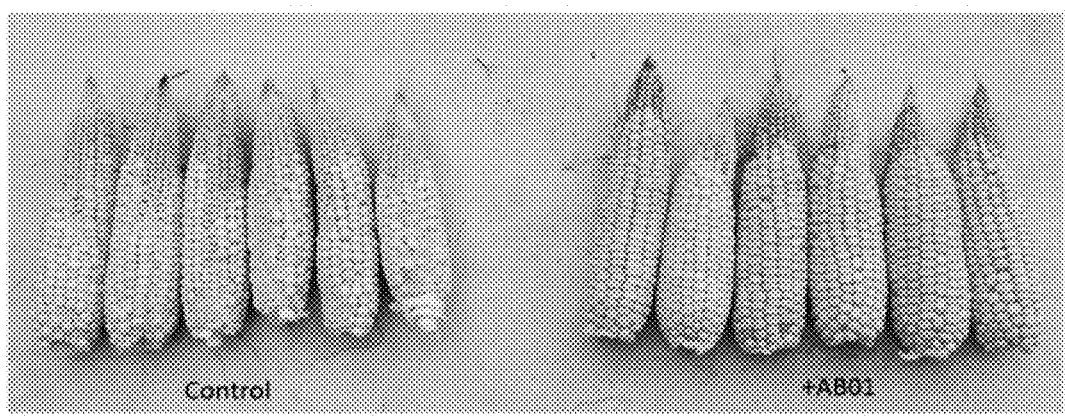

FIG. 15 shows AB01 enhances kernel set in corn field trial.

Figure 16:
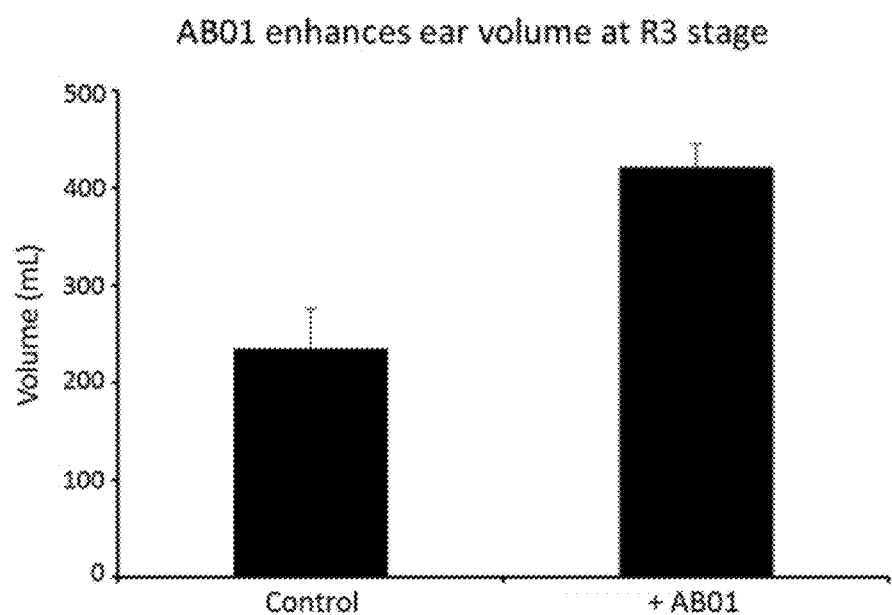

FIG. 16 shows AB01 enhances ear volume.

Figure 17:
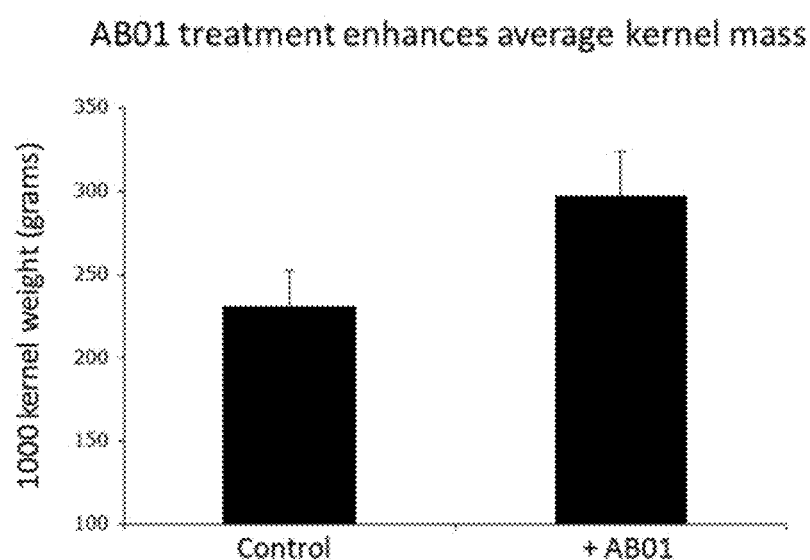

FIG. 17 AB01 treatment enhances average kernel weight.

Figure 18:
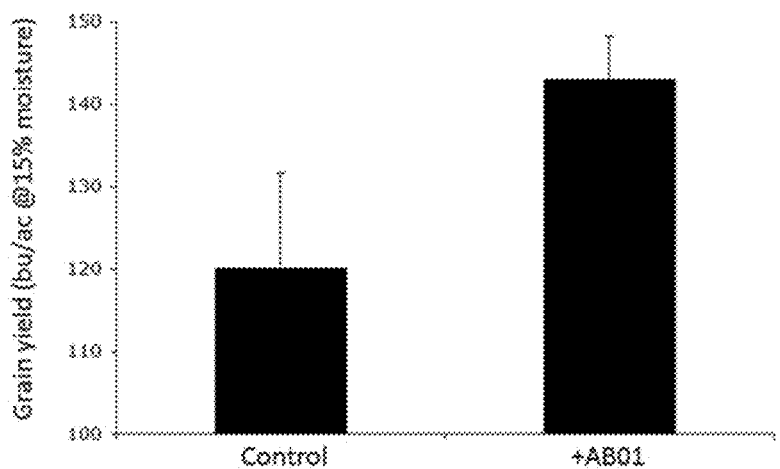

FIG. 18 shows AB01 treatment enhances harvest yield.

Figure 19:
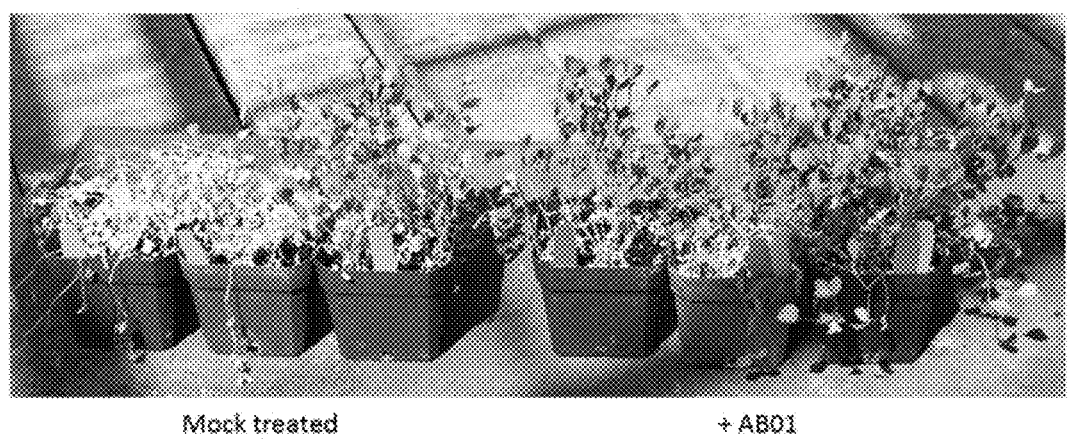

FIG. 19 shows AB01 treatment enables salinity tolerance in alfalfa.

Figure 20:

FIG. 20 shows AB01 treatment enables salinity tolerance in tomato.

Figure 21:
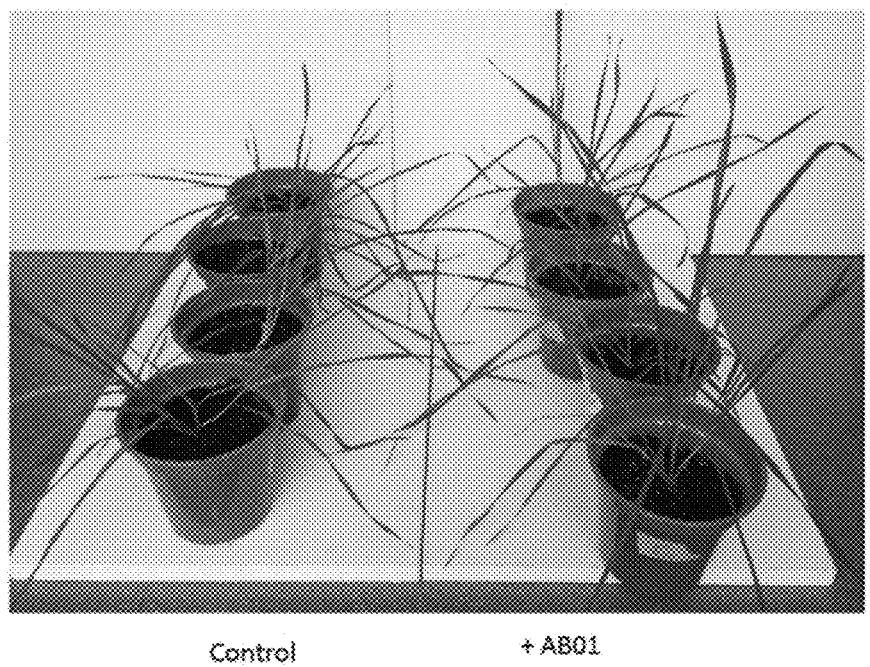

FIG. 21 shows AB01 treatment enhances drought tolerance in wheat.

Figure 22:
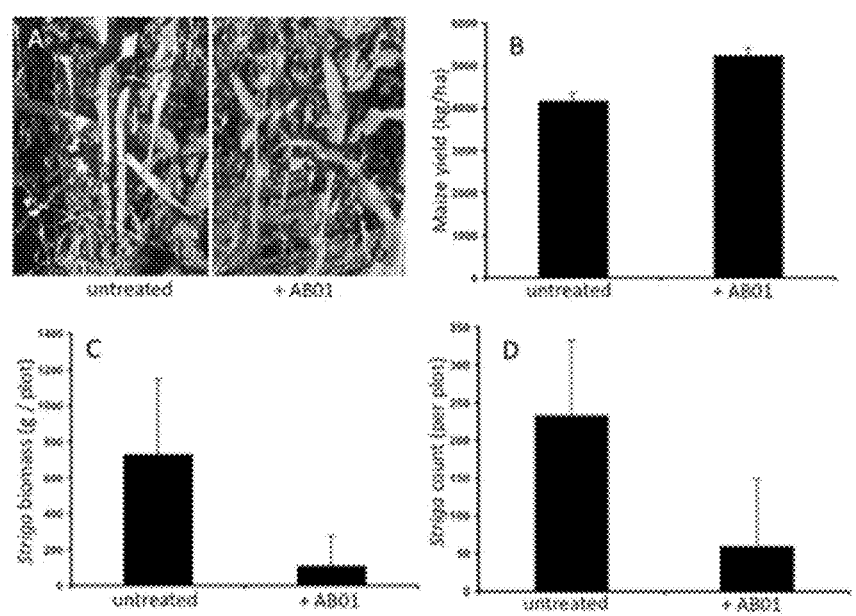

FIG. 22 shows reduction of *Striga* and enhancement of grain yield in AB01 treated fields (Siaya County, Kenya).

Figure 23:
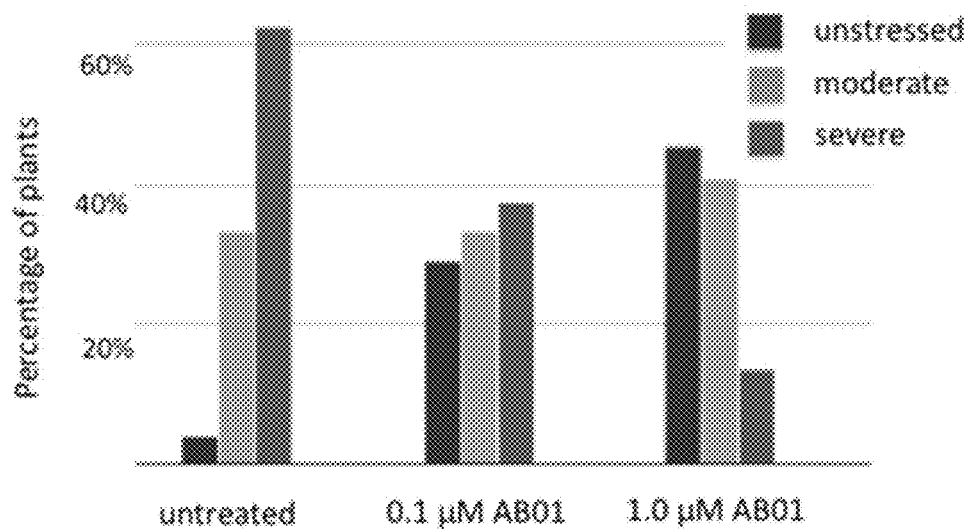

FIG. 23 shows reduction of acute water stress in AB01 treated corn.

INCORPORATION BY REFERENCE

All publications, patents, and patent applications herein are incorporated by reference to the same extent as if each individual publication, patent, or patent application was specifically and individually indicated to be incorporated by reference in its entirety. In the event of a conflict between a term herein and a term in an incorporated reference, the term herein controls.

DETAILED DESCRIPTION OF THE INVENTION

Unless defined otherwise, all technical and scientific terms used herein have the same meaning as commonly understood by one of the ordinary skill in the art to which this invention belongs. Although any methods and materials similar or equivalent to those described herein can be used in the practice or testing of the formulations or unit doses herein, some methods and materials are now described. Unless mentioned otherwise, the techniques employed or contemplated herein are standard methodologies. The materials, methods and examples are illustrative only and not limiting.

The details of one or more inventive embodiments are set forth in the accompanying drawings, the claims, and the description herein. Other features, objects, and advantages of the inventive embodiments disclosed and contemplated herein can be combined with any other embodiment unless explicitly excluded.

Unless otherwise indicated, open terms for example "contain," "containing," "include," "including," and the like mean comprising.

The singular forms "a", "an", and "the" are used herein to include plural references unless the context clearly dictates otherwise. Accordingly, unless the contrary is indicated, the numerical parameters set forth in this application are approximations that may vary depending upon the desired properties sought to be obtained by the present invention.

Unless otherwise indicated, some embodiments herein contemplate numerical ranges. When a numerical range is provided, unless otherwise indicated, the range includes the range endpoints. Unless otherwise indicated, numerical ranges include all values and subranges therein as if explicitly written out.

Unless otherwise indicated, formulations herein can be powdery.

Unless otherwise indicated, the genes listed herein may be heterologous genes.

Unless otherwise indicated, powder formulations herein can contain water in an amount from about 0% to about 15% w/w, for example 0-10%, 0-5%, or 0-1% w/w; or about: 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, 80%, 85%, 90% or 99% w/w, based on the weight of the formulation.

Unless otherwise indicated, "plant propagation material" can refer to any compound, salt, solvate, polymorph, diastereoisomer, stereoisomer, isomer, or formulation described herein.

Unless otherwise indicated, whenever there is a stereocenter in a structure disclosed or illustrated herein, the stereocenter can be R or S in each case.

Unless otherwise indicated, whenever there is a wavy bond

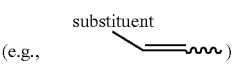

(e.g., in a structure disclosed or illustrated herein, the wavy bond can be

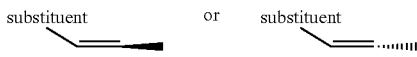

in each case.

Unless otherwise indicated, "amino" can refer be monosubstituted, disubstituted or trisubstituted.

Unless otherwise indicated, "alkyl" may comprise lower alkyl. In some embodiments, the alkyl can be from C1 to C8, for example, C1, C2, C3, C4, C5, C6, or C8. In some embodiments, the alkyl can be linear or branched. The alkyl may exclude cycloalkyl.

Unless otherwise indicated, "diastereomeric excess" (DE) may refer to the difference between the relative abundance of two diastereomers. For instance, if there are two diastereomers and their mole or weight percentages are A and B, then DE can be calculated as: DE=[(A−B)/(A+B)]*100%. For example, if a mixture contains 75% of one diastereomer and 25% of the other diastereomer, the diastereomers excess is 50%. In another example, if a mixture that is 95% of one diastereomer, the diastereomers excess is 90%.

Unless otherwise indicated, "treated" can be referred to "contacted." Similarly, "untreated" can be referred to "uncontacted."

Introduction

Drought is one of the most significant risks for farmers, rural economies, and the food supply chain; limited precipitation and irrigation acts as a major constraint on crop productivity. Climate change threatens to further exacerbate crop losses due to drought by shifting rainfall patterns and weather conditions across e.g. America's most productive agricultural regions. There is a need for tools and strategies to enable e.g. American farmers to adapt to climate change by reducing the water footprint of major commercial crops. While there have been promising advances in field management (such as low-till and no-till systems) and in the development of drought tolerant crops, there is currently no crop protection product that enhances the robustness of field crops to periods of prolonged drought and water-limitation stress. A product that could be applied to crops as a foliar spray or irrigation supplement to boost the health and productivity of plants during drought stress would allow farmers to reduce the risk of crop loss and maintain productivity throughout variable weather. Due to the large magnitude of drought-related crop losses and the substantial threats that climate change poses for the agricultural system, there is a significant opportunity for development of crop protection products that enhance drought tolerance.

Effect of Drought Upon Maize Productivity

Even with technologically advanced agriculture, weather is a prominent factor in determining crop yields and quality. Weather is especially critical for drought-sensitive crops, such as maize, where temperature and soil moisture during biologically critical developmental periods influence yields. Water stress at any growth stage can be deleterious to yield, but maize is particularly vulnerable to drought during the early reproductive stages [1]. Water stress during the period from two weeks prior to silking to two weeks after silking (the early reproductive stage) can reduce harvest yield by 3 to 8 percent for each day of stress [2]. This is because silks, which are essential for kernel fertilization, have the highest water content in maize plants and thus are highly sensitive to inadequate moisture levels [3]. Severe drought stress during the early stages of kernel development can also decrease yields as the maize plants abort developing kernels.

The biological effects of drought on maize plants translate into severe economic and productivity losses for the United States. Severe drought in the Midwestern US destroyed or damaged much of the field corn production during 2012. Field corn yield in the US in 2013 is expected to increase by 28% compared to 2012, largely because drought conditions have been relieved [4]. Even when these losses are not borne directly by farmers, the effects are felt by the US economy. The Federal Crop Insurance Program paid out a record $17.3 billion in insurance claims during 2012 [5]; 80% of these payments have been estimated to be for farmers whose crops were lost due to heat, drought or wind damage [6]. This outcome is particularly severe for US corn producers because 80% of maize is rainfed. The productivity losses are felt globally, as the US produces approximately 40% of maize worldwide and is a heavy exporter [7].

Strategies for Mitigating Drought Risk and Unmet Needs

The available strategies for drought mitigation in maize are effectively limited to soil management and crop choice. Irrigation, which is the only totally effective solution to drought, is not an option for the ~80% of U.S. corn production which relies on rain. Soil management for drought encourages no-till farming and cover cropping, and relies primarily on education and external incentives. Crop choice for maize farmers is primarily between drought tolerant genetic variants (both engineered and traditionally bred) that have become available in the past few years. These variants are still being evaluated, but early results show a 10-20% yield increase compared to similar non-drought tolerant strains under drought conditions [8, 9]. Importantly, these yields are still below the expected yields with sufficient watering. However, heat and drought tolerant variants have traditionally performed worse than standard variants under well-watered conditions. Recent evidence suggests that the newly developed strains may have mitigated this issue [10]. Crop insurance schemes are also used to mitigate drought risk. However, this mechanism is costly and does not address the nationwide productivity loss. All these mechanisms rely on forecasting or decisions made ahead of the onset of drought, which is difficult or impossible to predict. They notably do not include a crop protection product that can be added to fields (as a foliar spray, irrigation additive, or other method) as needed in order to mitigate risk or increase yield in response to drought that was not forecast.

Plant Growth Regulators Affect Plant Physiology and Water Stress Regulation

Plant hormones (also known as plant growth regulators, PGRs) are critical for adaptation to changing environments. Processes such as growth, development, and morphology are regulated by a stress-responsive hormone signaling network that includes the signaling molecules abscisic acid, cytokines, auxins, brassinosteroids, and strigolactones [11]. In addition to 'long term' plant responses such as morphology, the hormone-signaling network also orchestrates stress adaptive responses such as stomata opening, nutrient allocation, induction of innate immunity, and source-sink distribution [12]. The understanding of the interactions between environmental stress, PGRs, and plant physiology are important targets for biotechnological improvement of crops. For example, tobacco plants genetically modified to overproduce cytokines maintained their photosynthetic capacity under water limitation by inhibiting degradation of the photosynthetic machinery [13].

The PGR abscisic acid plays a major role in adaptation to drought conditions. Upon water limitation, abscisic acid biosynthesis is induced, with concentrations in cells reaching micromolar levels [14]. Abscisic acid triggers fast responses, such as stomata closure and cell cycle arrest, as well as slower responses such as transcriptional and epigenetic regulation of plant metabolism [15]. This coordinated response to water stress enables plants to adapt to periods of water limitation.

Strigolactones (SLs) are a recently discovered class of PGRs involved in the regulation of root and shoot morphology and interactions with rhizosphere-associated symbionts. SLs were first characterized as germination stimulants for seeds of the parasitic plants *Striga* and Orobanche [16]. SLs are derived from carotenoid biosynthesis, sharing a common precursor (beta-carotene) with abscisic acid [17]. The common pathway of abscisic acid and SL biosynthesis has lead to investigations into potential correlations in the levels of each PGR and their co-regulation of critical plant functions. A study with tomato mutants blocked at known abscisic acid biosynthesis steps revealed that SL levels were correlated with abscisic acid levels by an unknown mechanism [18]. Due to this correlation, we hypothesized that SLs may play a role in the regulation of stress response, either by influencing the levels and dynamics of abscisic acid signaling or by unknown mechanisms. SLs are among the few PGRs that have not been evaluated as crop protection products or as components of integrated crop management strategies.
Economic, Technical, and Social Benefits Crop failure, reduced crop harvest yields, and loss of pasture are the primary agricultural results of drought. The outcomes of drought affects individual farm revenues as well as the regional and national economies. The anticipated endpoint of the research and development project proposed here would deliver a product to protect crops from the effects of drought, increasing yields and reducing the risk of crop loss and failure. The development of this drought-protective product would have several benefits to society at large, including enhanced food security and food price stability. The secondary effects of drought and crop loss are increased food prices for consumers, which could be partially mitigated by deployment of a drought-protective product. It is also feasible that deployment of a drought-protective product will lower the water demands of agriculture, relieving existing and future stress on aquifers and fresh water supplies. For the federal government, tools for the mitigation of drought are used in the management of federal lands. In addition, the use of best practices and new technologies can reduce the magnitude of crop insurance liabilities. The development of SL as a drought-protective tool could further aid in reducing the magnitude of federal crop insurance.

There is a clear need for drought mitigation solutions which enhance yield and quality of crops during periods of water limitation stress. Currently available agricultural drought mitigation solutions rely on irrigation, conservation and crop management. Best practices require the use of low water profile crops or crops genetically enhanced for drought resistance, field management through no-till farming and the use of cover crops, and risk mitigation through crop insurance.

Disclosed herein are compounds for use in agriculture. The compounds may have the structure of Formula I-VI, or a salt, solvate, polymorph, stereoisomer, or isomer thereof. The compounds may comprise chemical mimics of strigolactone. Further disclosed are methods of producing the compounds and uses thereof.

Disclosed herein are compounds for use in preserving or extending the life of a plant. The compounds may have the structure of Formula I-VI, or a salt, solvate, polymorph, stereoisomer, or isomer thereof. The compounds may comprise chemical mimics of strigolactone. Further disclosed are methods of producing the compounds and uses thereof.

Further disclosed herein are plant propagation materials comprising strigolactone, or a salt, solvate, polymorph, stereoisomer, or isomer thereof. The strigolactone, or a salt, solvate, polymorph, stereoisomer, or isomer thereof may be obtained by chemical synthesis. Chemical synthesis methods are disclosed herein. The strigolactone, or a salt, solvate, polymorph, stereoisomer, or isomer thereof may be obtained by a biosynthetic process. Biosynthetic processes are disclosed herein.

Further disclosed herein are polynucleotides comprising one or more genes for use in a biosynthetic process. The one or more genes may encode one or more components of a strigolactone pathway. Further disclosed herein are vectors comprising the polynucleotides. Further disclosed herein are cells comprising the vectors comprising the polynucleotides.

Disclosed herein are methods of manufacturing said formulations. The methods may comprise a chemical synthesis. Alternatively, the method comprises a biosynthetic process.

Further disclosed herein are uses of the formulations and plant propagation materials disclosed herein. The plant propagation materials may be used to control the parasitic weeds of the *Striga* genus. The *Striga* genus may comprise species such as *Striga asiatica, S. gesnerioides*, and *S. hermonthica*. The plant propagation materials may be used to improve agriculture. The plant propagation material may be used to improve crop yield. The plant propagation material may be used to improve crop yield of staples such as maize, sorghum, rice, and cowpea. The plant propagation material may be use to preserve or extend the life of a plant. The plant propagation material may be used to prevent or reduce wilting of a plant. The plant propagation material may be used to delay the wilting of a plant. The plant propagation material may be used to maintain turgidity of a plant. The plant propagation material may be used to prolong the turgid state of a plant. The plant propagation material may be used to prevent or delay the loss of plant leaves or petals. The plant propagation material may be used to maintain the chlorophyll content of the plant. The plant propagation material may be used to reduce or delay the loss of the chlorophyll content of the plant.

Chemical Mimics of Strigolactone

Three key functionalities have been identified for strigolactone activity: the lactone C ring, the enol (vinyl) ether linkage and the D ring butenolide (Zwanenburg 2013). In studies of synthetic derivatives the α, β-unsaturated system and D ring were essential to retain activity (Magnus and Zwanenburg 1992, Zwanenburg et al 2009). Additionally, the C-4' methyl group of the D ring was established as essential for bioactivity (Zwanenburg 2013). The importance of stereochemistry is critical to the bioactivity, as illustrated by (+)-strigol. In germination studies of *Striga hermonthica* seeds, (+)-strigol shows 93% activity versus 22% for ent-strigol at 10-8 M concentrations (Zwanenburg 2013). Our synthetic strategy was guided by these features and by economics: simple methodology and low cost of goods is preferable for commercial scale-up. The chemical mimics of Strigolactone disclosed herein may be plant propagation materials.

Disclosed herein are chemical mimics of Strigolactone. A chemical mimic of strigolactone may be a compound of Formula (I), a salt, solvate, polymorph, stereoisomer, or isomer thereof:

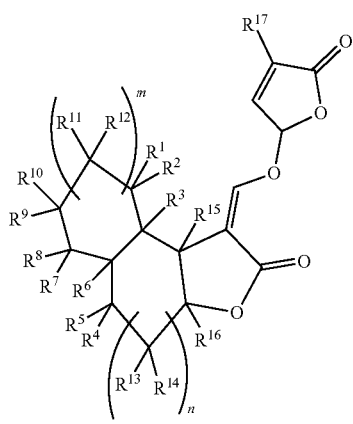

Formula (I)

wherein:

$R^1$, $R^2$, $R^4$, $R^5$, $R^7$, $R^8$, $R^9$, $R^{10}$, $R^{11}$, $R^{12}$, $R^{13}$, $R^{14}$, $R^{15}$, $R^{16}$, and $R^{17}$ are each independently H, alkyl, haloalkyl, amino, halo, or —$OR^{18}$;

$R^3$ and $R^6$ are each independently H, alkyl, haloalkyl, amino, halo, or —$OR^{18}$; or $R^3$ and $R^6$ together form a direct bond to provide a double bond;

each $R^{18}$ is independently H, alkyl, haloalkyl, aryl, heteroaryl, or —$C(O)R^{19}$;

each $R^{19}$ is independently alkyl, haloalkyl, aryl, or heteroaryl;

m is 0, 1, or 2; and n is 1 or 2.

The chemical mimic of strigolactone may be a compound of Formula (I) wherein m is 0 and n is 1. The chemical mimic of strigolactone may be a compound of Formula (I) wherein m is 0 and n is 2. The chemical mimic of strigolactone may be a compound of Formula (I) wherein m is 1 and n is 2. The chemical mimic of strigolactone may be a compound of Formula (I) wherein m is 2 and n is 1. The chemical mimic of strigolactone may be a compound of Formula (I) wherein m is 2 and n is 2. The chemical mimic of strigolactone may be a compound of Formula (I) wherein m is 1 or 2. The chemical mimic of strigolactone may be a compound of Formula (I) wherein m is 1 or 2.

The chemical mimic of strigolactone may be a compound of Formula (I) wherein $R^3$ and $R^6$ together form a direct bond to provide a double bond. The chemical mimic of strigolactone may be a compound of Formula (I) wherein $R^3$ and $R^6$ are each independently H, alkyl, haloalkyl, amino, halo, or —$OR^{18}$. The chemical mimic of strigolactone may be a compound of Formula (I) wherein $R^3$ and $R^6$ are each independently H or alkyl.

The chemical mimic of strigolactone may be a compound of Formula (I) wherein $R^1$, $R^2$, $R^4$, $R^5$, $R^7$, $R^8$, $R^9$, $R^{10}$, $R^{11}$, $R^{12}$, $R^{13}$, $R^{14}$, $R^{15}$, $R^{16}$, and $R^{17}$ are each independently H, alkyl, or —$OR^{18}$; $R^3$ and $R^6$ are each independently H or alkyl. The chemical mimic of strigolactone may be a compound of Formula (I) wherein $R^1$, $R^2$, $R^4$, $R^5$, $R^7$, $R^8$, $R^9$, $R^{10}$, $R^{11}$, $R^{12}$, $R^{13}$, $R^{14}$, $R^{15}$, and $R^{16}$ are each independently H, alkyl, or —$OR^{18}$; $R^3$ and $R^6$ are each independently H or alkyl; and $R^{17}$ is alkyl.

The chemical mimic of strigolactone may be a compound of Formula (I) wherein m is 1, n is 1, and the compound has the structure of Formula (II):

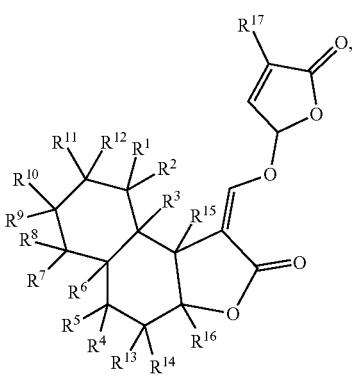

Formula (II)

or a salt, solvate, polymorph, stereoisomer, or isomer thereof.

The chemical mimic of strigolactone may be a compound of Formula (II) wherein $R^1$, $R^2$, $R^4$, $R^5$, $R^7$, $R^8$, $R^9$, $R^{10}$, $R^{11}$, $R^{12}$, $R^{13}$, $R^{14}$, $R^{15}$, $R^{16}$, and $R^{17}$ are each independently H, alkyl, or —$OR^{18}$. The chemical mimic of strigolactone may be a compound of Formula (II) wherein $R^1$, $R^2$, $R^4$, $R^5$, $R^7$, $R^8$, $R^9$, $R^{10}$, $R^{11}$, $R^{12}$, $R^{13}$, $R^{14}$, $R^{15}$, $R^{16}$, and $R^{17}$ are each independently H, alkyl, or —$OR^{18}$ and $R^{18}$ is H or alkyl.

The chemical mimic of strigolactone may be a compound of Formula (II) wherein $R^3$ and $R^6$ together form a direct bond to provide a double bond. The chemical mimic of strigolactone may be a compound of Formula (II) wherein $R^3$ and $R^6$ are each independently H, alkyl, haloalkyl, amino, halo, or —$OR^{18}$. The chemical mimic of strigolactone may be a compound of Formula (II) wherein $R^3$ and $R^6$ are each independently H or alkyl. The chemical mimic of strigolactone may be a compound of Formula (II) wherein $R^{17}$ is alkyl.

The chemical mimic of strigolactone may be a compound of Formula (I) wherein m is 1; n is 1; each of $R^4$, $R^5$, $R^9$, $R^{10}$, $R^{11}$, $R^{12}$, $R^{13}$, $R^{14}$, and $R^{15}$ are hydrogen; and the compound has the structure of Formula (III):

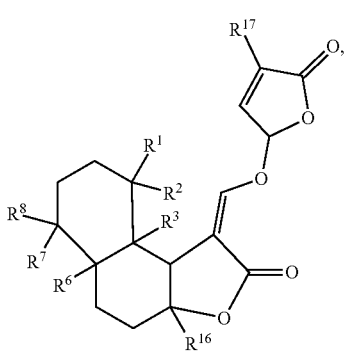

Formula (III)

or a salt, solvate, polymorph, stereoisomer, or isomer thereof.

The chemical mimic of strigolactone may be a compound of Formula (III) wherein $R^3$ and $R^6$ together form a direct bond to provide a double bond. The chemical mimic of strigolactone may be a compound of Formula (III) wherein $R^3$ and $R^6$ are each independently H, alkyl, haloalkyl, amino, halo, or —OR$^{18}$. The chemical mimic of strigolactone may be a compound of Formula (III) wherein R$^3$ and R$^6$ are each independently H or alkyl. The chemical mimic of strigolactone may be a compound of Formula (III) wherein R$^{17}$ is alkyl.

Disclosed herein can be another chemical mimic of Strigolactone. The chemical mimic of Strigolactone can be compound of Formula (VII), a salt, solvate, polymorph, diastereoisomer, stereoisomer, or isomer thereof:

Formula (VII)

wherein:

a, b, c are each independently 0, 1, or 2;

each A is independently O, or S;

each E is independently O, S, or —NR$^{18}$;

each G is independently C or N;

R$^5$, R$^6$, R$^{11}$, R$^{12}$, R$^{14}$, R$^{15}$ and R$^{17}$ are each independently H, alkyl, haloalkyl, amino, halo, or —OR$^{18}$;

R$^2$, R$^3$, R$^7$, R$^8$, R$^9$, and R$^{10}$ are each independently H, alkyl, haloalkyl, amino, halo, —OR$^{18}$ or a lone electron pair;

R$^1$ and R$^{16}$ are each independently H, alkyl, haloalkyl, amino, halo, lone electron pair, or —OR$^{18}$; or R$^1$ and R$^{16}$ together form a direct bond to provide a double bond;

R$^4$ and R$^{13}$ are each independently H, alkyl, haloalkyl, amino, halo, lone electron pair, or —OR$^{18}$; or R$^1$ and R$^{16}$ together form a direct bond to provide a double bond;

each R$^{18}$ is independently H, alkyl, haloalkyl, aryl, heteroaryl, —C(O)R$^{19}$ or and each R$^{19}$ is independently H, alkyl, haloalkyl, aryl, or heteroaryl.

Another chemical mimic of Strigolactone can be a compound of Formula (VIII), a salt, solvate, polymorph, diastereoisomer, stereoisomer, or isomer thereof:

Formula (VIII)

wherein:

a, b, c are each independently 0, 1, or 2;

each A is independently O, or S;

each E is independently O, S, or —NR$^{18}$;

each G is independently C or N;

R$^5$, R$^6$, R$^{11}$, R$^{12}$, R$^{14}$, R$^{15}$ and R$^{17}$ are each independently H, alkyl, haloalkyl, amino, halo, or —OR$^{18}$;

R$^2$, R$^3$, R$^7$, R$^8$, R$^9$, and R$^{10}$ are each independently H, alkyl, haloalkyl, amino, halo, —OR$^{18}$ or a lone electron pair;

R$^1$ and R$^{16}$ are each independently H, alkyl, haloalkyl, amino, halo, lone electron pair, or —OR$^{18}$; or R$^1$ and R$^{16}$ together form a direct bond to provide a double bond;

R$^4$ and R$^{13}$ are each independently H, alkyl, haloalkyl, amino, halo, lone electron pair, or —OR$^{18}$; or R$^1$ and R$^{16}$ together form a direct bond to provide a double bond;

each R$^{18}$ is independently H, alkyl, haloalkyl, aryl, heteroaryl, —C(O)R$^{19}$ or and each R$^{19}$ is independently H, alkyl, haloalkyl, aryl, or heteroaryl.

The chemical mimic of strigolactone may be a compound of Formula (VII) or (VIII) wherein a is 0, b is 0, and c is 0. The chemical mimic of strigolactone may be a compound of Formula (VII) or (VIII) wherein a is 0, b is 0, and c is 1. The chemical mimic of strigolactone may be a compound of Formula (VII) or (VIII) wherein a is 0, b is 0, and c is 2. The chemical mimic of strigolactone may be a compound of Formula (VII) or (VIII) wherein a is 0, b is 1, and c is 0. The chemical mimic of strigolactone may be a compound of Formula (VII) or (VIII) wherein a is 0, b is 1, and c is 1. The chemical mimic of strigolactone may be a compound of Formula (VII) or (VIII) wherein a is 0, b is 1, and c is 2. The chemical mimic of strigolactone may be a compound of Formula (VII) or (VIII) wherein a is 0, b is 2, and c is 0. The chemical mimic of strigolactone may be a compound of Formula (VII) or (VIII) wherein a is 0, b is 2, and c is 1. The chemical mimic of strigolactone may be a compound of Formula (VII) or (VIII) wherein a is 0, b is 2, and c is 2. The chemical mimic of strigolactone may be a compound of Formula (VII) or (VIII) wherein a is 1, b is 0, and c is 0. The chemical mimic of strigolactone may be a compound of Formula (VII) or (VIII) wherein a is 1, b is 0, and c is 1. The chemical mimic of strigolactone may be a compound of Formula (VII) or (VIII) wherein a is 1, b is 0, and c is 2. The chemical mimic of strigolactone may be a compound of Formula (VII) or (VIII) wherein a is 1, b is 1, and c is 0. The chemical mimic of strigolactone may be a compound of Formula (VII) or (VIII) wherein a is 1, b is 1, and c is 1. The chemical mimic of strigolactone may be a compound of Formula (VII) or (VIII) wherein a is 1, b is 1, and c is 2. The chemical mimic of strigolactone may be a compound of Formula (VII) or (VIII) wherein a is 1, b is 2, and c is 0. The chemical mimic of strigolactone may be a compound of Formula (VII) or (VIII) wherein a is 1, b is 2, and c is 1. The chemical mimic of strigolactone may be a compound of Formula (VII) or (VIII) wherein a is 1, b is 2, and c is 2. The chemical mimic of strigolactone may be a compound of Formula (VII) or (VIII) wherein a is 2, b is 0, and c is 0. The chemical mimic of strigolactone may be a compound of Formula (VII) or (VIII) wherein a is 2, b is 0, and c is 1. The chemical mimic of strigolactone may be a compound of Formula (VII) or (VIII) wherein a is 2, b is 0, and c is 2. The chemical mimic of strigolactone may be a compound of Formula (VII) or (VIII) wherein a is 2, b is 1, and c is 0. The chemical mimic of strigolactone may be a compound of Formula (VII) or (VIII) wherein a is 2, b is 1, and c is 1. The chemical mimic of strigolactone may be a compound of Formula (VII) or (VIII) wherein a is 2, b is 1, and c is 2. The chemical mimic of strigolactone may be a compound of Formula (VII) or (VIII) wherein a is 2, b is 2, and c is 0. The chemical mimic of strigolactone may be a compound of Formula (VII) or (VIII) wherein a is 2, b is 2, and c is 1. The chemical mimic of strigolactone may be a compound of Formula (VII) or (VIII) wherein a is 2, b is 2, and c is 2.

In one embodiment, the compound, salt, solvate, polymorph, diastereoisomer, stereoisomer, or isomer disclosed herein is not (+)-Strigol

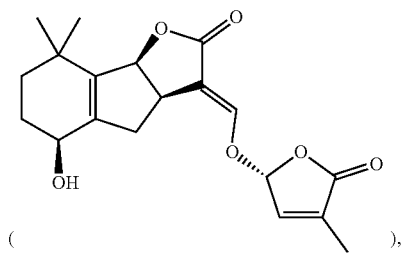 [SMILES: CC1=C[C@H](O/C=C2/C(=O)O[C@@H]3C4=C(C[C@H]23)[C@@H](O)CCC4(C)C)OC1=O]

(+)-Strigyl acetate

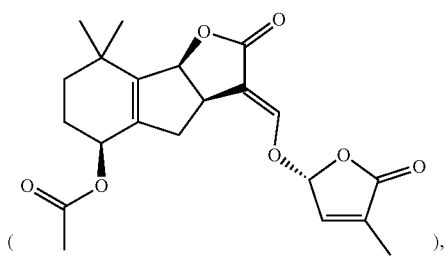 [SMILES: CC(=O)O[C@H]1CCC(C)(C)C2=C1C[C@@H]1/C(=C\O[C@H]3C=C(C)C(=O)O3)C(=O)O[C@H]21]

(+)-Orobanchol

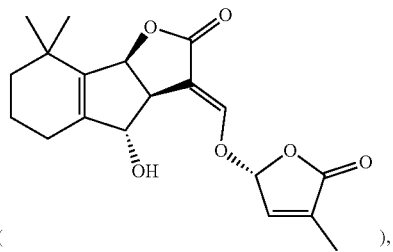

(+)-Orobanchyl acetate

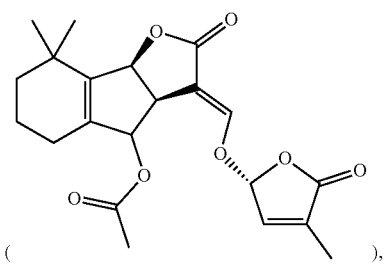 [SMILES: CC(=O)OC1C2=C([C@H]3OC(=O)/C(=C/O[C@H]4C=C(C)C(=O)O4)[C@@H]13)C(C)(C)CCC2]

(+)-5-Deoxystrigol

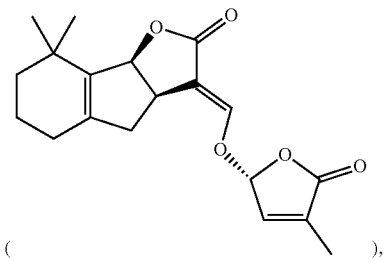 [SMILES: CC1=C[C@H](O/C=C2/C(=O)O[C@@H]3C4=C(CCCC4(C)C)C[C@H]23)OC1=O]

Sorgolactone

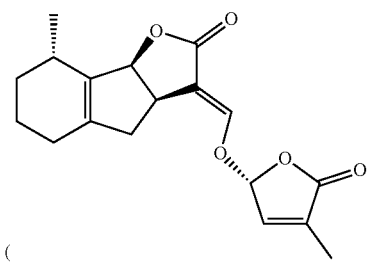

or any combination thereof.

In an embodiment, each A in the compound, salt, solvate, polymorph, diastereoisomer, stereoisomer, or isomer of the chemical mimic of strigolactone is independently O. In another embodiment, each E in the compound, salt, solvate, polymorph, diastereoisomer, stereoisomer, or isomer of the chemical mimic of strigolactone is independently O. In another embodiment, each G in the compound, salt, solvate, polymorph, diastereoisomer, stereoisomer, or isomer of the chemical mimic of strigolactone is independently C. In another embodiment, the compound, salt, solvate, polymorph, diastereoisomer, stereoisomer, or isomer of the chemical mimic of strigolactone, wherein $R^2$, $R^3$, $R^4$, $R^7$, $R^8$, $R^9$, $R^{10}$, $R^{11}$, $R^{12}$, and $R^{16}$ are each independently H. In another embodiment, the compound, salt, solvate, polymorph, diastereoisomer, stereoisomer, or isomer of the chemical mimic of strigolactone, wherein $R^1$, $R^5$, $R^6$, $R^{13}$, and $R^{17}$ are each independently alkyl. In another embodiment, the compound, salt, solvate, polymorph, diastereoisomer, stereoisomer, or isomer of the chemical mimic of strigolactone, wherein $R^1$, $R^5$, $R^6$, $R^{13}$, and $R^{17}$ are each independently methyl.

The chemical mimic of strigolactone may be a compound, salt, solvate, polymorph, diastereoisomer, stereoisomer, or isomer, having the structure of Formula (IX):

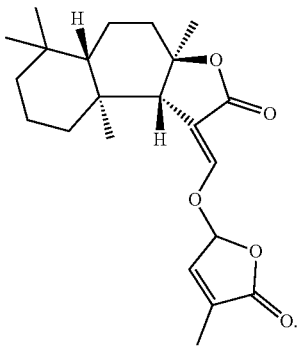

Formula (IX)

The chemical mimic of strigolactone may be a compound, salt, solvate, polymorph, diastereoisomer, stereoisomer, or isomer, having the structure of Formula (X):

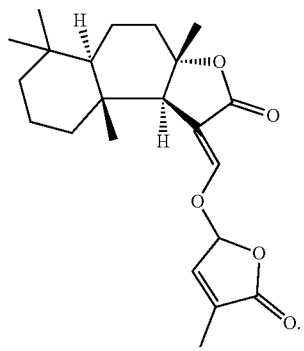

Formula (X)

The chemical mimic of strigolactone may be a compound having the structure of

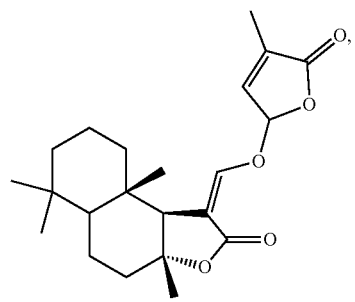 [SMILES: CC1=CC(O/C=C2\C(=O)O[C@]3(C)CCC4C(C)(C)CCC[C@]4(C)[C@@H]23)OC1=O]

or a salt, solvate, polymorph, stereoisomer, or isomer thereof.

A chemical mimic of strigolactone may be a compound, a salt, solvate, polymorph, stereoisomer, or isomer thereof, obtained by a process comprising a condensation reaction on a sesquiterpene lactone, salt, solvate, polymorph, stereoisomer, isomer or derivative thereof. The process may comprise a condensation reaction on a sesquiterpene lactone. The condensation reaction may comprise condensing the sesquiterpene lactone, salt, solvate, polymorph, stereoisomer, isomer or derivative thereof, with methyl formate to produce a hydroxymethylene lactone. The condensation reaction may comprise condesing the sesquiterpene lactone with methyl formate to produce a hydroxymethylene lactone. The condensation reaction may further comprise a base. The base may be potassium tert-butoxide. The base may be sodium tert-butoxide. The process may further comprise conducting an alkylation reaction. The alkylation reaction may comprise reaction of the condensation reaction product with an electrophilic butenolide. The alkylation reaction may comprise reaction of the condensation reaction product with a halobutenolide. The halobutenolide may be chlorobutenolide. The halobutenolide may be bromobutenolide. The halobutenolide may be iodobutenolide. The sesquiterpene lactone may be sclareolide. The bromobutenolide may be 5-bromo-3-methylfuran-2(5H)-one.

A chemical mimic of strigolactone may be a compound having the structure of

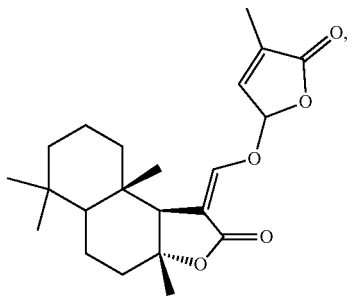 [SMILES: CC1=CC(O/C=C2\C(=O)O[C@]3(C)CCC4C(C)(C)CCC[C@]4(C)[C@@H]23)OC1=O]

a salt, solvate, polymorph, stereoisomer, or isomer thereof, obtained by a process comprising a condensation reaction on a sesquiterpene lactone, salt, solvate, polymorph, stereoisomer, isomer or derivative thereof. The chemical mimic of strigolactone may be obtained by a process comprising a condensation reaction on a sesquiterpene lactone. The sesquiterpene lactone may be sclareolide.

Further disclosed herein a plant propagation material comprising strigolactone, wherein the plant propagation material is produced by a recombinant cell; and wherein the recombinant cell comprises one or more foreign genes. The one or more foreign genes are genes that do not naturally occur in the cell. The one or more foreign genes may comprise one or more genes that encode a strigolactone pathway. The plant propagation material may comprise a mixture of strigolactones. Examples of strigolactone include, but are not limited to strigol, strigyl acetate, orobanchol, orobanchyl acetate, 7-orobanchyl acetate, 7-hydroxy-orobanchyl acetate, sorgomol, fabacyl acetate, 5-deoxystrigol, and sorgolactone. Examples of orobanchol include, but are not limited to, 7-oxo-orobanchol, 2'-epi-orobanchol, ent-2'-epi-orobanchol and ent-orobanchol. Examples of 5-deoxystrigol include, but are not limited to, 2'-epi-5-deoxystrigol, ent-2'-epi-5-deoxystrigol, and ent-5-deoxystrigol. The strigolactone may comprise strigol. The strigolactone may comprise strigyl acetate. The strigolactone may comprise orobanchol. The strigolactone may comprise orobanchyl acetate. The strigolactone may comprise 5-deoxystrigol. The strigolactone may comprise sorgolactone.

Further disclosed herein are plant propagation materials comprising a mixture of strigolactones. The plant propagation material may be obtained by a biosynthetic process. Examples of strigolactone include, but are not limited to strigol, strigyl acetate, orobanchol, orobanchyl acetate, 7-orobanchyl acetate, 7-hydroxy-orobanchyl acetate, sorgomol, fabacyl acetate, 5-deoxystrigol, and sorgolactone. Examples of orobanchol include, but are not limited to, 7-oxo-orobanchol, 2'epi-orobanchol, ent-2'-epi-orobanchol and ent-orobanchol. Examples of 5-deoxystrigol include, but are not limited to, 2'-epi-5-deoxystrigol, ent-2'-epi-5-deoxystrigol, and ent-5-deoxystrigol. The mixture of strigolactones may comprise one or more strigolactones selected from strigol, strigyl acetate, orobanchol, orobanchyl acetate, 5-deoxystrigol, and sorgolactone. The mixture of strigolactones may comprise two or more strigolactones selected from strigol, strigyl acetate, orobanchol, orobanchyl acetate, 5-deoxystrigol, and sorgolactone. The mixture of strigolactones may comprise three or more strigolactones selected from strigol, strigyl acetate, orobanchol, orobanchyl acetate, 5-deoxystrigol, and sorgolactone. The mixture of strigolactones may comprise four or more strigolactones selected from strigol, strigyl acetate, orobanchol, orobanchyl acetate, 5-deoxystrigol, and sorgolactone. The mixture of strigolactones may comprise five or more strigolactones selected from strigol, strigyl acetate, orobanchol, orobanchyl acetate, 5-deoxystrigol, and sorgolactone. The mixture of strigolactones may comprise six or more strigolactones selected from strigol, strigyl acetate, orobanchol, orobanchyl acetate, 5-deoxystrigol, and sorgolactone.

The mixture of strigolactones may comprise at least about 1% of strigol. The mixture of strigolactones may comprise at least about 2% of strigol. The mixture of strigolactones may comprise at least about 5% of strigol. The mixture of strigolactones may comprise at least about 7% of strigol. The mixture of strigolactones may comprise at least about 10% of strigol. The mixture of strigolactones may comprise at least about 20% of strigol. The mixture of strigolactones may comprise at least about 30% of strigol. The mixture of strigolactones may comprise at least about 40% of strigol. The mixture of strigolactones may comprise at least about 50% of strigol. The mixture of strigolactones may comprise at least about 60% of strigol. The mixture of strigolactones may comprise at least about 70% of strigol. The mixture of strigolactones may comprise at least about 80% of strigol. The mixture of strigolactones may comprise at least about 85% of strigol. The mixture of strigolactones may comprise at least about 90% of strigol. The mixture of strigolactones may comprise at least about 95% of strigol.

The mixture of strigolactones may comprise less than about 95% of strigol. The mixture of strigolactones may comprise less than about 90% of strigol. The mixture of strigolactones may comprise less than about 85% of strigol. The mixture of strigolactones may comprise less than about 80% of strigol. The mixture of strigolactones may comprise less than about 75% of strigol. The mixture of strigolactones may comprise less than about 70% of strigol. The mixture of strigolactones may comprise less than about 60% of strigol. The mixture of strigolactones may comprise less than about 55% of strigol. The mixture of strigolactones may comprise less than about 50% of strigol. The mixture of strigolactones may comprise less than about 40% of strigol. The mixture of strigolactones may comprise less than about 30% of strigol. The mixture of strigolactones may comprise less than about 25% of strigol. The mixture of strigolactones may comprise less than about 20% of strigol. The mixture of strigolactones may comprise less than about 15% of strigol. The mixture of strigolactones may comprise less than about 10% of strigol. The mixture of strigolactones may comprise less than about 5% of strigol. The mixture of strigolactones may comprise less than about 3% of strigol.

The mixture of strigolactones may comprise between about 1% and 90% of strigol. The mixture of strigolactones may comprise between about 1% and 80% of strigol. The mixture of strigolactones may comprise between about 1% and 70% of strigol. The mixture of strigolactones may comprise between about 1% and 60% of strigol. The mixture of strigolactones may comprise between about 1% and 50% of strigol. The mixture of strigolactones may comprise between about 1% and 40% of strigol. The mixture of strigolactones may comprise between about 1% and 30% of strigol. The mixture of strigolactones may comprise between about 1% and 20% of strigol. The mixture of strigolactones may comprise between about 1% and 10% of strigol. The mixture of strigolactones may comprise between about 1% and 5% of strigol. The mixture of strigolactones may comprise between about 5% and 90% of strigol. The mixture of strigolactones may comprise between about 10% and 90% of strigol. The mixture of strigolactones may comprise between about 20% and 90% of strigol. The mixture of strigolactones may comprise between about 30% and 90% of strigol. The mixture of strigolactones may comprise between about 40% and 90% of strigol. The mixture of strigolactones may comprise between about 50% and 90% of strigol. The mixture of strigolactones may comprise between about 60% and 90% of strigol. The mixture of strigolactones may comprise between about 70% and 90% of strigol. The mixture of strigolactones may comprise between about 80% and 90% of strigol. The mixture of strigolactones may comprise between about 10% and 80% of strigol. The mixture of strigolactones may comprise between about 20% and 70% of strigol. The mixture of strigolactones may comprise between about 30% and 60% of strigol. The mixture of strigolactones may comprise between about 20% and 50% of strigol. The mixture of strigolactones may comprise between about 25% and 50% of strigol.

The mixture of strigolactones may comprise at least about 1% of strigyl acetate. The mixture of strigolactones may comprise at least about 2% of strigyl acetate. The mixture of strigolactones may comprise at least about 5% of strigyl acetate. The mixture of strigolactones may comprise at least about 7% of strigyl acetate. The mixture of strigolactones may comprise at least about 10% of strigyl acetate. The mixture of strigolactones may comprise at least about 20% of strigyl acetate. The mixture of strigolactones may comprise at least about 30% of strigyl acetate. The mixture of strigolactones may comprise at least about 40% of strigyl acetate. The mixture of strigolactones may comprise at least about 50% of strigyl acetate. The mixture of strigolactones may comprise at least about 60% of strigyl acetate. The mixture of strigolactones may comprise at least about 70% of strigyl acetate. The mixture of strigolactones may comprise at least about 80% of strigyl acetate. The mixture of strigolactones may comprise at least about 85% of strigyl acetate. The mixture of strigolactones may comprise at least about 90% of strigyl acetate. The mixture of strigolactones may comprise at least about 95% of strigyl acetate.

The mixture of strigolactones may comprise less than about 95% of strigyl acetate. The mixture of strigolactones may comprise less than about 90% of strigyl acetate. The mixture of strigolactones may comprise less than about 85% of strigyl acetate. The mixture of strigolactones may comprise less than about 80% of strigyl acetate. The mixture of strigolactones may comprise less than about 75% of strigyl acetate. The mixture of strigolactones may comprise less than about 70% of strigyl acetate. The mixture of strigolactones may comprise less than about 60% of strigyl acetate. The mixture of strigolactones may comprise less than about 55% of strigyl acetate. The mixture of strigolactones may comprise less than about 50% of strigyl acetate. The mixture of strigolactones may comprise less than about 40% of strigyl acetate. The mixture of strigolactones may comprise less than about 30% of strigyl acetate. The mixture of strigolactones may comprise less than about 25% of strigyl acetate. The mixture of strigolactones may comprise less than about 20% of strigyl acetate. The mixture of strigolactones may comprise less than about 15% of strigyl acetate. The mixture of strigolactones may comprise less than about 10% of strigyl acetate. The mixture of strigolactones may comprise less than about 5% of strigyl acetate. The mixture of strigolactones may comprise less than about 3% of strigyl acetate.

The mixture of strigolactones may comprise between about 1% and 90% of strigyl acetate. The mixture of strigolactones may comprise between about 1% and 80% of strigyl acetate. The mixture of strigolactones may comprise between about 1% and 70% of strigyl acetate. The mixture of strigolactones may comprise between about 1% and 60% of strigyl acetate. The mixture of strigolactones may comprise between about 1% and 50% of strigyl acetate. The mixture of strigolactones may comprise between about 1% and 40% of strigyl acetate. The mixture of strigolactones may comprise between about 1% and 30% of strigyl acetate. The mixture of strigolactones may comprise between about 1% and 20% of strigyl acetate. The mixture of strigolactones may comprise between about 1% and 10% of strigyl acetate. The mixture of strigolactones may comprise between about 1% and 5% of strigyl acetate. The mixture of strigolactones may comprise between about 5% and 90% of strigyl acetate. The mixture of strigolactones may comprise between about 10% and 90% of strigyl acetate. The mixture of strigolactones may comprise between about 20% and 90% of strigyl acetate. The mixture of strigolactones may comprise between about 30% and 90% of strigyl acetate. The mixture of strigolactones may comprise between about 40% and 90% of strigyl acetate. The mixture of strigolactones may comprise between about 50% and 90% of strigyl acetate. The mixture of strigolactones may comprise between about 60% and 90% of strigyl acetate. The mixture of strigolactones may comprise between about 70% and 90% of strigyl acetate. The mixture of strigolactones may comprise between about 80% and 90% of strigyl acetate. The mixture of strigolactones may comprise between about 10% and 80% of strigyl acetate. The mixture of strigolactones may comprise between about 20% and 70% of strigyl acetate. The mixture of strigolactones may comprise between about 30% and 60% of strigyl acetate. The mixture of strigolactones may comprise between about 20% and 50% of strigyl acetate. The mixture of strigolactones may comprise between about 25% and 50% of strigyl acetate.

The mixture of strigolactones may comprise at least about 1% orobanchol. The mixture of strigolactones may comprise at least about 2% orobanchol. The mixture of strigolactones may comprise at least about 5% orobanchol. The mixture of strigolactones may comprise at least about 7% orobanchol. The mixture of strigolactones may comprise at least about 10% orobanchol. The mixture of strigolactones may comprise at least about 20% orobanchol. The mixture of strigolactones may comprise at least about 30% orobanchol. The mixture of strigolactones may comprise at least about 40% orobanchol. The mixture of strigolactones may comprise at least about 50% orobanchol. The mixture of strigolactones may comprise at least about 60% orobanchol. The mixture of strigolactones may comprise at least about 70% orobanchol. The mixture of strigolactones may comprise at least about 80% orobanchol. The mixture of strigolactones may comprise at least about 85% orobanchol. The mixture of strigolactones may comprise at least about 90% orobanchol. The mixture of strigolactones may comprise at least about 95% orobanchol.

The mixture of strigolactones may comprise less than about 95% orobanchol. The mixture of strigolactones may comprise less than about 90% orobanchol. The mixture of strigolactones may comprise less than about 85% orobanchol. The mixture of strigolactones may comprise less than about 80% orobanchol. The mixture of strigolactones may comprise less than about 75% orobanchol. The mixture of strigolactones may comprise less than about 70% orobanchol. The mixture of strigolactones may comprise less than about 60% orobanchol. The mixture of strigolactones may comprise less than about 55% orobanchol. The mixture of strigolactones may comprise less than about 50% orobanchol. The mixture of strigolactones may comprise less than about 40% orobanchol. The mixture of strigolactones may comprise less than about 30% orobanchol. The mixture of strigolactones may comprise less than about 25% orobanchol. The mixture of strigolactones may comprise less than about 20% orobanchol. The mixture of strigolactones may comprise less than about 15% orobanchol. The mixture of strigolactones may comprise less than about 10% orobanchol. The mixture of strigolactones may comprise less than about 5% orobanchol. The mixture of strigolactones may comprise less than about 3% orobanchol.

The mixture of strigolactones may comprise between about 1% and 90% orobanchol. The mixture of strigolactones may comprise between about 1% and 80% orobanchol. The mixture of strigolactones may comprise between about 1% and 70% orobanchol. The mixture of strigolactones may comprise between about 1% and 60% orobanchol. The mixture of strigolactones may comprise between about 1% and 50% orobanchol. The mixture of strigolactones may comprise between about 1% and 40% orobanchol. The mixture of strigolactones may comprise between about 1% and 30% orobanchol. The mixture of strigolactones may comprise between about 1% and 20% orobanchol. The mixture of strigolactones may comprise between about 1% and 10% orobanchol. The mixture of strigolactones may comprise between about 1% and 5% orobanchol. The mixture of strigolactones may comprise between about 5% and 90% orobanchol. The mixture of strigolactones may comprise between about 10% and 90% orobanchol. The mixture of strigolactones may comprise between about 20% and 90% orobanchol. The mixture of strigolactones may comprise between about 30% and 90% orobanchol. The mixture of strigolactones may comprise between about 40% and 90% orobanchol. The mixture of strigolactones may comprise between about 50% and 90% orobanchol. The mixture of strigolactones may comprise between about 60% and 90% orobanchol. The mixture of strigolactones may comprise between about 70% and 90% orobanchol. The mixture of strigolactones may comprise between about 80% and 90% orobanchol. The mixture of strigolactones may comprise between about 10% and 80% orobanchol. The mixture of strigolactones may comprise between about 20% and 70% orobanchol. The mixture of strigolactones may comprise between about 30% and 60% orobanchol. The mixture of strigolactones may comprise between about 20% and 50% orobanchol. The mixture of strigolactones may comprise between about 25% and 50% orobanchol.

The mixture of strigolactones may comprise at least about 1% of 2' epi-orobanchol. The mixture of strigolactones may comprise at least about 2% of 2' epi-orobanchol. The mixture of strigolactones may comprise at least about 5% of 2' epi-orobanchol. The mixture of strigolactones may comprise at least about 7% of 2' epi-orobanchol. The mixture of strigolactones may comprise at least about 10% of 2' epi-orobanchol. The mixture of strigolactones may comprise at least about 20% of 2' epi-orobanchol. The mixture of strigolactones may comprise at least about 30% of 2' epi-orobanchol. The mixture of strigolactones may comprise at least about 40% of 2' epi-orobanchol. The mixture of strigolactones may comprise at least about 50% of 2' epi-orobanchol. The mixture of strigolactones may comprise at least about 60% of 2' epi-orobanchol. The mixture of strigolactones may comprise at least about 70% of 2' epi-orobanchol. The mixture of strigolactones may comprise at least about 80% of 2' epi-orobanchol. The mixture of strigolactones may comprise at least about 85% of 2' epi-orobanchol. The mixture of strigolactones may comprise at least about 90% of 2' epi-orobanchol. The mixture of strigolactones may comprise at least about 95% of 2' epi-orobanchol.

The mixture of strigolactones may comprise less than about 95% of 2' epi-orobanchol. The mixture of strigolactones may comprise less than about 90% of 2' epi-orobanchol. The mixture of strigolactones may comprise less than about 85% of 2' epi-orobanchol. The mixture of strigolactones may comprise less than about 80% of 2' epi-orobanchol. The mixture of strigolactones may comprise less than about 75% of 2' epi-orobanchol. The mixture of strigolactones may comprise less than about 70% of 2' epi-orobanchol. The mixture of strigolactones may comprise less than about 60% of 2' epi-orobanchol. The mixture of strigolactones may comprise less than about 55% of 2' epi-orobanchol. The mixture of strigolactones may comprise less than about 50% of 2' epi-orobanchol. The mixture of strigolactones may comprise less than about 40% of 2' epi-orobanchol. The mixture of strigolactones may comprise less than about 30% of 2' epi-orobanchol. The mixture of strigolactones may comprise less than about 25% of 2' epi-orobanchol. The mixture of strigolactones may comprise less than about 20% of 2' epi-orobanchol. The mixture of strigolactones may comprise less than about 15% of 2' epi-orobanchol. The mixture of strigolactones may comprise less than about 10% of 2' epi-orobanchol. The mixture of strigolactones may comprise less than about 5% of 2' epi-orobanchol. The mixture of strigolactones may comprise less than about 3% of 2' epi-orobanchol.

The mixture of strigolactones may comprise between about 1% and 90% of 2' epi-orobanchol. The mixture of strigolactones may comprise between about 1% and 80% of 2' epi-orobanchol. The mixture of strigolactones may comprise between about 1% and 70% of 2' epi-orobanchol. The mixture of strigolactones may comprise between about 1% and 60% of 2' epi-orobanchol. The mixture of strigolactones may comprise between about 1% and 50% of 2' epi-orobanchol. The mixture of strigolactones may comprise between about 1% and 40% of 2' epi-orobanchol. The mixture of strigolactones may comprise between about 1% and 30% of 2' epi-orobanchol. The mixture of strigolactones may comprise between about 1% and 20% of 2' epi-orobanchol. The mixture of strigolactones may comprise between about 1% and 10% of 2' epi-orobanchol. The mixture of strigolactones may comprise between about 1% and 5% of 2' epi-orobanchol. The mixture of strigolactones may comprise between about 5% and 90% of 2' epi-orobanchol. The mixture of strigolactones may comprise between about 10% and 90% of 2' epi-orobanchol. The mixture of strigolactones may comprise between about 20% and 90% of 2' epi-orobanchol. The mixture of strigolactones may comprise between about 30% and 90% of 2' epi-orobanchol. The mixture of strigolactones may comprise between about 40% and 90% of 2' epi-orobanchol. The mixture of strigolactones may comprise between about 50% and 90% of 2' epi-orobanchol. The mixture of strigolactones may comprise between about 60% and 90% of 2' epi-orobanchol. The mixture of strigolactones may comprise between about 70% and 90% of 2' epi-orobanchol. The mixture of strigolactones may comprise between about 80% and 90% of 2' epi-orobanchol. The mixture of strigolactones may comprise between about 10% and 80% of 2' epi-orobanchol. The mixture of strigolactones may comprise between about 20% and 70% of 2' epi-orobanchol. The mixture of strigolactones may comprise between about 30% and 60% of 2' epi-orobanchol. The mixture of strigolactones may comprise between about 20% and 50% of 2' epi-orobanchol. The mixture of strigolactones may comprise between about 25% and 50% of 2' epi-orobanchol.

The mixture of strigolactones may comprise at least about 1% of ent-2'-epi-orobanchol. The mixture of strigolactones may comprise at least about 2% of ent-2'-epi-orobanchol. The mixture of strigolactones may comprise at least about 5% of ent-2'-epi-orobanchol. The mixture of strigolactones may comprise at least about 7% of ent-2'-epi-orobanchol. The mixture of strigolactones may comprise at least about 10% of ent-2'-epi-orobanchol. The mixture of strigolactones may comprise at least about 20% of ent-2'-epi-orobanchol. The mixture of strigolactones may comprise at least about 30% of ent-2'-epi-orobanchol. The mixture of strigolactones may comprise at least about 40% of ent-2'-epi-orobanchol. The mixture of strigolactones may comprise at least about 50% of ent-2'-epi-orobanchol. The mixture of strigolactones may comprise at least about 60% of ent-2'-epi-orobanchol. The mixture of strigolactones may comprise at least about 70% of ent-2'-epi-orobanchol. The mixture of strigolactones may comprise at least about 80% of ent-2'-epi-orobanchol. The mixture of strigolactones may comprise at least about 85% of ent-2'-epi-orobanchol. The mixture of strigolactones may comprise at least about 90% of ent-2'-epi-orobanchol. The mixture of strigolactones may comprise at least about 95% of ent-2'-epi-orobanchol.

The mixture of strigolactones may comprise less than about 95% of ent-2'-epi-orobanchol. The mixture of strigolactones may comprise less than about 90% of ent-2'-epi-orobanchol. The mixture of strigolactones may comprise less than about 85% of ent-2'-epi-orobanchol. The mixture of strigolactones may comprise less than about 80% of ent-2'-epi-orobanchol. The mixture of strigolactones may comprise less than about 75% of ent-2'-epi-orobanchol. The mixture of strigolactones may comprise less than about 70% of ent-2'-epi-orobanchol. The mixture of strigolactones may comprise less than about 60% of ent-2'-epi-orobanchol. The mixture of strigolactones may comprise less than about 55% of ent-2'-epi-orobanchol. The mixture of strigolactones may comprise less than about 50% of ent-2'-epi-orobanchol. The mixture of strigolactones may comprise less than about 40% of ent-2'-epi-orobanchol. The mixture of strigolactones may comprise less than about 30% of ent-2'-epi-orobanchol. The mixture of strigolactones may comprise less than about 25% of ent-2'-epi-orobanchol. The mixture of strigolactones may comprise less than about 20% of ent-2'-epi-orobanchol. The mixture of strigolactones may comprise less than about 15% of ent-2'-epi-orobanchol. The mixture of strigolactones may comprise less than about 10% of ent-2'-epi-orobanchol. The mixture of strigolactones may comprise less than about 5% of ent-2'-epi-orobanchol. The mixture of strigolactones may comprise less than about 3% of ent-2'-epi-orobanchol.

The mixture of strigolactones may comprise between about 1% and 90% of ent-2'-epi-orobanchol. The mixture of strigolactones may comprise between about 1% and 80% of ent-2'-epi-orobanchol. The mixture of strigolactones may comprise between about 1% and 70% of ent-2'-epi-orobanchol. The mixture of strigolactones may comprise between about 1% and 60% of ent-2'-epi-orobanchol. The mixture of strigolactones may comprise between about 1% and 50% of ent-2'-epi-orobanchol. The mixture of strigolactones may comprise between about 1% and 40% of ent-2'-epi-orobanchol. The mixture of strigolactones may comprise between about 1% and 30% of ent-2'-epi-orobanchol. The mixture of strigolactones may comprise between about 1% and 20% of ent-2'-epi-orobanchol. The mixture of strigolactones may comprise between about 1% and 10% of ent-2'-epi-orobanchol. The mixture of strigolactones may comprise between about 1% and 5% of ent-2'-epi-orobanchol. The mixture of strigolactones may comprise between about 5% and 90% of ent-2'-epi-orobanchol. The mixture of strigolactones may comprise between about 10% and 90% of ent-2'-epi-orobanchol. The mixture of strigolactones may comprise between about 20% and 90% of ent-2'-epi-orobanchol. The mixture of strigolactones may comprise between about 30% and 90% of ent-2'-epi-orobanchol. The mixture of strigolactones may comprise between about 40% and 90% of ent-2'-epi-orobanchol. The mixture of strigolactones may comprise between about 50% and 90% of ent-2'-epi-orobanchol. The mixture of strigolactones may comprise between about 60% and 90% of ent-2'-epi-orobanchol. The mixture of strigolactones may comprise between about 70% and 90% of ent-2'-epi-orobanchol. The mixture of strigolactones may comprise between about 80% and 90% of ent-2'-epi-orobanchol. The mixture of strigolactones may comprise between about 10% and 80% of ent-2'-epi-orobanchol. The mixture of strigolactones may comprise between about 20% and 70% of ent-2'-epi-orobanchol. The mixture of strigolactones may comprise between about 30% and 60% of ent-2'-epi-orobanchol. The mixture of strigolactones may comprise between about 20% and 50% of ent-2'-epi-orobanchol. The mixture of strigolactones may comprise between about 25% and 50% of ent-2'-epi-orobanchol.

The mixture of strigolactones may comprise at least about 1% of ent-orobanchol. The mixture of strigolactones may comprise at least about 2% of ent-orobanchol. The mixture of strigolactones may comprise at least about 5% of ent-orobanchol. The mixture of strigolactones may comprise at least about 7% of ent-orobanchol. The mixture of strigolactones may comprise at least about 10% of ent-orobanchol. The mixture of strigolactones may comprise at least about 20% of ent-orobanchol. The mixture of strigolactones may comprise at least about 30% of ent-orobanchol. The mixture of strigolactones may comprise at least about 40% of ent-orobanchol. The mixture of strigolactones may comprise at least about 50% of ent-orobanchol. The mixture of strigolactones may comprise at least about 60% of ent-orobanchol. The mixture of strigolactones may comprise at least about 70% of ent-orobanchol. The mixture of strigolactones may comprise at least about 80% of ent-orobanchol. The mixture of strigolactones may comprise at least about 85% of ent-orobanchol. The mixture of strigolactones may comprise at least about 90% of ent-orobanchol. The mixture of strigolactones may comprise at least about 95% of ent-orobanchol.

The mixture of strigolactones may comprise less than about 95% of ent-orobanchol. The mixture of strigolactones may comprise less than about 90% of ent-orobanchol. The mixture of strigolactones may comprise less than about 85% of ent-orobanchol. The mixture of strigolactones may comprise less than about 80% of ent-orobanchol. The mixture of strigolactones may comprise less than about 75% of ent-orobanchol. The mixture of strigolactones may comprise less than about 70% of ent-orobanchol. The mixture of strigolactones may comprise less than about 60% of ent-orobanchol. The mixture of strigolactones may comprise less than about 55% of ent-orobanchol. The mixture of strigolactones may comprise less than about 50% of ent-orobanchol. The mixture of strigolactones may comprise less than about 40% of ent-orobanchol. The mixture of strigolactones may comprise less than about 30% of ent-orobanchol. The mixture of strigolactones may comprise less than about 25% of ent-orobanchol. The mixture of strigolactones may comprise less than about 20% of ent-orobanchol. The mixture of strigolactones may comprise less than about 15% of ent-orobanchol. The mixture of strigolactones may comprise less than about 10% of ent-orobanchol. The mixture of strigolactones may comprise less than about 5% of ent-orobanchol. The mixture of strigolactones may comprise less than about 3% of ent-orobanchol.

The mixture of strigolactones may comprise between about 1% and 90% of ent-orobanchol. The mixture of strigolactones may comprise between about 1% and 80% of ent-orobanchol. The mixture of strigolactones may comprise between about 1% and 70% of ent-orobanchol. The mixture of strigolactones may comprise between about 1% and 60% of ent-orobanchol. The mixture of strigolactones may comprise between about 1% and 50% of ent-orobanchol. The mixture of strigolactones may comprise between about 1% and 40% of ent-orobanchol. The mixture of strigolactones may comprise between about 1% and 30% of ent-orobanchol. The mixture of strigolactones may comprise between about 1% and 20% of ent-orobanchol. The mixture of strigolactones may comprise between about 1% and 10% of ent-orobanchol. The mixture of strigolactones may comprise between about 1% and 5% of ent-orobanchol. The mixture of strigolactones may comprise between about 5% and 90% of ent-orobanchol. The mixture of strigolactones may comprise between about 10% and 90% of ent-orobanchol. The mixture of strigolactones may comprise between about 20% and 90% of ent-orobanchol. The mixture of strigolactones may comprise between about 30% and 90% of ent-orobanchol. The mixture of strigolactones may comprise between about 40% and 90% of ent-orobanchol. The mixture of strigolactones may comprise between about 50% and 90% of ent-orobanchol. The mixture of strigolactones may comprise between about 60% and 90% of ent-orobanchol. The mixture of strigolactones may comprise between about 70% and 90% of ent-orobanchol. The mixture of strigolactones may comprise between about 80% and 90% of ent-orobanchol. The mixture of strigolactones may comprise between about 10% and 80% of ent-orobanchol. The mixture of strigolactones may comprise between about 20% and 70% of ent-orobanchol. The mixture of strigolactones may comprise between about 30% and 60% of ent-orobanchol. The mixture of strigolactones may comprise between about 20% and 50% of ent-orobanchol. The mixture of strigolactones may comprise between about 25% and 50% of ent-orobanchol.

The mixture of strigolactones may comprise at least about 1% of 7-oxo-orobanchol. The mixture of strigolactones may comprise at least about 2% of 7-oxo-orobanchol. The mixture of strigolactones may comprise at least about 5% of 7-oxo-orobanchol. The mixture of strigolactones may comprise at least about 7% of 7-oxo-orobanchol. The mixture of strigolactones may comprise at least about 10% of 7-oxo-orobanchol. The mixture of strigolactones may comprise at least about 20% of 7-oxo-orobanchol. The mixture of strigolactones may comprise at least about 30% of 7-oxo-orobanchol. The mixture of strigolactones may comprise at least about 40% of 7-oxo-orobanchol. The mixture of strigolactones may comprise at least about 50% of 7-oxo-orobanchol. The mixture of strigolactones may comprise at least about 60% of 7-oxo-orobanchol. The mixture of strigolactones may comprise at least about 70% of 7-oxo-orobanchol. The mixture of strigolactones may comprise at least about 80% of 7-oxo-orobanchol. The mixture of strigolactones may comprise at least about 85% of 7-oxo-orobanchol. The mixture of strigolactones may comprise at least about 90% of 7-oxo-orobanchol. The mixture of strigolactones may comprise at least about 95% of 7-oxo-orobanchol.

The mixture of strigolactones may comprise less than about 95% of 7-oxo-orobanchol. The mixture of strigolactones may comprise less than about 90% of 7-oxo-orobanchol. The mixture of strigolactones may comprise less than about 85% of 7-oxo-orobanchol. The mixture of strigolactones may comprise less than about 80% of 7-oxo-orobanchol. The mixture of strigolactones may comprise less than about 75% of 7-oxo-orobanchol. The mixture of strigolactones may comprise less than about 70% of 7-oxo-orobanchol. The mixture of strigolactones may comprise less than about 60% of 7-oxo-orobanchol. The mixture of strigolactones may comprise less than about 55% of 7-oxo-orobanchol. The mixture of strigolactones may comprise less than about 50% of 7-oxo-orobanchol. The mixture of strigolactones may comprise less than about 40% of 7-oxo-orobanchol. The mixture of strigolactones may comprise less than about 30% of 7-oxo-orobanchol. The mixture of strigolactones may comprise less than about 25% of 7-oxo-orobanchol. The mixture of strigolactones may comprise less than about 20% of 7-oxo-orobanchol. The mixture of strigolactones may comprise less than about 15% of 7-oxo-orobanchol. The mixture of strigolactones may comprise less than about 10% of 7-oxo-orobanchol. The mixture of strigolactones may comprise less than about 5% of 7-oxo-orobanchol. The mixture of strigolactones may comprise less than about 3% of 7-oxo-orobanchol.

The mixture of strigolactones may comprise between about 1% and 90% of 7-oxo-orobanchol. The mixture of strigolactones may comprise between about 1% and 80% of 7-oxo-orobanchol. The mixture of strigolactones may comprise between about 1% and 70% of 7-oxo-orobanchol. The mixture of strigolactones may comprise between about 1% and 60% of 7-oxo-orobanchol. The mixture of strigolactones may comprise between about 1% and 50% of 7-oxo-orobanchol. The mixture of strigolactones may comprise between about 1% and 40% of 7-oxo-orobanchol. The mixture of strigolactones may comprise between about 1% and 30% of 7-oxo-orobanchol. The mixture of strigolactones may comprise between about 1% and 20% of 7-oxo-orobanchol. The mixture of strigolactones may comprise between about 1% and 10% of 7-oxo-orobanchol. The mixture of strigolactones may comprise between about 1% and 5% of 7-oxo-orobanchol. The mixture of strigolactones may comprise between about 5% and 90% of 7-oxo-orobanchol. The mixture of strigolactones may comprise between about 10% and 90% of 7-oxo-orobanchol. The mixture of strigolactones may comprise between about 20% and 90% of 7-oxo-orobanchol. The mixture of strigolactones may comprise between about 30% and 90% of 7-oxo-orobanchol. The mixture of strigolactones may comprise between about 40% and 90% of 7-oxo-orobanchol. The mixture of strigolactones may comprise between about 50% and 90% of 7-oxo-orobanchol. The mixture of strigolactones may comprise between about 60% and 90% of 7-oxo-orobanchol. The mixture of strigolactones may comprise between about 70% and 90% of 7-oxo-orobanchol. The mixture of strigolactones may comprise between about 80% and 90% of 7-oxo-orobanchol. The mixture of strigolactones may comprise between about 10% and 80% of 7-oxo-orobanchol. The mixture of strigolactones may comprise between about 20% and 70% of 7-oxo-orobanchol. The mixture of strigolactones may comprise between about 30% and 60% of 7-oxo-orobanchol. The mixture of strigolactones may comprise between about 20% and 50% of 7-oxo-orobanchol. The mixture of strigolactones may comprise between about 25% and 50% of 7-oxo-orobanchol.

The mixture of strigolactones may comprise at least about 1% of orobanchyl acetate. The mixture of strigolactones may comprise at least about 2% of orobanchyl acetate. The mixture of strigolactones may comprise at least about 5% of orobanchyl acetate. The mixture of strigolactones may comprise at least about 7% of orobanchyl acetate. The mixture of strigolactones may comprise at least about 10% of orobanchyl acetate. The mixture of strigolactones may comprise at least about 20% of orobanchyl acetate. The mixture of strigolactones may comprise at least about 30% of orobanchyl acetate. The mixture of strigolactones may comprise at least about 40% of orobanchyl acetate. The mixture of strigolactones may comprise at least about 50% of orobanchyl acetate. The mixture of strigolactones may comprise at least about 60% of orobanchyl acetate. The mixture of strigolactones may comprise at least about 70% of orobanchyl acetate. The mixture of strigolactones may comprise at least about 80% of orobanchyl acetate. The mixture of strigolactones may comprise at least about 85% of orobanchyl acetate. The mixture of strigolactones may comprise at least about 90% of orobanchyl acetate. The mixture of strigolactones may comprise at least about 95% of orobanchyl acetate.

The mixture of strigolactones may comprise less than about 95% of orobanchyl acetate. The mixture of strigolactones may comprise less than about 90% of orobanchyl acetate. The mixture of strigolactones may comprise less than about 85% of orobanchyl acetate. The mixture of strigolactones may comprise less than about 80% of orobanchyl acetate. The mixture of strigolactones may comprise less than about 75% of orobanchyl acetate. The mixture of strigolactones may comprise less than about 70% of orobanchyl acetate. The mixture of strigolactones may comprise less than about 60% of orobanchyl acetate. The mixture of strigolactones may comprise less than about 55% of orobanchyl acetate. The mixture of strigolactones may comprise less than about 50% of orobanchyl acetate. The mixture of strigolactones may comprise less than about 40% of orobanchyl acetate. The mixture of strigolactones may comprise less than about 30% of orobanchyl acetate. The mixture of strigolactones may comprise less than about 25% of orobanchyl acetate. The mixture of strigolactones may comprise less than about 20% of orobanchyl acetate. The mixture of strigolactones may comprise less than about 15% of orobanchyl acetate. The mixture of strigolactones may comprise less than about 10% of orobanchyl acetate. The mixture of strigolactones may comprise less than about 5% of orobanchyl acetate. The mixture of strigolactones may comprise less than about 3% of orobanchyl acetate.

The mixture of strigolactones may comprise between about 1% and 90% of orobanchyl acetate. The mixture of strigolactones may comprise between about 1% and 80% of orobanchyl acetate. The mixture of strigolactones may comprise between about 1% and 70% of orobanchyl acetate. The mixture of strigolactones may comprise between about 1% and 60% of orobanchyl acetate. The mixture of strigolactones may comprise between about 1% and 50% of orobanchyl acetate. The mixture of strigolactones may comprise between about 1% and 40% of orobanchyl acetate. The mixture of strigolactones may comprise between about 1% and 30% of orobanchyl acetate. The mixture of strigolactones may comprise between about 1% and 20% of orobanchyl acetate. The mixture of strigolactones may comprise between about 1% and 10% of orobanchyl acetate. The mixture of strigolactones may comprise between about 1% and 5% of orobanchyl acetate. The mixture of strigolactones may comprise between about 5% and 90% of orobanchyl acetate. The mixture of strigolactones may comprise between about 10% and 90% of orobanchyl acetate. The mixture of strigolactones may comprise between about 20% and 90% of orobanchyl acetate. The mixture of strigolactones may comprise between about 30% and 90% of orobanchyl acetate. The mixture of strigolactones may comprise between about 40% and 90% of orobanchyl acetate. The mixture of strigolactones may comprise between about 50% and 90% of orobanchyl acetate. The mixture of strigolactones may comprise between about 60% and 90% of orobanchyl acetate. The mixture of strigolactones may comprise between about 70% and 90% of orobanchyl acetate. The mixture of strigolactones may comprise between about 80% and 90% of orobanchyl acetate. The mixture of strigolactones may comprise between about 10% and 80% of orobanchyl acetate. The mixture of strigolactones may comprise between about 20% and 70% of orobanchyl acetate. The mixture of strigolactones may comprise between about 30% and 60% of orobanchyl acetate. The mixture of strigolactones may comprise between about 20% and 50% of orobanchyl acetate. The mixture of strigolactones may comprise between about 25% and 50% of orobanchyl acetate.

The mixture of strigolactones may comprise at least about 1% of 7-orobanchyl acetate. The mixture of strigolactones may comprise at least about 2% of 7-orobanchyl acetate. The mixture of strigolactones may comprise at least about 5% of 7-orobanchyl acetate. The mixture of strigolactones may comprise at least about 7% of 7-orobanchyl acetate. The mixture of strigolactones may comprise at least about 10% of 7-orobanchyl acetate. The mixture of strigolactones may comprise at least about 20% of 7-orobanchyl acetate. The mixture of strigolactones may comprise at least about 30% of 7-orobanchyl acetate. The mixture of strigolactones may comprise at least about 40% of 7-orobanchyl acetate. The mixture of strigolactones may comprise at least about 50% of 7-orobanchyl acetate. The mixture of strigolactones may comprise at least about 60% of 7-orobanchyl acetate. The mixture of strigolactones may comprise at least about 70% of 7-orobanchyl acetate. The mixture of strigolactones may comprise at least about 80% of 7-orobanchyl acetate. The mixture of strigolactones may comprise at least about 85% of 7-orobanchyl acetate. The mixture of strigolactones may comprise at least about 90% of 7-orobanchyl acetate. The mixture of strigolactones may comprise at least about 95% of 7-orobanchyl acetate.

The mixture of strigolactones may comprise less than about 95% of 7-orobanchyl acetate. The mixture of strigolactones may comprise less than about 90% of 7-orobanchyl acetate. The mixture of strigolactones may comprise less than about 85% of 7-orobanchyl acetate. The mixture of strigolactones may comprise less than about 80% of 7-orobanchyl acetate. The mixture of strigolactones may comprise less than about 75% of 7-orobanchyl acetate. The mixture of strigolactones may comprise less than about 70% of 7-orobanchyl acetate. The mixture of strigolactones may comprise less than about 60% of 7-orobanchyl acetate. The mixture of strigolactones may comprise less than about 55% of 7-orobanchyl acetate. The mixture of strigolactones may comprise less than about 50% of 7-orobanchyl acetate. The mixture of strigolactones may comprise less than about 40% of 7-orobanchyl acetate. The mixture of strigolactones may comprise less than about 30% of 7-orobanchyl acetate. The mixture of strigolactones may comprise less than about 25% of 7-orobanchyl acetate. The mixture of strigolactones may comprise less than about 20% of 7-orobanchyl acetate. The mixture of strigolactones may comprise less than about 15% of 7-orobanchyl acetate. The mixture of strigolactones may comprise less than about 10% of 7-orobanchyl acetate. The mixture of strigolactones may comprise less than about 5% of 7-orobanchyl acetate. The mixture of strigolactones may comprise less than about 3% of 7-orobanchyl acetate.

The mixture of strigolactones may comprise between about 1% and 90% of 7-orobanchyl acetate. The mixture of strigolactones may comprise between about 1% and 80% of 7-orobanchyl acetate. The mixture of strigolactones may comprise between about 1% and 70% of 7-orobanchyl acetate. The mixture of strigolactones may comprise between about 1% and 60% of 7-orobanchyl acetate. The mixture of strigolactones may comprise between about 1% and 50% of 7-orobanchyl acetate. The mixture of strigolactones may comprise between about 1% and 40% of 7-orobanchyl acetate. The mixture of strigolactones may comprise between about 1% and 30% of 7-orobanchyl acetate. The mixture of strigolactones may comprise between about 1% and 20% of 7-orobanchyl acetate. The mixture of strigolactones may comprise between about 1% and 10% of 7-orobanchyl acetate. The mixture of strigolactones may comprise between about 1% and 5% of 7-orobanchyl acetate. The mixture of strigolactones may comprise between about 5% and 90% of 7-orobanchyl acetate. The mixture of strigolactones may comprise between about 10% and 90% of 7-orobanchyl acetate. The mixture of strigolactones may comprise between about 20% and 90% of 7-orobanchyl acetate. The mixture of strigolactones may comprise between about 30% and 90% of 7-orobanchyl acetate. The mixture of strigolactones may comprise between about 40% and 90% of 7-orobanchyl acetate. The mixture of strigolactones may comprise between about 50% and 90% of 7-orobanchyl acetate. The mixture of strigolactones may comprise between about 60% and 90% of 7-orobanchyl acetate. The mixture of strigolactones may comprise between about 70% and 90% of 7-orobanchyl acetate. The mixture of strigolactones may comprise between about 80% and 90% of 7-orobanchyl acetate. The mixture of strigolactones may comprise between about 10% and 80% of 7-orobanchyl acetate. The mixture of strigolactones may comprise between about 20% and 70% of 7-orobanchyl acetate. The mixture of strigolactones may comprise between about 30% and 60% of 7-orobanchyl acetate. The mixture of strigolactones may comprise between about 20% and 50% of 7-orobanchyl acetate. The mixture of strigolactones may comprise between about 25% and 50% of 7-orobanchyl acetate.

The mixture of strigolactones may comprise at least about 1% of 7-hydroxy-orobanchyl acetate. The mixture of strigolactones may comprise at least about 2% of 7-hydroxy-orobanchyl acetate. The mixture of strigolactones may comprise at least about 5% of 7-hydroxy-orobanchyl acetate. The mixture of strigolactones may comprise at least about 7% of 7-hydroxy-orobanchyl acetate. The mixture of strigolactones may comprise at least about 10% of 7-hydroxy-orobanchyl acetate. The mixture of strigolactones may comprise at least about 20% of 7-hydroxy-orobanchyl acetate. The mixture of strigolactones may comprise at least about 30% of 7-hydroxy-orobanchyl acetate. The mixture of strigolactones may comprise at least about 40% of 7-hydroxy-orobanchyl acetate. The mixture of strigolactones may comprise at least about 50% of 7-hydroxy-orobanchyl acetate. The mixture of strigolactones may comprise at least about 60% of 7-hydroxy-orobanchyl acetate. The mixture of strigolactones may comprise at least about 70% of 7-hydroxy-orobanchyl acetate. The mixture of strigolactones may comprise at least about 80% of 7-hydroxy-orobanchyl acetate. The mixture of strigolactones may comprise at least about 85% of 7-hydroxy-orobanchyl acetate. The mixture of strigolactones may comprise at least about 90% of 7-hydroxy-orobanchyl acetate. The mixture of strigolactones may comprise at least about 95% of 7-hydroxy-orobanchyl acetate.

The mixture of strigolactones may comprise less than about 95% of 7-hydroxy-orobanchyl acetate. The mixture of strigolactones may comprise less than about 90% of 7-hydroxy-orobanchyl acetate. The mixture of strigolactones may comprise less than about 85% of 7-hydroxy-orobanchyl acetate. The mixture of strigolactones may comprise less than about 80% of 7-hydroxy-orobanchyl acetate. The mixture of strigolactones may comprise less than about 75% of 7-hydroxy-orobanchyl acetate. The mixture of strigolactones may comprise less than about 70% of 7-hydroxy-orobanchyl acetate. The mixture of strigolactones may comprise less than about 60% of 7-hydroxy-orobanchyl acetate. The mixture of strigolactones may comprise less than about 55% of 7-hydroxy-orobanchyl acetate. The mixture of strigolactones may comprise less than about 50% of 7-hydroxy-orobanchyl acetate. The mixture of strigolactones may comprise less than about 40% of 7-hydroxy-orobanchyl acetate. The mixture of strigolactones may comprise less than about 30% of 7-hydroxy-orobanchyl acetate. The mixture of strigolactones may comprise less than about 25% of 7-hydroxy-orobanchyl acetate. The mixture of strigolactones may comprise less than about 20% of 7-hydroxy-orobanchyl acetate. The mixture of strigolactones may comprise less than about 15% of 7-hydroxy-orobanchyl acetate. The mixture of strigolactones may comprise less than about 10% of 7-hydroxy-orobanchyl acetate. The mixture of strigolactones may comprise less than about 5% of 7-hydroxy-orobanchyl acetate. The mixture of strigolactones may comprise less than about 3% of 7-hydroxy-orobanchyl acetate.

The mixture of strigolactones may comprise between about 1% and 90% of 7-hydroxy-orobanchyl acetate. The mixture of strigolactones may comprise between about 1% and 80% of 7-hydroxy-orobanchyl acetate. The mixture of strigolactones may comprise between about 1% and 70% of 7-hydroxy-orobanchyl acetate. The mixture of strigolactones may comprise between about 1% and 60% of 7-hydroxy-orobanchyl acetate. The mixture of strigolactones may comprise between about 1% and 50% of 7-hydroxy-orobanchyl acetate. The mixture of strigolactones may comprise between about 1% and 40% of 7-hydroxy-orobanchyl acetate. The mixture of strigolactones may comprise between about 1% and 30% of 7-hydroxy-orobanchyl acetate. The mixture of strigolactones may comprise between about 1% and 20% of 7-hydroxy-orobanchyl acetate. The mixture of strigolactones may comprise between about 1% and 10% of 7-hydroxy-orobanchyl acetate. The mixture of strigolactones may comprise between about 1% and 5% of 7-hydroxy-orobanchyl acetate. The mixture of strigolactones may comprise between about 5% and 90% of 7-hydroxy-orobanchyl acetate. The mixture of strigolactones may comprise between about 10% and 90% of 7-hydroxy-orobanchyl acetate. The mixture of strigolactones may comprise between about 20% and 90% of 7-hydroxy-orobanchyl acetate. The mixture of strigolactones may comprise between about 30% and 90% of 7-hydroxy-orobanchyl acetate. The mixture of strigolactones may comprise between about 40% and 90% of 7-hydroxy-orobanchyl acetate. The mixture of strigolactones may comprise between about 50% and 90% of 7-hydroxy-orobanchyl acetate. The mixture of strigolactones may comprise between about 60% and 90% of 7-hydroxy-orobanchyl acetate. The mixture of strigolactones may comprise between about 70% and 90% of 7-hydroxy-orobanchyl acetate. The mixture of strigolactones may comprise between about 80% and 90% of 7-hydroxy-orobanchyl acetate. The mixture of strigolactones may comprise between about 10% and 80% of 7-hydroxy-orobanchyl acetate. The mixture of strigolactones may comprise between about 20% and 70% of 7-hydroxy-orobanchyl acetate. The mixture of strigolactones may comprise between about 30% and 60% of 7-hydroxy-orobanchyl acetate. The mixture of strigolactones may comprise between about 20% and 50% of 7-hydroxy-orobanchyl acetate. The mixture of strigolactones may comprise between about 25% and 50% of 7-hydroxy-orobanchyl acetate.

The mixture of strigolactones may comprise at least about 1% of 5-deoxystrigol. The mixture of strigolactones may comprise at least about 2% of 5-deoxystrigol. The mixture of strigolactones may comprise at least about 5% of 5-deoxystrigol. The mixture of strigolactones may comprise at least about 7% of 5-deoxystrigol. The mixture of strigolactones may comprise at least about 10% of 5-deoxystrigol. The mixture of strigolactones may comprise at least about 20% of 5-deoxystrigol. The mixture of strigolactones may comprise at least about 30% of 5-deoxystrigol. The mixture of strigolactones may comprise at least about 40% of 5-deoxystrigol. The mixture of strigolactones may comprise at least about 50% of 5-deoxystrigol. The mixture of strigolactones may comprise at least about 60% of 5-deoxystrigol. The mixture of strigolactones may comprise at least about 70% of 5-deoxystrigol. The mixture of strigolactones may comprise at least about 80% of 5-deoxystrigol. The mixture of strigolactones may comprise at least about 85% of 5-deoxystrigol. The mixture of strigolactones may comprise at least about 90% of 5-deoxystrigol. The mixture of strigolactones may comprise at least about 95% of 5-deoxystrigol.

The mixture of strigolactones may comprise less than about 95% of 5-deoxystrigol. The mixture of strigolactones may comprise less than about 90% of 5-deoxystrigol. The mixture of strigolactones may comprise less than about 85% of 5-deoxystrigol. The mixture of strigolactones may comprise less than about 80% of 5-deoxystrigol. The mixture of strigolactones may comprise less than about 75% of 5-deoxystrigol. The mixture of strigolactones may comprise less than about 70% of 5-deoxystrigol. The mixture of strigolactones may comprise less than about 60% of 5-deoxystrigol. The mixture of strigolactones may comprise less than about 55% of 5-deoxystrigol. The mixture of strigolactones may comprise less than about 50% of 5-deoxystrigol. The mixture of strigolactones may comprise less than about 40% of 5-deoxystrigol. The mixture of strigolactones may comprise less than about 30% of 5-deoxystrigol. The mixture of strigolactones may comprise less than about 25% of 5-deoxystrigol. The mixture of strigolactones may comprise less than about 20% of 5-deoxystrigol. The mixture of strigolactones may comprise less than about 15% of 5-deoxystrigol. The mixture of strigolactones may comprise less than about 10% of 5-deoxystrigol. The mixture of strigolactones may comprise less than about 5% of 5-deoxystrigol. The mixture of strigolactones may comprise less than about 3% of 5-deoxystrigol.

The mixture of strigolactones may comprise between about 1% and 90% of 5-deoxystrigol. The mixture of strigolactones may comprise between about 1% and 80% of 5-deoxystrigol. The mixture of strigolactones may comprise between about 1% and 70% of 5-deoxystrigol. The mixture of strigolactones may comprise between about 1% and 60% of 5-deoxystrigol. The mixture of strigolactones may comprise between about 1% and 50% of 5-deoxystrigol. The mixture of strigolactones may comprise between about 1% and 40% of 5-deoxystrigol. The mixture of strigolactones may comprise between about 1% and 30% of 5-deoxystrigol. The mixture of strigolactones may comprise between about 1% and 20% of 5-deoxystrigol. The mixture of strigolactones may comprise between about 1% and 10% of 5-deoxystrigol. The mixture of strigolactones may comprise between about 1% and 5% of 5-deoxystrigol. The mixture of strigolactones may comprise between about 5% and 90% of 5-deoxystrigol. The mixture of strigolactones may comprise between about 10% and 90% of 5-deoxystrigol. The mixture of strigolactones may comprise between about 20% and 90% of 5-deoxystrigol. The mixture of strigolactones may comprise between about 30% and 90% of 5-deoxystrigol. The mixture of strigolactones may comprise between about 40% and 90% of 5-deoxystrigol. The mixture of strigolactones may comprise between about 50% and 90% of 5-deoxystrigol. The mixture of strigolactones may comprise between about 60% and 90% of 5-deoxystrigol. The mixture of strigolactones may comprise between about 70% and 90% of 5-deoxystrigol. The mixture of strigolactones may comprise between about 80% and 90% of 5-deoxystrigol. The mixture of strigolactones may comprise between about 10% and 80% of 5-deoxystrigol. The mixture of strigolactones may comprise between about 20% and 70% of 5-deoxystrigol. The mixture of strigolactones may comprise between about 30% and 60% of 5-deoxystrigol. The mixture of strigolactones may comprise between about 20% and 50% of 5-deoxystrigol. The mixture of strigolactones may comprise between about 25% and 50% of 5-deoxystrigol.

The mixture of strigolactones may comprise at least about 1% of 2'-epi-5-deoxystrigol. The mixture of strigolactones may comprise at least about 2% of 2'-epi-5-deoxystrigol. The mixture of strigolactones may comprise at least about 5% of 2'-epi-5-deoxystrigol. The mixture of strigolactones may comprise at least about 7% of 2'-epi-5-deoxystrigol. The mixture of strigolactones may comprise at least about 10% of 2'-epi-5-deoxystrigol. The mixture of strigolactones may comprise at least about 20% of 2'-epi-5-deoxystrigol. The mixture of strigolactones may comprise at least about 30% of 2'-epi-5-deoxystrigol. The mixture of strigolactones may comprise at least about 40% of 2'-epi-5-deoxystrigol. The mixture of strigolactones may comprise at least about 50% of 2'-epi-5-deoxystrigol. The mixture of strigolactones may comprise at least about 60% of 2'-epi-5-deoxystrigol. The mixture of strigolactones may comprise at least about 70% of 2'-epi-5-deoxystrigol. The mixture of strigolactones may comprise at least about 80% of 2'-epi-5-deoxystrigol. The mixture of strigolactones may comprise at least about 85% of 2'-epi-5-deoxystrigol. The mixture of strigolactones may comprise at least about 90% of 2'-epi-5-deoxystrigol. The mixture of strigolactones may comprise at least about 95% of 2'-epi-5-deoxystrigol.

The mixture of strigolactones may comprise less than about 95% of 2'-epi-5-deoxystrigol. The mixture of strigolactones may comprise less than about 90% of 2'-epi-5-deoxystrigol. The mixture of strigolactones may comprise less than about 85% of 2'-epi-5-deoxystrigol. The mixture of strigolactones may comprise less than about 80% of 2'-epi-5-deoxystrigol. The mixture of strigolactones may comprise less than about 75% of 2'-epi-5-deoxystrigol. The mixture of strigolactones may comprise less than about 70% of 2'-epi-5-deoxystrigol. The mixture of strigolactones may comprise less than about 60% of 2'-epi-5-deoxystrigol. The mixture of strigolactones may comprise less than about 55% of 2'-epi-5-deoxystrigol. The mixture of strigolactones may comprise less than about 50% of 2'-epi-5-deoxystrigol. The mixture of strigolactones may comprise less than about 40% of 2'-epi-5-deoxystrigol. The mixture of strigolactones may comprise less than about 30% of 2'-epi-5-deoxystrigol. The mixture of strigolactones may comprise less than about 25% of 2'-epi-5-deoxystrigol. The mixture of strigolactones may comprise less than about 20% of 2'-epi-5-deoxystrigol. The mixture of strigolactones may comprise less than about 15% of 2'-epi-5-deoxystrigol. The mixture of strigolactones may comprise less than about 10% of 2'-epi-5-deoxystrigol. The mixture of strigolactones may comprise less than about 5% of 2'-epi-5-deoxystrigol. The mixture of strigolactones may comprise less than about 3% of 2'-epi-5-deoxystrigol.

The mixture of strigolactones may comprise between about 1% and 90% of 2'-epi-5-deoxystrigol. The mixture of strigolactones may comprise between about 1% and 80% of 2'-epi-5-deoxystrigol. The mixture of strigolactones may comprise between about 1% and 70% of 2'-epi-5-deoxystrigol. The mixture of strigolactones may comprise between about 1% and 60% of 2'-epi-5-deoxystrigol. The mixture of strigolactones may comprise between about 1% and 50% of 2'-epi-5-deoxystrigol. The mixture of strigolactones may comprise between about 1% and 40% of 2'-epi-5-deoxystrigol. The mixture of strigolactones may comprise between about 1% and 30% of 2'-epi-5-deoxystrigol. The mixture of strigolactones may comprise between about 1% and 20% of 2'-epi-5-deoxystrigol. The mixture of strigolactones may comprise between about 1% and 10% of 2'-epi-5-deoxystrigol. The mixture of strigolactones may comprise between about 1% and 5% of 2'-epi-5-deoxystrigol. The mixture of strigolactones may comprise between about 5% and 90% of 2'-epi-5-deoxystrigol. The mixture of strigolactones may comprise between about 10% and 90% of 2'-epi-5-deoxystrigol. The mixture of strigolactones may comprise between about 20% and 90% of 2'-epi-5-deoxystrigol. The mixture of strigolactones may comprise between about 30% and 90% of 2'-epi-5-deoxystrigol. The mixture of strigolactones may comprise between about 40% and 90% of 2'-epi-5-deoxystrigol. The mixture of strigolactones may comprise between about 50% and 90% of 2'-epi-5-deoxystrigol. The mixture of strigolactones may comprise between about 60% and 90% of 2'-epi-5-deoxystrigol. The mixture of strigolactones may comprise between about 70% and 90% of 2'-epi-5-deoxystrigol. The mixture of strigolactones may comprise between about 80% and 90% of 2'-epi-5-deoxystrigol. The mixture of strigolactones may comprise between about 10% and 80% of 2'-epi-5-deoxystrigol. The mixture of strigolactones may comprise between about 20% and 70% of 2'-epi-5-deoxystrigol. The mixture of strigolactones may comprise between about 30% and 60% of 2'-epi-5-deoxystrigol. The mixture of strigolactones may comprise between about 20% and 50% of 2'-epi-5-deoxystrigol. The mixture of strigolactones may comprise between about 25% and 50% of 2'-epi-5-deoxystrigol.

The mixture of strigolactones may comprise at least about 1% of ent-2'-epi-5-deoxystrigol. The mixture of strigolactones may comprise at least about 2% of ent-2'-epi-5-deoxystrigol. The mixture of strigolactones may comprise at least about 5% of ent-2'-epi-5-deoxystrigol. The mixture of strigolactones may comprise at least about 7% of ent-2'-epi-5-deoxystrigol. The mixture of strigolactones may comprise at least about 10% of ent-2'-epi-5-deoxystrigol. The mixture of strigolactones may comprise at least about 20% of ent-2'-epi-5-deoxystrigol. The mixture of strigolactones may comprise at least about 30% of ent-2'-epi-5-deoxystrigol. The mixture of strigolactones may comprise at least about 40% of ent-2'-epi-5-deoxystrigol. The mixture of strigolactones may comprise at least about 50% of ent-2'-epi-5-deoxystrigol. The mixture of strigolactones may comprise at least about 60% of ent-2'-epi-5-deoxystrigol. The mixture of strigolactones may comprise at least about 70% of ent-2'-epi-5-deoxystrigol. The mixture of strigolactones may comprise at least about 80% of ent-2'-epi-5-deoxystrigol. The mixture of strigolactones may comprise at least about 85% of ent-2'-epi-5-deoxystrigol. The mixture of strigolactones may comprise at least about 90% of ent-2'-epi-5-deoxystrigol. The mixture of strigolactones may comprise at least about 95% of ent-2'-epi-5-deoxystrigol.

The mixture of strigolactones may comprise less than about 95% of ent-2'-epi-5-deoxystrigol. The mixture of strigolactones may comprise less than about 90% of ent-2'-epi-5-deoxystrigol. The mixture of strigolactones may comprise less than about 85% of ent-2'-epi-5-deoxystrigol. The mixture of strigolactones may comprise less than about 80% of ent-2'-epi-5-deoxystrigol. The mixture of strigolactones may comprise less than about 75% of ent-2'-epi-5-deoxystrigol. The mixture of strigolactones may comprise less than about 70% of ent-2'-epi-5-deoxystrigol. The mixture of strigolactones may comprise less than about 60% of ent-2'-epi-5-deoxystrigol. The mixture of strigolactones may comprise less than about 55% of ent-2'-epi-5-deoxystrigol. The mixture of strigolactones may comprise less than about 50% of ent-2'-epi-5-deoxystrigol. The mixture of strigolactones may comprise less than about 40% of ent-2'-epi-5-deoxystrigol. The mixture of strigolactones may comprise less than about 30% of ent-2'-epi-5-deoxystrigol. The mixture of strigolactones may comprise less than about 25% of ent-2'-epi-5-deoxystrigol. The mixture of strigolactones may comprise less than about 20% of ent-2'-epi-5-deoxystrigol. The mixture of strigolactones may comprise less than about 15% of ent-2'-epi-5-deoxystrigol. The mixture of strigolactones may comprise less than about 10% of ent-2'-epi-5-deoxystrigol. The mixture of strigolactones may comprise less than about 5% of ent-2'-epi-5-deoxystrigol. The mixture of strigolactones may comprise less than about 3% of ent-2'-epi-5-deoxystrigol.

The mixture of strigolactones may comprise between about 1% and 90% of ent-2'-epi-5-deoxystrigol. The mixture of strigolactones may comprise between about 1% and 80% of ent-2'-epi-5-deoxystrigol. The mixture of strigolactones may comprise between about 1% and 70% of ent-2'-epi-5-deoxystrigol. The mixture of strigolactones may comprise between about 1% and 60% of ent-2'-epi-5-deoxystrigol. The mixture of strigolactones may comprise between about 1% and 50% of ent-2'-epi-5-deoxystrigol. The mixture of strigolactones may comprise between about 1% and 40% of ent-2'-epi-5-deoxystrigol. The mixture of strigolactones may comprise between about 1% and 30% of ent-2'-epi-5-deoxystrigol. The mixture of strigolactones may comprise between about 1% and 20% of ent-2'-epi-5-deoxystrigol. The mixture of strigolactones may comprise between about 1% and 10% of ent-2'-epi-5-deoxystrigol. The mixture of strigolactones may comprise between about 1% and 5% of ent-2'-epi-5-deoxystrigol. The mixture of strigolactones may comprise between about 5% and 90% of ent-2'-epi-5-deoxystrigol. The mixture of strigolactones may comprise between about 10% and 90% of ent-2'-epi-5-deoxystrigol. The mixture of strigolactones may comprise between about 20% and 90% of ent-2'-epi-5-deoxystrigol. The mixture of strigolactones may comprise between about 30% and 90% of ent-2'-epi-5-deoxystrigol. The mixture of strigolactones may comprise between about 40% and 90% of ent-2'-epi-5-deoxystrigol. The mixture of strigolactones may comprise between about 50% and 90% of ent-2'-epi-5-deoxystrigol. The mixture of strigolactones may comprise between about 60% and 90% of ent-2'-epi-5-deoxystrigol. The mixture of strigolactones may comprise between about 70% and 90% of ent-2'-epi-5-deoxystrigol. The mixture of strigolactones may comprise between about 80% and 90% of ent-2'-epi-5-deoxystrigol. The mixture of strigolactones may comprise between about 10% and 80% of ent-2'-epi-5-deoxystrigol. The mixture of strigolactones may comprise between about 20% and 70% of ent-2'-epi-5-deoxystrigol. The mixture of strigolactones may comprise between about 30% and 60% of ent-2'-epi-5-deoxystrigol. The mixture of strigolactones may comprise between about 20% and 50% of ent-2'-epi-5-deoxystrigol. The mixture of strigolactones may comprise between about 25% and 50% of ent-2'-epi-5-deoxystrigol.

The mixture of strigolactones may comprise at least about 1% of ent-5-deoxystrigol. The mixture of strigolactones may comprise at least about 2% of ent-5-deoxystrigol. The mixture of strigolactones may comprise at least about 5% of ent-5-deoxystrigol. The mixture of strigolactones may comprise at least about 7% of ent-5-deoxystrigol. The mixture of strigolactones may comprise at least about 10% of ent-5-deoxystrigol. The mixture of strigolactones may comprise at least about 20% of ent-5-deoxystrigol. The mixture of strigolactones may comprise at least about 30% of ent-5-deoxystrigol. The mixture of strigolactones may comprise at least about 40% of ent-5-deoxystrigol. The mixture of strigolactones may comprise at least about 50% of ent-5-deoxystrigol. The mixture of strigolactones may comprise at least about 60% of ent-5-deoxystrigol. The mixture of strigolactones may comprise at least about 70% of ent-5-deoxystrigol. The mixture of strigolactones may comprise at least about 80% of ent-5-deoxystrigol. The mixture of strigolactones may comprise at least about 85% of ent-5-deoxystrigol. The mixture of strigolactones may comprise at least about 90% of ent-5-deoxystrigol. The mixture of strigolactones may comprise at least about 95% of ent-5-deoxystrigol.

The mixture of strigolactones may comprise less than about 95% of ent-5-deoxystrigol. The mixture of strigolactones may comprise less than about 90% of ent-5-deoxystrigol. The mixture of strigolactones may comprise less than about 85% of ent-5-deoxystrigol. The mixture of strigolactones may comprise less than about 80% of ent-5-deoxystrigol. The mixture of strigolactones may comprise less than about 75% of ent-5-deoxystrigol. The mixture of strigolactones may comprise less than about 70% of ent-5-deoxystrigol. The mixture of strigolactones may comprise less than about 60% of ent-5-deoxystrigol. The mixture of strigolactones may comprise less than about 55% of ent-5-deoxystrigol. The mixture of strigolactones may comprise less than about 50% of ent-5-deoxystrigol. The mixture of strigolactones may comprise less than about 40% of ent-5-deoxystrigol. The mixture of strigolactones may comprise less than about 30% of ent-5-deoxystrigol. The mixture of strigolactones may comprise less than about 25% of ent-5-deoxystrigol. The mixture of strigolactones may comprise less than about 20% of ent-5-deoxystrigol. The mixture of strigolactones may comprise less than about 15% of ent-5-deoxystrigol. The mixture of strigolactones may comprise less than about 10% of ent-5-deoxystrigol. The mixture of strigolactones may comprise less than about 5% of ent-5-deoxystrigol. The mixture of strigolactones may comprise less than about 3% of ent-5-deoxystrigol.

The mixture of strigolactones may comprise between about 1% and 90% of ent-5-deoxystrigol. The mixture of strigolactones may comprise between about 1% and 80% of ent-5-deoxystrigol. The mixture of strigolactones may comprise between about 1% and 70% of ent-5-deoxystrigol. The mixture of strigolactones may comprise between about 1% and 60% of ent-5-deoxystrigol. The mixture of strigolactones may comprise between about 1% and 50% of ent-5-deoxystrigol. The mixture of strigolactones may comprise between about 1% and 40% of ent-5-deoxystrigol. The mixture of strigolactones may comprise between about 1% and 30% of ent-5-deoxystrigol. The mixture of strigolactones may comprise between about 1% and 20% of ent-5-deoxystrigol. The mixture of strigolactones may comprise between about 1% and 10% of ent-5-deoxystrigol. The mixture of strigolactones may comprise between about 1% and 5% of ent-5-deoxystrigol. The mixture of strigolactones may comprise between about 5% and 90% of ent-5-deoxystrigol. The mixture of strigolactones may comprise between about 10% and 90% of ent-5-deoxystrigol. The mixture of strigolactones may comprise between about 20% and 90% of ent-5-deoxystrigol. The mixture of strigolactones may comprise between about 30% and 90% of ent-5-deoxystrigol. The mixture of strigolactones may comprise between about 40% and 90% of ent-5-deoxystrigol. The mixture of strigolactones may comprise between about 50% and 90% of ent-5-deoxystrigol. The mixture of strigolactones may comprise between about 60% and 90% of ent-5-deoxystrigol. The mixture of strigolactones may comprise between about 70% and 90% of ent-5-deoxystrigol. The mixture of strigolactones may comprise between about 80% and 90% of ent-5-deoxystrigol. The mixture of strigolactones may comprise between about 10% and 80% of ent-5-deoxystrigol. The mixture of strigolactones may comprise between about 20% and 70% of ent-5-deoxystrigol. The mixture of strigolactones may comprise between about 30% and 60% of ent-5-deoxystrigol. The mixture of strigolactones may comprise between about 20% and 50% of ent-5-deoxystrigol. The mixture of strigolactones may comprise between about 25% and 50% of ent-5-deoxystrigol.

The mixture of strigolactones may comprise at least about 1% of sorgolactone. The mixture of strigolactones may comprise at least about 2% of sorgolactone. The mixture of strigolactones may comprise at least about 5% of sorgolactone. The mixture of strigolactones may comprise at least about 7% of sorgolactone. The mixture of strigolactones may comprise at least about 10% of sorgolactone. The mixture of strigolactones may comprise at least about 20% of sorgolactone. The mixture of strigolactones may comprise at least about 30% of sorgolactone. The mixture of strigolactones may comprise at least about 40% of sorgolactone. The mixture of strigolactones may comprise at least about 50% of sorgolactone. The mixture of strigolactones may comprise at least about 60% of sorgolactone. The mixture of strigolactones may comprise at least about 70% of sorgolactone. The mixture of strigolactones may comprise at least about 80% of sorgolactone. The mixture of strigolactones may comprise at least about 85% of sorgolactone. The mixture of strigolactones may comprise at least about 90% of sorgolactone. The mixture of strigolactones may comprise at least about 95% of sorgolactone.

The mixture of strigolactones may comprise less than about 95% of sorgolactone. The mixture of strigolactones may comprise less than about 90% of sorgolactone. The mixture of strigolactones may comprise less than about 85% of sorgolactone. The mixture of strigolactones may comprise less than about 80% of sorgolactone. The mixture of strigolactones may comprise less than about 75% of sorgolactone. The mixture of strigolactones may comprise less than about 70% of sorgolactone. The mixture of strigolactones may comprise less than about 60% of sorgolactone. The mixture of strigolactones may comprise less than about 55% of sorgolactone. The mixture of strigolactones may comprise less than about 50% of sorgolactone. The mixture of strigolactones may comprise less than about 40% of sorgolactone. The mixture of strigolactones may comprise less than about 30% of sorgolactone. The mixture of strigolactones may comprise less than about 25% of sorgolactone. The mixture of strigolactones may comprise less than about 20% of sorgolactone. The mixture of strigolactones may comprise less than about 15% of sorgolactone. The mixture of strigolactones may comprise less than about 10% of sorgolactone. The mixture of strigolactones may comprise less than about 5% of sorgolactone. The mixture of strigolactones may comprise less than about 3% of sorgolactone.

The mixture of strigolactones may comprise between about 1% and 90% of sorgolactone. The mixture of strigolactones may comprise between about 1% and 80% of sorgolactone. The mixture of strigolactones may comprise between about 1% and 70% of sorgolactone. The mixture of strigolactones may comprise between about 1% and 60% of sorgolactone. The mixture of strigolactones may comprise between about 1% and 50% of sorgolactone. The mixture of strigolactones may comprise between about 1% and 40% of sorgolactone. The mixture of strigolactones may comprise between about 1% and 30% of sorgolactone. The mixture of strigolactones may comprise between about 1% and 20% of sorgolactone. The mixture of strigolactones may comprise between about 1% and 10% of sorgolactone. The mixture of strigolactones may comprise between about 1% and 5% of sorgolactone. The mixture of strigolactones may comprise between about 5% and 90% of sorgolactone. The mixture of strigolactones may comprise between about 10% and 90% of sorgolactone. The mixture of strigolactones may comprise between about 20% and 90% of sorgolactone. The mixture of strigolactones may comprise between about 30% and 90% of sorgolactone. The mixture of strigolactones may comprise between about 40% and 90% of sorgolactone. The mixture of strigolactones may comprise between about 50% and 90% of sorgolactone. The mixture of strigolactones may comprise between about 60% and 90% of sorgolactone. The mixture of strigolactones may comprise between about 70% and 90% of sorgolactone. The mixture of strigolactones may comprise between about 80% and 90% of sorgolactone. The mixture of strigolactones may comprise between about 10% and 80% of sorgolactone. The mixture of strigolactones may comprise between about 20% and 70% of sorgolactone. The mixture of strigolactones may comprise between about 30% and 60% of sorgolactone. The mixture of strigolactones may comprise between about 20% and 50% of sorgolactone. The mixture of strigolactones may comprise between about 25% and 50% of sorgolactone.

The mixture of strigolactones may comprise at least about 1% of sorgomol. The mixture of strigolactones may comprise at least about 2% of sorgomol. The mixture of strigolactones may comprise at least about 5% of sorgomol. The mixture of strigolactones may comprise at least about 7% of sorgomol. The mixture of strigolactones may comprise at least about 10% of sorgomol. The mixture of strigolactones may comprise at least about 20% of sorgomol. The mixture of strigolactones may comprise at least about 30% of sorgomol. The mixture of strigolactones may comprise at least about 40% of sorgomol. The mixture of strigolactones may comprise at least about 50% of sorgomol. The mixture of strigolactones may comprise at least about 60% of sorgomol. The mixture of strigolactones may comprise at least about 70% of sorgomol. The mixture of strigolactones may comprise at least about 80% of sorgomol. The mixture of strigolactones may comprise at least about 85% of sorgomol. The mixture of strigolactones may comprise at least about 90% of sorgomol. The mixture of strigolactones may comprise at least about 95% of sorgomol.

The mixture of strigolactones may comprise less than about 95% of sorgomol. The mixture of strigolactones may comprise less than about 90% of sorgomol. The mixture of strigolactones may comprise less than about 85% of sorgomol. The mixture of strigolactones may comprise less than about 80% of sorgomol. The mixture of strigolactones may comprise less than about 75% of sorgomol. The mixture of strigolactones may comprise less than about 70% of sorgomol. The mixture of strigolactones may comprise less than about 60% of sorgomol. The mixture of strigolactones may comprise less than about 55% of sorgomol. The mixture of strigolactones may comprise less than about 50% of sorgomol. The mixture of strigolactones may comprise less than about 40% of sorgomol. The mixture of strigolactones may comprise less than about 30% of sorgomol. The mixture of strigolactones may comprise less than about 25% of sorgomol. The mixture of strigolactones may comprise less than about 20% of sorgomol. The mixture of strigolactones may comprise less than about 15% of sorgomol. The mixture of strigolactones may comprise less than about 10% of sorgomol. The mixture of strigolactones may comprise less than about 5% of sorgomol. The mixture of strigolactones may comprise less than about 3% of sorgomol.

The mixture of strigolactones may comprise between about 1% and 90% of sorgomol. The mixture of strigolactones may comprise between about 1% and 80% of sorgomol. The mixture of strigolactones may comprise between about 1% and 70% of sorgomol. The mixture of strigolactones may comprise between about 1% and 60% of sorgomol. The mixture of strigolactones may comprise between about 1% and 50% of sorgomol. The mixture of strigolactones may comprise between about 1% and 40% of sorgomol. The mixture of strigolactones may comprise between about 1% and 30% of sorgomol. The mixture of strigolactones may comprise between about 1% and 20% of sorgomol. The mixture of strigolactones may comprise between about 1% and 10% of sorgomol. The mixture of strigolactones may comprise between about 1% and 5% of sorgomol. The mixture of strigolactones may comprise between about 5% and 90% of sorgomol. The mixture of strigolactones may comprise between about 10% and 90% of sorgomol. The mixture of strigolactones may comprise between about 20% and 90% of sorgomol. The mixture of strigolactones may comprise between about 30% and 90% of sorgomol. The mixture of strigolactones may comprise between about 40% and 90% of sorgomol. The mixture of strigolactones may comprise between about 50% and 90% of sorgomol. The mixture of strigolactones may comprise between about 60% and 90% of sorgomol. The mixture of strigolactones may comprise between about 70% and 90% of sorgomol. The mixture of strigolactones may comprise between about 80% and 90% of sorgomol. The mixture of strigolactones may comprise between about 10% and 80% of sorgomol. The mixture of strigolactones may comprise between about 20% and 70% of sorgomol. The mixture of strigolactones may comprise between about 30% and 60% of sorgomol. The mixture of strigolactones may comprise between about 20% and 50% of sorgomol. The mixture of strigolactones may comprise between about 25% and 50% of sorgomol.

The mixture of strigolactones may comprise at least about 1% of fabacyl acetate. The mixture of strigolactones may comprise at least about 2% of fabacyl acetate. The mixture of strigolactones may comprise at least about 5% of fabacyl acetate. The mixture of strigolactones may comprise at least about 7% of fabacyl acetate. The mixture of strigolactones may comprise at least about 10% of fabacyl acetate. The mixture of strigolactones may comprise at least about 20% of fabacyl acetate. The mixture of strigolactones may comprise at least about 30% of fabacyl acetate. The mixture of strigolactones may comprise at least about 40% of fabacyl acetate. The mixture of strigolactones may comprise at least about 50% of fabacyl acetate. The mixture of strigolactones may comprise at least about 60% of fabacyl acetate. The mixture of strigolactones may comprise at least about 70% of fabacyl acetate. The mixture of strigolactones may comprise at least about 80% of fabacyl acetate. The mixture of strigolactones may comprise at least about 85% of fabacyl acetate. The mixture of strigolactones may comprise at least about 90% of fabacyl acetate. The mixture of strigolactones may comprise at least about 95% of fabacyl acetate.

The mixture of strigolactones may comprise less than about 95% of fabacyl acetate. The mixture of strigolactones may comprise less than about 90% of fabacyl acetate. The mixture of strigolactones may comprise less than about 85% of fabacyl acetate. The mixture of strigolactones may comprise less than about 80% of fabacyl acetate. The mixture of strigolactones may comprise less than about 75% of fabacyl acetate. The mixture of strigolactones may comprise less than about 70% of fabacyl acetate. The mixture of strigolactones may comprise less than about 60% of fabacyl acetate. The mixture of strigolactones may comprise less than about 55% of fabacyl acetate. The mixture of strigolactones may comprise less than about 50% of fabacyl acetate. The mixture of strigolactones may comprise less than about 40% of fabacyl acetate. The mixture of strigolactones may comprise less than about 30% of fabacyl acetate. The mixture of strigolactones may comprise less than about 25% of fabacyl acetate. The mixture of strigolactones may comprise less than about 20% of fabacyl acetate. The mixture of strigolactones may comprise less than about 15% of fabacyl acetate. The mixture of strigolactones may comprise less than about 10% of fabacyl acetate. The mixture of strigolactones may comprise less than about 5% of fabacyl acetate. The mixture of strigolactones may comprise less than about 3% of fabacyl acetate.

The mixture of strigolactones may comprise between about 1% and 90% of fabacyl acetate. The mixture of strigolactones may comprise between about 1% and 80% of fabacyl acetate. The mixture of strigolactones may comprise between about 1% and 70% of fabacyl acetate. The mixture of strigolactones may comprise between about 1% and 60% of fabacyl acetate. The mixture of strigolactones may comprise between about 1% and 50% of fabacyl acetate. The mixture of strigolactones may comprise between about 1% and 40% of fabacyl acetate. The mixture of strigolactones may comprise between about 1% and 30% of fabacyl acetate. The mixture of strigolactones may comprise between about 1% and 20% of fabacyl acetate. The mixture of strigolactones may comprise between about 1% and 10% of fabacyl acetate. The mixture of strigolactones may comprise between about 1% and 5% of fabacyl acetate. The mixture of strigolactones may comprise between about 5% and 90% of fabacyl acetate. The mixture of strigolactones may comprise between about 10% and 90% of fabacyl acetate. The mixture of strigolactones may comprise between about 20% and 90% of fabacyl acetate. The mixture of strigolactones may comprise between about 30% and 90% of fabacyl acetate. The mixture of strigolactones may comprise between about 40% and 90% of fabacyl acetate. The mixture of strigolactones may comprise between about 50% and 90% of fabacyl acetate. The mixture of strigolactones may comprise between about 60% and 90% of fabacyl acetate. The mixture of strigolactones may comprise between about 70% and 90% of fabacyl acetate. The mixture of strigolactones may comprise between about 80% and 90% of fabacyl acetate. The mixture of strigolactones may comprise between about 10% and 80% of fabacyl acetate. The mixture of strigolactones may comprise between about 20% and 70% of fabacyl acetate. The mixture of strigolactones may comprise between about 30% and 60% of fabacyl acetate. The mixture of strigolactones may comprise between about 20% and 50% of fabacyl acetate. The mixture of strigolactones may comprise between about 25% and 50% of fabacyl acetate.

The plant propagation material may be at least about 60%, 70%, 75%, 80%, 85%, 90%, 95% or more pure. The plant propagation material may be at least about 60% pure. The plant propagation material may be at least about 75% pure. The plant propagation material may be at least about 80% pure. The plant propagation material may be at least about 87% pure. The plant propagation material may be at least about 92% pure. The plant propagation material may be at least about 95% pure. The plant propagation material may be at least about 97% pure. The plant propagation material may be a chemical mimic of strigolactone. The chemical mimic of strigolactone may be a compound of Formula I, or a salt, solvate, polymorph, stereoisomer, or isomer thereof. The chemical mimic of strigolactone may be a compound of Formula II, or a salt, solvate, polymorph, stereoisomer, or isomer thereof. The chemical mimic of strigolactone may be a compound of Formula III, or a salt, solvate, polymorph, stereoisomer, or isomer thereof. The plant propagation material may comprise a mixture of chemical mimics of strigolactone. The mixture of chemical mimics of strigolactone may comprise the compounds of Formula IV and V. The plant propagation material may comprise strigolactone. The plant propagation material may comprise a mixture of strigolactones. The plant propagation material may comprise strigol. The plant propagation material may comprise strigyl acetate. The plant propagation material may comprise orobanchol. The plant propagation material may comprise orobanchyl acetate. The plant propagation material may comprise 5-deoxystrigol. The plant propagation material may comprise sorgolactone.

The plant propagation material may be characterized by having less than 30% impurities. The plant propagation material may be characterized by having less than 25% impurities. The plant propagation material may be characterized by having less than 20% impurities. The plant propagation material may be characterized by having less than 15% impurities. The plant propagation material may be characterized by having less than 10% impurities. The plant propagation material may be characterized by having less than 7% impurities. The plant propagation material may be characterized by having less than 5% impurities. The plant propagation material may be characterized by having less than 3% impurities. The plant propagation material may be characterized by having less than 2% impurities. The plant propagation material may be characterized by having less than 1% impurities. The plant propagation material may be characterized by having less than 0.5% impurities. The plant propagation material may be a chemical mimic of strigolactone. The chemical mimic of strigolactone may be a compound of Formula I, or a salt, solvate, polymorph, stereoisomer, or isomer thereof. The chemical mimic of strigolactone may be a compound of Formula II, or a salt, solvate, polymorph, stereoisomer, or isomer thereof. The chemical mimic of strigolactone may be a compound of Formula III, or a salt, solvate, polymorph, stereoisomer, or isomer thereof. The plant propagation material may comprise a mixture of chemical mimics of strigolactone. The mixture of chemical mimics of strigolactone may comprise the compounds of Formula IV and V. The plant propagation material may comprise strigolactone. The plant propagation material may comprise a mixture of strigolactones. The plant propagation material may comprise strigol. The plant propagation material may comprise strigyl acetate. The plant propagation material may comprise orobanchol. The plant propagation material may comprise orobanchyl acetate. The plant propagation material may comprise 5-deoxystrigol. The plant propagation material may comprise sorgolactone.

Formulations

Disclosed herein are formulations comprising plant propagation materials. The plant propagation material may comprise one or more chemical mimics of strigolactone as disclosed herein. The plant propagation material may comprise a compound of Formula I, or a salt, solvate, polymorph, stereoisomer, or isomer thereof. The plant propagation material may comprise a compound of Formula II, or a salt, solvate, polymorph, stereoisomer, or isomer thereof. The plant propagation material may comprise a compound of Formula III, or a salt, solvate, polymorph, stereoisomer, or isomer thereof. The plant propagation material may comprise a mixture of chemical mimics of strigolactone.

Further disclosed herein are formulations comprising a plant propagation material, wherein the plant propagation material comprises a mixture of two diastereomers. The two diastereomers may be (Formula IV)

(Formula V)

and

The two diastereomers may have a ratio of 1:1. Alternatively, the ratio of Formula IV to Formula V is 1:2. The ratio of Formula IV to Formula V may be 1:3. The ratio of Formula IV to Formula V may be 1:4. The ratio of Formula IV to Formula V may be 1:5. The ratio of Formula IV to Formula V may be at least about 1:6; 1:7; 1:8; 1:9; 1:10; 1:11; 1:12; 1:13; 1:14; 1:15: 1:16: 1:17; 1:18; 1:19; 1:20; 1:25; 1:30; 1:35; 1:40; 1:45; 1:50; 1:60; 1:70; 1:80; 1:90; or 1:100. The ratio of Formula IV to Formula V may be 1:10. The ratio of Formula IV to Formula V may be 1:20. The ratio of Formula IV to Formula V may be 1:40. The ratio of Formula V to Formula IV may be 1:2. The ratio of Formula V to Formula IV may be 1:3. The ratio of Formula V to Formula IV may be 1:4. The ratio of Formula V to Formula IV may be 1:5. The ratio of Formula V to Formula IV may be at least about 1:6; 1:7; 1:8; 1:9; 1:10; 1:11; 1:12; 1:13; 1:14; 1:15; 1:16: 1:17; 1:18; 1:19; 1:20; 1:25; 1:30; 1:35; 1:40; 1:45; 1:50; 1:60; 1:70; 1:80; 1:90; or 1:100. The ratio of Formula V to Formula IV may be 1:10. The ratio of Formula V to Formula IV may be 1:20. The ratio of Formula V to Formula IV may be 1:40.

The mixture of the two diastereomers may comprise at least about 1% of Formula IV. The mixture of the two diastereomers may comprise at least about 5% of Formula IV. The mixture of the two diastereomers may comprise at least about 10% of Formula IV. The mixture of the two diastereomers may comprise at least about 15% of Formula IV. The mixture of the two diastereomers may comprise at least about 20% of Formula IV. The mixture of the two diastereomers may comprise at least about 25% of Formula IV. The mixture of the two diastereomers may comprise at least about 30% of Formula IV. The mixture of the two diastereomers may comprise at least about 40% of Formula IV. The mixture of the two diastereomers may comprise at least about 50% of Formula IV. The mixture of the two diastereomers may comprise at least about 60% of Formula IV. The mixture of the two diastereomers may comprise at least about 70% of Formula IV. The mixture of the two diastereomers may comprise at least about 80% of Formula IV. The mixture of the two diastereomers may comprise at least about 85% of Formula IV. The mixture of the two diastereomers may comprise at least about 90% of Formula IV. The mixture of the two diastereomers may comprise at least about 95% of Formula IV.

The mixture of the two diastereomers may comprise less than about 97% of Formula IV. The mixture of the two diastereomers may comprise less than about 95% of Formula IV. The mixture of the two diastereomers may comprise less than about 90% of Formula IV. The mixture of the two diastereomers may comprise less than about 85% of Formula IV. The mixture of the two diastereomers may comprise less than about 80% of Formula IV. The mixture of the two diastereomers may comprise less than about 70% of Formula IV. The mixture of the two diastereomers may comprise less than about 60% of Formula IV. The mixture of the two diastereomers may comprise less than about 50% of Formula IV. The mixture of the two diastereomers may comprise less than about 40% of Formula IV. The mixture of the two diastereomers may comprise less than about 30% of Formula IV. The mixture of the two diastereomers may comprise less than about 20% of Formula IV. The mixture of the two diastereomers may comprise less than about 15% of Formula IV. The mixture of the two diastereomers may comprise less than about 10% of Formula IV. The mixture of the two diastereomers may comprise less than about 5% of Formula IV. The mixture of the two diastereomers may comprise less than about 1% of Formula IV.

The mixture of the two diastereomers may comprise between about 1% to about 90% of Formula IV. The mixture of the two diastereomers may comprise between about 5% to about 90% of Formula IV. The mixture of the two diastereomers may comprise between about 10% to about 90% of Formula IV. The mixture of the two diastereomers may comprise between about 20% to about 90% of Formula IV. The mixture of the two diastereomers may comprise between about 30% to about 90% of Formula IV. The mixture of the two diastereomers may comprise between about 50% to about 90% of Formula IV. The mixture of the two diastereomers may comprise between about 70% to about 90% of Formula IV. The mixture of the two diastereomers may comprise between about 1% to about 80% of Formula IV. The mixture of the two diastereomers may comprise between about 1% to about 70% of Formula IV. The mixture of the two diastereomers may comprise between about 1% to about 60% of Formula IV. The mixture of the two diastereomers may comprise between about 1% to about 50% of Formula IV. The mixture of the two diastereomers may comprise between about 5% to about 80% of Formula IV. The mixture of the two diastereomers may comprise between about 10% to about 80% of Formula IV. The mixture of the two diastereomers may comprise between about 10% to about 70% of Formula IV. The mixture of the two diastereomers may comprise between about 20% to about 70% of Formula IV. The mixture of the two diastereomers may comprise between about 30% to about 90% of Formula IV.

The mixture of the two diastereomers may comprise at least about 1% of Formula V. The mixture of the two diastereomers may comprise at least about 5% of Formula V. The mixture of the two diastereomers may comprise at least about 10% of Formula V. The mixture of the two diastereomers may comprise at least about 15% of Formula V. The mixture of the two diastereomers may comprise at least about 20% of Formula V. The mixture of the two diastereomers may comprise at least about 25% of Formula V. The mixture of the two diastereomers may comprise at least about 30% of Formula V. The mixture of the two diastereomers may comprise at least about 40% of Formula V. The mixture of the two diastereomers may comprise at least about 50% of Formula V. The mixture of the two diastereomers may comprise at least about 60% of Formula V. The mixture of the two diastereomers may comprise at least about 70% of Formula V. The mixture of the two diastereomers may comprise at least about 80% of Formula V. The mixture of the two diastereomers may comprise at least about 85% of Formula V. The mixture of the two diastereomers may comprise at least about 90% of Formula V. The mixture of the two diastereomers may comprise at least about 95% of Formula V.

The mixture of the two diastereomers may comprise less than about 97% of Formula V. The mixture of the two diastereomers may comprise less than about 95% of Formula V. The mixture of the two diastereomers may comprise less than about 90% of Formula V. The mixture of the two diastereomers may comprise less than about 85% of Formula V. The mixture of the two diastereomers may comprise less than about 80% of Formula V. The mixture of the two diastereomers may comprise less than about 70% of Formula V. The mixture of the two diastereomers may comprise less than about 60% of Formula V. The mixture of the two diastereomers may comprise less than about 50% of Formula V. The mixture of the two diastereomers may comprise less than about 40% of Formula V. The mixture of the two diastereomers may comprise less than about 30% of Formula V. The mixture of the two diastereomers may comprise less than about 20% of Formula V. The mixture of the two diastereomers may comprise less than about 15% of Formula V. The mixture of the two diastereomers may comprise less than about 10% of Formula V. The mixture of the two diastereomers may comprise less than about 5% of Formula V. The mixture of the two diastereomers may comprise less than about 1% of Formula V.

The mixture of the two diastereomers may comprise between about 1% to about 90% of Formula V. The mixture of the two diastereomers may comprise between about 5% to about 90% of Formula V. The mixture of the two diastereomers may comprise between about 10% to about 90% of Formula V. The mixture of the two diastereomers may comprise between about 20% to about 90% of Formula V. The mixture of the two diastereomers may comprise between about 30% to about 90% of Formula V. The mixture of the two diastereomers may comprise between about 50% to about 90% of Formula V. The mixture of the two diastereomers may comprise between about 70% to about 90% of Formula V. The mixture of the two diastereomers may comprise between about 1% to about 80% of Formula V. The mixture of the two diastereomers may comprise between about 1% to about 70% of Formula V. The mixture of the two diastereomers may comprise between about 1% to about 60% of Formula V. The mixture of the two diastereomers may comprise between about 1% to about 50% of Formula V. The mixture of the two diastereomers may comprise between about 5% to about 80% of Formula V. The mixture of the two diastereomers may comprise between about 10% to about 80% of Formula V. The mixture of the two diastereomers may comprise between about 10% to about 70% of Formula V. The mixture of the two diastereomers may comprise between about 20% to about 70% of Formula V. The mixture of the two diastereomers may comprise between about 30% to about 90% of Formula V.

Further disclosed herein are formulations comprising a plant propagation material, wherein the plant propagation material is obtained by a process comprising a condensation reaction on a sesquiterpene lactone, salt, solvate, polymorph, stereoisomer, isomer or derivative thereof. The condensation reaction may comprise condensing the sesquiterpene lactone, salt, solvate, polymorph, stereoisomer, isomer or derivative thereof, with methyl formate to produce a hydroxymethylene lactone. The condensation reaction may comprise condesing the sesquiterpene lactone with methyl formate to produce a hydroxymethylene lactone. The condensation reaction may further comprise a base. The base may be potassium tert-butoxide. The base may be sodium tert-butoxide. The process may further comprise conducting an alkylation reaction. The alkylation reaction may comprise reaction of the condensation reaction product with an electrophilic butenolide. The alkylation reaction may comprise reaction of the condensation reaction product with a halobutenolide. The halobutenolide may be chlorobutenolide. The halobutenolide may be bromobutenolide. The halobutenolide may be iodobutenolide. The sesquiterpene lactone may be sclareolide. The bromobutenolide may be 5-bromo-3-methylfuran-2(5H)-one. The plant propagation material may comprise a compound of Formula I, or a salt, solvate, polymorph, stereoisomer, or isomer thereof. The plant propagation material may comprise a compound of Formula II, or a salt, solvate, polymorph, stereoisomer, or isomer thereof. The plant propagation material may comprise a compound of Formula III, or a salt, solvate, polymorph, stereoisomer, or isomer thereof.

Further disclosed herein are formulations comprising a plant propagation material, wherein the plant propagation material is obtained by a process comprising conducting a hydroxymethylation and/or alkylation reaction on a sesquiterpene lactone, salt, solvate, polymorph, stereoisomer, isomer or derivative thereof. The sesquiterpene lactone may be sclareolide.

Further disclosed herein are formulations comprising a plant propagation material, wherein the plant propagation material is obtained by a process comprising conducting a hydroxymethylation and/or alkylation reaction on a sesquiterpene lactone. The sesquiterpene lactone may be sclareolide. The plant propagation material may comprise a compound of Formula I, or a salt, solvate, polymorph, stereoisomer, or isomer thereof. The plant propagation material may comprise a compound of Formula II, or a salt, solvate, polymorph, stereoisomer, or isomer thereof. The plant propagation material may comprise a compound of Formula III, or a salt, solvate, polymorph, stereoisomer, or isomer thereof.

Further disclosed herein are formulations comprising a plant propagation material, wherein the plant propagation material is obtained by a process comprising conducting a hydroxymethylation and alkylation reaction on a sesquiterpene lactone, salt, solvate, polymorph, stereoisomer, isomer or derivative thereof. The sesquiterpene lactone may be sclareolide. The hydroxymethylation and alkylation may be a one pot procedure. The hydroxymethylation may be a reaction between sclareolide and methyl formate in the presence of potassium tert-butoxide. The alkylation may be a reaction between the hydroxymethylation product and 5-bromo-3-methylfuran-2(5H)-one. The plant propagation material may comprise a compound of Formula I, or a salt, solvate, polymorph, stereoisomer, or isomer thereof. The plant propagation material may comprise a compound of Formula II, or a salt, solvate, polymorph, stereoisomer, or isomer thereof. The plant propagation material may comprise a compound of Formula III, or a salt, solvate, polymorph, stereoisomer, or isomer thereof.

Further disclosed herein are formulations comprising a plant propagation material, wherein the plant propagation material is obtained by a process comprising conducting a hydroxymethylation reaction on a sesquiterpene lactone, salt, solvate, polymorph, stereoisomer, isomer or derivative thereof. The sesquiterpene lactone may be sclareolide. The hydroxymethylation may be a reaction between sclareolide and methyl formate in the presence of potassium tert-butoxide. The plant propagation material may comprise a compound of Formula I, or a salt, solvate, polymorph, stereoisomer, or isomer thereof. The plant propagation material may comprise a compound of Formula II, or a salt, solvate, polymorph, stereoisomer, or isomer thereof. The plant propagation material may comprise a compound of Formula III, or a salt, solvate, polymorph, stereoisomer, or isomer thereof. The plant propagation material may comprise a compound of Formula IV. The plant propagation material may comprise a compound of Formula V.

Further disclosed herein are formulations comprising a plant propagation material, wherein the plant propagation material is obtained by a process comprising conducting an alkylation reaction on a sesquiterpene lactone, salt, solvate, polymorph, stereoisomer, isomer or derivative thereof. The sesquiterpene lactone may be sclareolide. The alkylation may be a reaction between the sesquiterpene lactone or product thereof and 5-bromo-3-methylfuran-2(5H)-one. The plant propagation material may comprise a compound of Formula I, or a salt, solvate, polymorph, stereoisomer, or isomer thereof. The plant propagation material may comprise a compound of Formula II, or a salt, solvate, polymorph, stereoisomer, or isomer thereof. The plant propagation material may comprise a compound of Formula III, or a salt, solvate, polymorph, stereoisomer, or isomer thereof. The plant propagation material may comprise a compound of Formula IV. The plant propagation material may comprise a compound of Formula V.

Further disclosed herein are formulations comprising a plant propagation material, wherein the plant propagation material is obtained by a biosynthetic process. The biosynthetic process may comprise introducing one or more genes into a cell. The biosynthetic process may further comprise culturing the cell. The biosynthetic process may further comprise inducing the cell to express one or more genes. Gene expression may result in production of the plant propagation material. The biosynthetic process may further comprise purifying the plant propagation material. The plant propagation material may comprise strigolactone. The plant propagation material may comprise a mixture of strigolactones. The plant propagation material may comprise strigol. The plant propagation material may comprise strigyl acetate. The plant propagation material may comprise orobanchol. The plant propagation material may comprise orobanchyl acetate. The plant propagation material may comprise 5-deoxystrigol. The plant propagation material may comprise sorgolactone.

Further disclosed herein are formulations comprising a plant propagation material, wherein the plant propagation material is obtained by a process comprising introducing one or more genes into a cell, wherein the one or more genes do not naturally occur in the cell. The one or more genes may be referred to as foreign genes. The one or more genes may encode a strigolactone pathway. The cell may be a eukaryotic cell. The one or more genes may be from a eukaryotic cell. The eukaryotice cell may be a yeast cell. The process may further comprise culturing the cell. The process may further comprise inducing the cell to express one or more genes. Gene expression may result in production of the plant propagation material. The process may further comprise purifying the plant propagation material. The plant propagation material may comprise strigolactone. The plant propagation material may comprise a mixture of strigolactones. The plant propagation material may comprise strigol. The plant propagation material may comprise strigyl acetate. The plant propagation material may comprise orobanchol. The plant propagation material may comprise orobanchyl acetate. The plant propagation material may comprise 5-deoxystrigol. The plant propagation material may comprise sorgolactone. The plant propagation material may comprise strigolactone. The plant propagation material may comprise a mixture of strigolactones. The plant propagation material may comprise strigol. The plant propagation material may comprise strigyl acetate. The plant propagation material may comprise orobanchol. The plant propagation material may comprise orobanchyl acetate. The plant propagation material may comprise 5-deoxystrigol. The plant propagation material may comprise sorgolactone.

Further disclosed herein are formulations comprising a plant propagation material comprising a mixture of strigolactones. The mixture of strigolactones may comprise two or more strigolactones selected from the group comprising strigol, strigyl acetate, orobanchol, orobanchyl acetate, 5-deoxystrigol, and sorgolactone. The mixture of strigolactones may comprise strigol. The mixture of strigolactones may comprise strigyl acetate. The mixture of strigolactones may comprise orobanchol. The mixture of strigolactones may comprise orobanchyl acetate. The mixture of strigolactones may comprise 5-deoxystrigol. The mixture of strigolactones may comprise sorgolactone.

The formulations may comprise at least about 1% of strigol. The formulations may comprise at least about 2% of strigol. The formulations may comprise at least about 5% of strigol. The formulations may comprise at least about 7% of strigol. The formulations may comprise at least about 10% of strigol. The formulations may comprise at least about 20% of strigol. The formulations may comprise at least about 30% of strigol. The formulations may comprise at least about 40% of strigol. The formulations may comprise at least about 50% of strigol. The formulations may comprise at least about 60% of strigol. The formulations may comprise at least about 70% of strigol. The formulations may comprise at least about 80% of strigol. The formulations may comprise at least about 85% of strigol. The formulations may comprise at least about 90% of strigol. The formulations may comprise at least about 95% of strigol.

The formulations may comprise less than about 95% of strigol. The formulations may comprise less than about 90% of strigol. The formulations may comprise less than about 85% of strigol. The formulations may comprise less than about 80% of strigol. The formulations may comprise less than about 75% of strigol. The formulations may comprise less than about 70% of strigol. The formulations may comprise less than about 60% of strigol. The formulations may comprise less than about 55% of strigol. The formulations may comprise less than about 50% of strigol. The formulations may comprise less than about 40% of strigol. The formulations may comprise less than about 30% of strigol. The formulations may comprise less than about 25% of strigol. The formulations may comprise less than about 20% of strigol. The formulations may comprise less than about 15% of strigol. The formulations may comprise less than about 10% of strigol. The formulations may comprise less than about 5% of strigol. The formulations may comprise less than about 3% of strigol.

The formulations may comprise between about 1% and 90% of strigol. The formulations may comprise between about 1% and 80% of strigol. The formulations may comprise between about 1% and 70% of strigol. The formulations may comprise between about 1% and 60% of strigol. The formulations may comprise between about 1% and 50% of strigol. The formulations may comprise between about 1% and 40% of strigol. The formulations may comprise between about 1% and 30% of strigol. The formulations may comprise between about 1% and 20% of strigol. The formulations may comprise between about 1% and 10% of strigol. The formulations may comprise between about 1% and 5% of strigol. The formulations may comprise between about 5% and 90% of strigol. The formulations may comprise between about 10% and 90% of strigol. The formulations may comprise between about 20% and 90% of strigol. The formulations may comprise between about 30% and 90% of strigol. The formulations may comprise between about 40% and 90% of strigol. The formulations may comprise between about 50% and 90% of strigol. The formulations may comprise between about 60% and 90% of strigol. The formulations may comprise between about 70% and 90% of strigol. The formulations may comprise between about 80% and 90% of strigol. The formulations may comprise between about 10% and 80% of strigol. The formulations may comprise between about 20% and 70% of strigol. The formulations may comprise between about 30% and 60% of strigol. The formulations may comprise between about 20% and 50% of strigol. The formulations may comprise between about 25% and 50% of strigol.

The formulations may comprise at least about 1% of strigyl acetate. The formulations may comprise at least about 2% of strigyl acetate. The formulations may comprise at least about 5% of strigyl acetate. The formulations may comprise at least about 7% of strigyl acetate. The formulations may comprise at least about 10% of strigyl acetate. The formulations may comprise at least about 20% of strigyl acetate. The formulations may comprise at least about 30% of strigyl acetate. The formulations may comprise at least about 40% of strigyl acetate. The formulations may comprise at least about 50% of strigyl acetate. The formulations may comprise at least about 60% of strigyl acetate. The formulations may comprise at least about 70% of strigyl acetate. The formulations may comprise at least about 80% of strigyl acetate. The formulations may comprise at least about 85% of strigyl acetate. The formulations may comprise at least about 90% of strigyl acetate. The formulations may comprise at least about 95% of strigyl acetate.

The formulations may comprise less than about 95% of strigyl acetate. The formulations may comprise less than about 90% of strigyl acetate. The formulations may comprise less than about 85% of strigyl acetate. The formulations may comprise less than about 80% of strigyl acetate. The formulations may comprise less than about 75% of strigyl acetate. The formulations may comprise less than about 70% of strigyl acetate. The formulations may comprise less than about 60% of strigyl acetate. The formulations may comprise less than about 55% of strigyl acetate. The formulations may comprise less than about 50% of strigyl acetate. The formulations may comprise less than about 40% of strigyl acetate. The formulations may comprise less than about 30% of strigyl acetate. The formulations may comprise less than about 25% of strigyl acetate. The formulations may comprise less than about 20% of strigyl acetate. The formulations may comprise less than about 15% of strigyl acetate. The formulations may comprise less than about 10% of strigyl acetate. The formulations may comprise less than about 5% of strigyl acetate. The formulations may comprise less than about 3% of strigyl acetate.

The formulations may comprise between about 1% and 90% of strigyl acetate. The formulations may comprise between about 1% and 80% of strigyl acetate. The formulations may comprise between about 1% and 70% of strigyl acetate. The formulations may comprise between about 1% and 60% of strigyl acetate. The formulations may comprise between about 1% and 50% of strigyl acetate. The formulations may comprise between about 1% and 40% of strigyl acetate. The formulations may comprise between about 1% and 30% of strigyl acetate. The formulations may comprise between about 1% and 20% of strigyl acetate. The formulations may comprise between about 1% and 10% of strigyl acetate. The formulations may comprise between about 1% and 5% of strigyl acetate. The formulations may comprise between about 5% and 90% of strigyl acetate. The formulations may comprise between about 10% and 90% of strigyl acetate. The formulations may comprise between about 20% and 90% of strigyl acetate. The formulations may comprise between about 30% and 90% of strigyl acetate. The formulations may comprise between about 40% and 90% of strigyl acetate. The formulations may comprise between about 50% and 90% of strigyl acetate. The formulations may comprise between about 60% and 90% of strigyl acetate. The formulations may comprise between about 70% and 90% of strigyl acetate. The formulations may comprise between about 80% and 90% of strigyl acetate. The formulations may comprise between about 10% and 80% of strigyl acetate. The formulations may comprise between about 20% and 70% of strigyl acetate. The formulations may comprise between about 30% and 60% of strigyl acetate. The formulations may comprise between about 20% and 50% of strigyl acetate. The formulations may comprise between about 25% and 50% of strigyl acetate.

The formulations may comprise at least about 1% of orobanchol. The formulations may comprise at least about 2% of orobanchol. The formulations may comprise at least about 5% of orobanchol. The formulations may comprise at least about 7% of orobanchol. The formulations may comprise at least about 10% of orobanchol. The formulations may comprise at least about 20% of orobanchol. The formulations may comprise at least about 30% of orobanchol. The formulations may comprise at least about 40% of orobanchol. The formulations may comprise at least about 50% of orobanchol. The formulations may comprise at least about 60% of orobanchol. The formulations may comprise at least about 70% of orobanchol. The formulations may comprise at least about 80% of orobanchol. The formulations may comprise at least about 85% of orobanchol. The formulations may comprise at least about 90% of orobanchol. The formulations may comprise at least about 95% of orobanchol.

The formulations may comprise less than about 95% of orobanchol. The formulations may comprise less than about 90% of orobanchol. The formulations may comprise less than about 85% of orobanchol. The formulations may comprise less than about 80% of orobanchol. The formulations may comprise less than about 75% of orobanchol. The formulations may comprise less than about 70% of orobanchol. The formulations may comprise less than about 60% of orobanchol. The formulations may comprise less than about 55% of orobanchol. The formulations may comprise less than about 50% of orobanchol. The formulations may comprise less than about 40% of orobanchol. The formulations may comprise less than about 30% of orobanchol. The formulations may comprise less than about 25% of orobanchol. The formulations may comprise less than about 20% of orobanchol. The formulations may comprise less than about 15% of orobanchol. The formulations may comprise less than about 10% of orobanchol. The formulations may comprise less than about 5% of orobanchol. The formulations may comprise less than about 3% of orobanchol.

The formulations may comprise between about 1% and 90% of orobanchol. The formulations may comprise between about 1% and 80% of orobanchol. The formulations may comprise between about 1% and 70% of orobanchol. The formulations may comprise between about 1% and 60% of orobanchol. The formulations may comprise between about 1% and 50% of orobanchol. The formulations may comprise between about 1% and 40% of orobanchol. The formulations may comprise between about 1% and 30% of orobanchol. The formulations may comprise between about 1% and 20% of orobanchol. The formulations may comprise between about 1% and 10% of orobanchol. The formulations may comprise between about 1% and 5% of orobanchol. The formulations may comprise between about 5% and 90% of orobanchol. The formulations may comprise between about 10% and 90% of orobanchol. The formulations may comprise between about 20% and 90% of orobanchol. The formulations may comprise between about 30% and 90% of orobanchol. The formulations may comprise between about 40% and 90% of orobanchol. The formulations may comprise between about 50% and 90% of orobanchol. The formulations may comprise between about 60% and 90% of orobanchol. The formulations may comprise between about 70% and 90% of orobanchol. The formulations may comprise between about 80% and 90% of orobanchol. The formulations may comprise between about 10% and 80% of orobanchol. The formulations may comprise between about 20% and 70% of orobanchol. The formulations may comprise between about 30% and 60% of orobanchol. The formulations may comprise between about 20% and 50% of orobanchol. The formulations may comprise between about 25% and 50% of orobanchol.

The formulations may comprise at least about 1% of orobanchol acetate. The formulations may comprise at least about 2% of orobanchol acetate. The formulations may comprise at least about 5% of orobanchol acetate. The formulations may comprise at least about 7% of orobanchol acetate. The formulations may comprise at least about 10% of orobanchol acetate. The formulations may comprise at least about 20% of orobanchol acetate. The formulations may comprise at least about 30% of orobanchol acetate. The formulations may comprise at least about 40% of orobanchol acetate. The formulations may comprise at least about 50% of orobanchol acetate. The formulations may comprise at least about 60% of orobanchol acetate. The formulations may comprise at least about 70% of orobanchol acetate. The formulations may comprise at least about 80% of orobanchol acetate. The formulations may comprise at least about 85% of orobanchol acetate. The formulations may comprise at least about 90% of orobanchol acetate. The formulations may comprise at least about 95% of orobanchol acetate.

The formulations may comprise less than about 95% of orobanchol acetate. The formulations may comprise less than about 90% of orobanchol acetate. The formulations may comprise less than about 85% of orobanchol acetate. The formulations may comprise less than about 80% of orobanchol acetate. The formulations may comprise less than about 75% of orobanchol acetate. The formulations may comprise less than about 70% of orobanchol acetate. The formulations may comprise less than about 60% of orobanchol acetate. The formulations may comprise less than about 55% of orobanchol acetate. The formulations may comprise less than about 50% of orobanchol acetate. The formulations may comprise less than about 40% of orobanchol acetate. The formulations may comprise less than about 30% of orobanchol acetate. The formulations may comprise less than about 25% of orobanchol acetate. The formulations may comprise less than about 20% of orobanchol acetate. The formulations may comprise less than about 15% of orobanchol acetate. The formulations may comprise less than about 10% of orobanchol acetate. The formulations may comprise less than about 5% of orobanchol acetate. The formulations may comprise less than about 3% of orobanchol acetate.

The formulations may comprise between about 1% and 90% of orobanchol acetate. The formulations may comprise between about 1% and 80% of orobanchol acetate. The formulations may comprise between about 1% and 70% of orobanchol acetate. The formulations may comprise between about 1% and 60% of orobanchol acetate. The formulations may comprise between about 1% and 50% of orobanchol acetate. The formulations may comprise between about 1% and 40% of orobanchol acetate. The formulations may comprise between about 1% and 30% of orobanchol acetate. The formulations may comprise between about 1% and 20% of orobanchol acetate. The formulations may comprise between about 1% and 10% of orobanchol acetate. The formulations may comprise between about 1% and 5% of orobanchol acetate. The formulations may comprise between about 5% and 90% of orobanchol acetate. The formulations may comprise between about 10% and 90% of orobanchol acetate. The formulations may comprise between about 20% and 90% of orobanchol acetate. The formulations may comprise between about 30% and 90% of orobanchol acetate. The formulations may comprise between about 40% and 90% of orobanchol acetate. The formulations may comprise between about 50% and 90% of orobanchol acetate. The formulations may comprise between about 60% and 90% of orobanchol acetate. The formulations may comprise between about 70% and 90% of orobanchol acetate. The formulations may comprise between about 80% and 90% of orobanchol acetate. The formulations may comprise between about 10% and 80% of orobanchol acetate. The formulations may comprise between about 20% and 70% of orobanchol acetate. The formulations may comprise between about 30% and 60% of orobanchol acetate. The formulations may comprise between about 20% and 50% of orobanchol acetate. The formulations may comprise between about 25% and 50% of orobanchol acetate.

The formulations may comprise at least about 1% of 5-deoxystrigol. The formulations may comprise at least about 2% of 5-deoxystrigol. The formulations may comprise at least about 5% of 5-deoxystrigol. The formulations may comprise at least about 7% of 5-deoxystrigol. The formulations may comprise at least about 10% of 5-deoxystrigol. The formulations may comprise at least about 20% of 5-deoxystrigol. The formulations may comprise at least about 30% of 5-deoxystrigol. The formulations may comprise at least about 40% of 5-deoxystrigol. The formulations may comprise at least about 50% of 5-deoxystrigol. The formulations may comprise at least about 60% of 5-deoxystrigol. The formulations may comprise at least about 70% of 5-deoxystrigol. The formulations may comprise at least about 80% of 5-deoxystrigol. The formulations may comprise at least about 85% of 5-deoxystrigol. The formulations may comprise at least about 90% of 5-deoxystrigol. The formulations may comprise at least about 95% of 5-deoxystrigol.

The formulations may comprise less than about 95% of 5-deoxystrigol. The formulations may comprise less than about 90% of 5-deoxystrigol. The formulations may comprise less than about 85% of 5-deoxystrigol. The formulations may comprise less than about 80% of 5-deoxystrigol. The formulations may comprise less than about 75% of 5-deoxystrigol. The formulations may comprise less than about 70% of 5-deoxystrigol. The formulations may comprise less than about 60% of 5-deoxystrigol. The formulations may comprise less than about 55% of 5-deoxystrigol. The formulations may comprise less than about 50% of 5-deoxystrigol. The formulations may comprise less than about 40% of 5-deoxystrigol. The formulations may comprise less than about 30% of 5-deoxystrigol. The formulations may comprise less than about 25% of 5-deoxystrigol. The formulations may comprise less than about 20% of 5-deoxystrigol. The formulations may comprise less than about 15% of 5-deoxystrigol. The formulations may comprise less than about 10% of 5-deoxystrigol. The formulations may comprise less than about 5% of 5-deoxystrigol. The formulations may comprise less than about 3% of 5-deoxystrigol.

The formulations may comprise between about 1% and 90% of 5-deoxystrigol. The formulations may comprise between about 1% and 80% of 5-deoxystrigol. The formulations may comprise between about 1% and 70% of 5-deoxystrigol. The formulations may comprise between about 1% and 60% of 5-deoxystrigol. The formulations may comprise between about 1% and 50% of 5-deoxystrigol. The formulations may comprise between about 1% and 40% of 5-deoxystrigol. The formulations may comprise between about 1% and 30% of 5-deoxystrigol. The formulations may comprise between about 1% and 20% of 5-deoxystrigol. The formulations may comprise between about 1% and 10% of 5-deoxystrigol. The formulations may comprise between about 1% and 5% of 5-deoxystrigol. The formulations may comprise between about 5% and 90% of 5-deoxystrigol. The formulations may comprise between about 10% and 90% of 5-deoxystrigol. The formulations may comprise between about 20% and 90% of 5-deoxystrigol. The formulations may comprise between about 30% and 90% of 5-deoxystrigol. The formulations may comprise between about 40% and 90% of 5-deoxystrigol. The formulations may comprise between about 50% and 90% of 5-deoxystrigol. The formulations may comprise between about 60% and 90% of 5-deoxystrigol. The formulations may comprise between about 70% and 90% of 5-deoxystrigol. The formulations may comprise between about 80% and 90% of 5-deoxystrigol. The formulations may comprise between about 10% and 80% of 5-deoxystrigol. The formulations may comprise between about 20% and 70% of 5-deoxystrigol. The formulations may comprise between about 30% and 60% of 5-deoxystrigol. The formulations may comprise between about 20% and 50% of 5-deoxystrigol. The formulations may comprise between about 25% and 50% of 5-deoxystrigol.

The formulations may comprise at least about 1% of sorgolactone. The formulations may comprise at least about 2% of sorgolactone. The formulations may comprise at least about 5% of sorgolactone. The formulations may comprise at least about 7% of sorgolactone. The formulations may comprise at least about 10% of sorgolactone. The formulations may comprise at least about 20% of sorgolactone. The formulations may comprise at least about 30% of sorgolactone. The formulations may comprise at least about 40% of sorgolactone. The formulations may comprise at least about 50% of sorgolactone. The formulations may comprise at least about 60% of sorgolactone. The formulations may comprise at least about 70% of sorgolactone. The formulations may comprise at least about 80% of sorgolactone. The formulations may comprise at least about 85% of sorgolactone. The formulations may comprise at least about 90% of sorgolactone. The formulations may comprise at least about 95% of sorgolactone.

The formulations may comprise less than about 95% of sorgolactone. The formulations may comprise less than about 90% of sorgolactone. The formulations may comprise less than about 85% of sorgolactone. The formulations may comprise less than about 80% of sorgolactone. The formulations may comprise less than about 75% of sorgolactone. The formulations may comprise less than about 70% of sorgolactone. The formulations may comprise less than about 60% of sorgolactone. The formulations may comprise less than about 55% of sorgolactone. The formulations may comprise less than about 50% of sorgolactone. The formulations may comprise less than about 40% of sorgolactone. The formulations may comprise less than about 30% of sorgolactone. The formulations may comprise less than about 25% of sorgolactone. The formulations may comprise less than about 20% of sorgolactone. The formulations may comprise less than about 15% of sorgolactone. The formulations may comprise less than about 10% of sorgolactone. The formulations may comprise less than about 5% of sorgolactone. The formulations may comprise less than about 3% of sorgolactone.

The formulations may comprise between about 1% and 90% of sorgolactone. The formulations may comprise between about 1% and 80% of sorgolactone. The formulations may comprise between about 1% and 70% of sorgolactone. The formulations may comprise between about 1% and 60% of sorgolactone. The formulations may comprise between about 1% and 50% of sorgolactone. The formulations may comprise between about 1% and 40% of sorgolactone. The formulations may comprise between about 1% and 30% of sorgolactone. The formulations may comprise between about 1% and 20% of sorgolactone. The formulations may comprise between about 1% and 10% of sorgolactone. The formulations may comprise between about 1% and 5% of sorgolactone. The formulations may comprise between about 5% and 90% of sorgolactone. The formulations may comprise between about 10% and 90% of sorgolactone. The formulations may comprise between about 20% and 90% of sorgolactone. The formulations may comprise between about 30% and 90% of sorgolactone. The formulations may comprise between about 40% and 90% of sorgolactone. The formulations may comprise between about 50% and 90% of sorgolactone. The formulations may comprise between about 60% and 90% of sorgolactone. The formulations may comprise between about 70% and 90% of sorgolactone. The formulations may comprise between about 80% and 90% of sorgolactone. The formulations may comprise between about 10% and 80% of sorgolactone. The formulations may comprise between about 20% and 70% of sorgolactone. The formulations may comprise between about 30% and 60% of sorgolactone. The formulations may comprise between about 20% and 50% of sorgolactone. The formulations may comprise between about 25% and 50% of sorgolactone.

The formulations disclosed herein may further comprise one or more pesticides. The pesticide may be a biopesticide. A biopesticide may be a form of a pesticide that is based on microorganisms or natural products. A biopesticide may include naturally occurring substances that control pests (biochemical pesticides), microorganisms that control pests (microbial pesticides), and pesticidal substances produced by plants containing added genetic material (plant-incorporated protectants) or PIPs. Examples of biopesticides include, but are not limited to, gluocosinolate, chitosan, spinosad, alkaloids, terpenoids, phenolics, pyrethroids, rotenoids, nicotinoids, strychnine, scilliroside, canola oil and baking soda. The pesticide may be an organophosphate pesticide, carbamate pesticide, organochlorine insecticide, pyrethroid pesticide, sulfonylurea pesticides, or a combination thereof. The pesticide may be a herbicide, algicide, avidicide, bactericide, fungicide, insecticide, miticide, molluscicide, nematicide, rodenticide, virucide, or a combination thereof.

The formulations disclosed herein may be formulated as a dry sprayable formulation. Examples of dry sprayable formulations include, but are not limited to, wettable powders and water dispersible granules. Wettable powders may comprise plant propagation materials that have been microionized to powder form. Wettable powders may be applied as suspended particles after dispertion into water. Water dispersible granules may consist of granules that are applied after disintegration or dispersion in water. The water dispersible granules may comprise particles within the range of 0.2 to 4 mm. Water dispersible granules may be formed by agglomeration, spray drying, or extrusion techniques.

The formulations may be formulated as a liquid sprayable formulation. Examples of liquid sprayable formulations include, but are not limited to, soluble concentrates, suspension concentrates, emulsifiable concentrates, microemulsions, oil dispersions, and microencapsulated particles. Suspension concentrates may comprise a stable suspension of the propagation material in a fluid usually intended for dilution with water before use. Emulsifiable concentrates may comprise a plant propagation material with an emulsifying agent in a water insoluble organic solvent which will form an emulsion when added to water. Microemulsions may comprise a plant propagation material with an emulsifying agent in a water insoluble organic solvent which will form a solution/emulsion when added to water.

The compositions may be formulated as a dry spreadable granule formulation. The dry spreadable granule formulation may comprise soil applied granule on inert or fertilizer carriers.

The formulations may be formulated as a seed treatment or seed dressing.

The formulations may be formulated for rapid release. The formulations may be formulated for slow release.

The formulations may further comprise one or more stabilizers and/or other additives. The stabilizers and/or additives include, but are not limited to, penetration agents, adhesives, anticaking agents, dyes, dispersants, wetting agents, emulsifying agents, defoamers, antimicrobials, antifreeze, pigments, colorants, buffers, and carriers. The formulations may further comprise surfanctans and/or adjuvants.

The formulations may further comprise one or more carriers. Examples of carriers include, but are not limited to, solid carriers, sponges, textiles, and synthetic materials. The synthetic material may be a porous synthetic material. Additional carriers include organic carriers, such as waxes, linolin, paraffin, dextrose granules, sucrose granules and maltose-dextrose granules. Alternatively, the carrier is an anorganic carrier such as natural clays, kaolin, pyrophyllite, bentonite, alumina, montmorillonite, kieselguhr, chalk, diatomaceous earths, calcium phosphates, calcium and magnesium carbonates, sulphur, lime, flours or talc. The formulation may be adsorbed into the carrier. The carrier may be characterized by enabling release of the plant propagation material.

The formulations may further comprise one or more dispersants. The dispersant may be an negatively charged anion dispersant. The dispersant may be a nonionic dispersant.

The formulations may further comprise fertilizer. The fertilizer may be a chemical fertilizer. The fertilizer may be an organic fertilizer. The fertilizer may be an inorganic fertilizer. The fertilizer may be a granulated or powdered fertilizers. The fertilizer may be a liquid fertilizer. The fertilizer may be a slow-release fertilizer.

Methods of Chemical Synthesis

Disclosed herein are methods of manufacturing a plant progation material. The method may comprise a chemical synthesis. The method may comprise (i) hydroxymethylation of an optionally substituted decahydronaphtho[2,1-b]furan-2(3aH)-one; and (ii) subsequent alkylation with

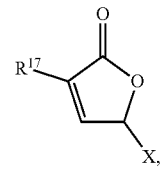

wherein $R^{17}$ is H, alkyl, halo, or haloalkyl and X is Cl, Br, or I. The plant propagation material may be a chemical mimic of strigolactone. The plant propagation material may be a compound of Formula I, II, III, IV, V, VI, VII, VIII, IX or X.

Further disclosed herein are methods of preparing a compound of Formula I, or a salt, solvate, polymorph, stereoisomer, or isomer thereof. The method of preparing a compound of Formula I, II, III, IV, V, VI, VII, VIII, IX or X may comprise (i) hydroxymethylation of an optionally substituted decahydronaphtho[2,1-b]furan-2(3aH)-one; and (ii) subsequent alkylation with

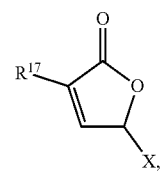

wherein $R^{17}$ is H, alkyl, halo, or haloalkyl and X is Cl, Br, or I.

The hydroxymethylation and alkylation may be a one pot procedure. The optionally substituted decahydronaphtho[2,1-b]furan-2(3aH)-one may be sclareolide. $R^{17}$ may be H or alkyl. $R^{17}$ may be H. $R^{17}$ may be alkyl. The hydroxymethylation may be a reaction between sclareolide and methyl formate in the presence of potassium tert-butoxide. The alkylation may be a reaction between the hydroxymethylation product and 5-bromo-3-methylfuran-2(5H)-one.

Examples of synthesizing the sclareolide is disclosed in Upar et al. (2001, *Tetrahedron: Asymmetry*, 20 (2009) 1637-1640). As shown in FIG. 7, an exemplary synthetic approach to (+)-sclareolide 710 from (E)-(+)-nerolidol 720 involves the [2,3] sigmatropic rearrangement of an allylic alcohol to the homologous amide followed by hydrolysis of the amide to the acid and biomimetic enantioselective cyclization of acid promoted by (R)-2-benzyloxy-20-hydroxy-1,10-binaphthyl[(R)-benzyl-BINOL] and SnCl4 (chiral LBA). The enantioselective synthesis of (+)-sclareolide and (+)-tetrahydroactinidiolid reaction conditions in FIG. 7 can be: (i) DMFDMA, xylene, reflux, 14 h; (ii) KOH, MeOH-water, reflux, 12 h; (iii) 2-benzyloxy-20-hydroxy-1,10-binaphthyl, SnCl4, toluene, −78° C., 3 h, and at −20° C., 3 d. In FIG. 7, (E)-(+)-Nerolidol 720 were heated with N,N-dimethylformamide dimethyl acetal (DMFDMA) to achieve one carbon homologation to the corresponding starting materials with incorporation of a terminal amide functionality. Thus, refluxing a mixture of (+)-(E)-nerolidol and DMFDMA in xylene for 14 h yielded an E/Z-mixture of the b,c-unsaturated amides 4a and 4b (2.2:1) in 79% yield, which were easily separated by silica gel column chromatography. The alkaline hydrolysis of amide 4a afforded homofarnesic acid 5,21 which was subjected to cyclization in the presence of (R)-benzyl-BINOL and SnCl4 at −78° C. for 3 h and subsequently at −20° C. for 3 d to give (+)-sclareolide 710 in 58.6% yield and 88% ee. The stereochemistry of the product compound can be changed by using a different catalyst, such as a chiral LBA.

Similar methods can also be used to synthesize compound I, II, III, IV, V, VI, VII, VIII, IX or X comprising a nitrogen atom. As shown in FIGS. 8A, 8B, 8C, 8D, 8E and 8F, compound I, II, III, IV, V, VI, VII, VIII, IX or X comprising one or more nitrogen atoms can be synthesized by substituting a carbon atom with a nitrogen atom in the starting compound in the disclosed synthetic approach.

Further disclosed herein are methods of producing a plant propagation material. A method of producing a plant propagation material may comprise conducting a condensation reaction on a sesquiterpene lactone, salt, solvate, polymorph, stereoisomer, isomer or derivative thereof, thereby producing a plant propagation material. A method of producing a plant propagation material may comprise conducting a condensation reaction on a sesquiterpene lactone, thereby producing a plant propagation material. The sesquiterpene lactone may be sclareolide. The plant propagation material may be a compound of Formula (I). The plant propagation material may be a compound of Formula (II). The plant propagation material may be a compound of Formula (III).

Alternatively, a method of producing a plant propagation material comprises conducting a hydroxymethylation and/or alkylation reaction on a sesquiterpene lactone, salt, solvate, polymorph, stereoisomer, isomer or derivative thereof, thereby producing a plant propagation material. A method of producing a plant propagation material may comprise conducting a hydroxymethylation and/or alkylation reaction on a sesquiterpene lactone, thereby producing a plant propagation material. A method of producing a plant propagation material may comprise conducting a hydroxymethylation and alkylation reaction on a sesquiterpene lactone, salt, solvate, polymorph, stereoisomer, isomer or derivative thereof, thereby producing a plant propagation material. A method of producing a plant propagation material may comprise conducting a hydroxymethylation and alkylation reaction on a sesquiterpene lactone, thereby producing a plant propagation material. A method of producing a plant propagation material may comprise conducting a hydroxymethylation reaction on a sesquiterpene lactone, salt, solvate, polymorph, stereoisomer, isomer or derivative thereof, thereby producing a plant propagation material. A method of producing a plant propagation material may comprise conducting a hydroxymethylation reaction on a sesquiterpene lactone, thereby producing a plant propagation material. A method of producing a plant propagation material may comprise conducting an alkylation reaction on a sesquiterpene lactone, salt, solvate, polymorph, stereoisomer, isomer or derivative thereof, thereby producing a plant propagation material. A method of producing a plant propagation material may comprise conducting an alkylation reaction on a sesquiterpene lactone, thereby producing a plant propagation material. The sesquiterpene lactone may be sclareolide. The plant propagation material may be a compound of Formula (I). The plant propagation material may be a compound of Formula (II). The plant propagation material may be a compound of Formula (III).

The plant propagation material may have the structure of Formula (I):

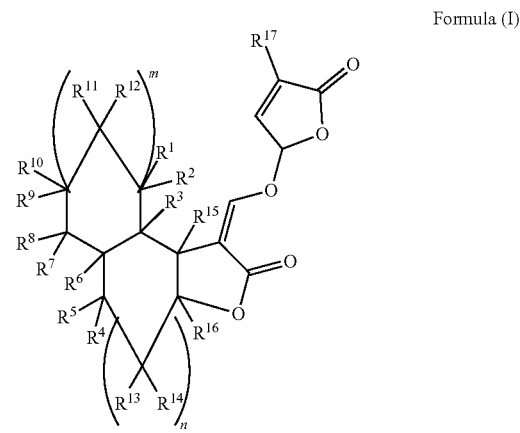

Formula (I)

or a salt, solvate, polymorph, stereoisomer, or isomer thereof, wherein:

$R^1$, $R^2$, $R^4$, $R^5$, $R^7$, $R^8$, $R^9$, $R^{10}$, $R^{11}$, $R^{12}$, $R^{13}$, $R^{14}$, $R^{15}$, $R^{16}$, and $R^{17}$ are each independently H, alkyl, haloalkyl, amino, halo, or —$OR^{18}$;

$R^3$ and $R^6$ are each independently H, alkyl, haloalkyl, amino, halo, or —$OR^{18}$; or $R^3$ and $R^6$ together form a direct bond to provide a double bond;

each $R^{18}$ is independently H, alkyl, haloalkyl, aryl, heteroaryl, or —$C(O)R^{19}$;

each $R^{19}$ is independently alkyl, haloalkyl, aryl, or heteroaryl;

m is 0, 1, or 2; and n is 1 or 2.

The methods disclosed herein may comprise one or more condensation reactions. The condensation reaction may comprise condensing the sesquiterpene lactone, salt, solvate, polymorph, stereoisomer, isomer or derivative thereof, with methyl formate to produce a hydroxymethylene lactone. The sesquiterpene lactone, salt, solvate, polymorph, stereoisomer, isomer or derivative thereof may be condensed with an excess of methyl formate. The sesquiterpene lactone, salt, solvate, polymorph, stereoisomer, isomer or derivative thereof may be condensed with two-fold excess of methyl formate. The sesquiterpene lactone, salt, solvate, polymorph, stereoisomer, isomer or derivative thereof may be condensed with three-fold excess of methyl formate. The sesquiterpene lactone, salt, solvate, polymorph, stereoisomer, isomer or derivative thereof may be condensed with four-fold excess of methyl formate. The sesquiterpene lactone, salt, solvate, polymorph, stereoisomer, isomer or derivative thereof may be condensed with five-fold excess of methyl formate. The condensation reaction may further comprise potassium tert-butoxide.

The methods disclosed herein may comprise one or more alkylation reactions. The method of producing a plant propagation material may further comprise conducting an alkylation reaction. The alkylation reaction may comprise alkylating the condensation reaction product with a bromobutenolide. The alkylation reaction may produce a mixture of two diastereomers. The two diastereomers may be

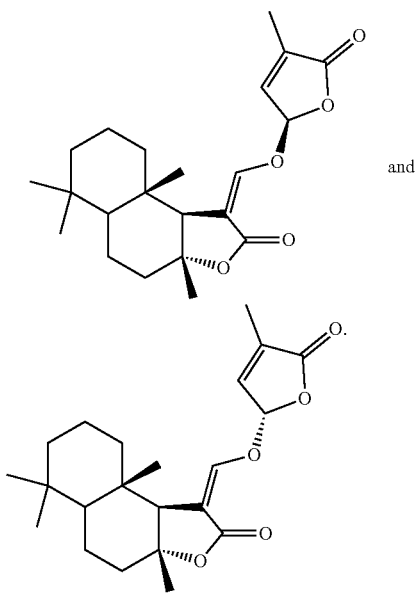

and

The methods disclosed herein may comprise the use of a terpene. The methods disclosed herein may comprise the use of a lactone. The methods disclosed herein may comprise the use of a sesquiterpene. The methods disclosed herein may comprise the use of a sesquiterpene lactone. The sesquiterpene lactone may be a germacranolide. Examples of germacranolides include, but are not limited to, germacranolides from Mikania guaco as disclosed in Rüngeler et al. (2001, *Phytochemistry*, 56(5):475-489). The sesquiterpene lactone may be a heliangolide. The sesquiterpene lactone may be a guaianolide. The sesquiterpene lactone may be a pseudoguaianolide. The sesquiterpene lactone may be a hypocretenolide. The sesquiterpene lactone may be an eudesmanolide. The sesquiterpene lactone may be an eudesmanolide α-santonin. The sesquiterpene lactone may be a β-santonin. The sesquiterpene lactone may be a parthenolide. The sesquiterpene lactone may be a lactuside A. The sesquiterpene lactone may be a helanalin. The sesquiterpene lactone may be a hymenin. The sesquiterpene lactone may be a lettucenin A. The sesquiterpene lactone may be a parthenin. The sesquiterpene lactone may be a tenulin. The sesquiterpene lactone may be a cadinanolide. The sesquiterpene lactone may be an artemisinin. The sesquiterpene lactone may be a seco-cadinanolide. The sesquiterpene lactone may be an artemisinic acid. The sesquiterpene lactone may be sclareolide. Additional sesquiterpene lactones include, but are not limited to, sesquiterpene lactones disclosed in Qin et al. (2012, *Planta Med*, 78(10):1002-9); Ren et al. (2012, *Tetrahedron*, 68(12):2671-2678); Shin et al. (2012, *ChemPharm Bull*, 60(3):306-14), Raupp and Spring (2013, *J Agric Food Chem*, 61(44):10481-7); and Chadwick et al. (2013, *Int J Mol Sci*, 14(6):12780-805).

The sesquiterpene lactone may be extracted or derived from a plant. The plant may be *Salvia sclarea*, *Salvia yosgadensis*, or cigar tobacco. The sesquiterpene lactone may be extracted or derived from one or more plants selected from laurus nobilis, chrysanthemum, pyrethrum, Star anise, Ragweed, Sneezeweed, Ironweed, Sagebrush, Wormwood, Mugwort, Boneset, Poverty weed, Marsh elder, Cocklebur, Burdock, Chamomile, Feverfew, Artichoke, Gaillardin, Parthenium, Sunflower, Lettuce, Spinach, Yellow star thistle, Ginkgo biloba, or a combination thereof. The sesquiterpene lactone may be extracted or derived from a sage plant. The sage plant may be a clary sage plant.

Methods of Biological Synthesis

Further disclosed herein are methods of preparing a plant propagation material. The method may comprise a biological synthesis. The method may comprise introducing one or more genes that encode a strigolactone pathway into a cell. The method may comprise introducing two or more genes that encode a strigolactone pathway into a cell. The method may comprise introducing three or more genes that encode a strigolactone pathway into a cell. The method may comprise introducing four or more genes that encode a strigolactone pathway into a cell. The method may comprise introducing five or more genes that encode a strigolactone pathway into a cell. The method may comprise introducing six or more genes that encode a strigolactone pathway into a cell. The method may comprise introducing 7, 8, 9, 10, 11, 12, 13, 14, 15 or more genes that encode a strigolactone pathway into a cell.

The method of preparing a plant propagation material may comprise introducing a plurality of genes into the cell. At least one of the plurality of genes may encode a strigolactone pathway. At least two of the plurality of genes may encode a strigolactone pathway. At least three of the plurality of genes may encode a strigolactone pathway. At least four of the plurality of genes may encode a strigolactone pathway. At least five of the plurality of genes may encode a strigolactone pathway. At least six of the plurality of genes may encode a strigolactone pathway. At least 7, 8, 9, 10, 11, 12, 13, 14, 15 or more of the plurality of genes may encode a strigolactone pathway.

The method of preparing the plant propagation material may comprise engineering a cell to produce a metabolite, wherein the metabolite is not a natural metabolite of the cell. The metabolite may be lycopene. Engineering the cell to produce the metabolite may comprise introducing one or more genes into the cell. The one or more genes may comprise crtE, crtB, crtI or a combination thereof. Engineering the cell to produce the metabolite may comprise introducing one or more genes into the cell, wherein the one or more genes are selected from crtE, crtB, crtI or a combination thereof. Engineering the cell to produce the metabolite may comprise introducing a plurality of genes into the cell, wherein at least two of the plurality of genes are selected from crtE, crtB, and crtI. Engineering the cell to produce the metabolite may comprise introducing a plurality of genes into the cell, wherein at least three of the plurality of genes are selected from crtE, crtB, and crtI.

The methods may further comprise introducing one or more additional genes into the engineered cell. The one or more genes may be introduced into the engineered cell by transformation. Introduction of the one or more genes into the engineered cell may comprise use of a gene cassette comprising the one or more genes. The one or more genes may comprise D27, CCD7, CCD8, P450 enzyme, or a combination thereof. The P450 enzyme may be MAX1. Transformation of the engineered cell with the one or more genes may result in production of the plant propagation material. The plant propagation material may be strigolactone. The plant propagation material may comprise a strigolactone analogue.

The methods may further comprise introducing a plurality of additional genes into the engineered cell. The plurality of additional genes may be introduced into the engineered cell by transformation. Introduction of the plurality of genes into the engineered cell may comprise use of a gene cassette comprising at least one of the plurality of genes. Introduction of the plurality of genes into the engineered cell may comprise use of a gene cassette comprising at least two of the plurality of genes. Introduction of the plurality of genes into the engineered cell may comprise use of a gene cassette comprising at least three of the plurality of genes. Introduction of the plurality of genes into the engineered cell may comprise use of a gene cassette comprising at least four of the plurality of genes. At least one of the plurality of genes may be selected from CCD7, CCD8, or P450 enzyme. At least two of the plurality of genes may be selected from CCD7, CCD8, or P450 enzyme. At least three of the plurality of genes may be selected from CCD7, CCD8 and P450 enzyme. The P450 enzyme may be MAX1.

Introduction of the plurality of genes may comprise use of a gene cassette comprising at least one of the plurality of genes. Introduction of the plurality of genes may comprise use of a gene cassette comprising at least two of the plurality of genes. Introduction of the plurality of genes may comprise use of a gene cassette comprising at least three of the plurality of genes. Introduction of the plurality of genes may comprise use of a gene cassette comprising at least four of the plurality of genes. Introduction of the plurality of genes may comprise use of a gene cassette comprising at least five of the plurality of genes. Introduction of the plurality of genes may comprise use of a gene cassette comprising at least six of the plurality of genes. Introduction of the plurality of genes may comprise use of a gene cassette comprising at least seven of the plurality of genes. Introduction of the plurality of genes may comprise use of two or more gene cassettes. Introduction of the plurality of genes may comprise use of three or more gene cassettes. Introduction of the plurality of genes may comprise use of four or more gene cassettes. Introduction of the plurality of genes may comprise use of five or more gene cassettes. Introduction of the plurality of genes may comprise use of six or more gene cassettes. Introduction of the plurality of genes may comprise use of 7, 8, 9, 10, 11, 12, 13, 14, 15 or more gene cassettes.

The plurality of genes may be introduced into the cell at the same time. Alternatively, the plurality of genes are introduced into the cell at two or more timepoints. The plurality of genes may be introduced into the cell at three or more timepoints. The plurality of genes may be introduced into the cell at four or more timepoints. The plurality of genes may be introduced into the cell at five or more timepoints. The plurality of genes may be introduced into the cell at six or more timepoints. The plurality of genes may be introduced into the cell at 7, 8, 9, 10, 11, 12, 13, 14, 15 or more timepoints.

The one or more genes may comprise crtE, crtB, crtI, CCD7, CCD8, P450 enzyme or a combination thereof. At least two of the plurality of genes may comprise crtE, crtB, crtI, CCD7, CCD8, or P450 enzyme. At least three of the plurality of genes may comprise crtE, crtB, crtI, CCD7, CCD8, or P450 enzyme. At least four of the plurality of genes may comprise crtE, crtB, crtI, CCD7, CCD8, or P450 enzyme. At least five of the plurality of genes may comprise crtE, crtB, crtI, CCD7, CCD8, or P450 enzyme. At least six of the plurality of genes may comprise crtE, crtB, crtI, CCD7, CCD8, and P450 enzyme. The one or more genes may comprise crtE, crtB, crtI or a combination thereof. At least two of the plurality of genes may be selected from crtE, crtB, or crtI. At least three of the plurality of genes may be selected from crtE, crtB, and crtI. The one or more genes may comprise CCD7, CCD8, P450 enzyme or a combination thereof. At least one of the plurality of genes may be selected from CCD7, CCD8, or P450 enzyme. At least two of the plurality of genes may be selected from CCD7, CCD8, or P450 enzyme. At least three of the plurality of genes may be selected from CCD7, CCD8 and P450 enzyme. The P450 enzyme may be MAXI.

The one or more genes may be introduced into the chromosome of the cell. The ono or more genes may be introduced episomally. The one or more genes may be introduced into the cell by transfection. Transfection may comprise physical treatment. Physical treatment may include, but is not limited to, electroporation, nanoparticles or magnetofection. Transfection may comprise chemical-based transfection. Chemical-based transfection may include, but is not limited to, cyclodextrin, polymers, liposomes, or nanoparticles. Chemical-based transfection may comprise calcium phosphate. Chemical-based transfection may comprise dendrimers. Chemical-based transfection may comprise cationic liposomes. Chemical-based transfection may comprise cationic polymers. Examples of cationic polymers include, but are not limited to, DEAE-dextran or polyethylenimine. Transfection may comprise non-chemical methods. Non-chemical methods include, but are not limited to, electroporation, sono-poration, optical transfection, protoplast fusion, impalefection, or hydrodynamic delivery. Transfection may comprise particle-based methods. Particle-based methods include, but are not limited to gene gun, mangentofection (e.g., magnet assisted transfection), or impalefection. Impalefection may comprise impaling cells by elongated nanostructures and arrays of such nanostructures. Examples of nanostructures include, but are not limited to, carbon nanofibers and silicon nanowires. Particle-based methods may also comprise particle bombardment. Particle bombardment may comprise delivery of the nucleic acid through membrane penetration at a high velocity. The nucleic acid may be connected to one or more microprojectiles. Alternatively, transfection may comprise nucleofection.

The one or more gene may be introduced into the cell by transduction. Transduction may comprise viral transduction. Viral transduction may comprise the use of one or more viral vectors. The viral vector may be an adenoviral vector. The viral vector may be a retroviral vector. Transduction may comprise the use of a bacteriophage virus.

The one or more genes may be introduced into the cell by transformation. Transformation may comprise electroporation. Transformation may comprise chemical-based transformation. Chemical-based transformation may comprise calcium phosphate. Transformation may comprise treating cells with one or more enzymes to degrade their cell walls. Transformation may comprise exposing cells to alkali cations. Alkali cations include, but are not limited to, cesium or lithium. Transformation may comprise exposing cells to lithium acetate, polyethylene glycole, or a combination thereof. Transformation may comprise enzymatic digestion.

Transformation may comprise agitation or agitation with glass beads. Transformation may comprise bacterial-mediated transformation.

Introducing the one or more genes may comprise transformation of the cell with a polynucleotide comprising the one or more genes. Introducing the one or more genes may comprise transformation of the cell with a vector comprising a polynucleotide comprising the one or more genes. The one or more genes may be introduced into the cell by a single polynucleotide or multiple polynucleotides. The one or more genes may be introduced into the cell by a single vector or multiple vectors.

The one or more genes may be under the control of one or more promoters. The one or more genes may be under the control of two or more promoters. The two or more promoters may be the same. The two or more promoters may be different. The one or more promoters may be constitutive. The promoter may be regulated. The promoter may be a GAP promoter.

Cells containing the one or more genes may be selected, isolated, and/or purified. The methods may further comprise drug selection. The methods may further comprise detection of a color change in cells containing the one or more genes. The methods may further comprise spectrophotometry. The methods may further comprise UV-Vis detection. The methods may further comprise chromatography. Examples of chromatography include, but are not limited to, column chromatography, planar chromatography, paper chromatography, thin layer chromatography, displacement chromatography, gas chromatography, liquid chromatograpy, affinity chromatography, supercritical fluid chromatography, ion exchange chromatography, size exclusion chromatography, expanded bed adsorption chromatographic separation, reversed-phase chromatography, two-dimensional chromatography, simulated moving-bed chromatography, pyrolysis gas chromatography, fast protein liquid chromatography, countercurrent chromatography, and chiral chromatography. Chromatography may comprise high performance liquid chromatography (HPLC). Selection may comprise the use of one or more known standards.

The method may further comprise culturing the cells. The cells may be cultured for at least 6, 8, 10, 12, 16, 18, 20, 24, 26, 28, 30, 32, 36, 40, 44, 48, 56, 60, 64, 72 or more hours. The cells may be cultured for at least 6 hours. The cells may be cultured for at least 12 hours. The cells may be cultured for at least 24 hours. The cells may be cultured for at least 36 hours. The cells may be cultured for at least 48 hours. The cells may be cultured for at least 56 hours. The cells may be cultured for at least 64 hours. The cells may be cultured for at least 72 hours. The cells may be cultured prior to introduction of the one or more genes. Alternatively, or additionally, the cells may be cultured after introduction of the one or more genes.

The cells may be cultured in a flask. The cells may be cultured in a petri dish. The cells may be cultured on a solid or semi-solid substrate. The cells may be cultured in a fermentor.

The cells may be cultured in a cell culture media. The cell culture media may comprise one or more sugars and/or alcohols. The cell culture media may comprise one or more sugars. The sugars may be simple sugars. The sugar may be a monosaccharide. The monosaccharide may be linear. The monosaccharide may be cyclic. Examples of monosaccharides include pyranoses, furanoses, heptoses, deoxyribose, ribose, arabinose, gulose, allose, altrose, iodose, galactose, talose, mannose, lyxose, and xylose. The monosaccharide may be glucose. The sugar may be a disaccharide. Examples of disaccharides include, but are not limited to, sucrose, lactulose, lactose, maltose, trehalose, and cellobiose. The sugar may be lactose. The sugar may be a polysaccharide. Examples of polysaccharides include, but are not limited to, storage polysaccharides, starches, glycogen, structural polysaccharides, arabinoxylans, cellulose, chitin, pectin, acidic polysaccharides, and bacterial capsular polysaccharides.

Alternatively, or additionally, the cell culture media comprises one or more alcohols. Examples of alcohols include, but are not limited to, methanol, ethanol, propanol, isopropanol, and butanol. The alcohol may be methanol. The alcohol may be ethanol.

The cells may be cultured with agitation. The cells may be cultured without agitation.

The cells may be cultured at about 23° C. The cells may be cultured at about 25° C. The cells may be cultured at about 30° C. The cells may be cultured at about 37° C. The cells may be cultured at about 42° C.

The method may further comprise purification of the plant propagation material from the cells or cell culture media. Purification may comprise solvent extraction. Solvent extraction may comprise ethyl acetate extraction. Purification may comprise a batchwise single stage extraction. Purification may comprise a multistage countercurrent continuous process. Purification may comprise the use of multistage countercurrent arrays. Purification may comprise an ion exchange mechanism. Purification may comprise aqueous two-phase extraction. Aqueous two-phase extraction may include, but is not limited to, polymer-polymer systems, polymer-salt systems, and ionic liquids.

Further disclosed herein are engineered cells comprising one or more polynucleotides and uses thereof. The engineered cells may be obtained by a process comprising introducing one or more polynucleotides into one or more cells. The engineered cells may be used to manufacture a plant propagation material.

The one or more cells may be a prokaryotic cell. The one or more genes may be from a prokaryotic cell. The prokaryotic cell may be a bacterial cell. The bacterial cell may be a Gram negative cell. The Gram negative cell may be a Gram negative cocci. The Gram negative cell may be a Gram negative bacilli. The bacterial cell may be a Gram positive cell. The Gram positive cell may be a Gram positive cocci. The Gram positive cell may be a Gram positive bacilli. Examples of bacteria include, but are not limited to, chlamydiae, green nonsulfure bacteria, acinobacteria, planctomycetes, spirochaetes, fusobacteria, cyanobacteria, thermophilic bacteria, acidobacteria, and proteobacteria. The prokaryotic cell may be an archae. Examples of archae include, but are not limited to, crenarchaeota, nanoarchaeota, and euryarchaeota.

The one or more cells may be an eukaryotic cell. The one or more genes may be from an eukaryotic cell. Examples of eukaryotes include, but are not limited to, fungi, animals, slime moulds, plants, algae, and protzoa. The eukaryotic cell may be a fungal cell. Examples of fungi include, but are not limited to, glomeromycota, chytridomycota, zygomycota, ascomycota, basidiomycota, and deuteromycetes. The eukaryotic cell may be a yeast cell. The yeast cell may be *Saccharomyces, Cryptococcus, Candida*. The yeast cell may be *Pichia*. The yeast cell may be *P. pastoris*. The yeast cell may be *Pantoea*. The yeast cell may be *P. ananatis*. The yeast cell may be *Saccharomyces*. The yeast cell may be *S. cerevisia*.

The eukaryote may be an animal. The animal may be a mammal. Examples of mammals include, but are not limited to, humans, goats, monkeys, dogs, sheep, cows, cats, rodents, rabbits and lions. The animal may be an avian. Avians include, but are not limited to, eagles, hawks, chickens, and penguins. The animal may be a reptile. Examples of reptiles include, but are not limited to, lizards, alligators, crocodiles, turtles, snakes and tortoises. The animal may be a fish. Fish include, but are not limited to, trout, sharks, whales, dolphins and bass.

The cells from which the genes are from and the cells in which the genes are introduced may be of the same species. The cells from which the genes are from and the cells in which the genes are introduced may be of different species. The cells from which the genes are from and the cells in which the genes are introduced may be of different cell types.

Applications and Uses

The plant propagation materials and formulations disclosed herein may be used in agriculture. The plant propagation materials and formulations may be used to promote plant growth. The plant propagation materials and formulations disclosed herein may be used for enhancing shoot stability in plants. The plant propagation materials and formulations may be used for increasing transport capacity in plants. The plant propagation materials and formulations may be used for increasing drought tolerance of a plant.

Further disclosed herein are methods of improving agriculture comprising applying a formulation comprising a plant propagation material to a plant, thereby improving agriculture. Improving agriculture may comprise promoting plant growth. Improving agriculture may comprise enhancing shoot stability in plants. Improving agriculture may comprise increasing transport capacity in plants. Improving agriculture may comprise increasing drought tolerance. Improving agriculture may comprise reducing an application of one or more pesticides. Improving agriculture may comprise terminating application of one or more pesticides. Improving agriculture may comprise reducing watering amounts applied to the plants. Improving agriculture may comprise reducing watering frequency to the plants. Improving agriculture may comprise controlling phytopathogenic fungi. Improving agriculture may comprise controlling unwanted plant growth. Improving agriculture may comprise controlling unwanted insect or mite infestation. Improving agriculture may comprise regulating growth of the plant. Improving agriculture may comprise promoting or stimulating activity in one or more fungi.

Further disclosed herein are methods of controlling phytopathogenic fungi and/or unwanted plant growth and/or unwanted insect or mite infestation and/or for regulating the growth of plants. The methods may comprise use of a formulation comprising a propagation plant propagation material disclosed herein to act on the respective pests, their habitat or the plants to be protected from the respective pest, to the soil and/or to unwanted plants and/or the crop plants and/or their habitat.

The plant propagation materials may increase plant growth by at least about 5%. The plant propagation materials may increase plant growth by at least about 10%. The plant propagation materials may increase plant growth by at least about 15%. The plant propagation materials may increase plant growth by at least about 20%. The plant propagation materials may increase plant growth by at least about 25%. The plant propagation materials may increase plant growth by at least about 30%. The plant propagation materials may increase plant growth by at least about 50%. The plant propagation materials may increase plant growth by at least about 60%, 70%, 80%, 90%, 95%. 100% or more.

The plant propagation materials may increase plant growth by at least about 1.5, 2, 3, 4, 5, 6, 7, 8, 9, 10, 11, 12, 13, 14, 15, 16, 17, 18, 19, 20, 25, 30, 40, 50-fold or more. The plant propagation materials may increase plant growth by at least about 1.5-fold or more. The plant propagation materials may increase plant growth by at least about 2-fold or more. The plant propagation materials may increase plant growth by at least about 3-fold or more. The plant propagation materials may increase plant growth by at least about 5-fold or more. The plant propagation materials may increase plant growth by at least about 10-fold or more. Plant growth may comprise secondary plant growth.

The plant propagation materials may enhance shoot growth by at least about 5%. The plant propagation materials may enhance shoot growth by at least about 10%. The plant propagation materials may enhance shoot growth by at least about 15%. The plant propagation materials may enhance shoot growth by at least about 20%. The plant propagation materials may enhance shoot growth by at least about 25%. The plant propagation materials may enhance shoot growth by at least about 30%. The plant propagation materials may enhance shoot growth by at least about 50%. The plant propagation materials may enhance shoot growth by at least about 60%, 70%, 80%, 90%, 95%. 100% or more. The plant propagation materials may enhance shoot growth by at least about 1.5, 2, 3, 4, 5, 6, 7, 8, 9, 10, 11, 12, 13, 14, 15, 16, 17, 18, 19, 20, 25, 30, 40, 50-fold or more.

The plant propagation materials may enhance shoot growth by at least about 1.5-fold or more. The plant propagation materials may enhance shoot growth by at least about 2-fold or more. The plant propagation materials may enhance shoot growth by at least about 3-fold or more. The plant propagation materials may enhance shoot growth by at least about 5-fold or more. The plant propagation materials may enhance shoot growth by at least about 10-fold or more.

The plant propagation materials may increase transport capacity in plants by at least about 5%. The plant propagation materials may increase transport capacity in plants by at least about 10%. The plant propagation materials may increase transport capacity in plants by at least about 15%. The plant propagation materials may increase transport capacity in plants by at least about 20%. The plant propagation materials may increase transport capacity in plants by at least about 25%. The plant propagation materials may increase transport capacity in plants by at least about 30%. The plant propagation materials may increase transport capacity in plants by at least about 50%. The plant propagation materials may increase transport capacity in plants by at least about 60%, 70%, 80%, 90%, 95%. 100% or more.

The plant propagation materials may increase transport capacity in plants by at least about 1.5, 2, 3, 4, 5, 6, 7, 8, 9, 10, 11, 12, 13, 14, 15, 16, 17, 18, 19, 20, 25, 30, 40, 50-fold or more. The plant propagation materials may increase transport capacity in plants by at least about 1.5-fold or more. The plant propagation materials may increase transport capacity in plants by at least about 2-fold or more. The plant propagation materials may increase transport capacity in plants by at least about 3-fold or more. The plant propagation materials may increase transport capacity in plants by at least about 5-fold or more. The plant propagation materials may increase transport capacity in plants by at least about 10-fold or more.

The plant propagation materials may increase drought tolerance in plants by at least about 5%. The plant propagation materials may increase drought tolerance in plants by at least about 10%. The plant propagation materials may increase drought tolerance in plants by at least about 15%.

The plant propagation materials may increase drought tolerance in plants by at least about 20%. The plant propagation materials may increase drought tolerance in plants by at least about 25%. The plant propagation materials may increase drought tolerance in plants by at least about 30%. The plant propagation materials may increase drought tolerance in plants by at least about 50%. The plant propagation materials may increase drought tolerance in plants by at least about 60%, 70%, 80%, 90%, 95%. 100% or more.

The plant propagation materials may increase drought tolerance in plants by at least about 1.5, 2, 3, 4, 5, 6, 7, 8, 9, 10, 11, 12, 13, 14, 15, 16, 17, 18, 19, 20, 25, 30, 40, 50-fold or more. The plant propagation materials may increase drought tolerance in plants by at least about 1.5-fold or more. The plant propagation materials may increase drought tolerance in plants by at least about 2-fold or more. The plant propagation materials may increase drought tolerance in plants by at least about 3-fold or more. The plant propagation materials may increase drought tolerance in plants by at least about 5-fold or more. The plant propagation materials may increase drought tolerance in plants by at least about 10-fold or more.

The plant propagation materials may reduce the application of one or more pesticides. Reducing the application of one or more pesticides may comprise reducing an amount of the one or more pesticides that are applied to the plant. The amount of the one or more pesticides applied to the plant may be reduced by at least about 1%, 5%, 10%, 15%, 20%, 25%, 30%, 35%, 40%, 50%, 60%, 70%, 80%, 90%, 95%, or 100%. The amount of the one or more pesticides applied to the plant may be reduced by at least about 10%. The amount of the one or more pesticides applied to the plant may be reduced by at least about 20%. The amount of the one or more pesticides applied to the plant may be reduced by at least about 30%. The amount of the one or more pesticides applied to the plant may be reduced by at least about 50%.

Alternatively, or additionally, reducing the application of the one or more pesticides may comprise reducing a frequency of which the one or more pesticides are applied to the plant. The frequency of which the one or more pesticides are applied to the plant may be reduced by at least about 1%, 5%, 10%, 15%, 20%, 25%, 30%, 35%, 40%, 50%, 60%, 70%, 80%, 90%, 95%, or 100%. The frequency of which the one or more pesticides are applied to the plant may be reduced by at least about 10%. The frequency of which the one or more pesticides are applied to the plant may be reduced by at least about 20%. The frequency of which the one or more pesticides are applied to the plant may be reduced by at least about 30%. The frequency of which the one or more pesticides are applied to the plant may be reduced by at least about 40%. The frequency of which the one or more pesticides are applied to the plant may be reduced by at least about 50%.

Use of the plant propagation materials may allow a reduction in the amount of water applied to the plants. The amount of the water applied to the plant may be reduced by at least about 1%, 5%, 10%, 15%, 20%, 25%, 30%, 35%, 40%, 50%, 60%, 70%, 80%, 90%, 95%, or 100%. The amount of the water applied to the plant may be reduced by at least about 10%. The amount of the water applied to the plant may be reduced by at least about 20%. The amount of the water applied to the plant may be reduced by at least about 30%. The amount of the water applied to the plant may be reduced by at least about 50%.

Use of the plant propagation materials may allow a reduction in the frequency of which the water is applied to the plant. The frequency of which the water is applied to the plant may be reduced by at least about 1%, 5%, 10%, 15%, 20%, 25%, 30%, 35%, 40%, 50%, 60%, 70%, 80%, 90%, 95%, or 100%. The frequency of which the water is applied to the plant may be reduced by at least about 10%. The frequency of which the water is applied to the plant may be reduced by at least about 20%. The frequency of which the water is applied to the plant may be reduced by at least about 30%. The frequency of which the water is applied to the plant may be reduced by at least about 40%. The frequency of which the water is applied to the plant may be reduced by at least about 50%.

The plant propagation material disclosed herein may be used to control phytopathogenic fungi. Improving agriculture may comprise controlling unwanted plant growth. Controlling unwanted plant growth may comprise stimulating germination activity of the unwanted plant. The unwanted plant may be a parasitic plant. The unwanted plant may be a root parasitic plant. Examples of parasitic plants include, but are not limited to, witchweeds (*Striga* spp.), broomrapes (*Orobanche* spp, *Phelipanche* spp), *Alectra*, dodders, and mistletoes. The unwanted plant may belong to the family Orobanchaceae. The unwanted plant may be witchweed. The unwanted plant may be *Orobanche* spp. The plant propagation material may be applied directly to the unwanted plant. The plant propagation material may be applied indirectly to the unwanted plant.

The plant propagation material disclosed herein may be used to control unwanted insect or mite infestation. Examples of insects and mites include, but are not limited to spiders, gnats, mealybugs, whiteflies, predator mites, spider mites and aphids.

The plant propagation material disclosed herein may be used to regulate growth of the plant. Regulating plant growth may comprise regulating plant breeding Regulating plant growth may comprise inhibiting shoot branching. Regulating plant growth may comprise regulating one or more plant products. Regulating plant growth may comprise inhibiting root development.

The plant propagation material disclosed herein may be used to promote or stimulate activity in fungi. The plant propagation material may stimulate hyphal branching activity of one or more fungi. The plant propagation material may induce spore germination of one or more fungi. The one or more fungi may be arbuscular mycorrhizal (AM) fungi.

Further disclosed herein are methods of preserving or extending the life of a plant. Generally, the method may comprise contacting the plant with a plant propagation material disclosed herein. The plant propagation material may comprise a compound of Formula (I) or a salt, solvate, polymorph, stereoisomer, or isomer thereof. The plant propagation material may comprise a compound of Formula (II) or a salt, solvate, polymorph, stereoisomer, or isomer thereof. The plant propagation material may comprise a compound of Formula (III) or a salt, solvate, polymorph, stereoisomer, or isomer thereof. The plant propagation material may comprise a strigolactone or a salt, solvate, polymorph, stereoisomer, or isomer thereof. The plant propagation material may comprise a strigolactone mimic or a salt, solvate, polymorph, stereoisomer, or isomer thereof.

The plant propagation material for use in preserving or extending the life of a plant may be produced by any of the methods disclosed herein. The plant propagation material may be produced by chemical synthesis. For example, the plant propagation material is produced by conducting a condensation reaction on a sesquiterpene lactone, salt, solvate, polymorph, stereoisomer, isomer or derivative thereof. The plant propagation material may be produced by conducting a hydroxymethylation on a sesquiterpene lactone, salt, solvate, polymorph, stereoisomer, isomer or derivative thereof. The plant propagation material may be produced by (a) conducting a hydroxymethylation on a sesquiterpene lactone, salt, solvate, polymorph, stereoisomer, isomer or derivative thereof to produce a first product; and (b) conducting an alkylation reaction on the first product. Alternatively, the plant propagation material is produced by biological synthesis. Biological synthesis may comprise the use of one or more cells, genes, or vectors disclosed herein.

The plant propagation material may be used to preserve or extend the life of a cut plant. The cut plant may be a flower. The cut plant may be a tree. The cut plant may be bush or shrub. The cut plant may be a vegetable. The plant propagation material may be used to preserve or extend the life of an uncut plant. The uncut plant may be a flower. The uncut plant may be a tree. The uncut plant may be bush or shrub. The uncut plant may be a vegetable. The plant propagation material may be used to preserve or extend the life of a potted plant. The potted plant may be a flower. The potted plant may be a tree. The potted plant may be bush or shrub. The potted plant may be a vegetable.

The plant propagation material may be used to preserve or extend the life of a flower. Examples of flowers include, but are not limited to, lilies, daisies, roses, marigolds, Angel's trumpet, phlox, vinca, snapdragons, toadflax, orchids, ferns, black-eyed Susans, blood flowers, blue lobelias, morning glories, poppies, calendulas, geraniums, impatiens, lantanas, larkspurs, calla lilies, hyacinths, azaleas, pointsettias, and begonias.

The plant propagation material may be used to preserve or extend the life of a bush or shrub. Examples of bushes and shrubs include, but are not limited to, forsynthia, fuchsia, hibiscus, currant, lilac, rose, hydrangea, willow, magnolia, thyme, snowberry, dogwood and holly.

The plant propagation material may be used to preserve or extend the life of a tree. Examples of trees include, but are not limited to, cypress, poinsettia, palm, fir, pine, spruce, cedar, oak, mulberry, chestnut, hawthorn, poplar, and maple. The tree may be a fir tree. The fir tree may be a Douglas, Balsam or Fraser fir tree. The tree may be a pine tree. The pine tree may be a Scotch or White pine tree. The tree may be a spruce tree. The spruce tree may be a White, Norway or Blue spruce tree. The tree may be a cedar tree. The cedar tree may be a Deodara or Eastern red cedar. The tree may be a cypress tree. The cypress tree may be an Arizona or Leland cypress tree.

The plant may be contacted with a plant propagation material disclosed herein, thereby extending or preserving the life of the plant. Contacting the plant with the plant propagation material may comprise administering the plant propagation material as a spray. Contacting the plant with the plant propagation material may comprise adding the plant growth material to the irrigation water of the plant. Contacting the plant with the plant propagation material may comprise applying the plant propagation material to the habitat of the plant. Contacting the plant with the plant propagation material may comprise adding the plant propagation material to a plant container (e.g., vase) and placing the plant in the plant container. Contacting the plant with the plant propagation material may comprise adding the plant propagation material to soil.

The life of the plant may be extended by at least about 1%, 5%, 10%, 15%, 20%, 25%, 30%, 35%, 40%, 45%, 50%, 55%, 60%, 65%, 70%, 75%, 80%, 85%, 90%, 95%, or 97% as compared to an untreated plant. The life of the plant may be extended by at least about 20% as compared to an untreated plant. The life of the plant may be extended by at least about 30% as compared to an untreated plant. The life of the plant may be extended by at least about 40% as compared to an untreated plant. The life of the plant may be extended by at least about 50% as compared to an untreated plant. The life of the plant may be extended by at least about 55% as compared to an untreated plant. The life of the plant may be extended by at least about 60% as compared to an untreated plant. The life of the plant may be extended by at least about 65% as compared to an untreated plant. The life of the plant may be extended by at least about 70% as compared to an untreated plant. The life of the plant may be extended by at least about 75% as compared to an untreated plant. The life of the plant may be extended by at least about 80% as compared to an untreated plant.

The life of the plant may be extended by at least about 6, 12, 24, 30, 36, 42, 48, 54, 60, 66, 72, 78, 84, 90, 96, 102, 108, 114, or 120 hours as compared to an untreated plant. The life of the plant may be extended by at least about 24 hours as compared to an untreated plant. The life of the plant may be extended by at least about 36 hours as compared to an untreated plant. The life of the plant may be extended by at least about 48 hours as compared to an untreated plant. The life of the plant may be extended by at least about 72 hours as compared to an untreated plant. The life of the plant may be extended by at least about 96 hours as compared to an untreated plant.

The life of the plant may be extended by at least about 1, 1.5, 2, 2.5, 3, 3.5, 4, 4.5, 5, 5.5, 6, 6.5, or 7 days as compared to an untreated plant. The life of the plant may be extended by at least about 8, 9, 10, 11, 12, 13, 14, 15, 16, 17, 18, 19, or 20 days as compared to an untreated plant. The life of the plant may be extended by at least about 1 day as compared to an untreated plant. The life of the plant may be extended by at least about 2 days as compared to an untreated plant. The life of the plant may be extended by at least about 2.5 days as compared to an untreated plant. The life of the plant may be extended by at least about 3 days as compared to an untreated plant. The life of the plant may be extended by at least about 3.5 days as compared to an untreated plant. The life of the plant may be extended by at least about 4 days as compared to an untreated plant. The life of the plant may be extended by at least about 4.5 days as compared to an untreated plant.

The life of the plant may be extended by at least about 1, 1.5, 2, 2.5, 3, 3.5, 4, 4.5, 5, 5.5, 6, 6.5, or 7 weeks as compared to an untreated plant. The life of the plant may be extended by at least about 8, 9, 10, 11, 12, 13, 14, 15, 16, 17, 18, 19, or 20 weeks as compared to an untreated plant. The life of the plant may be extended by at least about 1, 1.5, 2, 2.5, 3, 3.5, 4, 4.5, 5, 5.5, 6, 6.5, or 7 months as compared to an untreated plant. The life of the plant may be extended by at least about 8, 9, 10, 11, 12, 13, 14, 15, 16, 17, 18, 19, or 20 months as compared to an untreated plant.

Preserving or extending the life of the plant may comprise reducing wilting of the plant. Reducing wilting of the plant may comprise reducing flower or leaf rolling of the plant. The wilting of the plant may be reduced by at least about 1%, 5%, 10%, 15%, 20%, 25%, 30%, 35%, 40%, 45%, 50%, 55%, 60%, 65%, 70%, 75%, 80%, 85%, 90%, 95%, or 97% as compared to an untreated plant. The wilting of the plant may be reduced by at least about 10% as compared to an untreated plant. The wilting of the plant may be reduced by at least about 30% as compared to an untreated plant. The wilting of the plant may be reduced by at least about 50% as compared to an untreated plant. The wilting of the plant may be reduced by at least about 70% as compared to an untreated plant. The wilting of the plant may be reduced by at least about 80% as compared to an untreated plant.

A sign of plant stress may include wilting of the plant. For example, stressed plants may have rolled leaves or petals. The plant growth materials disclosed herein may promote the life of the plant by reducing the wilting of the plant. Reducing the wilting of the plant may comprise delaying the wilting of the plant as compared to an untreated plant. For example, an untreated cut plant may show signs of wilting within 36 hours of being cut, however, a cut plant treated with a plant growth material may have delayed wilting. The wilting of the plant may be delayed by at least about 2, 3, 4, 5, 6, 7, 8, 9, 10, 11, 12, 13, 14, 15, 16, 17, 18, 19, 20, 21, 22, 23, or 24 hours as compared to an untreated plant. The wilting of the plant may be delayed by at least about 12 hours as compared to an untreated plant. The wilting of the plant may be delayed by at least about 24 hours as compared to an untreated plant. The wilting of the plant may be delayed by at least about 36 hours as compared to an untreated plant. The wilting of the plant may be delayed by at least about 48 hours as compared to an untreated plant.

An additional sign of plant stress may include reduced turgidity. Turgidity may refer to pressure caused by the osmotic flow of water from an area of low solute concentration outside of the cell into the cell cell's vacuole. Turgidity may be used by plants to maintain rigidity. Often, healthy plants are turgid, whereas, unhealthy plants are less turgid. Preserving or extending the life of the plant may comprise prolonging or maintaining the turgidity of the plant. The turgidity of the plant may be greater than the turgidity of an untreated plant. The turgidity of the plant may be at least about 1%, 5%, 10%, 15%, 20%, 25%, 30%, 35%, 40%, 45%, 50%, 55%, 60%, 65%, 70%, 75%, 80%, 85%, 90%, 95%, or 97% greater than the turgidity of an untreated plant. The turgidity of the plant may be at least about 10% greater than the turgidity of an untreated plant. The turgidity of the plant may be at least about 15% greater than the turgidity of an untreated plant. The turgidity of the plant may be at least about 25% greater than the turgidity of an untreated plant. The turgidity of the plant may be at least about 35% greater than the turgidity of an untreated plant. The turgidity of the plant may be at least about 45% greater than the turgidity of an untreated plant. The turgidity of the plant may be at least about 60% greater than the turgidity of an untreated plant. The turgidity of the plant may be at least about 75% greater than the turgidity of an untreated plant.

A stressed plant may also show a reduction in the turgid state. The turgid state may refer to a period of time in which the plant maintains its rigidity. The rigidity of the plant may refer to the rigidity of the stem of the plant. For example, as cut plants die, the stem of the plant may be less rigid, thereby causing the cut plant to fall over or bend. A stressed plant may be unable to hold itself upright. Preserving or extending the life of the plant may comprise prolonging the turgid state of the plant. The turgid state of the plant may be increased by at least about 1%, 5%, 10%, 15%, 20%, 25%, 30%, 35%, 40%, 45%, 50%, 55%, 60%, 65%, 70%, 75%, 80%, 85%, 90%, 95%, or 97% as compared to an untreated plant. The turgid state of the plant may be increased by at least about 20% as compared to an untreated plant. The turgid state of the plant may be increased by at least about 30% as compared to an untreated plant. The turgid state of the plant may be increased by at least about 40% as compared to an untreated plant. The turgid state of the plant may be increased by at least about 50% as compared to an untreated plant.

The turgid state of the plant may be increased by at least about 2, 3, 4, 5, 6, 7, 8, 9, 10, 11, 12, 13, 14, 15, 16, 17, 18, 19, 20, 21, 22, 23, or 24 hours as compared to an untreated plant. The turgid state of the plant may be increased by at least about 6 hours as compared to an untreated plant. The turgid state of the plant may be increased by at least about 12 hours as compared to an untreated plant. The turgid state of the plant may be increased by at least about 24 hours as compared to an untreated plant.

A stressed plant may lose leaves or petals. Contacting a plant with a plant growth material may reduce or delay the loss of one or more petals or leaves of the plant. For example, an untreated plant may lose 50% of its leaves or petals, whereas a treated plant may lose 10-25% of its leaves or petals. The loss of the one or more petals of the plant may be reduced by least about 1%, 5%, 10%, 15%, 20%, 25%, 30%, 35%, 40%, 45%, 50%, 55%, 60%, 65%, 70%, 75%, 80%, 85%, 90%, 95%, or 97% as compared to the loss of the one or more petals of an untreated plant. The loss of the one or more petals of the plant may be reduced by least about 10% as compared to the loss of the one or more petals of an untreated plant. The loss of the one or more petals of the plant may be reduced by least about 20% as compared to the loss of the one or more petals of an untreated plant. The loss of the one or more petals of the plant may be reduced by least about 35% as compared to the loss of the one or more petals of an untreated plant. The loss of the one or more petals of the plant may be reduced by least about 50% as compared to the loss of the one or more petals of an untreated plant. The loss of the one or more petals of the plant may be reduced by least about 60% as compared to the loss of the one or more petals of an untreated plant. The loss of the one or more petals of the plant may be reduced by least about 70% as compared to the loss of the one or more petals of an untreated plant.

The loss of the one or more petals of the plant may be delayed by at least about 2, 3, 4, 5, 6, 7, 8, 9, 10, 11, 12, 13, 14, 15, 16, 17, 18, 19, 20, 21, 22, 23, or 24 hours as compared to the loss of one or more petals of an untreated plant. The loss of the one or more petals of the plant may be delayed by at least about 25, 30, 35, 40, 45, 50, 55, 60, 65, 70, 75, 80, 85, 90, 95 or 100 hours as compared to the loss of one or more petals of an untreated plant. The loss of the one or more petals of the plant may be delayed by at least about 6 hours as compared to the loss of one or more petals of an untreated plant. The loss of the one or more petals of the plant may be delayed by at least about 12 hours as compared to the loss of one or more petals of an untreated plant. The loss of the one or more petals of the plant may be delayed by at least about 18 hours as compared to the loss of one or more petals of an untreated plant. The loss of the one or more petals of the plant may be delayed by at least about 36 hours as compared to the loss of one or more petals of an untreated plant. The loss of the one or more petals of the plant may be delayed by at least about 48 hours as compared to the loss of one or more petals of an untreated plant. The loss of the one or more petals of the plant may be delayed by at least about 60 hours as compared to the loss of one or more petals of an untreated plant. The loss of the one or more petals of the plant may be delayed by at least about 72 hours as compared to the loss of one or more petals of an untreated plant. The loss of the one or more petals of the plant may be delayed by at least about 96 hours as compared to the loss of one or more petals of an untreated plant.

A stressed plant may show signs of discoloration. The stressed plant may appear brownish. Alternatively, or additionally, the stressed plant shows a reduction in the appearance of green leaves. The chlorophyll content of the stressed plant may also be reduced. Preserving or extending the life of the plant may comprise maintaining the chlorophyll content of the plant. For example, a reduction in the chlorophyll content of an untreated plant may appear within 48 hours of being cut. However, a reduction in the chlorophyll content of a treated plant may appear after 60 hours of being cut. The chlorophyll content of the plant may be maintained for at least about 2, 3, 4, 5, 6, 7, 8, 9, 10, 11, 12, 13, 14, 15, 16, 17, 18, 19, 20, 21, 22, 23, or 24 hours. The chlorophyll content of the plant may be maintained for at least about 6 hours. The chlorophyll content of the plant may be maintained for at least about 12 hours. The chlorophyll content of the plant may be maintained for at least about 24 hours.

Preserving or extending the life of the plant may comprise reducing or delaying the loss of the chlorophyll content of the plant. The chlorophyll content of the plant may be greater than the chlorophyll content of an untreated plant. The chlorophyll content of the plant may be at least about 1%, 5%, 10%, 15%, 20%, 25%, 30%, 35%, 40%, 45%, or 50% greater than the content of an untreated plant. The chlorophyll content of the plant may be at least about 55%, 60%, 65%, 70%, 75%, 80%, 85%, 90%, 95% or 97% greater than the content of an untreated plant. The chlorophyll content of the plant may be at least about 20% greater than the content of an untreated plant. The chlorophyll content of the plant may be at least about 30% greater than the content of an untreated plant. The chlorophyll content of the plant may be at least about 40% greater than the content of an untreated plant. The chlorophyll content of the plant may be at least about 50% greater than the content of an untreated plant. The chlorophyll content of the plant may be at least about 60% greater than the content of an untreated plant. The chlorophyll content of the plant may be at least about 1.5, 2, 2.5, 3, 3.5, 4, 4.5, 5, 5.5, 6, 6.5, 7, 8, 9, or 10-fold greater than the content of an untreated plant. The chlorophyll content of the plant may be at least about 11, 12, 13, 14, 15, 16, 17, 18, 19, 20, 25, 30, 35, 40, 45, 50, 55, 60, 65, 70, 75, 80, 85, 90, 95 or 100-fold greater than the content of an untreated plant. The chlorophyll content of the plant may be at least about 2-fold greater than the content of an untreated plant. The chlorophyll content of the plant may be at least about 3-fold greater than the content of an untreated plant. The chlorophyll content of the plant may be at least about 4-fold greater than the content of an untreated plant. The chlorophyll content of the plant may be at least about 5-fold greater than the content of an untreated plant. The chlorophyll content of the plant may be at least about 10-fold greater than the content of an untreated plant.

The loss of the chlorophyll content of the plant may be delayed by at least about 2, 3, 4, 5, 6, 7, 8, 9, 10, 11, 12, 13, 14, 15, 16, 17, 18, 19, 20, 21, 22, 23, or 24 hours as compared to the loss of the chlorophyll content of an untreated plant. The loss of the chlorophyll content of the plant may be delayed by at least about 30, 35, 40, 45, 50, 55, 60, 65, 70, 75, 80, 85, 90, 95, or 100 hours as compared to the loss of the chlorophyll content of an untreated plant. The loss of the chlorophyll content of the plant may be delayed by at least about 6 hours as compared to the loss of the chlorophyll content of an untreated plant. The loss of the chlorophyll content of the plant may be delayed by at least about 12 hours as compared to the loss of the chlorophyll content of an untreated plant. The loss of the chlorophyll content of the plant may be delayed by at least about 24 hours as compared to the loss of the chlorophyll content of an untreated plant. The loss of the chlorophyll content of the plant may be delayed by at least about 36 hours as compared to the loss of the chlorophyll content of an untreated plant. The loss of the chlorophyll content of the plant may be delayed by at least about 48 hours as compared to the loss of the chlorophyll content of an untreated plant. The loss of the chlorophyll content of the plant may be delayed by at least about 60 hours as compared to the loss of the chlorophyll content of an untreated plant. The loss of the chlorophyll content of the plant may be delayed by at least about 72 hours as compared to the loss of the chlorophyll content of an untreated plant.

The loss of the chlorophyll content of the plant may be less than the loss of the chlorophyll content of an untreated plant. The loss of the chlorophyll content of the plant may be at least about 1%, 5%, 10%, 15%, 20%, 25%, 30%, 35%, 40%, 45%, 50%, 55%, or 60% less than the loss of the chlorophyll content of an untreated plant. The loss of the chlorophyll content of the plant may be at least about 65%, 70%, 72%, 75%, 77%, 80%, 85%, 90%, 92%, 95%, or 97% less than the loss of the chlorophyll content of an untreated plant. The loss of the chlorophyll content of the plant may be at least about 5% less than the loss of the chlorophyll content of an untreated plant. The loss of the chlorophyll content of the plant may be at least about 10% less than the loss of the chlorophyll content of an untreated plant. The loss of the chlorophyll content of the plant may be at least about 20% less than the loss of the chlorophyll content of an untreated plant. The loss of the chlorophyll content of the plant may be at least about 30% less than the loss of the chlorophyll content of an untreated plant. The loss of the chlorophyll content of the plant may be at least about 40% less than the loss of the chlorophyll content of an untreated plant. The loss of the chlorophyll content of the plant may be at least about 50% less than the loss of the chlorophyll content of an untreated plant. The loss of the chlorophyll content of the plant may be at least about 60% less than the loss of the chlorophyll content of an untreated plant.

The loss of the chlorophyll content of the plant may be at least about 1.5, 2, 2.5, 3, 3.5, 4, 4.5, 5, 5.5, 6, 6.5, 7, 7.5, 8, 8.5, 9, 9.5, or 10-fold less than the loss of the chlorophyll content of an untreated plant. The loss of the chlorophyll content of the plant may be at least about 11, 12, 13, 14, 15, 16, 17, 18, 19, 20, 25, 30, 35, 40, 45, 50, 55, 60, 65, 70, 75, 80, 85, 90, 95 or 100-fold less than the loss of the chlorophyll content of an untreated plant. The loss of the chlorophyll content of the plant may be at least about 2-fold less than the loss of the chlorophyll content of an untreated plant. The loss of the chlorophyll content of the plant may be at least about 3-fold less than the loss of the chlorophyll content of an untreated plant. The loss of the chlorophyll content of the plant may be at least about 5-fold less than the loss of the chlorophyll content of an untreated plant. The loss of the chlorophyll content of the plant may be at least about 10-fold less than the loss of the chlorophyll content of an untreated plant.

The plant propagation material or a formulation thereof may be applied directly to the plant. The plant propagation material or a formulation thereof may be applied to one or more parts of the plant. The one or more parts of the plant may comprise a terminal bud, flower, lateral bud, leaf blade, leaf axil, node, internode, petiole, primary root, lateral root, root hair, root cap, or a combination thereof. The formulations may be applied to the leaf blade of the plant. The formulations may be applied to the root of the plant.

Alternatively, or additionally, the plant propagation material or a formulation thereof is applied indirectly to the plant. The formulation may be applied to an area around the plant.

The area around the plant may comprise soil. The area around the plant may comprise an adjacent plant.

The plant propagation material or a formulation thereof may be applied to a plant that is susceptible to a parasitic weed. Examples of plants include, but are not limited to, corn, rice, sorghum, millets, and sugar cane. The plant may be corn. The plant may be tobacco. The plant may be rice.

The plant propagation material or a formulation thereof may be applied as a seed coating. The plant propagation material or a formulation thereof may be applied as a seed treatment. The plant propagation material or a formulation thereof may be applied as a seed dressing. The plant propagation material or a formulation thereof may be applied as a spray. The plant propagation material or a formulation thereof may be applies as a foliar spray. The plant propagation material or a formulation thereof may be applied as a powder.

The plant propagation material or a formulation thereof may be applied 1, 2, 3, 4, 5, 6, 7, 8, 9, 10 or more times a day. The plant propagation material or a formulation thereof may be applied once a day. The plant propagation material or a formulation thereof may be applied twice a day. The plant propagation material or a formulation thereof may be applied 1, 2, 3, 4, 5, 6, 7, 8, 9, 10 or more times per week. The plant propagation material or a formulation thereof may be applied once a week. The plant propagation material or a formulation thereof may be applied twice a week. The plant propagation material or a formulation thereof may be applied three times a week. The plant propagation material or a formulation thereof may be applied four times a week. The formulations may be applied 1, 2, 3, 4, 5, 6, 7, 8, 9, 10 or more times a month. The formulations may be applied once a month. The plant propagation material or a formulation thereof may be applied twice a month. The plant propagation material or a formulation thereof may be applied three times a month. The plant propagation material or a formulation thereof may be applied four times a month. The formulations may be applied ten times a month. The plant propagation material or a formulation thereof may be applied 15 times a month. The formulations may be applied 20 times a month.

EXAMPLES

The following illustrative examples are representative of embodiments of the compounds, formulations, compositions and methods described herein and are not meant to be limiting in any way.

Example 1—Synthesis of Plant Propagation Material

Chemical Synthesis of a Chemical Mimic of Strigolactone

Figure 1:
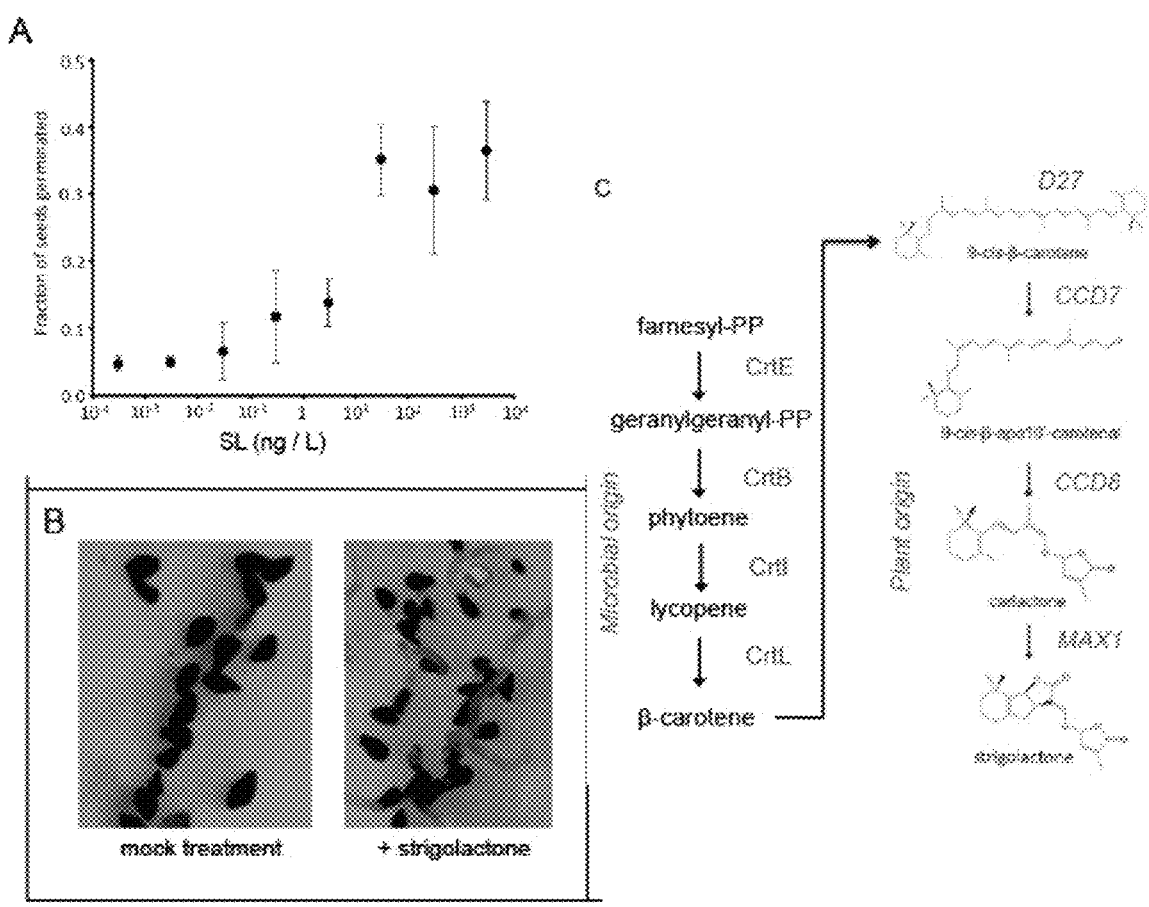
FIG. 1 (A) Synthetic SL shows potent bioactivity, with nanograms of material inducing germination of *Striga* seeds. (B) Bioactivity of synthetic SL. Seeds of *Striga asiatica* were exposed to SL (right) or a mock treatment (left). SL induces *Striga* germination as evident by radicle emergence from seeds. (C) Synthetic biological pathway for the production of SL in yeast, consisting of enzymes of plant and microbial origin.

The use of natural plant growth regulators as crop protection products is well established. For example, gibberellins are widely used in agriculture for fruit setting, ethylene and ethylene analogs are used as defoliants, and recently Valent Biosciences Corporation has commercialized abscisic acid for enhancing color in table grapes [19]. However, the high cost of chemical synthesis and/or extraction from plant materials has precluded the testing and adoption of strigolactone (SL) as a useful tool for agriculture. To address these problems, we developed a synthetic route to a SL mimic compound starting from a readily available sesquiterpene lactone, sclareolide. Sclareolide is economically extracted from the clary sage plant and is currently used in industrial production of perfumes. Global production of the sclareolide is estimated at 50-100 metric tons [20]. Our synthesis of the sclareolide strigolactone mimic is a straightforward hydroxymethylation and alkylation in a one-pot procedure. Sclareolide is condensed with a three-fold excess of methyl formate in the presence of potassium tert-butoxide and the solution of hydroxymethylene lactone is then alkylated with bromobutenolide to give a mixture of two diastereomers. Unlike previously published synthetic routes, the strategy described here does not require costly catalysts or reagents, complicated workup and purification, and gives good yields. We found that a millimolar scale synthesis routinely yielded several hundred milligrams of product, with 80% efficiency. We found that synthetic SL also displayed bioactivity in assays with the plant *Striga* (FIG. 1).

Biosynthesis of Strigolactone

We have also developed a complementary biosynthetic route to SL using genetically engineered yeast. We initially pursued both a chemical synthetic and biosynthetic route, as each approach has distinct advantages and risks in the economics of scale-up. We have engineered the industrial yeast *Pichia pastoris* to produce SL by introducing foreign genes that encode the known pathway to SL. Metabolic engineering microbial cells to produce valuable natural products has been used for the production of antimalarial therapeutics, polymers, and fuels [21]. The advantage of this approach is that *Pichia* can be grown to high cell densities on simple sugars and/or methanol in fermentors, with each cell acting as a microbial cell 'factory' for the synthesis of SL-type compounds.

To accomplish this, we first introduced the known metabolic pathway to SL into *P. pastoris*. SL is produced in plants starting from β-carotene. β-carotene is cleaved into 9-cis-β-apo carotenol and carlactone by the enzymes CCD7 and CCD8, respectively [17]. We first engineered *P. pastoris* to produce lycopene, as it is not a natural metabolite in this yeast. We introduced the genes crtE, crtB, crtI from *P. ananatis* into the chromosome of *P. pastoris* under the control of a constitutive GAP promoter. Transformed colonies appeared red due to the production of lycopene, which was also verified by HPLC against a known standard. We next introduced the gene cassette containing D27, CCD7, CCD8, and the P450 enzyme MAX1. D27 is required to isomerize trans β-carotene to cis β-carotene, which is the substrate for CCD7 [17]. MAX1 has previously been reported to be essential for strigolactone biosynthesis, but had not been shown conclusively. Upon transformation of cells with these constructs we observed the accumulation of SL. In addition, an ethyl acetate purified extract from cultures of engineered yeast showed bioactivity in assays with the weed *Striga asiatica* (FIG. 1—see Example 6 for details).

We have performed initial proof of concept experiments to determine if SLs are able to enhance plant health in water limited conditions. In these experiments, a single application of SL in irrigation water was followed by withholding irrigation for several weeks. In experiments with mature pepper plants (*Capsicum annum*), we observed that SL-treated plants displayed few signs of water stress compared to untreated plants. In this experiment we applied 1 milligram of SL to plants by resuspending the SL in 1 liter of water, which was then used to irrigate the potted plant. The control plant was similarly irrigated with water lacking SL. Plants were then maintained at 22 degrees under natural day-night cycles for 4 weeks. After 4 weeks, we observed qualitative signs of water stress in the untreated plant, such as the beginning stages of chlorosis and severe wilting (FIG.

2). In contrast, the SL treated plant did not display these characteristics. While these results are preliminary, they are support the hypothesis that SL plays a role in water stress regulation and are suggestive that exogenously applied SL could be used as a drought protective product. We have unambiguously shown our SL mimic has specific biological activity expected from SL, and preliminary indications of a drought-resistance effect.

Example 2—Lab-scale Validation of SL as a Drought Tolerance-enhancing Product

This example evaluates the ability of SL to mitigate the negative effects of water stress in maize. Several standard metrics are used to determine efficacy of SL treatment, including onset of water stress symptoms (leaf rolling, reduction in chlorophyll) and grain yield. Using these metrics to evaluate efficacy in enhancing drought tolerance, we are evaluating (1) the best methods for application of SL, (2) the dose concentration of SL, and (3) the dose schedule of SL, thereby determining the stage of plant growth where application has the largest effect. Taken together, this data enables us to estimate the magnitude improvement in crop health and harvest yield to expect in future phases of the project. The overall efficacy of SL treatment on harvest yield (per plant and bushels per acre) is key in determining the value proposition of technology adoption for growers.

Example 3—Development of a Prototype Product for Use in Field Trials

This example focuses on formulation, initial safety testing (both toxicology and environmental fate), and field efficacy of SL under different conditions. Data from Example 2 on the application method and dose with the highest efficacy guides product formulation efforts. Formulation of the SL active ingredient with inert carriers is tested for effective delivery to maize fields. For either a foliar spray or an irrigation supplement, it is likely that a wettable powder is the preferred formulation. Wettable powders contain relatively low amounts of the active ingredient along with inert carriers such as surfactants to allow even spraying. Formulations are tested for active ingredient release profiles using analytical chemistry (GC-MS), while formulation efficacy is measured in greenhouse maize and small-scale field experiments. Initial safety testing are focused on generating mammalian toxicology data and environmental fate data to support registration of SL as a new active ingredient with the Environmental Protection Agency. This work is performed using certified contract research organizations, and can also be used to request an Experimental Use Permit from the EPA for use of SL in field trials larger than 10 acres. The field trials with formulated SL are also performed, wherein the effects of SL treatment on harvest yield with different maize hybrid varieties, soil conditions, weather conditions, and drought severity are examined. The positive impacts of SL as a product for enhancing drought tolerance and improving harvest yield is determined.

Example 4—Effect of Strigolactone on Corn Plants

Given the impacts of drought on agricultural productivity, the lack of crop protection products for addressing the consequences of drought, and our preliminary investigations, this example tests whether strigolactone has a positive effect on water stressed corn plants.

Measure the Effects of SL Application on the Vegetative Growth of Unstressed Plants.

This experiment examines whether SL application affects growth and/or morphology in healthy plants experiencing adequate irrigation. The rationale for this experiment is two-fold: first, due to the historical high costs of SL and mimic synthesis, it is unknown what effect the exogenous application of SL will have on vegetative growth. While there is no prior evidence to suggest deleterious effects, a crop protection product that negatively modulates vegetative growth would have a difficult path to adoption. Second, observation of the growth rates of morphology of SL-treated, unstressed plants provides a baseline for downstream experiments.

These experiments are performed on seedlings of Pioneer 34M95, a high yielding variety with moderate drought tolerance that has been successfully grown to maturity in the greenhouse [25, 26]. Experiments are performed at the V8 stage plants, approximately 4 weeks post-emergence. Plants are grown under best practice conditions as determined by Purdue University greenhouse specialists [25-31]. Maize are grown in 8-inch pots in Turface calcined clay media under natural day-night cycles in a climate controlled greenhouse. Plants are regularly irrigated using an automated drip irrigation system, with an irrigation schedule of 12 waterings daily of 2 minutes each [27]. We add SL directly to the irrigation water of each plant, as we have observed plant physiological responses using this application method in previous data. We test a range of SL dose concentrations, as the amount of active ingredient applied to elicit a drought protective response directly impact the cost-benefit ratio of deploying this technology. We apply SL doses corresponding to an application rate of 200 grams per acre and 10 serial dilutions of 10-fold each (spanning a dose concentration range from 200 grams per acre to 20 picograms per acre). As a plant growth regulator, we expect SL to show high potency, requiring low amounts of active ingredient per plant and per acre to induce a plant response. We measure (i) the height of each plant before the SL application and every 3 days post-application; (ii) the leaf chlorophyll content of each plant, as assayed by a Spad 502 chlorophyll meter; and (iii) vegetative growth stage, as determined by leaf number and morphology. Plants will be maintained with regular irrigation. Each experimental condition (strigolactone dose concentration) is performed in replicate (n=5) to gauge significance of any observed differences using appropriate statistical tests.

Measure the Onset of Water Stress Symptoms in SL-Treated and Untreated Plants.

This experiment tests and quantifies the drought protective effect of SL treatment in terms of the appearance of drought stress symptoms in plants in the vegetative stage of growth. Water stress in growing maize is manifest as leaf rolling (wilting), reductions in chlorophyll and photosynthetic activity, and plant height in severe cases. The experiments involve growing plants under adequate irrigation, applying a range of SL concentrations or a mock treatment, and stopping irrigation to impose water limitation. We then measure the appearance of the above drought stress indicators over time using standard assays and accepted literature practices [23, 24], with an expectation that SL treatment delays the onset of water stress indicators. We perform these experiments to provide the range of SL concentrations that elicit a drought protective response, the duration of the drought protective response, and the magnitude of the drought protective response. This data may be used in determining the impact of SL application on grain yield in water stressed and unstressed corn and in validating SL as a drought protective product.

Measure the Impact of SL Application on Grain Yield in Water Stressed and Unstressed Corn.

This experiment seeks to determine directly whether SL application affects harvest grain yield, both for plants experiencing adequate irrigation and for plants subjected to water stress. These experiments are performed in a greenhouse for maximum control over conditions. We impose a severe water stress during the early reproductive phase of the maize growth cycle, starting at tasseling and continuing to early grain fill. From these results, we determine the best application method, dose, and application timing to enhance grain yields. This data also provides a foundation for scale up and field trials of SL as a drought protective product.

Examining the Effects of Strigolactone on Water-Stressed Corn

This experiment determines the effect of SL application on the onset of water-stress symptoms in corn during the vegetative growth stage. We test a wide range of SL concentrations to focus our investigations of the effects of strigolactone on water-stressed corn. Indicators of water-limitation stress in V8 stage plants are measured (approximately 4 weeks post-emergence). We grow seedlings under regular irrigation, apply SL in irrigation water at V8, and stop irrigation. SL spans a concentration range from 200 grams per acre to 20 picograms per acre. We then monitor plants daily for the presence of drought stress indicators, such as leaf rolling (wilting), height of plants, and chlorophyll content. We expect to observe a subset of SL concentrations that are able to delay the onset of drought stress indicators, as we have observed in our preliminary investigations. These experiments narrow the concentration range of SL that elicit a drought-protective effect. Data from these experiments may provide an indication of the period of drought protection afforded by SL use.

Exploring the Effects of Strigolactone Application on Grain Yield

The efficacy of SL to provide a protective effect to corn under drought stress is evaluated. One key metric to determine economic and technical feasibility is the grain yield of drought stressed plants treated with SL. Maize are grown under greenhouse conditions for precise control of irrigation and conditions.

We evaluate two SL concentrations plus a mock-treated control. Each SL application condition is tested under an irrigated and a water stressed condition. Water stress is applied by halting irrigation for 12 consecutive days [23], which results in severe water stress for the plant. The initial symptoms of drought stress are manifested as leaf tissue wilting and 'rolling' during daylight hours when water demand is high, and return to normal turgor pressure at night. Further severity of water limitation results in leaf wilting both day and night. If drought stress continues, leaf tissue begins to die, starting from the margins of upper leaves and progressing through the plant. While water stress at any stage of growth is detrimental for harvest yield, the corn plant is particularly susceptible to drought during the early reproductive stages. For example, water stress during the period from two weeks prior to silking to two weeks after silking (R1 stage) can reduce harvest yield by 3 to 8 percent for each day of stress [2]. We apply water stress (by stopping irrigation) at the onset of tasseling. Silking occurs 4 to 8 days after tasseling, with pollination 1 to 3 days after the emergence of silk. Subjecting plants to water limitation stress at this time results in significantly lower kernel number as well as kernel weight, due to desiccation of the silks and poor pollination efficiency. These effects ultimately impact grain yield at harvest.

We investigate the efficacy of different application methods to determine the best practice of crop treatment and to inform commercial considerations in future efforts. We focus on common application methods of crop protection products, including use of SL through (i) irrigation systems and as a (ii) foliar spray. Application through irrigation is commonly used for in-season application of crop inputs such as nitrogen and pesticides via center pivot irrigation systems or furrow irrigation [32]. In this experiment, a dose of SL is dissolved in a small volume (0.1 mL) of acetone, diluted into the unit irrigation volume of water, and applied to the base of the plant. For untreated control plants, a mock application of diluted acetone will be performed. Foliar sprays are widely used to apply fertilizers, pesticides, and micronutrients to maize and other crops. Foliar sprays are particularly advantageous during drought conditions where soil moisture does not support efficient uptake of nutrients. Typical foliar spray application volumes use 3-10 gallons of liquid per acre for micronutrients, which we will follow here. We apply the SL dose as a foliar spray using a hand sprayer, with the SL dissolved in acetone and diluted in water as before. Plants receiving the spray application will be physically separated from control plants using temporary plastic barriers. Spray is applied in the evening to follow standard grower practices.

Focused Investigation of 'Best Practice' Application Method, Dose, and Scheduling This experiment incorporates the knowledge gained from previous experiments to test the 'best practice' application method with a higher number of experimental replicates in order to generate highly statistically significant data. We utilize the application conditions that display the largest positive effect on grain yield under simulated drought and reproducing the experiment over multiple plants. This experiment has one delivery method, one application time, two SL concentrations (an experimental and a mock-treatment), and two water stress conditions (halted irrigation and normal irrigation). Thus, there are 4 experimental conditions, allowing each condition to be performed in replicates of n=50. The data from this experiment test the utility of SL as a drought-protective product and provide the foundation for field trials in the next phase of this project.

Taken together, the experiments evaluate application timing, application method, and two application concentrations on irrigated and water-stressed corn. In addition to monitoring symptoms of stress such as rolling, timing of tasseling and silking, and leaf chlorosis, we measure kernel morphology and grain yield at maturity. Severely water-stressed plants are known to have both unfertilized kernels and aborted kernels. We also measure the weight of kernels to evaluate grain fill and the overall yield of grain for each condition.

We have found that synthetically produced SL is effective at germinating seeds of *Striga asiatica* and providing crop protective effects in the lab. We have field trials underway outside of Kisumu, Kenya to test the efficacy of this treatment on maize yields in *Striga* infested fields.

Example 5—Synthesis of Strigolactone

We have developed a chemical mimic (AB01, FIG. 5) of the plant hormone strigolactone displaying biological activity similar to the natural product and potencies several orders of magnitude greater than those of previously described mimics.

The synthesis of AB01 starts from a readily available sesquiterpene lactone, sclareolide. Sclareolide is extracted from species of the *Salvia* plant and is currently used in industrial production of perfumes. The synthesis of AB01 is a straightforward hydroxymethylation and alkylation in a one-pot procedure. Sclareolide is condensed with a three-fold excess of methyl formate in the presence of potassium tert-butoxide and the solution of hydroxymethylene lactone is then alkylated with bromobutenolide to give a mixture of two diastereomers. Resolution of stereomers is not necessary for downstream application. Unlike previously published synthetic routes, the strategy described here does not require costly catalysts or reagents, complicated workup and purification, and gives good yields. We found that a millimolar scale synthesis routinely yielded several hundred milligrams of AB01 product, with 80% efficiency.

Protocol: Synthesis of Bromobutenolide

A 250 mL round bottom flask was charged with N-bromosuccinimide (8.90 g, 1.0 equiv, 50 mmol) and suspended as a yellow mixture in CCl4 (125 mL)-MeCN can substitute for CCl4 here.

3-methyl-2(5H)-furanone (4.90 g, 1.0 equiv, 50 mmol) (see comments on purity) was added, followed by benzoyl peroxide (126.7 mg, 0.01 equiv, 0.5 mmol).

The suspension was flushed under nitrogen and brought to reflux. The progress of the reaction was monitored by periodically halting stirring and allowing the reaction mixture to settle. Due to impurities present, reaction times required up to 20 hours instead of the previously stated 1.5 hours (see note below). Additional benzoyl peroxide and the use of yellow impure NBS increased the rate of reaction.

Once complete, as noted by white/orange solid succinimide present on sides of flask and floating on solvent surface, the reaction mixture was filtered to remove succinimide to provide a clear orange solution. Mixture was concentrated to provide an orange oil that was partitioned between toluene (150 mL) and de-ionized water (150 mL). Rapid stirring of the yellow emulsion for 30 minutes, then the toluene layer was separated, dried with Na2SO4, filtered and concentrated to give a deep orange oil. Passage of this oil through a plug of CH2Cl2 moistened silica gel and elution with CH2Cl2 (200 mL) gave a clear pale yellow solution, concentrated to yield a bright orange liquid (7.25 g, 82% yield) matching known properties that was stored cold.

Note on purity: 3-methyl-2(5H)-furanone is commercially available (Aldrich, 90% technical grade) and by synthesis via bromination/elimination of 3-methyl-2,3-dihydro-2 (3H)-furanone (α-methyl-γ-butyrolactone)1, from citraconic anhydride via a retro Diels-Alder sequence2 or by regio-controlled ring opening and reduction3 and finally by ring-closing methathesis of allyl methyacrylate4. In our hands, commercial material contains polar impurities that are not readily removed by column chromatography or distillation at the cost of considerable loss of material. While these polar impurities severely retard the rate of the radical bromination3, they are removed from the desired bromobutenolide as detailed above. Material without distillation performs well in the alkylation and it is stable over periods of months when stored cold protected from light.

Protocol: Synthesis of Synthetic Lactone

An oven-dried 100 mL 2-necked round bottom flask (2×14j) with stir bar was capped with a rubber septa and nitrogen bubbler was cooled under nitrogen flow.

The flask was charged with sclareolide (0.4126 g, 2.0 mmol, Sigma-Aldrich) and dissolved in dry THF (20 mL).

The clear, colourless solution was cooled under inert gas to –0° C. using an ice-water bath.

Solid potassium tert-butoxide (0.2693 g, 2.4 mmol, 1.2 equivalents, Sigma-Aldrich) was added under nitrogen flow, followed by methyl formate (0.370 mL, 6.0 mmol, 3 equivalents, Sigma-Aldrich) added neat via syringe.

The pale yellow-white suspension was stirred under nitrogen at ~0° C. for 3 hours.

Bromobutenolide (0.3540 g, 2.0 mmol, 1 equivalent) was added as a solution in dry THF (6 mL) via syringe.

The reaction suspension was left to stir overnight, warming to room temperature.

The suspension was quenched with distilled water (50 mL) and diluted with EtOAc (100 mL).

The organics were separated and the aqueous layer extracted with EtOAc (2×50 mL). Combined organics were washed with brine (1×75 mL) and dried with K2CO3. Filtration and concentration provided golden oil (0.780 g) that solidified on standing.

Example 6—Bioactivity of Strigolactone

Bioactivity: Triggering *Striga* Germination

We tested the ability of AB01 to trigger the germination of *Striga* seeds. Seeds of *Striga asiatica* were conditioned by incubation in the dark at 30 degrees for 7 days, and dilutions of the AB01 material in water were applied. We observed that concentrations of 1 nanogram per liter and greater were able to trigger germination of approximately 30% of the seeds, which is similar to published efficiencies and activity for plant-derived strigolactone (FIG. 1A-B). Germination showed a graded dose-response behavior.

Bioactivity: Complementation of *Arabidopsis* Mutant

To further validate the bioactivity of AB01 we tested whether the compound could complement mutants of the model plant *Arabidopsis thaliana* that are deficient in strigolactone biosynthesis. *A. thaliana* mutants with lacking MAX1 cytochrome P450 activity do not synthesize strigolactones, and display phenotypes characterized by increased tillering (branching) of leaf and roots as well as stunting. We grew MAX1 *A. thaliana* under standard conditions and added 1 uM AB01 as an irrigation supplement, or a mock treatment. We observed that the AB01 treatment had a visible impact on the phenotype of the mutant (FIG. 6A-B). Thus, the synthetic AB01 is sufficiently similar to strigolactone to both to trigger *Striga* germination as well as substitute for the natural compound in a model plant.

Example 7—Effect of Plant Propagation Materials on Water-stress

This example determines the effect of the application of a plant propagation material comprising strigolactone or analogs or mimics thereof on the onset of water-stress symptoms in cut flowers during storage, shipping, and/or life in retail or consumer environment. We test a wide range of concentrations to focus our investigations of the effects of the plant propagation material on cut flowers. Indicators of water-limitation stress in flowers are measured (approximately daily). We take cut flowers, apply a plant propagation material in irrigation water, and place in a normal storage environment (e.g., regular day-night cycles, room temperature). The concentration of the strigolactone or analog or mimic thereof in the plant propagation material spanned a concentration range from 1 gram per liter to 1 picogram per liter. We then monitor plants daily for the presence of water stress indicators and shelf life, such as flower and leaf rolling (wilting), turgor of stems, chlorophyll content, and loss of petals.

FIG. 3 shows the results from a preliminary experiment in which cut floweres were treated with a water-only control or a plant propagation material comprising a strigolactone mimic (e.g., AB01). Various concentrations of the strigolactone mimic were added to the irrigation water of the cut flowers. The vase life for cut flowers treated with water-only was approximately 4 days, whereas the vase life for the cut flowers treated with the plant propagation material was approximately 6-7 days. These experiments demonstrated that the addition of the plant propagation material to the cut flowers resulted in a vase life extension of 50-60%. As shown in FIG. 3, the plant on the left is treated with water-only and the plant on the right is treated with the plant propagation material.

Additional experiments with plant propagation materials comprising strigolactone or analogs or mimics thereof are anticipated to reveal a subset of SL concentrations that are able to delay the onset of water stress indicators and prolong shelf life, as we have observed in our preliminary investigations. These experiments narrow the concentration range of strigolactone or analog or mimic thereof that elicit a protective effect. Data from these experiments may provide an indication of the period of shelf life extension afforded by the use of a plant propagation material comprising strigolactone or analog or mimic thereof.

In addition to determining optimal concentration ranges of the plant propagation materials, the purpose of this example is to also determine the best practice of cut flower treatment and to inform commercial considerations. We focus on common application methods of vase life extension and preservative products, including use of the plant propagation material through (i) irrigation, and as a (ii) foliar spray. Application through irrigation is commonly used for cut flower preservation, including granule or liquid-based formulations that can be added to irrigation water. In this experiment, a dose of the plant propagation material comprising strigolactone or analog or mimic thereof is dissolved in a small volume (0.1 mL) of acetone, diluted into the unit irrigation volume of water, and applied in the vase of cut flowers. For untreated control plants, a mock application of diluted acetone is performed. We apply the plant propagation material dose as a foliar spray using a hand sprayer, with the plant propagation material dissolved in acetone and diluted in water as before. Plants receiving the spray application are physically separated from control plants using temporary plastic barriers. Each formulation is tested in combination with other cut flower preservative and shelf life extension products, such as nutrients, antimicrobials, surfactants, and plant growth regulators.

Example 8—Synthesis of Strigolactone

Overview

A chemical mimic of the plant hormone strigolactone has been developed displaying biological activity similar to the natural product and potencies several orders of magnitude greater than those of previously described mimics. The synthesis of AB01 (MW: 374.47, C22H30O5) starts from a readily available sesquiterpene, lactone, sclareolide. Sclareolide is extracted from species of the *Salvia* plant and is currently used in industrial production of perfumes. Sclareolide is condensed with a two-fold excess of methyl formate in the presence of lithium diisopropylamide. The isolated formyl lactone is then alkylated with chlorobutenolide to give a mixture of two diastereomers. A concise synthesis of chlorobutenolide is provided here. Resolution of stereomers is not necessary for downstream application.

Synthesis of Formyl Sclareolide

As shown in FIG. 9, an oven-dried 100 mL 2-necked round bottom flask (2×14j) with stirbar, capped with a rubber septa and nitrogen bubbler was cooled under nitrogen flow. The flask was charged with sclareolide (1.50 g, 6.0 mmol, Sigma-Aldrich) and dissolved in dry THF (42 mL). The clear, colourless solution was cooled under inert gas to ~0° C. using an ice water bath. LDA solution (3.60 mL, 7.20 mmol, 1.2 equivalents, 2.0M solution Sigma-Aldrich) was added dropwise via syringe to give a yellow-orange solution. Stirred at ~78° C. for 30 minutes to ensure deprotonation. Methyl formate (0.74 mL, 12.00 mmol, 2.0 equivalents) was added neat via syringe. The pale yellow solution was left to stir overnight, warming to room temperature. The orange solution was quenched with distilled water (25 mL) and diluted with ethyl acetate (25 mL). The organic layer was separated and the aqueous layer extracted with ethyl acetate (3×25 mL). Combined organics were washed with 1N HCl (2×25 mL), brine (1×25 mL) and dried with Na2SO4. Filtration and concentration provided a golden oil (2.28 g). Purified by flash chromatography (silica gel, gradient 2-20% ethyl acetate:hexane) to provide a white solid (1.57 g) in 94% yield. Rf=0.18 in 10% ethyl acetate:hexane.

Synthesis of Chlorobutenolide

Step 1: TiCl4 aldol (FIG. 10A)

A 1000 mL 3-necked (19j, 34j, 19j) round bottom flask was equipped with an oversized stirbar, nitrogen bubbler (19j), reducing adapter (19j to 34j) topped with a pressure equalizing dropping funnel capped with 19j rubber septa (34j) and rubber septa (19j). The assembled glassware was flushed under nitrogen and flame-dried under nitrogen purge. CH$_2$Cl$_2$ was charged to the flask (212 mL, anhydrous) and dropping funnel (106 mL). At room temperature, TiCl$_4$ (16.5 mL, 150 mmol) was added to the flask to give a clear, colourless solution. The titanium tetrachloride solution was cooled in an ice water bath and the dropping funnel charged with ethyl pyruvate (16.7 mL, 150 mmol) and vinyl acetate (13.8 mL, 150 mmol). The carbonyl solution in CH$_2$Cl$_2$ was added dropwise to the titanium tetrachloride solution over two hours, generating a bright yellow-orange suspension. When addition is complete, the suspension was further stirred for two hours at 0° C. (ice water bath). The clear orange-red solution was quenched with deionized water (140 mL) (caution: exothermic with vigorous gas production). CH$_2$Cl$_2$ separated and the aqueous layer extracted with CH$_2$Cl$_2$ (2×100 mL). Combined CH$_2$Cl$_2$ extracts were washed with deionized water (1×100 mL), brine (1×100 mL) and dried with Na$_2$SO$_4$. Filtered to give a clear golden yellow solution, concentrated to give a bright yellow oil (30.55 g, 85%). The yellow oil darkens on standing and decomposes releasing acrid fumes; these deformulation products complicate downstream purification. Can be stored cold in the refrigerator and is used directly in the following step without purification.

Step 2: Hydrolysis and cyclization (FIG. 10B)

A 1000 mL round bottom flask containing the crude aldol product (30.55 g, 128 mmol) was equipped with an oversized stirbar and taken up in absolute ethanol (345 mL) to give a yellow solution. To the stirred solution was added glacial acetic acid (17 mL) and concentrated HCl (17 mL). A reflux condenser was fitted to the flask and the solution heated to reflux for 4 hours. At this time, deionized water (430 mL) was added and the ethanol removed by fractional distillation until distillation rate slows and internal temperature rises to approximately 90° C. and volume of distillate is approximately 135% of initially added ethanol. The condenser was returned to reflux set up and the deep golden reaction mixture heated at reflux for 45 minutes. The cooled reaction mixture was extracted with ethyl acetate (3×150 mL). Combined extracts were washed with brine (1×100 mL) and dried $Na_2SO_4$. Filtered to give a golden solution, concentrated to give an orange oil (15.19 g). The crude orange oil was subjected to bulb-to-bulb distillation, collecting material at 120-135° C./8 mbar. The pale yellow oil (9.47 g, 65%) slowly solidified on standing.

Step 3: Chlorination (FIG. 10C)

A 25 mL 19j rbf was capped with a take-off head (2 necked, 2×19j), capped with a 19 j glass stopper and 19j reflux condenser. The flask was charged with $CH_2Cl_2$ (5 mL), $SOCl_2$ (1 mL, 14 mmol, 1.4 equiv) and a drop of DMF, then heated to reflux. A golden solution of hydroxybutenolide (1.15 g, 10 mmol) in $CH_2Cl_2$ (5 mL) was added dropwise to the refluxing vapours at such a rate to maintain reflux with immediate gas evolution. After two hours of reflux, the reaction mixture was cooled to rt, diluted with $CH_2Cl_2$ (20 mL) and poured into saturated $NaHCO_3$ (~50 mL) containing ice and rapidly stirred to destroy excess $SOCl_2$. When gas evolution has ceased the $CH_2Cl_2$ layer was separated and the aqueous extracted with $CH_2Cl_2$ (2×20 mL). Combined $CH_2Cl_2$ extracts were washed with brine (1×50 mL) and dried with freshly pulverized $MgSO_4$. The clear orange solution was filtered and concentrated to give a thin red liquid (1.106 g). The crude liquid was subjected to bulb-to-bulb distillation, collecting a clear colourless distillate (0.73 g, 53%) at 120-122° C./5 mbar.

Synthesis of AB01

As shown in FIG. 11, a 100 mL round bottom flask containing the formyl sclareolide (1.57 g, 5.64 mmol) was flushed under nitrogen and dissolved in DMF (15 mL, anhydrous, Sigma-Aldrich) at room temperature. The clear yellow solution was treated with potassium carbonate (858 mg, 6.2 mmol, 1.1 equivalents) under nitrogen flow to give a yellow-white suspension. To the suspension was added dropwise via syringe a clear golden solution of chlorobutenolide (5.52 mmol, 1.2 equivalents) in DMF (5 mL, anhydrous). Addition of the chlorobutenolide solution causes a colour change of the reaction mixture from yellow to orange to brown. Left to stir under nitrogen at room temperature for 24 hours. The dark suspension was diluted with distilled water (50 mL) and ethyl acetate (50 mL). Organic layer separated and the aqueous layer extracted with ethyl acetate (3×40 mL). The combined organics were washed with saturated $NaHCO_3$ (1×50 mL), distilled water (1×50 mL), brine (1×50 mL) and dried $K_2CO_3$. Filtration and concentration gave a viscous brown oil (2.63 g) that solidifies on standing Purified by flash chromatography (silica gel, gradient 6-50% ethyl acetate:hexane) to provide a white solid (1.67 g) in 80% yield. Rf=0.18 in 25% ethyl acetate:hexane. The material tenaciously retains ethyl acetate and requires prolonged drying under vacuum to remove trace solvent.

Synthesis of Nitrogen-Substituted Sclareolide

As shown in FIG. 8A to 8F, the nitrogen-substituted sclareolides are synthesised using an approach similar to FIG. 7. To a solution of (R)-2-benzyloxy-20-hydroxy-1,10-binaphthyl (260 mg, 0.69 mmol) in toluene (9 mL) is added tin(IV) chloride (0.4 mL, 3.37 mmol) at −20° C. and the solution is stirred for 30 min. This complex of 2-benzyloxy-20-hydroxy-1,10-binapthyl-SnCl4 prepared in situ is cooled to −78° C. and nitrogen-substituted homofarnesic acid (600 mg, 2.4 mmol) in toluene (9 mL) is added dropwise over a period of 5 min. The reaction mixture is stirred at −78° C. for 3 h and kept at −20° C. for 3 d, quenched with saturated aqueous $NaHCO_3$, and extracted with ethyl acetate. The combined organic extracts are dried over anhydrous MgSO4 and concentrated. The crude product is purified by column chromatography on silica gel to yield the nitrogen-substituted (+)-sclareolide. Then similar to FIG. 11, the nitrogen-substituted sclareolide is used to the synthesis of nitrogen-substituted AB01. The stereochemistry of the product compound can be changed by using a different catalyst, such as a chiral LBA.

Example 9—Field Trial of AB01

Field trial was performed from April to July 2014 in Hays County, Tex. Dekalb hybrid 68-05 was planted at a density of 25,000 plants per acre (30" rows with 8" spacing). The field was top-dressed with 80 lbs/ac nitrogen. The field was not irrigated. AB01 treated plots were sprayed with a 2 gram per acre dose at the tasseling (VT) stage. Spraying was accomplished by resuspending solid AB01 in 0.5 mL of acetone, and diluting in water for a spray volume of 1 gallon per 500 square feet. Experiments were performed in triplicate Improved Germination Triggering of Parasitic Weeds (FIG. 12)

Significant differences in germination triggering efficiency between the plant-derived natural compound 5-deoxystrigol (5-dS) and the synthetic compound AB01 were observed. Seeds of *O. cumana* were primed by incubation on glass fiber filters in darkness at room temperature for 3 days. Specified concentrations of AB01 or 5-dS were applied and seeds were monitored at 48 hours post-treatment. Germination was evident by appearance of haustoria. Experiments were performed in triplicate.

Drought Tolerance in Alfalfa Enabled by AB01 Treatment (FIG. 13)

Alfalfa was grown from seeds for 14 days. Seedlings were treated with 1 mg/mL AB01 or mock treated. Irrigation was stopped after treatment and seedlings were monitored for symptoms of water limitation stress. At approximately 7 days post-treatment, the untreated seedlings appeared dessicated (left), while treated seedlings appeared robust (right).

AB01 Enhances Ear Fertilization in Corn Field Trial (FIG. 14).

The fraction of fertilized ears was measured by visual inspection of the ear silk at the R2-R3 stage. Unfertilized silks that appear yellow/green, while fertilized silks appear reddish brown. Completely unfertilized ears have silks that are completely yellow/green, fertilized ears appear brown, while ears with an incomplete degree of fertilized silks have a mixed population of silks. We found that AB01 treatment decreased the fraction of unfertilized ears while increasing the fraction of fertilized ears, compared to the mock treated control.

AB01 Enhances Kernel Set in Corn Field Trial (FIG. 15).

Ears were visually inspected at harvest to monitor kernel set (the number of fully formed kernels in the mature ear). Control (mock treated, left) ears showed incomplete kernel set and kernel abortion, symptoms of severe drought stress. AB01 treated ears (right) showed more complete kernel set and few signs of kernel abortion.

AB01 Enhances Ear Volume (FIG. 16).

Ears volume was measured in the field at the R3 stage to calculate ear volume. The length and circumference of each ear was measure, and volume was calculated by treating the ear as a cylinder. Approximately 100 ears from each plot were measured. AB01 treated ears averaged significantly higher volumes in mid-season as compared to the mock treated control.

AB01 Treatment Enhances Average Kernel Weight (FIG. 17).

After harvest, ears were shelled and kernels counted and weighed to quantitate the 'thousand kernel weight' (TKW), or average mass of kernels in the trial. AB01 treated plots yielded kernels averaging 30% higher mass than control plots.

AB01 Treatment Enhances Harvest Yield (FIG. 18).

Ears from control and treated plots were harvested, shelled, and moisture tested to quantitate dry mass. Control plots averaged 120 bushels per acre, while AB01 treated plots averaged 143 bushels per acre, a 19% increase. Grain yield is calculated at 15% moisture, a standard measure of harvest output.

AB01 Treatment Enables Salinity Tolerance in Alfalfa (FIG. 19).

Alfalfa was grown from seeds for 14 days. Seedlings were treated with 1 mg/mL AB01 or mock treated. After treatment, plants were irrigated with 100 mL water containing 35 g/L dissolved salt (NaCl). Irrigation was performed every 48 hours and plants monitored for symptoms of salinity stress. After 5 days, control plants (left) displayed near complete chlorosis, while treated plants (right) displayed significantly higher vigor.

AB01 Treatment Enables Salinity Tolerance in Tomato (FIG. 20).

Tomato seedlings were treated with 10 mg/mL AB01 or mock treated. 24 hours after treatment, they were irrigated with 250 mL water containing 29.2 g/L salt (NaCl). At 6 hours after salt irrigation, the control seedling (left) displayed symptoms of salinity shock which are manifest as severe wilting. The treated seedling (right) appeared unstressed.

AB01 Treatment Enhances Drought Tolerance in Wheat (FIG. 21).

Wheat was grown in greenhouse conditions from seed for 6 weeks with adequate irrigation. Plants were treated with 1 mg of AB01 resuspended in acetone and diluted in 100 mL water, or mock treated as a control. Irrigation was stopped and plants monitored for symptoms of drought stress. At 7 days post treatment, control plants (left) showed signs of water limitation stress (evident by wilting), while treated plants (right) appeared vigorous.

Reduction of *Striga* and Enhancement of Grain Yield in AB01 Treated Fields (Siaya County, Kenya) (FIG. 22).

Field trial was performed from August 2013 to January 2014 in Siaya County, Kenya. AB01 treated plots were sprayed with a 1 gram per acre dose 1 week prior to planting. Treatment was accomplished by resuspending solid AB01 in 1 mL of acetone, and diluting in 4000 L of water. 3 replicate treated and untreated plots (100 m2 each) were performed. (A) *Striga* emergence was observed in the untreated plots during the season and prior to harvest, while treated plots showed few signs of *Striga*-related stress and parasite emergence. (B) Grain yields from treated plots showed a 25% increase compared to the untreated plots. (C) The biomass of *Striga* from each plot was collected and measured after harvest. Treated plots show a significant reduction in the mass of *Striga* present. (D) Emergent *Striga* was counted in each plot, with few parasites in treated plots.

Reduction of Acute Water Stress in AB01 Treated Corn (FIG. 23).

Corn seedlings were scored as unstressed, moderately water stressed and severely water stressed as measured by visual inspection of leaf rolling, a response of corn to water stress. Dekalb 67-86 RR corn seeds were planted and then irrigated through 7 days after emergence in a greenhouse setting. Seedlings were then treated with 40 mL of water, 0.1 mM AB01 or 1.0 mM AB01 and irrigation ceased. On the 6th day without irrigation, seedlings were scored for water stress. Seedlings with open leaves were scored as unstressed; seedlings with partial leaf rolling were scored as moderately stressed; seedlings with completely rolled leaves were scored as severely stressed. We found that AB01 treatment decreased the fraction of severely stressed seedlings while increasing the fraction of unstressed seedlings in a dose-dependent manner.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

REFERENCES CITED

1. Boyer, J. S. and M. E. Westgate, *Grain yields with limited water*. J Exp Bot, 2004. 55(407): p. 2385-94.
2. Nielsen, R., *Corn growth and development, what goes on from planting to harvest?* Extension University, 1997.
3. Schoper, J. B., et al., *Plant factors controlling seed set in maize: the influence of silk, pollen, and ear-leaf water status and tassel heat treatment at pollination*. Plant Physiol, 1987. 83(1): p. 121-5.
4. United States Department of Agriculture, National Agricultural Statistics Service Crop production report released September 2013.
5. United States Department of Agriculture, Risk Management Agency *RMA Indemnities* (As of Jul. 8, 2013). Accessed 26 Sep. 2013 from: http://www.rma.usda.gov/data/indemnity/2013/070813table.pdf.
6. O'Connor, C., *Soil Matters: How the Federal Crop Insurance Program should be reformed to encourage low-risk farming methods with high-reward environmental outcomes*. 2013.
7. *Climate Stabilization Targets: Emissions, Concentrations, and Impacts over Decades to Millennia*. 2011: The National Academies Press.
8. Bruce, W. B., G. O. Edmeades, and T. C. Barker, *Molecular and physiological approaches to maize improvement for drought tolerance*. J Exp Bot, 2002. 53(366): p. 13-25.
9. Harrigan, G. G., et al., *The forage and grain of MON 87460, a drought-tolerant corn hybrid, are formulationally equivalent to that of conventional corn*. J Agric Food Chem, 2009. 57(20): p. 9754-63.
10. Tollefson, J., *Drought-tolerant maize gets US debut*. Nature, 2011. 469(7329): p. 144.
11. Peleg, Z. and E. Blumwald, *Hormone balance and abiotic stress tolerance in crop plants*. Curr Opin Plant Biol, 2011. 14(3): p. 290-5.
12. Prasch, C. M. and U. Sonnewald, *Simultaneous application of heat, drought, and virus to Arabidopsis plants reveals significant shifts in signaling networks*. Plant Physiol, 2013. 162(4): p. 1849-66.
13. Rivero, R. M., et al., *Enhanced cytokinin synthesis in tobacco plants expressing PSARK::IPT prevents the degradation of photosynthetic protein complexes during drought*. Plant Cell Physiol, 2010. 51(11): p. 1929-41.
14. Harris, M. J., et al., *Water-stress-induced changes in the abscisic acid content of guard cells and other cells of*

*Vicia faba* L. *leaves as determined by enzyme-amplified immunoassay.* Proc Natl Acad Sci USA, 1988. 85(8): p. 2584-8.
15. Kim, T. H., et al., *Guard cell signal transduction network: advances in understanding abscisic acid, CO2, and Ca2+ signaling.* Annu Rev Plant Biol, 2010. 61: p. 561-91.
16. Tsuchiya, Y. and P. McCourt, *Strigolactones: a new hormone with a past.* Curr Opin Plant Biol, 2009. 12(5): p. 556-61.
17. Alder, A., et al., *The path from beta-carotene to carlactone, a strigolactone-like plant hormone.* Science, 2012. 335(6074): p. 1348-51.
18. Lopez-Raez, J. A., et al., *Does abscisic acid affect strigolactone biosynthesis?* New Phytol, 2010. 187(2): p. 343-54.
19. Peppi, M. C., M. W. Fidelibus, and N. Dokoozlian, *Abscisic Acid Application Timing and Concentration Affect Firmness, Pigmentation, and Color of Flame Seedless' Grapes.* HortScience, 2006. 41(6): p. 1440-1445.
20. Lawrence, B. *Production of clary sage oil and sclareol in North America.* In *Proceedings of the 4th international symposium on medicinal and aromatic plants.* 1994.
21. Stephanopoulos, G., *Synthetic biology and metabolic engineering.* ACS Synth Biol, 2012. 1(11): p. 514-25.
22. Clark, M., et al., *Agronomic, economic, and environmental comparison of pest management in conventional and alternative tomato and corn systems in northern California.* Agriculture, Ecosystems & Environment, 1998. 68(1): p. 51-71.
23. Witt, S., et al., *Metabolic and phenotypic responses of greenhouse-grown maize hybrids to experimentally controlled drought stress.* Mol Plant, 2012. 5(2): p. 401-17.
24. Chugh, V., et al., *Differential antioxidative response of tolerant and sensitive maize (Zea mays L.) genotypes to drought stress at reproductive stage.* Indian J Biochem Biophys, 2013. 50(2): p. 150-8.
25. Eddy, R. and D. T Hahn, *Optimizing Greenhouse Corn Production: Materials and Methods.* Purdue Methods for Corn Growth, 2010.
26. Eddy, R. and D. T Hahn, *Optimizing Greenhouse Corn Production: Summary.* Purdue Methods for Corn Growth, 2012.
27. Rink, W., et al., *Optimizing Greenhouse Corn Production: What Is the Best Irrigation Strategy?* Purdue Methods for Corn Growth, 2010.
28. Eddy, R. and D. T Hahn, *Optimizing Greenhouse Corn Production: What Is the Best Lighting and Plant Density?* Purdue Methods for Corn Growth, 2010.
29. Leonberger, A., R. Eddy, and D. T Hahn, *Optimizing Greenhouse Corn Production: What Is the Best Open Pollination Method?* Purdue Methods for Corn Growth, 2010.
30. Gambrel, D., R. Eddy, and D. T Hahn, *Optimizing Greenhouse Corn Production: What Is the Best Pot Size?* Purdue Methods for Corn Growth, 2010.
31. Gambrel, D., et al., *Optimizing Greenhouse Corn Production: What Is the Best Root Medium?* Purdue Methods for Corn Growth, 2010.
32. Tarkalson, D. D., S. J. Van Donk, and J. L. Petersen, *Effect of nitrogen application timing on corn production using subsurface drip irrigation.* Soil Science, 2009. 174(3): p. 174-179.
33. Yoshida, S. and K. Shirasu, *Plants that attack plants: molecular elucidation of plant parasitism.* Curr Opin Plant Biol, 2012. 15(6): p. 708-13.
34. Wigchert, S. C., et al., *Dose-response of seeds of the parasitic weeds Striga and Orobanche toward the synthetic germination stimulants GR 24 and Nijmegen 1.* J Agric Food Chem, 1999. 47(4): p. 1705-10.
35. Pimentel, D., et al., *Environmental and economic costs of pesticide use.* BioScience, 1992. 42(10): p. 750-760.
36. Lake, L. K., et al., *Regulation of Biochemical Plant Growth Regulators at the US Environmental Protection Agency.* HortTechnology, 2002. 12(1): p. 55-58.
37. Okamoto, M., et al., *Activation of dimeric ABA receptors elicits guard cell closure, ABA-regulated gene expression, and drought tolerance.* Proc Natl Acad Sci USA, 2013. 110(29): p. 12132-7.
38. E. M. Magnus, B. Zwanenburg. *J. Agric. Food. Chem.* 1992, 40, 1066-1070.
39. B. Zwanenburg, A. S. Mwakaboko, A. Reizelman, G. Anilkumar, D. Sethumadhavan. *Pest Manag. Sci.* 2009, 65, 478-491.
40. B. Zwanenburg, T. Pospisil. *Molecular Plant* 2013, 6, 38-62.

What is claimed is:

1. A method of making a compound of Formula (I), comprising:
   a) contacting sclareolide with methyl formate to form a mixture; and
   b) contacting said mixture with

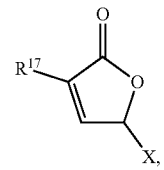

wherein $R^{17}$ is H, alkyl, halo, or haloalkyl, and X is Cl, Br, or I,
wherein Formula (I) has the structure of:

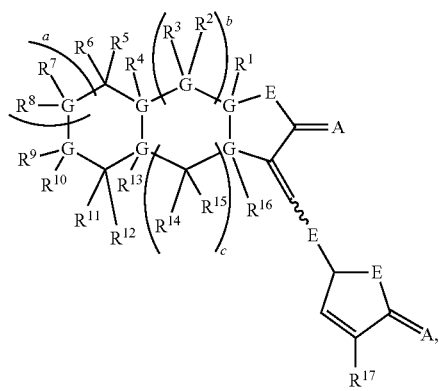

wherein:
a is 1, b is 2, and c is 0;
each A is independently O;
each E is independently O;
each G is independently C;
$R^1$, $R^5$, $R^6$, and $R^{13}$ are methyl; and
$R^2$, $R^3$, $R^4$, $R^7$, $R^8$, $R^9$, $R^{10}$, $R^{11}$, $R^{12}$, $R^{14}$, $R^{15}$ and $R^{16}$ are H.

2. The method of claim 1, wherein said sclareolide comprises

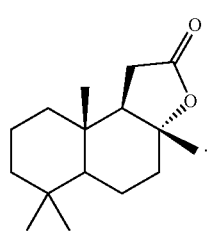 [SMILES: CC1(C)CCC[C@@]2(C)C1CC[C@@]1(C)OC(=O)C[C@@H]12]

3. The method of claim 1, wherein said methyl formate is at least two fold excess of said sclareolide.
4. The method of claim 1, further comprising dissolving said sclareolide in a tetrahydrofuran (THF) solution.
5. The method of claim 1, further comprising contacting said sclareolide with a base solution.
6. The method of claim 5, wherein said base solution comprises lithium diisopropylamide (LDA).
7. The method of claim 5, wherein said base solution comprises potassium tert-butoxide.
8. The method of claim 1, further comprising dissolving the mixture in a dimethylformamide (DMF) solution.
9. The method of claim 1, further comprising contacting the mixture with potassium carbonate.
10. The method of claim 1, wherein $R^{17}$ is alkyl.
11. The method of claim 1, wherein $R^{17}$ is methyl.
12. The method of claim 1, wherein X is Cl.
13. The method of claim 1, wherein X is Br.
14. A method of making a compound of Formula (II), comprising:
   a) contacting sclareolide with a base solution comprising lithium diisopropylamide (LDA) or potassium tert-butoxide;
   b) contacting said sclareolide with methyl formate to form a mixture; and
   c) contacting said mixture with

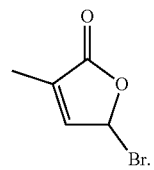

wherein Formula (II) has the structure of:

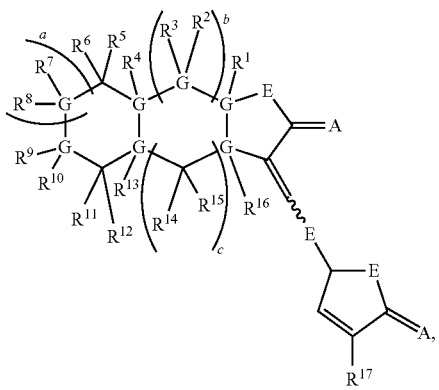

wherein:
a is 1, b is 2, and c is 0;
each A is independently O;
each E is independently O;
each G is independently C;
$R^1$, $R^5$, $R^6$, $R^{13}$, and $R^{17}$ are methyl; and
$R^2$, $R^3$, $R^4$, $R^7$, $R^8$, $R^9$, $R^{10}$, $R^{11}$, $R^{12}$, $R^{14}$, $R^{15}$ and $R^{16}$ are H.

* * * * *